US006475778B1

(12) United States Patent
Roberts et al.

(10) Patent No.: US 6,475,778 B1
(45) Date of Patent: Nov. 5, 2002

(54) DIFFERENTIATION ENHANCING FACTORS AND USES THEREFOR

(75) Inventors: Thomas M. Roberts, Cambridge; Frederick J. King, Brookline, both of MA (US); David F. Harris, Gales Ferry, CT (US); Erding Hu, King of Prussia, PA (US); Bruce Spiegelman, Waban; Joanne Chan, Brookline, both of MA (US)

(73) Assignee: Dana-Farber Cancer Institute, Boston, MA (US)

( * ) Notice: Subject to any disclaimer, the term of this patent is extended or adjusted under 35 U.S.C. 154(b) by 0 days.

(21) Appl. No.: 09/023,905

(22) Filed: Feb. 13, 1998

Related U.S. Application Data

(60) Provisional application No. 60/038,191, filed on Feb. 14, 1997.

(51) Int. Cl.$^7$ ........................... C12N 15/00; C12N 5/00; C12P 21/06; C07H 21/02; C07H 21/04
(52) U.S. Cl. .................... 435/320.1; 435/69.1; 435/325; 435/455; 536/23.1; 536/23.5
(58) Field of Search ............................. 536/23.1, 23.5; 435/320.1, 325, 455, 69.1

(56) References Cited

FOREIGN PATENT DOCUMENTS

WO    WO 95/19779    7/1995

OTHER PUBLICATIONS

King et al, Mol. Cell. Bio. 19(3):2330–2337, 1999.*
Weng et al, Mol. Cell. Bio. 15(10):5627–5634, 1995.*
Database EMBL—EMEST13 Entry MMW336, Ac NO. W89336, Marra, M. et al.: "mf62d06.r1 Soares Mouse Embryo NbME13.5 14.5 Mus Musculus cDNA Clone 418859 5'Similar to SW:GCS1_YeastP35197 Zinc Finger Protein GCS1," XP002066666 (Jul. 7, 1996).
Ishikawa, K. et al., "Prediction of the Coding Sequences of Unidentified Human Genes. VIII. 78 New cDNA Clones from Brain Which Code for Large Proteins in vitro," *DNA Research*, vol. 4, 307–13 (1997).
Williams, R. and Katan, M., "Structural Views of Phosphoinositide–specific Phosholipase C: Signalling the Way Ahead," *Structure*, vol. 4, No. 12, 1387–94 (1996).
Wong, K. and Cantley, L., "Cloning and Characterization of Human Phosphatidylinositol 4–Kinase," *Journal of Biological Chemistry*, vol. 269, No. 46, 28878–84 (Nov. 18, 1994).
Kitamura, T. et al., "Molecular Cloning of p.125$^{Nap1}$, Protein That Associates with an SH3 Domain of Nick," *Biochemical and Biophysical Research Communications*, vol. 219, 509–514 (1996).
Williamson, Michael P., "The Structure and Function of Proline–rich Regions in Proteins", vol. *Biochem. J.*, 297, 249–260 (1994).
Spiegelman, Bruce M. and Flier, Jeffrey S., "Adipogenesis and Obesity: Rounding Out the Big Picture," *Cell* vol. 87, 377–389 (1994).
Cohen, George B. et al., "Modular Binding Domains in Signal Transduction Proteins," *Cell* vol. 80, 237–248 (1995).

Yu, Hongtau et al., "Structural Basis for the Binding of Proline–Rich Peptides to SH3 Domains," *Cell* vol. 76, 933–945 (1994).
Dai, Zonghan and Pedergast, Ann Marie, "Abi–2, a Novel SH3–containing Protein Interacts with the c–Abl Tyrosine Kinase and Modulates c–Abl Transforming Activity", *Genes & Development* 9:2569–2582.
Yeh, Wen–Chen et al., "Cascade Regulation of Terminal Adipocyte Differentiation by Three Members of the C/EBP Family of Leucine Zipper Proteins," *Genes & Development* 9:168–181.
Sudol, Marius, Yes–Associated Protein (YAP65) is a Proline–Rich Phosphoprotein that Binds to the SH3 Domain of the Yes Proto–Oncogene Product, *Oncogene* 92145–52 (1994).
Alexandropoulos, Konstantina et al., Proline–rich Sequences that Bind to Src Homology and 3 Domains With Individual Specificities, *Proc. Natl. Acad. Sci. USA* vol. 92, 3110–3114 (1995).
Courtneidge, Sara A., "Protein Tyrosine Kinases, with Emphasis on the SRC Family," *Seminars in Cancer Biology* vol. 5, 239–246 (1994).
Lim, Wendell A. et al., "Structural Determinants of Peptide–Binding Orienttion and of Sequence Specificity in SH3 Domains," *Nature* vol. 372, 375–379 (1994).
Michaely, Peter and Bennett, Vann, "The Membrane–binding Domain of Ankyrin Contains Four Independently Folded Subdomains, Each Comprised of Six Ankyrin Repeats," *The Journal of Biological Chemistry*, vol. 268, 22703–22709 (1993).
Weng, Zhigang et al., "Structure–function Analysis of SH3 Domains: SH3 Binding Specificity Altered by Single Amino Acid Substitutions," *Molecule and Cellular Biology*, vol. 15, 5627–5634 (1995).
Feng, Sibo et al., Two Binding Orientations for Peptides to the Src Sh3 Domain: Development of a General Model for SH3–Ligand Interactions, *Science* vol. 266, 1241–1247 (1994).
Trainor, Cecelia et al., "Structure and Evolution of a Human Erythroid Transcription Factor," *Nature*, vol 343, 92–96 (1990).
Pawson, Tony et al., "Protein Modules and Signaling Networks," *Nature* vol. 373, 573–580 (1995).

* cited by examiner

*Primary Examiner*—Scott D. Priebe
*Assistant Examiner*—Sumesh Kaushal
(74) *Attorney, Agent, or Firm*—Amy E. Mandragouras; DeAnn F. Smith

(57) ABSTRACT

The present invention relates to novel SH3 domain binding protein, referred to herein a DEF polypeptides. The DEF polypeptides comprise several motifs including a src SH3 consensus binding sequence, four ankyrin repeats, one zinc finger domain and six copies of a proline-rich tandem repeat. DEF polypeptides may function as mediators of SH3 domain-dependent signal transduction pathways and, thus may mediate multiple signaling events such as cellular gene expression, cytoskeletal architecture, protein trafficking and endocytosis, cell adhesion, migration, proliferation and differentiation. Described herein are isolated and antisense nucleic acids molecules, recombinant expression vectors, host cells and non-human transgenic animals containing an insertion or a disruption of the DEF gene. Diagnostic, screening and therapeutic methods utilizing the compositions of the invention are also provided

12 Claims, 34 Drawing Sheets

```
CCCGGtCCGcGCCTCCCGCCCCGCCGGCTGCTCCCGCCGCCGCCGCCGtCgcCTCCCgCTTTCCGCTGcGAGAG
CCGCGATCGGCCGGCCGAGGGGAGcGGGGCGtGGGCGTCTGCGCCGCCGCCAGGGAGCCGCCGCCGAATC
CGCGATGGAATAATGCCCAGCGGCCCGCCCGGTCCCGGTAATTTTCTGATGTGACGGCTGAGACATGAGA
TCTTCAGCCTCCAGGCTCTCCAGTTTTTCATCAAGAGATTCGCTATGGAATCGGATGCCGGACCAGATCTC
CGTCTCCGAGTTCATCGCCGAGACCACCGAGGACTACAACTCGCCCACCACGTCCAGCTTCACTACGCGG
CTGCACAACTGCAGGAACACCGTCACGCTGCTGGAGGAGGCTCTAGACCAAGATAGAACAGcCTTACAGA
AAGTTAAGAAGTCTGTAAAAGCAATATACAATTCCGGTCAAGACCATGTACAAAATGAAGAAAACTATG
CGCAAGTTCTTGATAAGTTTGGGAGTAATTTTTTAAGTCGAGACAACCCAGATCTTGGCACCGCTTTTGTC
AAGTTTTCTACGCTTACAAAGGAACTGTCCACACTGCTGAAAAATCTGCTCCAGGGCCTGAGcCACAATGT
GATCTTCACCTTGGATTCCTTGTTGAAAGGAGACCTGAAGGGAGTCAAAGGCGATCTCAAGAAACCATTT
GACAAAGCTTGGAAAGATTATGAGACGAAGTTTACCAAAATTGAGAAGGAGAAGAGGGAGCACGCCAA
GCAGCACGGGATGaTCCGCACGGAGATCACCGGCGCCGAGATCGCGGAGGAAATGGAAAAGGAGCGGCG
CCTCTTCCAGCTCCAGATGTGCGAGTATCTCATTAAAGTTAATGAAATCAAGACCAAAAAGGGTGTGGAT
CTGCTGCAGAACCTGATAAAGTATTATCACGCACAGTGCAATTTCTTTCAAGATGGTTTGAAAACAGCTG
ATAAATTGAAACAGTACATTGAAAAGCTGGCTGCTGATTTGTATAATATCAAACAGACCCAGGACGAAG
AAAAGAAACAGCTGACCGCACTCCGAGACCTAATAAAGTCCTCGCTCCAACTCGATCAGAAGGAGTCTaG
GAGAGATTCCCAGAGCCGGCAGGGAGGCTACAGCATGCACCAGCTGCAGGGCAACAAGGAATaCGGCAG
CGAGAAGAAGGGCTACCTgCTGAAGAAGAGTGACGGGATCCGGAAAGTGTGGCAGAGAAGGAAGTGCTC
CGTCAAGAACGGGATCCTGACCATCTCCCACGCCACGTCCAACAGACAGCCAGCCAAGCTGAACCTTCTC
ACTTGCCAGGTGAAGCCGAATGCCGAGGACAAGAAGTCTTTTGACCTGATATCACATAACAGGACGTATC
ACTTTCAGGCCGAAGATGAGCAGGATTATGTAGCGTGGATCTCGGTGCTGACAAACAGCAAAGAGGAGG
CCCTCACCATGGCCTTCCGGGGGAACAGAGTGCTGGGGAGAGCAGCCTGGAGGAGCTGACGAAGGCCA
TCATCGAGGACGTGCAGCGGCTCCCGGGCAACGACGTCTGCTGCGACTGCGGCTCGGCAGAACCCACCTG
GCTGTCCACCAACTTGGGCATCTTGACCTGTATAGAATGTTCCGGCATCCATAGAGAAATGGGGGTTCAT
ATTTCTCGCATCCAGTCTTTGGAACTAGACAAATTAGGAACTTCTGAACTCTTGCTGGCCAAGAATGTAGG
AAACAATAGTTTTAATGATATTATGGAAGCAAATTTACCCAGTCCCTCACCAAAACCCACCCCTTCAAGT
GATATGaCTGTACGGAAGGAATATATCaCTGCAAAGTATGTAGATCATAGGTTTTCACGGAAGACCTGTTC
ATCGTCATCAGCTAAACTGAACGAATTGCTTGAGGCCATCAAATCCAGGGATTTACTTGCACTAATTCAA
GTCTATGCAGAGGGGGTGGAGCTAATGGAACCGCTGCTGGAACCCGGACAGGAGCTTGGGGAGACAGCC
CTTCATCTTGCAGTCCGAACGCAGACCAGACATCTCTCCATTTGGTGGACTTCCTTGTACAAAACTGTGGG
AACCTAGATAAGCAGACGGCCCTGGGGAACACGGCCCTGCACTACTGTAGTATGTACAGTAAACCAGAG
TGTTTGAAGCTGCTGCTCAGGAGCAAGCCCACTGTGGACGTCGTTAATCAGGCTGGAGAGACCGCCCTGG
ACATAGCAAAGAGACTGAAAGCCACTCAGTGTGAAGACCTGCTTTCCCAAGCTAAATCTGGAAAGTTCAA
TCCACACGTCCACGTGGAATATGAGTGGAATCTTCGACAGGAGGAGATGGATGAGAGCGATGACGACCT
GGATGACAAACCGAGCCCCATCAAGAAGGAGCGCTCCCCCCGACCGCAGAGCTTCTGCCACTCCTCCAGC
ATCTCCCCcCAGGACAAGCTCTCACTGCCGGGCTTCAGCACGCCAAGGGACAAGCAACGACTCTCCTACG
GCGCCTTCACCAACCAGATCTTCGTCTCCACAAGCACAGACTCACCCACGTCACCGATCGCAGAGGCGCC
CCCGCTGCCTCCCAGAAACGCCACGAAAGGTCCACCTGGCCCACCTTCAACACTCCCTCTAAGCACCCAG
ACCTCTAGTGGCAGCTCCACCCTGTCCAAGAAGCGGTCTCCTCCCCCACCACCCGGACACAAGAGAACCC
TGTCTGACCCTCCCAGCCCACTACCTCACGGGCCCCAAACAAAGGCGCAGTTCCTTGGGGTAACGACGT
GGGTCCCTCATCGTCCAGTAAGACCACGAACAAGTTCGAGGGCCTGTCCCAGCAGTCGAGCACCGGTTCT
GCaAAGACTGCACTTGtCCCAAGAGTTCTTCCTAAACTACCTCAGAAAGTGGCACTAAGGAAAACAGAGA
CCAGCCATCATCTCTCCCTCGACAAAGCCAACGTCCCACCTGAGATCTTCCAGAAGTCGTCCCAGTTGACA
GAGTTACCGCAGAAGCCGCCACCCGGGGACCTGCCCCGAAGCCCACGGAACTGGCTCCCAAACCCCCA
TTGGAGACTTACCACCTAAGCCAGGCGAGCTGCCCCGAAGCCACAGCTGGGCGACCTGCCCCCAAGCC
CCAGCTCGCAGaCTTGCCCCCAAGCCCCAGGTGAAAGACCTGCCTCCCAAGCCACAACTGGGGGAGCTG
CTGGCAAAACCCCAGACGGGAGACGCCTCGCCCAAGGCCCAGCCACCCCTGGAGCTCACCCCCAAGTCAC
ACCCGGCGGACCTGTCCCCGAACGTCCCCAAGCAGGCGTCTGAGGACACCAACGACCTCACGCCCACCCT
GCCAGAGACACCCGTGCCTCTGCCCAGGAAGATCAACACGGGGAAGAGCAAGGTGAGGCGAGTGAAGAC
CATCTACGACTGCCAGGCGGACAACGATGACGAGCTGACTTTCATGGAGGGCGAGGTGATCGTGGTCACC
GGGGAGGAGGACCAGGAGTGGTGGATTGGGCACATCGAGGGGCAGCCCGAGAGGAAGGGCGTCTTCCCA
GTGTCCTTTGTCCACATCCTGTCGGACTAGCAAAAAAAGCAGAGCCTTCAGACTGTCCGCACCCGTCATG
```

Fig. 2A

```
CCAGACTGCTGCCTCCCTGGGACCCCGTGCGCACCGTGTAAATAGCTGCTGTTGCCGAGTGGAAGCTCCC
GGAGGGGCCGCCTCAGGAGGGGAACGGAGCACGTGTTGTAAATACCCTATGGTCTCTGCCTTCGCCAGTA
TTAGGGTAGCCTTGGGACCCGGTGCGCCTTACTGGTTTGCCAAAGCCATCCTTGGCATCTAGCACTTACAT
CTCTCTCTATGCTGTTTTCCAAGCAAACAAACAAGCAGGAATATAGGAACTGCTGGCTTTGCAAATAGAA
ATGGTGTCCAGCAACCGTTGAAGGGCACAGCATTGCCTCTCTGTTCCTAACCTGACAGTATTCTCCATTGT
GTTACTGAAAAATGCAACATTAGCAAAGAGGTGGGTACTGTCTTCCAGGTGAATCTTTCCGCTCCGTGAC
AGACCAGCCTGTCGTTATCCGTGTACACAGTTTACAGTACAAAAACCGACTTTGGTATTTATTACAGAAA
AGCGCTCAGTTCCGTGTAAGTGTTATTCCTTCAGCAAAGTATCCACTGACCCAGAACGTTGGGTGGCATTT
TACAGTGCCCACAGcCTCACGCAGGTTTAGACACGTGGGTTTATGCTGTCTTAAGAAGATGAGTGCCCGCC
CCTGATATTACCTCATTATGCAAAAATAACATATCCTTCATGACTATTTTCACAGAAGTTTAAGACACATC
TGATGAAGTTCAACTTTCAAGAACCAAGGACTGCCAGAAAATATTAGCCTCTACATTATGCATGCATTTA
GAAGCTTACCTGAAATCTGCCTTTTATAAAGGGAATAGTATGGATAAGTTGAACTGTACATTTTTTTTAA
AACTTGATTGCCATTAAAGCAGAAATTATAAGGTTGCAACAAATATTTGTTTCCAGTCAGTCATTTGGCTt
TCCTCAAGAGTATGAATGCACATATCACATTATGAATTAGCATCCTTCAACTATGTTAACACCTCTAACAT
GTCCGTTTTAAATTCCTTTCTTAGTTTTCGTTCTGGATAAATTTAAACTTTCAAAAGAGTGTTCAAGAAGAT
GACTAATTCAGAAATCAGTTCTGCCCACCGTTTTCCCCCGCCCACCCCCGCTGTAGAATTCAGGTGCTGAA
ACCAGCCTTCTTTTTTTTTTTCTTCATTTCCTTTAGTAAACTCCAATCATAGATAAGTTTCCCAGCTCTGTT
GAACAGACACTTCATCTTCAAGTCGATTCATAACCAAGTTTCTGAACGCTGCTATGAATTGCACTGTGAAA
CATGCTTTTCTGCCAGGGGTCCCTGCCCCTCCCAGTTTTTTTCTCATCCCAGCCGCTTTCATCAGACCATC
AAGACCATCCTCAGTTTTTCAGTCTTTTACATCAGCCTGAATGTGGGGAGAGAATACCGCTCCGCTCCCCA
GTCAGTGGGACTGCTCTCGGATTCCGAGGCCCACGTGTCGTCCTTGCAGTGCGCTTGCTTAAACGGCTACG
TTGGCAGCAGCGCAGGAAGCTAATATTTTAAGCAGATCATCCTGGCAACGAGTGAGAAATGTTCATTTC
ACAGAAGCACAGCTCCCAACCAGACCCTTAGGGGAGCCCTCTGTAATCGAGTCGCAGTGCTCGGCGAGCA
TTACCTTAGCTCTGCTCACGTGATCACTGAACCAATAAACCTTGCATGACAAACCTGCGGCA
```

Fig. 2B

```
MRSSASRLSSFSSRDSLWNRMPDQISVSEFIAETTEDYNS   40
PTTSSFTTRLHNCRNTVTLLEEALDQDRTALQKVKKSVKA   80
IYNSGQDHVQNEENYAQVLDKFGSNFLSRDNPDLGTAFVK  120
FSTLTKELSTLLKNLLQGLSHNVIFTLDSLLKGDLKGVKG  160
DLKKPFDKAWKDYETKFTKIEKEKREHAKQHGMIRTEITG  200
AEIAEEMEKERRLFQLQMCEYLIKVNEIKTKKGVDLLQNL  240
IKYYHAQCNFFQDGLKTADKLKQYIEKLAADLYNIKQTQD  280
EEKKQLTALRDLIKSSLQLDQKESRRDSQSRQGGYSMHQL  320
QGNKEYGSEKKGYLLKKSDGIRKVWQRRKCSVKNGILTIS  360
HATSNRQPAKLNLLTCQVKPNAEDKKSFDLISHNRTYHFQ  400
AEDEQDYVAWISVLTNSKEEALTMAFRGEQSAGESSLEEL  440
TKAIIEDVQRLPGNDVCCDCGSAEPTWLSTNLGILTCIEC  480
SGIHREMGVHISRIQSLELDKLGTSELLLAKNVGNNSFND  520
IMEANLPSPSPKPTPSSDMTVRKEYITAKYVDHRFSRKTC  560
SSSSAKLNELLEAIKSRDLLALIQVYAEGVELMEPLLEPG  600
QELGETALHLAVRTADQTSLHLVDFLVQNCGNLDKQTALG  640
NTALHYCSMYSKPECLKLLLRSKPTVDVVNQAGETALDIA  680
KRLKATQCEDLLSQAKSGKFNPHVHVEYEWNLRQEEMDES  720
DDDLDDKPSPIKKERSPRPQSFCHSSSISPQDKLSLPGFS  760
TPRDKQRLSYGAFTNQIFVSTSTDSPTSPIAEAPPLPPRN  800
ATKGPPGPPSTLPLSTQTSSGSSTLSKKRSPPPPPGHKRT  840
LSDPPSPLPHGPPNKGAVPWGNDVGPSSSSKTTNKFEGLS  880
QQSSTGSAKTALVPRVLPKLPQKVALRKTETSHHLSLDKA  920
NVPPEIFQKSSQLTELPQKPPPGDLPPKPTELAPKPPIGD  960
LPPKPGELPPKPQLGDLPPKPQLADLPPKPQVKDLPPKPQ 1000
LGELLAKPQTGDASPKAQPPLELTPKSHPADLSPNVPKQA 1040
SEDTNDLTPTLPETPVPLPRKINTGKSKVRRVKTIYDCQA 1080
DNDDELTFMEGEVIVVTGEEDQEWWIGHIEGQPERKGVFP 1120
VSFVHILSD
```

Fig. 3

```
Chicken c-src  (88) ALYDYESRTETDLSFKKGERLQIVNNTEGDWWLAHLSTTGQT--GYIPSNY
Murine c-fgr   (72) ......A..GD..T.T...KFH.L....Y...E.RSLSS.HR--..V....
Human c-fyn    (88) ......A......FH..EKFQIL.SS...W.E.RSL...E.--........
Murine c-abl   (68) .....FVASGDNT..IT...K.RVLGYNHNGE.CEAQTKN.----,WV....
Human p85      ( 9) .....KRER.E.IDLHL.DI.TVNKGSLVALGFSDGQEARPEEI.WLNG..
Human grb-2N   ( 5) .K..FKATADDE....R.DI.KVL.EECDQN.YKAELNGKD---.F..K..
```

Fig. 12B

```
         10        20        30        40
         |         |         |         |
GACAAAAGCTGGAGCTCGCGCGCCTGCAGGTCGACACTAG  40
TGGATCCAAAGAATTCGGCACGAGCTCCGGCCCCCTCCAA  80
ACTCACATGCCGGACTCCCGCTTCCTGTCCAGCAGCTCCA 120
GATGGGGCAGATCAATGCGCGCATTCCTGCTCATTGTAAC 160
TGTAGCGGCATGTGATTTCAGCCCGTAATGTCCGCGCT   200

210       220       230       240
         |         |         |         |
GGACGGAGCACAATGCGCTGAATATGGTGCCACTCGGAAA 240
CACGGAGCTGTACGCACAATCTGCTTTGCAATTACTTTTT 280
AATCTGTTAATACGGAGTGAAACCGCAGCTGTCTCGCTCA 320
GGGTTGTTTTGCTGAGGTGACTACAGAGCCATGAGGTCCT 360
CGTCCTCGCGTTTGTCAAGTTTTTCCTCCAGGGATTCATT 400

410       420       430       440
         |         |         |         |
ATGGAGTCGGATGCCGGATCAGATCTCCGTGTCCGAGTTT 440
CTCTCGGAGACGACGGAGGATTACAATTCCCCCACGACCT 480
CGAGCTTCACCACCCGCCTGCAGAGCTGCCGGAACACGGT 520
CAATGTTCTGGAAGAGGCTTTGGATCAGGACCGAACTGCT 560
TTACAGAAGGTCAAGAAATCTGTCAAAGCAATCTACAACT 600

610       620       630       640
         |         |         |         |
CGGGTCAAGAACATGTGCAGAATGAAGAGAATTATGGACA 640
GGCACTGGACAAGTTTGGCAGCAACTTCATCAGCCGAGAT 680
AACTCTGATCTGGGAACAGCCTTCATCAAGTTTTCTGGAC 720
TTATCAAAGAGCTGGCTGCTCTCCTCAAGAACCTGCTCCA 760
GAGCCTCAGCCACAACGTCATCTTCACCCTGGACTCTCTG 800

810       820       830       840
         |         |         |         |
CTCAAAGGAGATCTAAAGGGAGTGAAGGGGACCTTAAAA  840
AGCCTTTCGACAAGGCCTGGAAAGACTATGAAACCAAGTT 880
CACAAAGATCGAGAAGGAGAAGAGAACATGCCAAGCAG   920
CACGGCATGATCCGCACAGAAATCACCGGCGCAGAGATTG 960
CAGAAGAGATGGAGAAGGAGCGGAGGATCTTTCAGCTGCA 1000
```

Fig. 13A

```
              1010        1020        1030        1040
         |||||||||||||||||||||||||||||||||||||||||
GATGTGTGAGTACCTGATCAAAGTCAATGAGATTAAGACC 1040
AAGAAGGGAGTGGATCTCCTCCAGAATCTCATCAAGTATT 1080
ATCATGCACAGTGCAATTTCTTCCAGGATGGCTTGAAAAC 1120
TGCTGACAAGTTGAAGCAGTATATTGAAAAATTAGCAGCT 1160
GATCTTTATAATATAAACAGACTCAGGATGAGGAGAAAA 1200

1210        1220        1230        1240
         |||||||||||||||||||||||||||||||||||||||||
AACAGCTCACAGCTCTCAGAGACCTCATCAAATCTTCCTT 1240
ACAGCTGGACCAGAAGGAGGATTCTCAGAGTAAGCAGAGC 1280
GGGTACAGCATGCACCAGCTGCAGGGCAATAAGGAGTTTG 1320
GCAGTGAGAAGAAGGGCTATCTCTTCAAGAAGAGTGATGG 1360
GATCCGTAAGGTGTGGCAGAGGAGGAAGTGCTCAGTGAAA 1400

1410        1420        1430        1440
         |||||||||||||||||||||||||||||||||||||||||
AATGGCATCCTCACCATCTCTCATGCCACATCCAACAGGC 1440
AGCCGGTGAGACTGAATCTGCTGACCTGCCAGGTTAAACC 1480
CAGTGGAGAGGATAAGAAGTGCTTTGACCTCATCTCTCAT 1520
AATCGAACATATCATTTCCAGGCAGAGGACGAACAGGAGT 1560
TTGTGATATGGATCTCGGTGCTGACTAATAGTAAGGAGGA 1600

1610        1620        1630        1640
         |||||||||||||||||||||||||||||||||||||||||
GGCTCTGAACATGGCATTTCGTGGGGAGCAGAGTGCTGGA 1640
GATGACAGTTTGGAGGACTTGACCAAAGCCATCATCGAGG 1680
ACGTGCTGCGCATTCCTGGAAACGAAGTCTGCTGTGACTG 1720
TGGGGTTCCAGAGCCCAAATGGTTATCCACTAACCTCGGC 1760
ATCCTGACGTGCATCGAGTGTTCAGGAATCCACAGGGAAA 1800

1810        1820        1830        1840
         |||||||||||||||||||||||||||||||||||||||||
TGGGAGTCCATATTTCGCGCATCCAATCCATGGAGCTTGA 1840
CAAACTTGGAACCTCTGAACTCTTGCTGGCTAAGAACGTG 1880
GGCAACAGTAGTTTCAACGAAATATTAGAAGGGAATCTGC 1920
CGAGTCCTTCACCAAAGCCAGCGCCATCAAGTGACATGAC 1960
CGAGAGGAAGGAGTACATCAATGCGAAGTACGTGGAGCAC 2000
```

Fig.13B

```
        2010      2020      2030      2040
AGGTTCGCTCGGCGAACGGCCACTACAGCCACAGCCAGAC 2040
AGGGCGACTTGTACGAGGCGGTGAGAACGCGAGACTTGAT 2080
GGCTCTCATTCAGCTCTATGCAGATG5AGTGGAGCTAATG 2120
GATCCTTTCCCAGAAGCAGGACAGGACCCGGGAGAGACAG 2160
CTCTGCACTTTGCTGTTCGGACATCAGACCAGACTTCCCT 2200

2210      2220      2230      2240
GCACCTGGTGGACTTTCTTGTCCAAAACAGTGGGACTCTA 2240
GACAGACAGACGGAGAGTGGAAACGCTGCTCTCCATTACT 2280
GCTGCACATATGAGAAGCCAGAGTGTCTCAAACTGCTGCT 2320
CAGS3GAAAACCGTCTATT5ACCTG&TTAATCARAACG55 2360
GAGACAGCATTGGATATCGCCAGACGACTGAGAAATGTAC 2400

2410      2420      2430      2440
AGTGTGAAGAGCTACTGGTGGAGGCAGCAGCCGGGAGGTT 2440
TAATCCTCATGTGCATGTGGAGTATGAGTGGAATCTGCGG 2480
CTGGAGGAGATTGATGAGAGTGACGATGACCTGGATGACA 2520
AGCCTAGTCCAGTGAAGAAGGAGCGTTCTCCTCGTCCTCA 2560
GAGCTTCTGTCATTCGTCCAGCGTGTCTCCTCAGGAGAAG 2600

2610      2620      2630      2640
TTAACCCTGCCGGGGTATCTAGGACACAGGGACAAGCAGA 2640
GACTGTCCTATGGAGCCTTTGCCAACCCCGTCTACAGCAC 2680
CTCCACCGAAACCCCTGCATCTCCAGTGTCAGAGGGACCC 2720
ACCATAGCCAGCAAGACCCCTGCAAAAGCTCCGTCCTGTG 2760
GGCCGCCCACCTCTCTGCCGCTGGGATCTCAATCGAGTGC 2800

2810      2820      2830      2840
AGGAGGCAGCTCCACTTTGTCTAAGAAGAGAGCTCCTCCT 2840
CCACCTCCCGGACACAAGCGCACCCACTCAGATCCCCCCA 2880
GTCCCGTACTGCAGGGTCCGCAGAGCAAAGGAAGTGAGTC 2920
CACACCTCCTTCTGCAAATCGGACATCCCCGGCCAACAAG 2960
TTTGAGGGAATCCAGCAGCAGCAAAGCACTACGTCTATGA 3000
```

Fig.13C

```
          3010        3020        3030        3040
ACACAAAAGCAACATTTGGCCCACGAGTTCTTCCCAAACT 3040
ACCTCAAAAAGTGGCACTACGAAAGATTGACACAATCCAC 3080
CTCCCATCAGTGGACAAGTCTGGTCCTGATGTGCTTCAGA 3120
AACCCCCACAGGCCCAGGATGCACCTCCCACCAGAGCCTC 3160
AGATACAATAACCAGACCCACTGAACCTCCACCTAAAATT 3200
          3210        3220        3230        3240
CCACAGGTCGCAGAACGATCCCAGCCTGTGGATGTCCCGC 3240
AGAAACCGCACATCTCAGACCTTCCTCCCAAACCGCAACT 3280
ATCAGATCTTCCCCCCAAACCCCAATTGTCGGATTTACCA 3320
CCAAAACCTCAGCTTTCTGACCTGCCCCGAAGCCTCAGC 3360
TTAAGGATCTTCCCCCTAAGCCGCAGATCAGTGATCTGCC 3400
          3410        3420        3430        3440
ATCCAAACCGGCCGTGTGTTCTGCGTCTGAGGCCACACAG 3440
AGGCAGTCAACGCAGGAGGAAACCAGTCCGAAGCCCCAGC 3480
TGACGGAGACACAGTCATTCAGCCAGCAGGAGGAGCTCTC 3520
ACCCCGACAGGCCAGCGAGGACACCAATGGAGCGCCCGCA 3560
GGAGCCTTGGAAATGCCAGTCCCAATGCCACGCAAAATTA 3600
          3610        3620        3630        3640
ACACAGTAGCAAAGAACAAAGCGAAGCGTGTGAAAACCAT 3640
CTATGATTGCCAGGCAGACAATGACGATGAGCTGACTTTT 3680
GTGGAGGGCGAGGTTATAATTGTCACAGGAGAGGAAGACC 3720
AGGAGTGGTGGATCGGGCACATAGAGGGTCAGCCTGAAAG 3760
GAAAGGGGTCTTCCCAATGTCCTTCGTGCACATTCTGTCA 3800
          3810        3820        3830        3840
GACTGACAGTGCATGACCGGCAGCCGAGAGGCTCTCTAAC 3840
TAGCACAAGCTCCGCTCTCTCTGGCCTCACACTGGACTGT 3880
GGGCATTGCCTCTGTACATAGCTGCTGAAACCCAAACGGT 3920
CTCCAAACACATACAAAACNTGAAGTATCAAACCCATGCT 3960
CCCTTAATCCTCAAGGGTGAAATGTGTAAACTATGTGTTG 4000
```

Fig.13D

```
                4010          4020          4030          4040
       |||||||||||||||||||||||||||||||||||||||||||||||
       TTCATAAACTGTGTTATCCTGCCTACCAGTATTATCGTAG 4040
       CCATGGCAGCCCAGCATGCCATAACTGGGTTTGCAGTAGC 4080
       TATACTTGGAAATCTAGCACTTAACATGTATGCTGTAACT 4120
       TTGTGTATGTGTACACATATAGAATTATATGTATGTCCAT 4160
       TTTAAGTGTGTCTTTGTACATACATATGCACAGACGTAAG 4200

4210          4220          4230          4240
       |||||||||||||||||||||||||||||||||||||||||||||||
       TGTATATTTATGTACGTATGTATAATGTACAAGTGTGCAA 4240
       ATGTATGTTAACCCTGCTTGCTTATGGAGCCAGAGTGACT 4280
       CTAGACATTTTAGTGTACTGTTTTAAAAAAAAAAAAAAAA 4320
       AAACTCGAGAGTACTTCTAGAGCGGCCGCGGGCCCATCGA 4360
       TTTTCCACCCGGGTGGGGTACCA 4383
```

Fig.13E

```
          10        20        30        40
   |||||||||||||||||||||||||||||||||||||||||
GGAGCTCGCGCGCCTGCAGGTCGACACTAGTGGATCCAAA   40
GAATTCGGCACGAGGCAAAATCCAGCACGACAACCTACAC   80
TCCTGTCCCAAAACAGAAGAGAAGCACATCACCGCACTGC  120
TTTATTATCAAACGAGTGGACTAAATTCCTACTTAAACTG  160
GAAGAAGTGAGATCCGTGAAAGAAAGAGGGAAAAAGAG    200

210       220       230       240
   |||||||||||||||||||||||||||||||||||||||||
AGAGATTTCCCCGTCGTACAAGCCGCACTTCAGTGTAGTT  240
GGCTAATGATTTGTATTAATTCCAACTTGTTTTAATCCA   280
CCGAGGACAAAACACCGCGATGATAAGACTCCAGGACGCT  320
CATGAGAGTTTTAATTCGGCGTTTCATCTCTGAATTTCGA  360
CATTAAGTGCACCGCGACCGGCCAAATCAAGGATTAAACA  400

410       420       430       440
   |||||||||||||||||||||||||||||||||||||||||
CGACATTTGTGGATTTCGCCAAAGGAGATACAATGCCTGA  440
CCAGATAACAGTGGCGGAGTTTGTCACGGAGACAAATGAA  480
GATTATAAATCGCCCACCGCCTCAAACTTCACCACCAGAA  520
TGACTCACTGCAGGAACACAGTATCCGCACTGGAGGAGGC  560
CCTGGATGTGGACCGCAGTGTCCTTTACAAGATGAAGAAG  600

610       620       630       640
   |||||||||||||||||||||||||||||||||||||||||
TCAGTTAAGGCTATTTACGCCTCGGGTCTGGCTCATGTGG  640
AGAATGAGGAGCAGTACACTCAAGCTCTGGAGAAGTTCGG  680
AGAGAACTGTGTGTACAGAGATGACCCGGACCTGGGATCA  720
GCCTTCCTGAAGTTCTCCGTCTTCACCAAGGAGCTCACGG  760
CACTCTTCAAGAACCTGTTTCAGAACATGAATAATATCAT  800

810       820       830       840
   |||||||||||||||||||||||||||||||||||||||||
TACCTTCCCATTGGACAGTCTGCTGAAGGGAGATCTGAAA  840
GGGGTTAAAGGGGATCTCAAGAAGCCCTTCGATAAAGCCT  880
GGAAAGACTACGAGACTAAAGTCTCTAAATAGAGAAGGA   920
GAAAAAGAGCACGCCCGGCAGCACGGAATGATCCGGACG   960
GAGATCAGCGGAGCAGAGATAGCAGAAGAGATGGAAAAAG 1000
```

Fig. 14A

```
          1010      1020      1030      1040
     |||||||||||||||||||||||||||||||||||||||||
     AGCGGCGTTTCTTCCAGCTTCAGATGTGTGAGTACCTCCT 1040
     CAAAGTCAATGAAATCAAGATCAAAAAGGTGTCGACCTG  1080
     CTCCAGAATCTCATCAAATACTTCCACGCACAGTGCAACT 1120
     TCTTTCAGGATGGTCTCAAAGCGGTGGACAACCTCAAACC 1160
     CTCAATAGAAAAACTGGCCACAGACTTGCACTCGATCAAA 1200

1210      1220      1230      1240
     |||||||||||||||||||||||||||||||||||||||||
     CAGGTACAGGATGAAGAACGCAGACAGCTAACCCAGTTAC 1240
     GGGATGTGCTAAAAACTGCTCTGCAAGTGGAGCAGAAGGA 1280
     GGACTCTCAGGTTAGACAGAGCGCCACCTACAGTCTGCAC 1320
     CAGCCGCAGGGCAACAAAGAGCATGGGACTGAGCGCAGCG 1360
     GCAACCTTTACAAGAAGAGTGACGGGCTGCGGAAAGTGTG 1400

1410      1420      1430      1440
     |||||||||||||||||||||||||||||||||||||||||
     GCAGAAGAGAAAGTGCACAGTAAAGAATGGATATTTGACC 1440
     ATCTCACATGGGACGGCAAACAGACCTCCCGCCAAACTCA 1480
     ATCTTCTCACCTGTCAGGTGAAGCACAACCCAGAGGAGAA 1520
     GAAAAGTTTTGACCTCATCTCACATGACAGAACATATCAT 1560
     TTCCAGGCAGAAGATGAGCCAGAGTGTCAAATATGGATCT 1600

1610      1620      1630      1640
     |||||||||||||||||||||||||||||||||||||||||
     CAGTGCTGCAGAACAGTAAAGAAGAGGCGCTCAACAACGC 1640
     CTTCAAGGGCGACCAGCATGTTGGTGAAAATAACATTGIG 1680
     CAGGAGCTCACCAAGGCCATCCTGGGAGAGGTGAAGCGGA 1720
     TGGCGGGGAACGATGTCTGCTGCGACTGCGGTGCTCCCGG 1760
     CCCCACATGGCTCTCCACCAACCTGGGCATCCTGACCTGC 1800

1810      1820      1830      1840
     |||||||||||||||||||||||||||||||||||||||||
     ATCGAGTGTTCGGGGATCCACAGAGAGCTGGGCGTCCATT 1840
     ACTCCCGAATCCAGTCCCTCACACTCGACGTCCTCAGCAC 1880
     CTCCGAGCTCTTGCTGGCCAAGAACGTGGGGAATCCTGGC 1920
     TTCAATGAGATCATGGAGGCCTGTCTGACGGCAGAAGATG 1960
     TGATCAAACCGAATCCAGCCAGTGACATGCAGGCGAGGAA 2000
```

Fig. 14B

```
              2010        2020        2030        2040
   |||||||||||||||||||||||||||||||||||||||||||
  GGACTTTATCATGGCCAAATACACAGAGAAACGCTTCGCT 2040
  CGTAAGAAGTGTCCAGACGCACTGTCGAAGCTGCACACGC 2080
  TCTGTGATGCTGTGAAGGCCCGGGACATTTTCTCTCTCAT 2120
  CCAGGTCTATGCTGAAGGAGTGGATCTGATGGAGCCCATT 2160
  CCTCTGGCTAATGGACATGAACAAGGTGAGACGGCTCTTC 2200
              2210        2220        2230        2240
   |||||||||||||||||||||||||||||||||||||||||||
  ATCTGGCCGTGAGACTGGTGGACAGAACTTCCCTACACAT 2240
  CATCGACTTCCTCACCCAAAACAGTTTAAACCTGGATAAG 2280
  CAAACGGCTAAAGGAAGCACAGCTCTGCATTACTGCTGCC 2320
  TGACGGACAACAGCGAGTGTCTCAAACTGCTGCTCAGAGG 2360
  AAAAGCCTCCATAGATATCGCTAATGAAGCTGGAGAGACC 2400
              2410        2420        2430        2440
   |||||||||||||||||||||||||||||||||||||||||||
  CCGTTGGACATCGCCAGGCGACTCAAACATCTGCAGTGTG 2440
  AGGAACTGCTGAACCAGGCTCTTGCAGGGAAGTTCAATGC 2480
  TCATGTGCATGTGGAGTATGAGTGGAGACTTCAGCATGAA 2520
  GACCTGGACGAGAGTGATGAAGATCTGGATGAGAAGTCGA 2560
  GTCCTCACCGGCGGGATGAGCGGCCCATCAGCTGCTACAC 2600
              2610        2620        2630        2640
   |||||||||||||||||||||||||||||||||||||||||||
  ACCGGGCAGTAACTCCCTTCAGCTGAGTCCAGCCAGCCTG 2640
  AGCCGAGACGGTCGAGACCTGGTTAAAGACAAGCAACGCT 2680
  TGTGCCAAACCTGGTCAACAATGAAACCTACGGGACCAT 2720
  CATTAACACCAGCTCACCCGTCAGCCTGTCCTCTTCTGCT 2760
  CCACCTCTACCACCCCGAAACCTAGTTCAGCCGTCTGCTC 2800
              2810        2820        2830        2840
   |||||||||||||||||||||||||||||||||||||||||||
  TTGCAGGACTGACTCAAGGATCTCCCGGCTGGAAGCCTGG 2840
  CTCTCTGGATCTGAGCGGCAGACAGAGATCCTCCTCTGAC 2880
  CCTCCCAACATGCATCCTCCTGCGCCTCCCTTACGGGTCA 2920
  CTTCCACCTCCCTTCTAATGCCCAGCGGTGCTGCTCCTCC 2960
  TCTGGCTAAAGCTACTGGTATGATGGAGACCATGAATATG 3000
```

Fig. 14C

```
         3010      3020      3030      3040
CAACCCAAACCCGGACAGGGGCCTCCTGGACAGAACATCA 3040
ACCGGGCTACAAGTGCGGACAAAAACTTCAGCAAAAGCAC 3080
ACTGATGCGCTCCGGATCCATCGAGAGACCAGCTAAAGAA 3120
GTCCCAGGAGGCCCACAAAACACCACTGGTCAAACTCTGC 3160
CTGCGACCCACATGCCCAGGAAACGTATTTGAAGCCGAA 3200
         3210      3220      3230      3240
GCGTGTGAAGGCCATGTATAACTGTGTGGCCGATAATCCA 3240
GACGAGCTGACCTTCTCTGAGGGAGAGCTTATCGTGGTGG 3280
ATGGAGAGGAGGACCAGGAGTGGTGGCTGGGCCACATTGA 3320
GGGAGAGCCAATGAGAAGAGGAGCGTTTCCTGTCACGTTT 3360
GTACAGTTCATTATGGACTGAAGCTCGAGAGATCACACAC 3400
         3410      3420      3430      3440
TGAACTGATGACGGCACTTCTCTGCCTCTGTGTGGCCTCA 3440
CTAACCACCACTATCTTCATCATCATCGTTGTTCTTCCCT 3480
TTATGGTGAGGCCTGTATCTTCACCAATCTTCCACAAGTC 3520
CTGCCTCTGGAGAAATCAGCCTTCTGGGCAATAAACGCAC 3560
TTTTGAACTTAATTTATCATGAACACAATGCTAATGAATG 3600
         3610      3620      3630      3640
TCACCAAGATGAAGGTTTTGTTTCAGGATCATTCACATCC 3640
TTATTTCTTTAGACAGATCTGTGAATATAGTCTTATATGC 3680
CCACATTCCACATCTGGCAAGGAAAGACGGAAGCATAGTA 3720
GTGAAATGACAGCCTTTTTGGAGGACTCTGTTGGATAAGA 3760
CGGCTCTGTTAATGGTGCTAAAGCAGGAATATGCTACAGG 3800
         3810      3820      3830      3840
AGCTGTCTGTCCTAGGAGGAGCGCACTGATGTCCCGTTT 3840
TCACACTACCTGCCCCAGTGCTGAGTGCAGAAATAGGTTT 3880
TCTCCAGCACTCGCACATGGGAAATCTCTGAAGTGCACTG 3920
TGTGATGGAGAAACTGACAGACTGAAGAGTGCTTTTGCGC 3960
TGGCTGAGGGACGTGAAGATTAAATGAAAGTAATCTTGAC 4000
```

Fig. 14D

```
                4010      4020      4030      4040
         |||||||||||||||||||||||||||||||||||||||
         CCTGAAGCTGCTGGGATTTTGGAGCGTTGTGAATGTTCTC 4040
         TGGCCTCCAGGGAAAGGAGAGGAAGAGCATCCAGGAGCTT 4080
         TTTTTCTGTATAGGTATTTATAAATCGGAGCTGTTCTGTT 4120
         TTAGACTCTCGTTGATTTTAACGATCTTCCGCAGAACTTG 4160
         CTTCATTGTGCGAGCAATCTGCTGAATGATGTCATTTCTT 4200

4210      4220      4230      4240
         |||||||||||||||||||||||||||||||||||||||
         TTTAAAGAGACAGACCAAACCTTCAAANTAATTAATTTAC 4240
         TCCAGGAGTGTCAAAGTTCCTGGAGGGCCACAGCCCTGCA 4280
         CAGTTTAGTTCCAACCCTGCTCCAACACACTTACCTGCAA 4320
         GTTTCAAACAAGCCTGAAGAACTTAATTAGTTTGATCAGG 4360
         TGTTTAATCAGGGTTGTGCAGAGCTGCGGCCCTCCAGGAA 4400

4410      4420      4430      4440
         |||||||||||||||||||||||||||||||||||||||
         CTCAGTTTGACACCTGTGATTTACTCAATTTACAAAATGT 4440
         CCAGAGTGCTCTATATCAGCATTTCCCAACCCTCTTCTTG 4480
         AAGGCACACCAACAGTACACATTTTCAACCTCTTCCTAAG 4520
         CAAACACGCCTCAATCAACTCAACAGACCATTAGAAGAGA 4560
         CTCTAAACCTGAAGTAAATGAGTCAGATAAGGGAGACTC 4600

4610      4620      4630      4640
         |||||||||||||||||||||||||||||||||||||||
         CCAAAATATGAACTGTTGGTGTGCCTCCAGGAACACTGTT 4640
         TGGAAACCTTCTCTATATGCTCAATTTGATGTAATCCAAG 4680
         TTGTCTGAAGACATACAGTAAACTTAAATGAGTAAATAGA 4720
         TGGGTTTTAGAGGAAAACTAAACATTTATTCTCAAGTCTT 4760
         TACAAACCTTACTTCAGTGTTTATTTGGAGCAATGTGGGT 4800

4810      4820      4830      4840
         |||||||||||||||||||||||||||||||||||||||
         ACTAAATGTAGGAATCTGTTCATATGGAAATATATATATA 4840
         TATATATATATATATATATATATATATTCAAAAAAG 4880
         GTAATAGTGACTTTAATCGTACCAGTTCTGCTTATTTTAT 4920
         ATATGAAAGATTTGCAACAGAAAAGTGCAAAATTGAGGTG 4960
         GCACAAATGGATTTCAATACACTGATCCAATTCTCTAAAT 5000
```

Fig. 14E

```
                5010        5020        5030        5040
ATTGTCTTATACAATGAAATCCTACAGGATTGTAATAGCA 5040
AATTAAGTTATTTTCTGAAAATCATTCACTGTCATTGTCA 5080
AACAAGGTCAAATCATCAACTTCACATTTGAATATGGATT 5120
CAGCTTTGGTTTGAGTATTCTGGTTACAGGGTGAACATGT 5160
TTCATCAATCATACTGATTAAAGCACTCTTGCCATTTTTC 5200
                5210        5220        5230        5240
ACTAATCATCCTCTGGTTCAATGGAAGAAAAAGTCATAC 5240
TTTTGGCATGACGGTGAGCAAATGACAGCATTTACATTTG 5280
TGGAGGGGGAGTGACTGTCTTTTAAGATGCTTTTGCACAG 5320
TTTTAAATAGAGTCTGTTTTAATTTAAACCTTTGGATAAA 5360
AGCGTCTGCTAAATTAATAAATTTAAACAGATTACGAAGT 5400
                5410        5420        5430        5440
GTGAATGACAGCTATTTTCTACTAGACCGTTTTGGTGTAA 5440
CCCTGACGGTTGTTCCCTGTAGCAGTAATAACTCTCTTTC 5480
TCTCTCTAGCGCTCTAATTGTATTCCAGAGAAAATGAAAA 5520
TCTCTCTCATCACTTCTCCTAATCCTTTGTAAAGCTCATC 5560
CATCAGTGAGTGTGTGCAGGAGTAACACAGCAGAGCGTTT 5600
                5610        5620        5630        5640
TCTGTCAAGAGTGTTTGATGTCGTTGCAGAGCAACTTAGC 5640
GTCTGTTATGTAACTTTTAATTACAGTCATGTTAGTCTTG 5680
ATTGAGCTCAGGCCAGTGTGTATACGGCCTGCAGTGATTG 5720
TAAATAACTGTAGACTTTTGCTTTGTGCATATTTAATTG 5760
TAAACAGAGAGCTAAACTGATACTGACTGATGTGTTGACG 5800
                5810        5820        5830        5840
TATTGTTAGATAAGACTGTTACAGTACACTTTTAACTACT 5840
CACCCCTTTACCATAAACATTGTTGACGCTAATATATAAT 5880
TCATATATGTACAAATAAAGAGTACTTCTAGAGCGGCCGC 5920
GGGCCCATCGATTTTCCACCCGGGTGGGTACCAGG 5955
```

Fig. 14F

```
              10        20        30        40
    |....|....|....|....|....|....|....|....|
    GGAGCTCGCGCGCCTGCAGGTCGACACTAGTGGATCCAAA   40
    GAATTCGGCACGAGCAGAAGTGTTGATCTTGTCAGCTGCT   80
    CGTGTGATGGAGTTGTTTAACGCTTGTGTTCAAAGGCAAA  120
    TCCTCTCCTCATCGGCCGTTTACATTTTAACTTCACGCGG  160
    AAATTTAAACTGAACTAATCTCTAAGGAATGACTGAAAT   200
              210       220       230       240
    |....|....|....|....|....|....|....|....|
    GGACTTGAGTTGAAGTCTGGTTTTTGAGCGCGAAGCTACA  240
    ACTTTAAGCAAACTTTCTTTCTTTTTGGATCTATTGTGT   280
    AGATTTAAAAGGAATAATCATGCCTGATCAGCTGACAGTG  320
    ACTGAGTTTGTGGATATTACCCATGAGGACTATAAAGCAC  360
    CGACAACATCAGTGTTCTGCACGCGCATGGCTCACTGCAG  400
              410       420       430       440
    |....|....|....|....|....|....|....|....|
    GAATACAGTCGCCGCTCTGGAAGAGGCGCTGGATCTGGAC  440
    CGCAGTGTACTGCACAAAATGAAGAAGTCAGTCAAGGCCA  480
    TAAACAGCTCTGGTCAGACTCATGTAGAGAACGAGGAGCA  520
    GTACATCCAGGCCATAGAGAGGTTTACGGATAACACTGTG  560
    TACAAAGATGACCCTGAGATGTCCAATTACTTCCTCACAT  600
              610       620       630       640
    |....|....|....|....|....|....|....|....|
    TCGCTGGTTTCACCAAGGAGCTTACTGCTCTTTTCAAGAA  640
    CTTGCTACAGAACATGAATAACATCATCACTTTTCCACTA  680
    GACAGTCTGCTAAAGGGAGACCTCAAAGGAGTCAAAGGGG  720
    ATTTGAAAAGCCATTTGATAAAGCATGGAAGGATTATGA   760
    AACCAAACTGAGCAAGATTGAGAAAGAAAGCGAGAACAT   800
              810       820       830       840
    |....|....|....|....|....|....|....|....|
    GCCAAACAGCACGGTCTGATCCGAACAGAGATCAGTGGAG  840
    GAGAGATCGCAGAAGAGATGGAGAAAGAGAGACGCCTCTT  880
    TCAGCTTCAGATGTGTGAGTACCTCATTAAAGTGAATGAA  920
    ATCAAAGTCAAAAGGGGGTCGACCTGCTTCACAACCTCA   960
    TCAAATACTTTCATGCCCAGTGCAATTTCTTTCAGGATGG 1000
```

Fig. 15A

```
            1010          1020          1030          1040
      |||||||||||||||||||||||||||||||||||||||||||||
      GCTAAAGGTCGTGGACAATCTGAAACCTTTCATGGAAAAG  1040
      CTTGCCACAGACTTAACCGGAACAAACAGACTCAAGATGT  1080
      CAGAAAGGAAACAGTTGCTGCAGCTGAAAGAAACTCTTAA  1120
      ATCTGCTCTACAGTCTGAGTGTAAGGAGGATGCTCAGTCA  1160
      AAGCAGAACGCAGGCTACAGTCTTCACCAGTTGCAGGGCA  1200

1210          1220          1230          1240
      |||||||||||||||||||||||||||||||||||||||||||||
      ATAAAGCTCACGGCACGGAGCGCTCTGGGATGCTCCTCAA  1240
      ACGCAGCGAGGGACTGAGGAAAGTTTGGCAGAAAAGGAAG  1280
      TGCTCTGTGAAAAATGGATTGTTGACTATTTCACATGGAA  1320
      CGCCCAATGCACCGCCAGCAAACCTGAACCTCTTAACCTG  1360
      CCAAGTGAAGCGTAACCCAGATGAGAAAAATGCTTTGAT   1400

1410          1420          1430          1440
      |||||||||||||||||||||||||||||||||||||||||||||
      CTCATATCACATGACAGAACGTATCACTTCCAGACTGAGG  1440
      ATGAGGCAGAGTGTCAGGTATGGGTTTCTGTTCTCCAGAA  1480
      CAGTAAAGAAGAGGCGCTGAACAATGCCTTTAAAGACGAT  1520
      CAGAATGAGGGAGAAAATAACATTGTTCGAGAGCTCACTA  1560
      AGGCCATCGTGGGGGAAGTGAAGAAAATGAGCGGCAATGA  1600

1610          1620          1630          1640
      |||||||||||||||||||||||||||||||||||||||||||||
      CGTGTGCTGTGACTGTGGAGCTTCCAATCCAACATGGCTC  1640
      TCCACAAACCTGGGTGTGTTGATTTGCATTGAATGCTCTG  1680
      GGATCCATCGGGAAATGGGCGTCCACTACTCCCGAATACA  1720
      GTCTCTGACACTGGACCTCTTAGGCACATCTGAACTATTG  1760
      CTTGCTAACAGTGTGGGAAATGCAGCATTCAATGAAATCA  1800

1810          1820          1830          1840
      |||||||||||||||||||||||||||||||||||||||||||||
      TGGAAGCAAAACTGTCTTCAGAGATCCCAAAACCCTACCC  1840
      TTCTAGTGACATGCAGGTACGAAAAGACTTCATCACAGCC  1880
      AAATACACAGAGAAGCGTTTCGCTCAGAAGAAGTATGCAG  1920
      ATAACGCAGCTCGACTGCATGCACTGTGTGATGCAGTGAA  1960
      GTCTCGGGACATCTTCTCCCTGATCCAGGTCTATGCTGAA  2000
```

Fig. 15B

```
               2010        2020        2030        2040
          |||||||||||||||||||||||||||||||||||||||||||||
          GGACTGGACCTGATGGAGACCATTAATCAGCCTAACCAAC 2040
          ATGAACCAGGCGAGACATCACTACATCTTGCGGTACGAAT 2080
          GGTGGACCGAAACTCCCTCCATATTGTGGACTTTCTTGTA 2120
          CAGAACAGTGGCAATTTAGACAAGCAGACAGCCAAAGGAA 2160
          GCACAGCGCTACATTATTGCTGCTTGACTGATAACAGTGA 2200

2210        2220        2230        2240
          |||||||||||||||||||||||||||||||||||||||||||||
          ATGTATGAAGCTGCTGCTGCGGGGGAAAGCATCTGTCAGC 2240
          ATTACTAATGATGCTGGAGAGACTGCTCTGGATTTGGCGC 2280
          AGCGTCTCAAACACTCCAAATGCGAGGAGCTGCTGACTCA 2320
          GGCGCAGACGGGGAAGTTCAATGTCCATGTGCATGTGGAA 2360
          TATGACTGGCGTCTGCATAATGAGGATCTGGACGAGAGCG 2400

2410        2420        2430        2440
          |||||||||||||||||||||||||||||||||||||||||||||
          AAGATGAGATGGAGGACAAGCCCATTCCCATCAGGCGTGA 2440
          GGAGCGTCCAATAAGCTGTATAGTTCCAGGCAGTGGCCCC 2480
          ATGATGCCCAACATGAGCGCTCTGGCTCGGGACGTGGCCA 2520
          ATGTGGTCAATAATAAGCAGAGGGCTTTTATTCCGAGCAT 2560
          GATGATGAACGAGACTTACGGCACCATGCTCGATCCCAAC 2600

2610        2620        2630        2640
          |||||||||||||||||||||||||||||||||||||||||||||
          TCTCCACCACTGGGTTTACCAGGAGTACCTGGCATTCCTC 2640
          TTTTACCCCCTCGGCCCTTGGGAAGGGGATGGAGTCCACC 2680
          AATGGAGAACATCGGTAGACAGAGGTCATGTTCAGATCCT 2720
          GCAAACCCTCAAACTCCTGAACAAAATAACTCTGTGTATG 2760
          TTCTGCCTCCTGCTCCTCCACCTCCTCCTGCACCCAAGAG 2800

2810        2820        2830        2840
          |||||||||||||||||||||||||||||||||||||||||||||
          ACCTCCACCTCCAGATCCAAAGGCCAGTCTTCTTCCTCCA 2840
          GCAGCCACGGCTCCTCCTGCACCATCCGCACCGCTCCTTA 2880
          TTCCACCTGCTCCTCTCAGGCCAGCGCCTGTAGTGCCCCC 2920
          TGCACCAGTTATGCCCACTTCGTCACTGACTGATGTCAAA 2960
          AGTCTGCTGTCTAAAGCCCAGCTCACATTGTGCGATTTCG 3000
```

Fig. 15C

```
              3010      3020      3030      3040
            |....|....|....|....|....|....|....|....|
            AATACTACTAAATGATTGTAGCATCAGAGTGCACAAGTAT 3040
            GATCCGCATGTGTCCCTCAGTTTTCATAATGTCAGATTGA 3080
            ACCACAGTTAAGATGCACCAAACATGGACACGCAAGAAAA 3120
            CTCACCCTGGAGTTTGGCATCATCCATCTGTGACACCTTC 3160
            ACTCTACTGCATCCTGACATGAAACCTCACGGTAAACATA 3200

3210      3220      3230      3240
            |....|....|....|....|....|....|....|....|
            AACAAACTGTAGCAACACTTTTACTTACAACACGTCTCAG 3240
            TGATAACCGGAAAAGGCAGTGGTTTGAAAGTGTCGTTCTG 3280
            ATTGCGTCATCAGATATACCGCTCCTATTGATTCTTGGTT 3320
            AGACGCTCGTCTTAACTGAATTCACACTTCAGCCAAGAGT 3360
            CTGAACGCCCGACACCACCAGAACTTCTTCATCAGAGGGA 3400

3410      3420      3430      3440
            |....|....|....|....|....|....|....|....|
            AAATCTGATCGTAGAGGCCATCAATCAAGGAATCAAAAAC 3440
            TACAGATTTTAGGCTAGGATTACTGGAATCTTTTAGGATT 3480
            TTCCATATTAGTCTCAGATGGCCAAATCATCTCTGAAATT 3520
            GCACAGTGTGAGCAGGGCTTAAATCAGATCACCAAACTAT 3560
            TGTTGAGACCTAACACCACTGAATATTTAACAATCAATAC 3600

3610      3620      3630      3640
            |....|....|....|....|....|....|....|....|
            ACCCCTCAGCCATCCGTGTGGCTAATTGGTGGTGTACGAG 3640
            ACATTCACAAGCATTAAGACCTCAGGAAGTGTTACTTTGA 3680
            TTACTTTGATTCTAAGTGCAATTACCTCTACCTTTAATAC 3720
            GGAAATCGTTTATGAACTGTGATGAGTGATATGCATTATA 3760
            CGGGGACGGTTTGGTTTTATTAAGCGAGATGTGGTTGGAT 3800

3810      3820      3830      3840
            |....|....|....|....|....|....|....|....|
            GAGCTTTTTGTGTTTTCAGACAGCAGTGGCAGAGTGACT 3840
            CCTATTTGGCAAGTGTTTAAAGGCACAATATGTAATATTC 3880
            ACCACAAGGGGGCACATATTCACAACAAACAAATGGTTAT 3920
            GTCTGTTAGGGTGCTGCACTTTGCAGTGTAATAAAACGCA 3960
            CAACATTTTAAAGCGTCTTTGGAGTTTTTCTGTTTTCTAG 4000
```

Fig. 15D

```
              4010          4020          4030          4040
    |,,,,|,,,,|,,,,|,,,,|,,,,|,,,,|,,,,|,,,,|,,,,|,,,,|,,,,|
    AAAACCAAACTAGAAATCGAAGGTGATGAGCAACTGGAAA  4040
    ATGCAGGTGTATGATGTCATAAGCATGGAGACACTAGTTA  4080
    AAATAACTTATATCTCTGGATTTGAACATTCTTCCTAACC  4120
    TTTGGGATAATGCAAGTACTCAAGCCAAAATATATCACAC  4160
    TGTTTTAGTGATTTTAGGATATTTGAAAGAAAATAATCGT  4200

4210          4220          4230          4240
    |,,,,|,,,,|,,,,|,,,,|,,,,|,,,,|,,,,|,,,,|,,,,|,,,,|,,,,|
    ACATATTGTGCCTTTAAGTAACATGATGAACCAGGTAGGT  4240
    TGCTTCTCAAGATTTGTTACCAGACAAGCCATTAAACTTA  4280
    CTCTGCTTCATTTTCAGCCTTAATATTTTTTTTTACAAA   4320
    ATGTTATAGTGGCTTAGAAAACGTTTTTAGTAACATTCA   4360
    TGATTTTTGTGGAACCAGATTGAATAGAAAGAAGTATGG   4400

4410          4420          4430          4440
    |,,,,|,,,,|,,,,|,,,,|,,,,|,,,,|,,,,|,,,,|,,,,|,,,,|,,,,|
    AATTTATTTTAAATAATATATTACATGACTGTAATATTCT  4440
    TAATGTGTGTACTGTCATTTTTCATCAGTGTAATGCATCC  4480
    TTGCTCAATAAAAACATGTATTTTTTTTTTAAAAAAAAAA  4520
    AAAAAAAAAAAACTCGAGAGTACTTCTAGAGCGGCCGCGG  4560
    GCCCATCGATTTTCCACCCGGGTGGGGTACCAGGT       4595
```

Fig. 15E

SEQUENCE LISTING

```
<160> NUMBER OF SEQ ID NOS: 39

<210> SEQ ID NO 1
<211> LENGTH: 5330
<212> TYPE: DNA
<213> ORGANISM: Bos sp.
<220> FEATURE:
<221> NAME/KEY: CDS
<222> LOCATION: (209)...(3595)

<400> SEQUENCE: 1
cccggtccgc gcctcccgcc ccgccggctg ctcccgccgc cgccgccgtc gcctcccgct       60
ttccgctgcg agagccgcga tcggccggcc gaggggagcg gggcgtgggc gtctgcgccg      120
ccgccaggga gccgccgccg aatccgcgat ggaataatgc ccagcggccc gcccggtccc      180
ggtaattttc tgatgtgacg gctgagac atg aga tct tca gcc tcc agg ctc         232
                                Met Arg Ser Ser Ala Ser Arg Leu
                                  1               5 tcc agt ttt tca tca aga gat tcg cta tgg aat cgg atg ccg gac cag        280
Ser Ser Phe Ser Ser Arg Asp Ser Leu Trp Asn Arg Met Pro Asp Gln
         10                  15                  20 atc tcc gtc tcc gag ttc atc gcc gag acc acc gag gac tac aac tcg        328
Ile Ser Val Ser Glu Phe Ile Ala Glu Thr Thr Glu Asp Tyr Asn Ser
 25                  30                  35                  40 ccc acc acg tcc agc ttc act acg cgg ctg cac aac tgc agg aac acc        376
Pro Thr Thr Ser Ser Phe Thr Thr Arg Leu His Asn Cys Arg Asn Thr
                 45                  50                  55 gtc acg ctg ctg gag gag gct cta gac caa gat aga aca gcc tta cag        424
Val Thr Leu Leu Glu Glu Ala Leu Asp Gln Asp Arg Thr Ala Leu Gln
             60                  65                  70 aaa gtt aag aag tct gta aaa gca ata tac aat tcc ggt caa gac cat        472
Lys Val Lys Lys Ser Val Lys Ala Ile Tyr Asn Ser Gly Gln Asp His
         75                  80                  85 gta caa aat gaa gaa aac tat gcg caa gtt ctt gat aag ttt ggg agt        520
Val Gln Asn Glu Glu Asn Tyr Ala Gln Val Leu Asp Lys Phe Gly Ser
     90                  95                 100 aat ttt tta agt cga gac aac cca gat ctt ggc acc gct ttt gtc aag        568
Asn Phe Leu Ser Arg Asp Asn Pro Asp Leu Gly Thr Ala Phe Val Lys
105                 110                 115                 120 ttt tct acg ctt aca aag gaa ctg tcc aca ctg aaa aat ctg ctc            616
Phe Ser Thr Leu Thr Lys Glu Leu Ser Thr Leu Leu Lys Asn Leu Leu
                125                 130                 135 cag ggc ctg agc cac aat gtg atc ttc acc ttg gat tcc ttg ttg aaa        664
Gln Gly Leu Ser His Asn Val Ile Phe Thr Leu Asp Ser Leu Leu Lys
            140                 145                 150 gga gac ctg aag gga gtc aaa ggc gat ctc aag aaa cca ttt gac aaa        712
Gly Asp Leu Lys Gly Val Lys Gly Asp Leu Lys Lys Pro Phe Asp Lys
```

|   |   |   |
|---|---|---|
| gct tgg aaa gat tat gag acg aag ttt acc aaa att gag aag gag aag<br>Ala Trp Lys Asp Tyr Glu Thr Lys Phe Thr Lys Ile Glu Lys Glu Lys<br>    170                     175                   180 | 760 |
| agg gag cac gcc aag cag cac ggg atg atc cgc acg gag atc acc ggc<br>Arg Glu His Ala Lys Gln His Gly Met Ile Arg Thr Glu Ile Thr Gly<br>185                     190                   195                   200 | 808 |
| gcc gag atc gcg gag gaa atg gaa aag gag cgg cgc ctc ttc cag ctc<br>Ala Glu Ile Ala Glu Glu Met Glu Lys Glu Arg Arg Leu Phe Gln Leu<br>                   205                   210                   215 | 856 |
| cag atg tgc gag tat ctc att aaa gtt aat gaa atc aag acc aaa aag<br>Gln Met Cys Glu Tyr Leu Ile Lys Val Asn Glu Ile Lys Thr Lys Lys<br>         220                   225                   230 | 904 |
| ggt gtg gat ctg ctg cag aac ctg ata aag tat tat cac gca cag tgc<br>Gly Val Asp Leu Leu Gln Asn Leu Ile Lys Tyr Tyr His Ala Gln Cys<br>             235                   240                   245 | 952 |
| aat ttc ttt caa gat ggt ttg aaa aca gct gat aaa ttg aaa cag tac<br>Asn Phe Phe Gln Asp Gly Leu Lys Thr Ala Asp Lys Leu Lys Gln Tyr<br>       250                   255                   260 | 1000 |
| att gaa aag ctg gct gct gat ttg tat aat atc aaa cag acc cag gac<br>Ile Glu Lys Leu Ala Ala Asp Leu Tyr Asn Ile Lys Gln Thr Gln Asp<br>265                     270                   275                   280 | 1048 |
| gaa gaa aag aaa cag ctg acc gca ctc cga gac cta ata aag tcc tcg<br>Glu Glu Lys Lys Gln Leu Thr Ala Leu Arg Asp Leu Ile Lys Ser Ser<br>                   285                   290                   295 | 1096 |
| ctc caa ctc gat cag aag gag tct agg aga gat tcc cag agc cgg cag<br>Leu Gln Leu Asp Gln Lys Glu Ser Arg Arg Asp Ser Gln Ser Arg Gln<br>         300                   305                   310 | 1144 |
| gga ggc tac agc atg cac cag ctg cag ggc aac aag gaa tac ggc agc<br>Gly Gly Tyr Ser Met His Gln Leu Gln Gly Asn Lys Glu Tyr Gly Ser<br>             315                   320                   325 | 1192 |
| gag aag aag ggc tac ctg ctg aag aag agt gac ggg atc cgg aaa gtg<br>Glu Lys Lys Gly Tyr Leu Leu Lys Lys Ser Asp Gly Ile Arg Lys Val<br>       330                   335                   340 | 1240 |
| tgg cag aga agg aag tgc tcc gtc aag aac ggg atc ctg acc atc tcc<br>Trp Gln Arg Arg Lys Cys Ser Val Lys Asn Gly Ile Leu Thr Ile Ser<br>345                     350                   355                   360 | 1288 |
| cac gcc acg tcc aac aga cag cca gcc aag ctg aac ctt ctc act tgc<br>His Ala Thr Ser Asn Arg Gln Pro Ala Lys Leu Asn Leu Leu Thr Cys<br>             365                   370                   375 | 1336 |
| cag gtg aag ccg aat gcc gag gac aag aag tct ttt gac ctg ata tca<br>Gln Val Lys Pro Asn Ala Glu Asp Lys Lys Ser Phe Asp Leu Ile Ser<br>         380                   385                   390 | 1384 |
| cat aac agg acg tat cac ttt cag gcc gaa gat gag cag gat tat gta<br>His Asn Arg Thr Tyr His Phe Gln Ala Glu Asp Glu Gln Asp Tyr Val<br>             395                   400                   405 | 1432 |
| gcg tgg atc tcg gtg ctg aca aac agc aaa gag gag gcc ctc acc atg<br>Ala Trp Ile Ser Val Leu Thr Asn Ser Lys Glu Glu Ala Leu Thr Met<br>       410                   415                   420 | 1480 |
| gcc ttc cgg ggg gaa cag agt gct ggg gag agc agc ctg gag gag ctg<br>Ala Phe Arg Gly Glu Gln Ser Ala Gly Glu Ser Ser Leu Glu Glu Leu<br>425                     430                   435                   440 | 1528 |
| acg aag gcc atc atc gag gac gtg cag cgg ctc ccg ggc aac gac gtc<br>Thr Lys Ala Ile Ile Glu Asp Val Gln Arg Leu Pro Gly Asn Asp Val<br>                   445                   450                   455 | 1576 |
| tgc tgc gac tgc ggc tcg gca gaa ccc acc tgg ctg tcc acc aac ttg<br>Cys Cys Asp Cys Gly Ser Ala Glu Pro Thr Trp Leu Ser Thr Asn Leu<br>         460                   465                   470 | 1624 |
| ggc atc ttg acc tgt ata gaa tgt tcc ggc atc cat aga gaa atg ggg | 1672 |

```
                    -continued

Gly Ile Leu Thr Cys Ile Glu Cys Ser Gly Ile His Arg Glu Met Gly
              475                 480                 485 gtt cat att tct cgc atc cag tct ttg gaa cta gac aaa tta gga act     1720
Val His Ile Ser Arg Ile Gln Ser Leu Glu Leu Asp Lys Leu Gly Thr
        490                 495                 500 tct gaa ctc ttg ctg gcc aag aat gta gga aac aat agt ttt aat gat     1768
Ser Glu Leu Leu Leu Ala Lys Asn Val Gly Asn Asn Ser Phe Asn Asp
505                 510                 515                 520 att atg gaa gca aat tta ccc agt ccc tca cca aaa ccc acc cct tca     1816
Ile Met Glu Ala Asn Leu Pro Ser Pro Ser Pro Lys Pro Thr Pro Ser
                525                 530                 535 agt gat atg act gta cgg aag gaa tat atc act gca aag tat gta gat     1864
Ser Asp Met Thr Val Arg Lys Glu Tyr Ile Thr Ala Lys Tyr Val Asp
            540                 545                 550 cat agg ttt tca cgg aag acc tgt tca tcg tca tca gct aaa ctg aac     1912
His Arg Phe Ser Arg Lys Thr Cys Ser Ser Ser Ser Ala Lys Leu Asn
        555                 560                 565 gaa ttg ctt gag gcc atc aaa tcc agg gat tta ctt gca cta att caa     1960
Glu Leu Leu Glu Ala Ile Lys Ser Arg Asp Leu Leu Ala Leu Ile Gln
570                 575                 580 gtc tat gca gag ggg gtg gag cta atg gaa ccg ctg ctg gaa ccc gga     2008
Val Tyr Ala Glu Gly Val Glu Leu Met Glu Pro Leu Leu Glu Pro Gly
585                 590                 595                 600 cag gag ctt ggg gag aca gcc ctt cat ctt gca gtc cga acc gca gac     2056
Gln Glu Leu Gly Glu Thr Ala Leu His Leu Ala Val Arg Thr Ala Asp
                605                 610                 615 cag aca tct ctc cat ttg gtg gac ttc ctt gta caa aac tgt ggg aac     2104
Gln Thr Ser Leu His Leu Val Asp Phe Leu Val Gln Asn Cys Gly Asn
            620                 625                 630 cta gat aag cag acg gcc ctg ggg aac acg gcc ctg cac tac tgt agt     2152
Leu Asp Lys Gln Thr Ala Leu Gly Asn Thr Ala Leu His Tyr Cys Ser
        635                 640                 645 atg tac agt aaa cca gag tgt ttg aag ctg ctc tc agg agc aag ccc      2200
Met Tyr Ser Lys Pro Glu Cys Leu Lys Leu Leu Arg Ser Lys Pro
650                 655                 660 act gtg gac gtc gtt aat cag gct gga gag acc gcc ctg gac ata gca     2248
Thr Val Asp Val Val Asn Gln Ala Gly Glu Thr Ala Leu Asp Ile Ala
665                 670                 675                 680 aag aga ctg aaa gcc act cag tgt gaa gac ctg ctt tcc caa gct aaa     2296
Lys Arg Leu Lys Ala Thr Gln Cys Glu Asp Leu Leu Ser Gln Ala Lys
                685                 690                 695 tct gga aag ttc aat cca cac gtc cac gtg gaa tat gag tgg aat ctt     2344
Ser Gly Lys Phe Asn Pro His Val His Val Glu Tyr Glu Trp Asn Leu
            700                 705                 710 cga cag gag gag atg gat gag agc gat gac gac ctg gat gac aaa ccg     2392
Arg Gln Glu Glu Met Asp Glu Ser Asp Asp Asp Leu Asp Asp Lys Pro
        715                 720                 725 agc ccc atc aag aag gag cgc tcc ccc cga ccg cag agc ttc tgc cac     2440
Ser Pro Ile Lys Lys Glu Arg Ser Pro Arg Pro Gln Ser Phe Cys His
730                 735                 740 tcc tcc agc atc tcc ccc cag gac aag ctc tca ctg ccg ggc ttc agc     2488
Ser Ser Ser Ile Ser Pro Gln Asp Lys Leu Ser Leu Pro Gly Phe Ser
745                 750                 755                 760 acg cca agg gac aag caa cga ctc tcc tac ggc gcc ttc acc aac cag     2536
Thr Pro Arg Asp Lys Gln Arg Leu Ser Tyr Gly Ala Phe Thr Asn Gln
                765                 770                 775 atc ttc gtc tcc aca agc aca gac tca ccc acg tca ccg atc gca gag     2584
Ile Phe Val Ser Thr Ser Thr Asp Ser Pro Thr Ser Pro Ile Ala Glu
            780                 785                 790
```

-continued

| | |
|---|---|
| gcg ccc ccg ctg cct ccc aga aac gcc acg aaa ggt cca cct ggc cca<br>Ala Pro Pro Leu Pro Pro Arg Asn Ala Thr Lys Gly Pro Pro Gly Pro<br>795                          800                    805 | 2632 |
| cct tca aca ctc cct cta agc acc cag acc tct agt ggc agc tcc acc<br>Pro Ser Thr Leu Pro Leu Ser Thr Gln Thr Ser Ser Gly Ser Ser Thr<br>    810                          815                    820 | 2680 |
| ctg tcc aag aag cgg tct cct ccc cca cca ccc gga cac aag aga acc<br>Leu Ser Lys Lys Arg Ser Pro Pro Pro Pro Gly His Lys Arg Thr<br>825                          830                    835                    840 | 2728 |
| ctg tct gac cct ccc agc cca cta cct cac ggg ccc cca aac aaa ggc<br>Leu Ser Asp Pro Pro Ser Pro Leu Pro His Gly Pro Pro Asn Lys Gly<br>                  845                    850                    855 | 2776 |
| gca gtt cct tgg ggt aac gac gtg ggt ccc tca tcg tcc agt aag acc<br>Ala Val Pro Trp Gly Asn Asp Val Gly Pro Ser Ser Ser Ser Lys Thr<br>                  860                    865                    870 | 2824 |
| acg aac aag ttc gag ggc ctg tcc cag cag tcg agc acc ggt tct gca<br>Thr Asn Lys Phe Glu Gly Leu Ser Gln Gln Ser Ser Thr Gly Ser Ala<br>           875                        880                    885 | 2872 |
| aag act gca ctt gtc cca aga gtt ctt cct aaa cta cct cag aaa gtg<br>Lys Thr Ala Leu Val Pro Arg Val Leu Pro Lys Leu Pro Gln Lys Val<br>890                          895                    900 | 2920 |
| gca cta agg aaa aca gag acc agc cat cat ctc tcc ctc gac aaa gcc<br>Ala Leu Arg Lys Thr Glu Thr Ser His His Leu Ser Leu Asp Lys Ala<br>905                          910                    915                    920 | 2968 |
| aac gtc cca cct gag atc ttc cag aag tcg tcc cag ttg aca gag tta<br>Asn Val Pro Pro Glu Ile Phe Gln Lys Ser Ser Gln Leu Thr Glu Leu<br>                  925                    930                    935 | 3016 |
| ccg cag aag ccg cca ccc ggg gac ctg ccc ccg aag ccc acg gaa ctg<br>Pro Gln Lys Pro Pro Pro Gly Asp Leu Pro Pro Lys Pro Thr Glu Leu<br>                  940                    945                    950 | 3064 |
| gct ccc aaa ccc ccc att gga gac tta cca cct aag cca ggc gag ctg<br>Ala Pro Lys Pro Pro Ile Gly Asp Leu Pro Pro Lys Pro Gly Glu Leu<br>           955                        960                    965 | 3112 |
| ccc ccg aag cca cag ctg ggc gac ctg ccc ccc aag ccc cag ctc gca<br>Pro Pro Lys Pro Gln Leu Gly Asp Leu Pro Pro Lys Pro Gln Leu Ala<br>970                          975                    980 | 3160 |
| gac ttg ccc ccc aag ccc cag gtg aaa gac ctg cct ccc aag cca caa<br>Asp Leu Pro Pro Lys Pro Gln Val Lys Asp Leu Pro Pro Lys Pro Gln<br>985                          990                    995               1000 | 3208 |
| ctg ggg gag ctg ctg gca aaa ccc cag acg gga gac gcc tcg ccc aag<br>Leu Gly Glu Leu Leu Ala Lys Pro Gln Thr Gly Asp Ala Ser Pro Lys<br>                 1005                 1010                 1015 | 3256 |
| gcc cag cca ccc ctg gag ctc acc ccc aag tca cac ccg gcg gac ctg<br>Ala Gln Pro Pro Leu Glu Leu Thr Pro Lys Ser His Pro Ala Asp Leu<br>                1020                1025                 1030 | 3304 |
| tcc ccg aac gtc ccc aag cag gcg tct gag gac acc aac gac ctc acg<br>Ser Pro Asn Val Pro Lys Gln Ala Ser Glu Asp Thr Asn Asp Leu Thr<br>           1035                 1040                 1045 | 3352 |
| ccc acc ctg cca gag aca ccc gtg cct ctg ccc agg aag atc aac acg<br>Pro Thr Leu Pro Glu Thr Pro Val Pro Leu Pro Arg Lys Ile Asn Thr<br>1050                         1055                 1060 | 3400 |
| ggg aag agc aag gtg agg cga gtg aag acc atc tac gac tgc cag gcg<br>Gly Lys Ser Lys Val Arg Arg Val Lys Thr Ile Tyr Asp Cys Gln Ala<br>1065                         1070                 1075                 1080 | 3448 |
| gac aac gat gac gag ctg act ttc atg gag ggc gag gtg atc gtg gtc<br>Asp Asn Asp Asp Glu Leu Thr Phe Met Glu Gly Glu Val Ile Val Val<br>                1085                1090                1095 | 3496 |
| acc ggg gag gag gac cag gag tgg tgg att ggg cac atc gag ggg cag<br>Thr Gly Glu Glu Asp Gln Glu Trp Trp Ile Gly His Ile Glu Gly Gln<br>           1100                 1105                 1110 | 3544 |

```
ccc gag agg aag ggc gtc ttc cca gtg tcc ttt gtc cac atc ctg tcg        3592
Pro Glu Arg Lys Gly Val Phe Pro Val Ser Phe Val His Ile Leu Ser
        1115                1120                1125 gac tagcaaaaaa agcagagcct tcagactgtc cgcacccgtc atgccagact             3645
Asp gctgcctccc tgggacccccg tgcgcaccgt gtaaatagct gctgttgccg agtggaagct     3705
cccggagggg ccgcctcagg aggggaacgg agcacgtgtt gtaaataccc tatggtctct     3765
gccttcgcca gtattagggt agccttggga cccggtgcgc cttactggtt tgccaaagcc     3825
atccttggca tctagcactt acatctctct ctatgctgtt ttccaagcaa acaaacaagc     3885
aggaatatag gaactgctgg ctttgcaaat agaaatggtg tccagcaacc gttgaagggc     3945
acagcattgc ctctctgttc ctaacctgac agtattctcc attgtgttac tgaaaaatgc     4005
aacattagca aagaggtggg tactgtcttc caggtgaatc tttccgctcc gtgacagacc     4065
agcctgtcgt tatccgtgta cacagtttac agctacaaaa accgactttg gtatttatta     4125
cagaaaagcg ctcagttccg tgtaagtgtt attccttcag caaagtatcc actgacccag     4185
aacgttgggt ggcattttac agtgcccaca gcctcacgca ggtttagaca cgtgggttta     4245
tgctgtctta agaagatgag tgcccgcccc tgatattacc tcattatgca aaaataacat     4305
atccttcatg actattttca cagaagttta agacacatct gatgaagttc aactttcaag     4365
aaccaaggac tgccagaaaa tattagcctc tacattatgc atgcatttag aagcttacct     4425
gaaatctgcc ttttataaag ggaatagtat ggataagttg aactgtacat ttttttttaa     4485
aacttgattg ccattaaagc agaaattata aggttgcaac aaatatttgt ttccagtcag     4545
tcatttggct ttcctcaaga gtatgaatgc acatatcaca ttatgaatta gcatccttca     4605
actatgttaa cacctctaac atgtccgttt taaattcctt tcttagtttt cgttctggat     4665
aaatttaaac tttcaaaaga gtgttcaaga agatgactaa ttcagaaatc agttctgccc     4725
accgttttcc cccgcccacc cccgctgtag aattcaggtg ctgaaaccag ccttctttt      4785 tttttttctt catttccttt agtaaactcc aatcatagat aagtttccca gctctgttga     4845
acagacactt catcttcaag tcgattcata accaagtttc tgaacgctgc tatgaattgc     4905
actgtgaaac atgcttttct gccagggggtc cctgcccctc ccagtttttt ttctcatccc    4965
agccgctttc atcagaccat caagaccatc ctcagttttt cagtcttta catcagcctg      5025 aatgtgggga gagaataccg ctccgctccc cagtcagtgg gactgctctc ggattccgag     5085
gcccacgtgt cgtccttgca gtgcgcttgc ttaaacggct acgttggcag cagcgcagga     5145
agctaatatt tttaagcaga tcatcctggc aacgagtgag aaatgttcat ttcacagaag     5205
cacagctccc aaccagaccc ttaggggagc cctctgtaat cgagtcgcag tgctcggcga     5265
gcattacctt agctctgctc acgtgatcac tgaaccaata aaccttgcat gacaaacctg     5325
cggca                                                                  5330

<210> SEQ ID NO 2
<211> LENGTH: 1129
<212> TYPE: PRT
<213> ORGANISM: Bos sp.

<400> SEQUENCE: 2

Met Arg Ser Ser Ala Ser Arg Leu Ser Ser Phe Ser Ser Arg Asp Ser
 1               5                  10                  15

Leu Trp Asn Arg Met Pro Asp Gln Ile Ser Val Ser Glu Phe Ile Ala
        20                  25                  30
```

```
Glu Thr Thr Glu Asp Tyr Asn Ser Pro Thr Thr Ser Ser Phe Thr Thr
             35                  40                  45

Arg Leu His Asn Cys Arg Asn Thr Val Thr Leu Leu Glu Glu Ala Leu
 50                  55                  60

Asp Gln Asp Arg Thr Ala Leu Gln Lys Val Lys Lys Ser Val Lys Ala
 65                  70                  75                  80

Ile Tyr Asn Ser Gly Gln Asp His Val Gln Asn Glu Asn Tyr Ala
                 85                  90                  95

Gln Val Leu Asp Lys Phe Gly Ser Asn Phe Leu Ser Arg Asp Asn Pro
                100                 105                 110

Asp Leu Gly Thr Ala Phe Val Lys Phe Ser Thr Leu Thr Lys Glu Leu
            115                 120                 125

Ser Thr Leu Leu Lys Asn Leu Leu Gln Gly Leu Ser His Asn Val Ile
            130                 135                 140

Phe Thr Leu Asp Ser Leu Leu Lys Gly Asp Leu Lys Gly Val Lys Gly
145                 150                 155                 160

Asp Leu Lys Lys Pro Phe Asp Lys Ala Trp Lys Asp Tyr Glu Thr Lys
                165                 170                 175

Phe Thr Lys Ile Glu Lys Glu Lys Arg Glu His Ala Lys Gln His Gly
            180                 185                 190

Met Ile Arg Thr Glu Ile Thr Gly Ala Glu Ile Ala Glu Glu Met Glu
            195                 200                 205

Lys Glu Arg Arg Leu Phe Gln Leu Gln Met Cys Glu Tyr Leu Ile Lys
            210                 215                 220

Val Asn Glu Ile Lys Thr Lys Lys Gly Val Asp Leu Leu Gln Asn Leu
225                 230                 235                 240

Ile Lys Tyr Tyr His Ala Gln Cys Asn Phe Phe Gln Asp Gly Leu Lys
                245                 250                 255

Thr Ala Asp Lys Leu Lys Gln Tyr Ile Glu Lys Leu Ala Ala Asp Leu
            260                 265                 270

Tyr Asn Ile Lys Gln Thr Gln Asp Glu Glu Lys Lys Gln Leu Thr Ala
            275                 280                 285

Leu Arg Asp Leu Ile Lys Ser Ser Leu Gln Leu Asp Gln Lys Glu Ser
            290                 295                 300

Arg Arg Asp Ser Gln Ser Arg Gln Gly Gly Tyr Ser Met His Gln Leu
305                 310                 315                 320

Gln Gly Asn Lys Glu Tyr Gly Ser Glu Lys Lys Gly Tyr Leu Leu Lys
                325                 330                 335

Lys Ser Asp Gly Ile Arg Lys Val Trp Gln Arg Arg Lys Cys Ser Val
            340                 345                 350

Lys Asn Gly Ile Leu Thr Ile Ser His Ala Thr Ser Asn Arg Gln Pro
            355                 360                 365

Ala Lys Leu Asn Leu Leu Thr Cys Gln Val Lys Pro Asn Ala Glu Asp
            370                 375                 380

Lys Lys Ser Phe Asp Leu Ile Ser His Asn Arg Thr Tyr His Phe Gln
385                 390                 395                 400

Ala Glu Asp Glu Gln Asp Tyr Val Ala Trp Ile Ser Val Leu Thr Asn
                405                 410                 415

Ser Lys Glu Glu Ala Leu Thr Met Ala Phe Arg Gly Glu Gln Ser Ala
            420                 425                 430

Gly Glu Ser Ser Leu Glu Glu Leu Thr Lys Ala Ile Ile Glu Asp Val
            435                 440                 445
```

-continued

```
Gln Arg Leu Pro Gly Asn Asp Val Cys Cys Asp Cys Gly Ser Ala Glu
    450                 455                 460
Pro Thr Trp Leu Ser Thr Asn Leu Gly Ile Leu Thr Cys Ile Glu Cys
465                 470                 475                 480
Ser Gly Ile His Arg Glu Met Gly Val His Ile Ser Arg Ile Gln Ser
                485                 490                 495
Leu Glu Leu Asp Lys Leu Gly Thr Ser Glu Leu Leu Ala Lys Asn
            500                 505                 510
Val Gly Asn Asn Ser Phe Asn Asp Ile Met Glu Ala Asn Leu Pro Ser
        515                 520                 525
Pro Ser Pro Lys Pro Thr Pro Ser Ser Asp Met Thr Val Arg Lys Glu
    530                 535                 540
Tyr Ile Thr Ala Lys Tyr Val Asp His Arg Phe Ser Arg Lys Thr Cys
545                 550                 555                 560
Ser Ser Ser Ser Ala Lys Leu Asn Glu Leu Leu Glu Ala Ile Lys Ser
                565                 570                 575
Arg Asp Leu Leu Ala Leu Ile Gln Val Tyr Ala Glu Gly Val Glu Leu
            580                 585                 590
Met Glu Pro Leu Leu Glu Pro Gly Gln Glu Leu Gly Glu Thr Ala Leu
    595                 600                 605
His Leu Ala Val Arg Thr Ala Asp Gln Thr Ser Leu His Leu Val Asp
        610                 615                 620
Phe Leu Val Gln Asn Cys Gly Asn Leu Asp Lys Gln Thr Ala Leu Gly
625                 630                 635                 640
Asn Thr Ala Leu His Tyr Cys Ser Met Tyr Ser Lys Pro Glu Cys Leu
                645                 650                 655
Lys Leu Leu Leu Arg Ser Lys Pro Thr Val Asp Val Val Asn Gln Ala
            660                 665                 670
Gly Glu Thr Ala Leu Asp Ile Ala Lys Arg Leu Lys Ala Thr Gln Cys
    675                 680                 685
Glu Asp Leu Leu Ser Gln Ala Lys Ser Gly Lys Phe Asn Pro His Val
        690                 695                 700
His Val Glu Tyr Glu Trp Asn Leu Arg Gln Glu Glu Met Asp Glu Ser
705                 710                 715                 720
Asp Asp Asp Leu Asp Asp Lys Pro Ser Pro Ile Lys Lys Glu Arg Ser
                725                 730                 735
Pro Arg Pro Gln Ser Phe Cys His Ser Ser Ser Ile Ser Pro Gln Asp
            740                 745                 750
Lys Leu Ser Leu Pro Gly Phe Ser Thr Pro Arg Asp Lys Gln Arg Leu
    755                 760                 765
Ser Tyr Gly Ala Phe Thr Asn Gln Ile Phe Val Ser Thr Ser Thr Asp
        770                 775                 780
Ser Pro Thr Ser Pro Ile Ala Glu Ala Pro Pro Leu Pro Pro Arg Asn
785                 790                 795                 800
Ala Thr Lys Gly Pro Pro Gly Pro Ser Thr Leu Pro Leu Ser Thr
                805                 810                 815
Gln Thr Ser Ser Gly Ser Ser Thr Leu Ser Lys Lys Arg Ser Pro Pro
            820                 825                 830
Pro Pro Pro Gly His Lys Arg Thr Leu Ser Asp Pro Pro Ser Pro Leu
    835                 840                 845
Pro His Gly Pro Pro Asn Lys Gly Ala Val Pro Trp Gly Asn Asp Val
        850                 855                 860
Gly Pro Ser Ser Ser Ser Lys Thr Thr Asn Lys Phe Glu Gly Leu Ser
```

```
                            865                 870                 875                 880
Gln Gln Ser Ser Thr Gly Ser Ala Lys Thr Ala Leu Val Pro Arg Val
                885                 890                 895
Leu Pro Lys Leu Pro Gln Lys Val Ala Leu Arg Lys Thr Glu Thr Ser
                900                 905                 910
His His Leu Ser Leu Asp Lys Ala Asn Val Pro Pro Glu Ile Phe Gln
                915                 920                 925
Lys Ser Ser Gln Leu Thr Glu Leu Pro Gln Lys Pro Pro Gly Asp
        930                 935                 940
Leu Pro Pro Lys Pro Thr Glu Leu Ala Pro Lys Pro Ile Gly Asp
945                 950                 955                 960
Leu Pro Pro Lys Pro Gly Glu Leu Pro Lys Pro Gln Leu Gly Asp
                965                 970                 975
Leu Pro Pro Lys Pro Gln Leu Ala Asp Leu Pro Pro Lys Pro Gln Val
                980                 985                 990
Lys Asp Leu Pro Pro Lys Pro Gln Leu Gly Glu Leu Leu Ala Lys Pro
            995                 1000                1005
Gln Thr Gly Asp Ala Ser Pro Lys Ala Gln Pro Pro Leu Glu Leu Thr
        1010                1015                1020
Pro Lys Ser His Pro Ala Asp Leu Ser Pro Asn Val Pro Lys Gln Ala
1025                1030                1035                1040
Ser Glu Asp Thr Asn Asp Leu Thr Pro Thr Leu Pro Glu Thr Pro Val
                1045                1050                1055
Pro Leu Pro Arg Lys Ile Asn Thr Gly Lys Ser Lys Val Arg Arg Val
                1060                1065                1070
Lys Thr Ile Tyr Asp Cys Gln Ala Asp Asn Asp Glu Leu Thr Phe
            1075                1080                1085
Met Glu Gly Glu Val Ile Val Val Thr Gly Glu Glu Asp Gln Glu Trp
        1090                1095                1100
Trp Ile Gly His Ile Glu Gly Gln Pro Glu Arg Lys Gly Val Phe Pro
1105                1110                1115                1120
Val Ser Phe Val His Ile Leu Ser Asp
            1125

<210> SEQ ID NO 3
<211> LENGTH: 4382
<212> TYPE: DNA
<213> ORGANISM: Danio rerio
<220> FEATURE:
<221> NAME/KEY: CDS
<222> LOCATION: (351)...(3803)

<400> SEQUENCE: 3
gacaaaagct ggagctcgcg cgcctgcagg tcgacactag tggatccaaa gaattcggca      60
cgagctccgg ccccctccaa actcacatgc cggactcccg cttcctgtcc agcagctcca     120
gatgggcag atcaatgcgc gcattcctgc tcattgtaac tgtagcggca tgtgatttca     180
gcccgtaatg tccgcgcgct ggacggagca caatgcgctg aatatggtgc cactcggaaa     240
cacggagctg tacgcacaat ctgctttgca attacttttt aatctgttaa tacggagtga     300
aaccgcagct gtctcgctca gggttgtttt gctgaggtga ctacagagcc atg agg      356
                                                     Met Arg
                                                       1 tcc tcg tcc tcg cgt ttg tca agt ttt tcc tcc agg gat tca tta tgg      404
Ser Ser Ser Ser Arg Leu Ser Ser Phe Ser Ser Arg Asp Ser Leu Trp
         5                  10                  15
```

-continued

| | |
|---|---|
| agt cgg atg ccg gat cag atc tcc gtg tcc gag ttt ctc tcg gag acg<br>Ser Arg Met Pro Asp Gln Ile Ser Val Ser Glu Phe Leu Ser Glu Thr<br>    20                          25                      30 | 452 |
| acg gag gat tac aat tcc ccc acg acc tcg agc ttc acc acc cgc ctg<br>Thr Glu Asp Tyr Asn Ser Pro Thr Thr Ser Ser Phe Thr Thr Arg Leu<br>35                      40                    45                  50 | 500 |
| cag agc tgc cgg aac acg gtc aat gtt ctg gaa gag gct ttg gat cag<br>Gln Ser Cys Arg Asn Thr Val Asn Val Leu Glu Glu Ala Leu Asp Gln<br>                  55                    60                  65 | 548 |
| gac cga act gct tta cag aag gtc aag aaa tct gtc aaa gca atc tac<br>Asp Arg Thr Ala Leu Gln Lys Val Lys Lys Ser Val Lys Ala Ile Tyr<br>            70                    75                  80 | 596 |
| aac tcg ggt caa gaa cat gtg cag aat gaa gag aat tat gga cag gca<br>Asn Ser Gly Gln Glu His Val Gln Asn Glu Glu Asn Tyr Gly Gln Ala<br>        85                    90                  95 | 644 |
| ctg gac aag ttt ggc agc aac ttc atc agc cga gat aac tct gat ctg<br>Leu Asp Lys Phe Gly Ser Asn Phe Ile Ser Arg Asp Asn Ser Asp Leu<br>100                    105                110 | 692 |
| gga aca gcc ttc atc aag ttt tct gga ctt atc aaa gag ctg gct gct<br>Gly Thr Ala Phe Ile Lys Phe Ser Gly Leu Ile Lys Glu Leu Ala Ala<br>115                    120                125                130 | 740 |
| ctc ctc aag aac ctg ctc cag agc ctc agc cac aac gtc atc ttc acc<br>Leu Leu Lys Asn Leu Leu Gln Ser Leu Ser His Asn Val Ile Phe Thr<br>                  135                140                145 | 788 |
| ctg gac tct ctg ctc aaa gga gat cta aag gga gtg aag ggg gac ctt<br>Leu Asp Ser Leu Leu Lys Gly Asp Leu Lys Gly Val Lys Gly Asp Leu<br>              150                155                160 | 836 |
| aaa aag cct ttc gac aag gcc tgg aaa gac tat gaa acc aag ttc aca<br>Lys Lys Pro Phe Asp Lys Ala Trp Lys Asp Tyr Glu Thr Lys Phe Thr<br>                  165                170                175 | 884 |
| aag atc gag aag gag aag aga gaa cat gcc aag cag cac ggc atg atc<br>Lys Ile Glu Lys Glu Lys Arg Glu His Ala Lys Gln His Gly Met Ile<br>180                    185                190 | 932 |
| cgc aca gaa atc acc ggc gca gag att gca gaa gag atg gag aag gag<br>Arg Thr Glu Ile Thr Gly Ala Glu Ile Ala Glu Glu Met Glu Lys Glu<br>195                    200                205                210 | 980 |
| cgg agg atc ttt cag ctg cag atg tgt gag tac ctg atc aaa gtc aat<br>Arg Arg Ile Phe Gln Leu Gln Met Cys Glu Tyr Leu Ile Lys Val Asn<br>                  215                220                225 | 1028 |
| gag att aag acc aag aag gga gtg gat ctc ctc cag aat ctc atc aag<br>Glu Ile Lys Thr Lys Lys Gly Val Asp Leu Leu Gln Asn Leu Ile Lys<br>                    230                235                240 | 1076 |
| tat tat cat gca cag tgc aat ttc ttc cag gat ggc ttg aaa act gct<br>Tyr Tyr His Ala Gln Cys Asn Phe Phe Gln Asp Gly Leu Lys Thr Ala<br>              245                250                255 | 1124 |
| gac aag ttg aag cag tat att gaa aaa tta gca gct gat ctt tat aat<br>Asp Lys Leu Lys Gln Tyr Ile Glu Lys Leu Ala Ala Asp Leu Tyr Asn<br>260                    265                270 | 1172 |
| ata aaa cag act cag gat gag gag aaa aaa cag ctc aca gct ctc aga<br>Ile Lys Gln Thr Gln Asp Glu Glu Lys Lys Gln Leu Thr Ala Leu Arg<br>275                    280                285                290 | 1220 |
| gac ctc atc aaa tct tcc tta cag ctg gac cag aag gag gat tct cag<br>Asp Leu Ile Lys Ser Ser Leu Gln Leu Asp Gln Lys Glu Asp Ser Gln<br>                  295                300                305 | 1268 |
| agt aag cag agc ggg tac agc atg cac cag ctg cag ggc aat aag gag<br>Ser Lys Gln Ser Gly Tyr Ser Met His Gln Leu Gln Gly Asn Lys Glu<br>              310                315                320 | 1316 |
| ttt ggc agt gag aag aag ggc tat ctc ttc aag aag agt gat ggg atc<br>Phe Gly Ser Glu Lys Lys Gly Tyr Leu Phe Lys Lys Ser Asp Gly Ile<br>325                    330                335 | 1364 |

-continued

| | |
|---|---|
| cgt aag gtg tgg cag agg agg aag tgc tca gtg aaa aat ggc atc ctc<br>Arg Lys Val Trp Gln Arg Arg Lys Cys Ser Val Lys Asn Gly Ile Leu<br>340                         345                     350 | 1412 |
| acc atc tct cat gcc aca tcc aac agg cag ccg gtg aga ctg aat ctg<br>Thr Ile Ser His Ala Thr Ser Asn Arg Gln Pro Val Arg Leu Asn Leu<br>355                   360                   365               370 | 1460 |
| ctg acc tgc cag gtt aaa ccc agt gga gag gat aag aag tgc ttt gac<br>Leu Thr Cys Gln Val Lys Pro Ser Gly Glu Asp Lys Lys Cys Phe Asp<br>                   375                   380               385 | 1508 |
| ctc atc tct cat aat cga aca tat cat ttc cag gca gag gac gaa cag<br>Leu Ile Ser His Asn Arg Thr Tyr His Phe Gln Ala Glu Asp Glu Gln<br>         390                   395                   400 | 1556 |
| gag ttt gtg ata tgg atc tcg gtg ctg act aat agt aag gag gag gct<br>Glu Phe Val Ile Trp Ile Ser Val Leu Thr Asn Ser Lys Glu Glu Ala<br>405                         410                     415 | 1604 |
| ctg aac atg gca ttt cgt ggg gag cag agt gct gga gat gac agt ttg<br>Leu Asn Met Ala Phe Arg Gly Glu Gln Ser Ala Gly Asp Asp Ser Leu<br>         420                   425                   430 | 1652 |
| gag gac ttg acc aaa gcc atc atc gag gac gtg ctg cgc att cct gga<br>Glu Asp Leu Thr Lys Ala Ile Ile Glu Asp Val Leu Arg Ile Pro Gly<br>435                         440                   445               450 | 1700 |
| aac gaa gtc tgc tgt gac tgt ggg gtt cca gag ccc aaa tgg tta tcc<br>Asn Glu Val Cys Cys Asp Cys Gly Val Pro Glu Pro Lys Trp Leu Ser<br>                   455                   460               465 | 1748 |
| act aac ctc ggc atc ctg acg tgc atc gag tgt tca gga atc cac agg<br>Thr Asn Leu Gly Ile Leu Thr Cys Ile Glu Cys Ser Gly Ile His Arg<br>         470                   475                   480 | 1796 |
| gaa atg gga gtc cat att tcg cgc atc caa tcc atg gag ctt gac aaa<br>Glu Met Gly Val His Ile Ser Arg Ile Gln Ser Met Glu Leu Asp Lys<br>485                         490                     495 | 1844 |
| ctt gga acc tct gaa ctc ttg ctg gct aag aac gtg ggc aac agt agt<br>Leu Gly Thr Ser Glu Leu Leu Leu Ala Lys Asn Val Gly Asn Ser Ser<br>         500                   505                   510 | 1892 |
| ttc aac gaa ata tta gaa ggg aat ctg ccg agt cct tca cca aag cca<br>Phe Asn Glu Ile Leu Glu Gly Asn Leu Pro Ser Pro Ser Pro Lys Pro<br>515                         520                   525               530 | 1940 |
| gcg cca tca agt gac atg acc gag agg aag gag tac atc aat gcg aag<br>Ala Pro Ser Ser Asp Met Thr Glu Arg Lys Glu Tyr Ile Asn Ala Lys<br>                   535                   540               545 | 1988 |
| tac gtg gag cac agg ttc gct cgg cga acg gcc act aca gcc aca gcc<br>Tyr Val Glu His Arg Phe Ala Arg Arg Thr Ala Thr Thr Ala Thr Ala<br>         550                   555                   560 | 2036 |
| aga cag ggc gac ttg tac gag gcg gtg aga acg cga gac ttg atg gct<br>Arg Gln Gly Asp Leu Tyr Glu Ala Val Arg Thr Arg Asp Leu Met Ala<br>565                         570                     575 | 2084 |
| ctc att cag ctc tat gca gat gga gtg gag cta atg gat cct ttc cca<br>Leu Ile Gln Leu Tyr Ala Asp Gly Val Glu Leu Met Asp Pro Phe Pro<br>         580                   585                   590 | 2132 |
| gaa gca gga cag gac ccg gga gag aca gct ctg cac ttt gct gtt cgg<br>Glu Ala Gly Gln Asp Pro Gly Glu Thr Ala Leu His Phe Ala Val Arg<br>595                         600                   605               610 | 2180 |
| aca tca gac cag act tcc ctg cac ctg gtg gac ttt ctt gtc caa aac<br>Thr Ser Asp Gln Thr Ser Leu His Leu Val Asp Phe Leu Val Gln Asn<br>                   615                   620               625 | 2228 |
| agt ggg act cta gac aga cag acg gag agt gga aac gct gct ctc cat<br>Ser Gly Thr Leu Asp Arg Gln Thr Glu Ser Gly Asn Ala Ala Leu His<br>         630                   635                   640 | 2276 |
| tac tgc tgc aca tat gag aag cca gag tgt ctc aaa ctg ctg ctc agg<br>Tyr Cys Cys Thr Tyr Glu Lys Pro Glu Cys Leu Lys Leu Leu Leu Arg | 2324 |

```
                    -continued
         645                 650                 655
gga aaa ccg tct att gac ctg gtt aat caa aac ggg gag aca gca ttg    2372
Gly Lys Pro Ser Ile Asp Leu Val Asn Gln Asn Gly Glu Thr Ala Leu
        660                 665                 670 gat atc gcc aga cga ctg aga aat gta cag tgt gaa gag cta ctg gtg    2420
Asp Ile Ala Arg Arg Leu Arg Asn Val Gln Cys Glu Glu Leu Leu Val
675                 680                 685                 690 gag gca gca gcc ggg agg ttt aat cct cat gtg cat gtg gag tat gag    2468
Glu Ala Ala Ala Gly Arg Phe Asn Pro His Val His Val Glu Tyr Glu
                695                 700                 705 tgg aat ctg cgg ctg gag gag att gat gag agt gac gat gac ctg gat    2516
Trp Asn Leu Arg Leu Glu Glu Ile Asp Glu Ser Asp Asp Asp Leu Asp
            710                 715                 720 gac aag cct agt cca gtg aag aag gag cgt tct cct cgt cct cag agc    2564
Asp Lys Pro Ser Pro Val Lys Lys Glu Arg Ser Pro Arg Pro Gln Ser
        725                 730                 735 ttc tgt cat tcg tcc agc gtg tct cct cag gag aag tta acc ctg ccg    2612
Phe Cys His Ser Ser Ser Val Ser Pro Gln Glu Lys Leu Thr Leu Pro
    740                 745                 750 ggg tat cta gga cac agg gac aag cag aga ctg tcc tat gga gcc ttt    2660
Gly Tyr Leu Gly His Arg Asp Lys Gln Arg Leu Ser Tyr Gly Ala Phe
755                 760                 765                 770 gcc aac ccc gtc tac agc acc tcc acc gaa acc cct gca tct cca gtg    2708
Ala Asn Pro Val Tyr Ser Thr Ser Thr Glu Thr Pro Ala Ser Pro Val
                775                 780                 785 tca gag gga ccc acc ata gcc agc aag acc cct gca aaa gct ccg tcc    2756
Ser Glu Gly Pro Thr Ile Ala Ser Lys Thr Pro Ala Lys Ala Pro Ser
            790                 795                 800 tgt ggg ccg ccc acc tct ctg ccg ctg gga tct caa tcg agt gca gga    2804
Cys Gly Pro Pro Thr Ser Leu Pro Leu Gly Ser Gln Ser Ser Ala Gly
        805                 810                 815 ggc agc tcc act ttg tct aag aag aga gct cct cct cca cct ccc gga    2852
Gly Ser Ser Thr Leu Ser Lys Lys Arg Ala Pro Pro Pro Pro Pro Gly
    820                 825                 830 cac aag cgc acc cac tca gat ccc ccc agt ccc gta ctg cag ggt ccg    2900
His Lys Arg Thr His Ser Asp Pro Pro Ser Pro Val Leu Gln Gly Pro
835                 840                 845                 850 cag agc aaa gga agt gag tcc aca cct cct tct gca aat cgg aca tcc    2948
Gln Ser Lys Gly Ser Glu Ser Thr Pro Pro Ser Ala Asn Arg Thr Ser
                855                 860                 865 ccg gcc aac aag ttt gag gga atc cag cag cag caa agc act acg tct    2996
Pro Ala Asn Lys Phe Glu Gly Ile Gln Gln Gln Gln Ser Thr Thr Ser
            870                 875                 880 atg aac aca aaa gca aca ttt ggc cca cga gtt ctt ccc aaa cta cct    3044
Met Asn Thr Lys Ala Thr Phe Gly Pro Arg Val Leu Pro Lys Leu Pro
        885                 890                 895 caa aaa gtg gca cta cga aag att gac aca atc cac ctc cca tca gtg    3092
Gln Lys Val Ala Leu Arg Lys Ile Asp Thr Ile His Leu Pro Ser Val
    900                 905                 910 gac aag tct ggt cct gat gtg ctt cag aaa ccc cca gcc cag gat        3140
Asp Lys Ser Gly Pro Asp Val Leu Gln Lys Pro Pro Gln Ala Gln Asp
915                 920                 925                 930 gca cct ccc acc aga gcc tca gat aca ata acc aga ccc act gaa cct    3188
Ala Pro Pro Thr Arg Ala Ser Asp Thr Ile Thr Arg Pro Thr Glu Pro
                935                 940                 945 cca cct aaa att cca cag gtc gca gaa cga tcc cag cct gtg gat gtc    3236
Pro Pro Lys Ile Pro Gln Val Ala Glu Arg Ser Gln Pro Val Asp Val
            950                 955                 960 ccg cag aaa ccg cac atc tca gac ctt cct ccc aaa ccg caa cta tca    3284
```

|  |  |
|---|---|
| Pro Gln Lys Pro His Ile Ser Asp Leu Pro Pro Lys Pro Gln Leu Ser<br>         965                970                    975 |  |
| gat ctt ccc ccc aaa ccc caa ttg tcg gat tta cca cca aaa cct cag<br>Asp Leu Pro Pro Lys Pro Gln Leu Ser Asp Leu Pro Pro Lys Pro Gln<br>980                   985                    990 | 3332 |
| ctt tct gac ctg ccc ccg aag cct cag ctt aag gat ctt ccc cct aag<br>Leu Ser Asp Leu Pro Pro Lys Pro Gln Leu Lys Asp Leu Pro Pro Lys<br>995                   1000              1005             1010 | 3380 |
| ccg cag atc agt gat ctg cca tcc aaa ccg gcc gtg tgt tct gcg tct<br>Pro Gln Ile Ser Asp Leu Pro Ser Lys Pro Ala Val Cys Ser Ala Ser<br>                  1015              1020              1025 | 3428 |
| gag gcc aca cag agg cag tca acg cag gag gaa acc agt ccg aag ccc<br>Glu Ala Thr Gln Arg Gln Ser Thr Gln Glu Glu Thr Ser Pro Lys Pro<br>            1030              1035              1040 | 3476 |
| cag ctg acg gag aca cag tca ttc agc cag cag gag gag ctc tca ccc<br>Gln Leu Thr Glu Thr Gln Ser Phe Ser Gln Gln Glu Glu Leu Ser Pro<br>            1045              1050              1055 | 3524 |
| cga cag gcc agc gag gac acc aat gga gcg ccc gca gga gcc ttg gaa<br>Arg Gln Ala Ser Glu Asp Thr Asn Gly Ala Pro Ala Gly Ala Leu Glu<br>            1060              1065              1070 | 3572 |
| atg cca gtc cca atg cca cgc aaa att aac aca gta gca aag aac aaa<br>Met Pro Val Pro Met Pro Arg Lys Ile Asn Thr Val Ala Lys Asn Lys<br>1075                  1080              1085              1090 | 3620 |
| gcg aag cgt gtg aaa acc atc tat gat tgc cag gca gac aat gac gat<br>Ala Lys Arg Val Lys Thr Ile Tyr Asp Cys Gln Ala Asp Asn Asp Asp<br>                  1095              1100              1105 | 3668 |
| gag ctg act ttt gtg gag ggc gag gtt ata att gtc aca gga gag gaa<br>Glu Leu Thr Phe Val Glu Gly Glu Val Ile Ile Val Thr Gly Glu Glu<br>            1110              1115              1120 | 3716 |
| gac cag gag tgg tgg atc ggg cac ata gag ggt cag cct gaa agg aaa<br>Asp Gln Glu Trp Trp Ile Gly His Ile Glu Gly Gln Pro Glu Arg Lys<br>            1125              1130              1135 | 3764 |
| ggg gtc ttc cca atg tcc ttc gtg cac att ctg tca gac tgacagtgca<br>Gly Val Phe Pro Met Ser Phe Val His Ile Leu Ser Asp<br>            1140              1145              1150 | 3813 |
| tgaccggcag ccgagaggct ctctaactag cacaagctcc gctctctctg gcctcacact | 3873 |
| ggactgtggg cattgcctct gtacatagct gctgaaaccc aaacggtctc caaacacata | 3933 |
| caaaactgaa gtatcaaacc catgctccct taatcctcaa gggtgaaatg tgtaaactat | 3993 |
| gtgttgttca taaactgtgt tatcctgcct accagtatta tcgtagccat ggcagcccag | 4053 |
| catgccataa ctgggtttgc agtagctata cttggaaatc tagcacttaa catgtatgct | 4113 |
| gtaactttgt gtatgtgtac acatatagaa ttatatgtat gtccatttta agtgtgtctt | 4173 |
| tgtacataca tatgcacaga cgtaagtgta tatttatgta cgtatgtata atgtacaagt | 4233 |
| gtgcaaatgt atgttaaccc tgcttgctta tggagccaga gtgactctag acattttagt | 4293 |
| gtactgtttt aaaaaaaaaa aaaaaaaaac tcgagagtac ttctagagcg gccgcgggcc | 4353 |
| catcgatttt ccacccgggt ggggtacca | 4382 |

<210> SEQ ID NO 4
<211> LENGTH: 1151
<212> TYPE: PRT
<213> ORGANISM: Danio rerio
<400> SEQUENCE: 4

Met Arg Ser Ser Ser Arg Leu Ser Ser Phe Ser Ser Arg Asp Ser
1               5                   10                   15

Leu Trp Ser Arg Met Pro Asp Gln Ile Ser Val Ser Glu Phe Leu Ser

-continued

```
             20                  25                  30
Glu Thr Thr Glu Asp Tyr Asn Ser Pro Thr Thr Ser Ser Phe Thr Thr
                 35                  40                  45
Arg Leu Gln Ser Cys Arg Asn Thr Val Asn Val Leu Glu Glu Ala Leu
 50                  55                  60
Asp Gln Asp Arg Thr Ala Leu Gln Lys Val Lys Lys Ser Val Lys Ala
 65                  70                  75                  80
Ile Tyr Asn Ser Gly Gln Glu His Val Gln Asn Glu Glu Asn Tyr Gly
                 85                  90                  95
Gln Ala Leu Asp Lys Phe Gly Ser Asn Phe Ile Ser Arg Asp Asn Ser
                100                 105                 110
Asp Leu Gly Thr Ala Phe Ile Lys Phe Ser Gly Leu Ile Lys Glu Leu
                115                 120                 125
Ala Ala Leu Leu Lys Asn Leu Leu Gln Ser Leu Ser His Asn Val Ile
130                 135                 140
Phe Thr Leu Asp Ser Leu Leu Lys Gly Asp Leu Lys Gly Val Lys Gly
145                 150                 155                 160
Asp Leu Lys Lys Pro Phe Asp Lys Ala Trp Lys Asp Tyr Glu Thr Lys
                165                 170                 175
Phe Thr Lys Ile Glu Lys Glu Lys Arg Glu His Ala Lys Gln His Gly
                180                 185                 190
Met Ile Arg Thr Glu Ile Thr Gly Ala Glu Ile Ala Glu Glu Met Glu
                195                 200                 205
Lys Glu Arg Arg Ile Phe Gln Leu Gln Met Cys Glu Tyr Leu Ile Lys
                210                 215                 220
Val Asn Glu Ile Lys Thr Lys Lys Gly Val Asp Leu Leu Gln Asn Leu
225                 230                 235                 240
Ile Lys Tyr Tyr His Ala Gln Cys Asn Phe Phe Gln Asp Gly Leu Lys
                245                 250                 255
Thr Ala Asp Lys Leu Lys Gln Tyr Ile Glu Lys Leu Ala Ala Asp Leu
                260                 265                 270
Tyr Asn Ile Lys Gln Thr Gln Asp Glu Glu Lys Lys Gln Leu Thr Ala
                275                 280                 285
Leu Arg Asp Leu Ile Lys Ser Ser Leu Gln Leu Asp Gln Lys Glu Asp
    290                 295                 300
Ser Gln Ser Lys Gln Ser Gly Tyr Ser Met His Gln Leu Gln Gly Asn
305                 310                 315                 320
Lys Glu Phe Gly Ser Glu Lys Lys Gly Tyr Leu Phe Lys Lys Ser Asp
                325                 330                 335
Gly Ile Arg Lys Val Trp Gln Arg Arg Lys Cys Ser Val Lys Asn Gly
                340                 345                 350
Ile Leu Thr Ile Ser His Ala Thr Ser Asn Arg Gln Pro Val Arg Leu
                355                 360                 365
Asn Leu Leu Thr Cys Gln Val Lys Pro Ser Gly Glu Asp Lys Lys Cys
    370                 375                 380
Phe Asp Leu Ile Ser His Asn Arg Thr Tyr His Phe Gln Ala Glu Asp
385                 390                 395                 400
Glu Gln Glu Phe Val Ile Trp Ile Ser Val Leu Thr Asn Ser Lys Glu
                405                 410                 415
Glu Ala Leu Asn Met Ala Phe Arg Gly Glu Gln Ser Ala Gly Asp Asp
                420                 425                 430
Ser Leu Glu Asp Leu Thr Lys Ala Ile Ile Glu Asp Val Leu Arg Ile
    435                 440                 445
```

-continued

```
Pro Gly Asn Glu Val Cys Cys Asp Cys Gly Val Pro Glu Pro Lys Trp
    450                 455                 460
Leu Ser Thr Asn Leu Gly Ile Leu Thr Cys Ile Glu Cys Ser Gly Ile
465                 470                 475                 480
His Arg Glu Met Gly Val His Ile Ser Arg Ile Gln Ser Met Glu Leu
                485                 490                 495
Asp Lys Leu Gly Thr Ser Glu Leu Leu Leu Ala Lys Asn Val Gly Asn
                500                 505                 510
Ser Ser Phe Asn Glu Ile Leu Glu Gly Asn Leu Pro Ser Pro Ser Pro
            515                 520                 525
Lys Pro Ala Pro Ser Ser Asp Met Thr Glu Arg Lys Glu Tyr Ile Asn
    530                 535                 540
Ala Lys Tyr Val Glu His Arg Phe Ala Arg Arg Thr Ala Thr Thr Ala
545                 550                 555                 560
Thr Ala Arg Gln Gly Asp Leu Tyr Glu Ala Val Arg Thr Arg Asp Leu
                565                 570                 575
Met Ala Leu Ile Gln Leu Tyr Ala Asp Gly Val Glu Leu Met Asp Pro
                580                 585                 590
Phe Pro Glu Ala Gly Gln Asp Pro Gly Glu Thr Ala Leu His Phe Ala
            595                 600                 605
Val Arg Thr Ser Asp Gln Thr Ser Leu His Leu Val Asp Phe Leu Val
    610                 615                 620
Gln Asn Ser Gly Thr Leu Asp Arg Gln Thr Glu Ser Gly Asn Ala Ala
625                 630                 635                 640
Leu His Tyr Cys Cys Thr Tyr Glu Lys Pro Glu Cys Leu Lys Leu Leu
                645                 650                 655
Leu Arg Gly Lys Pro Ser Ile Asp Leu Val Asn Gln Asn Gly Glu Thr
                660                 665                 670
Ala Leu Asp Ile Ala Arg Arg Leu Arg Asn Val Gln Cys Glu Glu Leu
            675                 680                 685
Leu Val Glu Ala Ala Gly Arg Phe Asn Pro His Val His Val Glu
    690                 695                 700
Tyr Glu Trp Asn Leu Arg Leu Glu Glu Ile Asp Glu Ser Asp Asp Asp
705                 710                 715                 720
Leu Asp Asp Lys Pro Ser Pro Val Lys Lys Glu Arg Ser Pro Arg Pro
                725                 730                 735
Gln Ser Phe Cys His Ser Ser Val Ser Pro Gln Gly Lys Leu Thr
                740                 745                 750
Leu Pro Gly Tyr Leu Gly His Arg Asp Lys Gln Arg Leu Ser Tyr Gly
            755                 760                 765
Ala Phe Ala Asn Pro Val Tyr Ser Thr Ser Thr Glu Thr Pro Ala Ser
    770                 775                 780
Pro Val Ser Glu Gly Pro Thr Ile Ala Ser Lys Thr Pro Ala Lys Ala
785                 790                 795                 800
Pro Ser Cys Gly Pro Pro Thr Ser Leu Pro Leu Gly Ser Gln Ser Ser
                805                 810                 815
Ala Gly Gly Ser Ser Thr Leu Ser Lys Lys Arg Ala Pro Pro Pro Pro
                820                 825                 830
Pro Gly His Lys Arg Thr His Ser Asp Pro Pro Ser Pro Val Leu Gln
            835                 840                 845
Gly Pro Gln Ser Lys Gly Ser Glu Ser Thr Pro Pro Ser Ala Asn Arg
    850                 855                 860
```

-continued

| | | | | | | | | | | | | |
|---|---|---|---|---|---|---|---|---|---|---|---|---|
|Thr|Ser|Pro|Ala|Asn|Lys|Phe|Glu|Gly|Ile|Gln|Gln|Gln|Ser|Thr|
|865| | | |870| | | |875| | | |880|

Thr Ser Met Asn Thr Lys Ala Thr Phe Gly Pro Arg Val Leu Pro Lys
            885            890            895

Leu Pro Gln Lys Val Ala Leu Arg Lys Ile Asp Thr Ile His Leu Pro
         900             905            910

Ser Val Asp Lys Ser Gly Pro Asp Val Leu Gln Lys Pro Pro Gln Ala
         915             920            925

Gln Asp Ala Pro Pro Thr Arg Ala Ser Asp Thr Ile Thr Arg Pro Thr
930                935            940

Glu Pro Pro Lys Ile Pro Gln Val Ala Glu Arg Ser Gln Pro Val
945              950            955            960

Asp Val Pro Gln Lys Pro His Ile Ser Asp Leu Pro Pro Lys Pro Gln
         965             970            975

Leu Ser Asp Leu Pro Pro Lys Pro Gln Leu Ser Asp Leu Pro Pro Lys
         980             985            990

Pro Gln Leu Ser Asp Leu Pro Pro Lys Pro Gln Leu Lys Asp Leu Pro
         995            1000            1005

Pro Lys Pro Gln Ile Ser Asp Leu Pro Ser Lys Pro Ala Val Cys Ser
     1010             1015            1020

Ala Ser Glu Ala Thr Gln Arg Gln Ser Thr Gln Glu Glu Thr Ser Pro
1025              1030            1035            1040

Lys Pro Gln Leu Thr Glu Thr Gln Ser Phe Ser Gln Gln Glu Glu Leu
             1045            1050            1055

Ser Pro Arg Gln Ala Ser Glu Asp Thr Asn Gly Ala Pro Ala Gly Ala
             1060            1065            1070

Leu Glu Met Pro Val Pro Met Pro Arg Lys Ile Asn Thr Val Ala Lys
             1075            1080            1085

Asn Lys Ala Lys Arg Val Lys Ser Thr Ile Tyr Asp Cys Gln Ala Asp Asn
             1090            1095            1100

Asp Asp Glu Leu Thr Phe Val Glu Gly Glu Val Ile Ile Val Thr Gly
1105              1110            1115            1120

Glu Glu Asp Gln Glu Trp Trp Ile Gly His Ile Glu Gly Gln Pro Glu
             1125            1130            1135

Arg Lys Gly Val Phe Pro Met Ser Phe Val His Ile Leu Ser Asp
         1140             1145            1150

<210> SEQ ID NO 5
<211> LENGTH: 3456
<212> TYPE: DNA
<213> ORGANISM: Danio rerio

<400> SEQUENCE: 5

| | | |
|---|---|---|
|atgaggtcct cgtcctcgcg tttgtcaagt ttttcctcca gggattcatt atggagtcgg|  60|
|atgccggatc agatctccgt gtccgagttt ctctcggaga cgacggagga ttacaattcc| 120|
|cccacgacct cgagcttcac cacccgcctg cagagctgcc ggaacacggt caatgttctg| 180|
|gaagaggctt tggatcagga ccgaactgct ttacagaagg tcaagaaatc tgtcaaagca| 240|
|atctacaact cgggtcaaga acatgtgcag aatgaagaga attatggaca ggcactggac| 300|
|aagtttggca gcaacttcat cagccgagat aactctgatc tgggaacagc cttcatcaag| 360|
|ttttctggac ttatcaaaga gctggctgct ctcctcaaga acctgctcca gagcctcagc| 420|
|cacaacgtca tcttcaccct ggactctctg ctcaaaggag atctaaaggg agtgaagggg| 480|
|gaccttaaaa agcctttcga caaggcctgg aaagactatg aaaccaagtt cacaaagatc| 540|

```
gagaaggaga agagagaaca tgccaagcag cacggcatga tccgcacaga aatcaccggc    600
gcagagattg cagaagagat ggagaaggag cggaggatct ttcagctgca gatgtgtgag    660
tacctgatca aagtcaatga gattaagacc aagaagggag tggatctcct ccagaatctc    720
atcaagtatt atcatgcaca gtgcaatttc ttccaggatg gcttgaaaac tgctgacaag    780
ttgaagcagt atattgaaaa attagcagct gatctttata atataaaaca gactcaggat    840
gaggagaaaa aacagctcac agctctcaga gacctcatca aatcttcctt acagctggac    900
cagaaggagg attctcagag taagcagagc gggtacagca tgcaccagct gcagggcaat    960
aaggagtttg gcagtgagaa gaagggctat ctcttcaaga agagtgatgg gatccgtaag   1020
gtgtggcaga ggaggaagtg ctcagtgaaa aatggcatcc tcaccatctc tcatgccaca   1080
tccaacaggc agccggtgag actgaatctg ctgacctgcc aggttaaacc cagtggagag   1140
gataagaagt gctttgacct catctctcat aatcgaacat atcatttcca ggcagaggac   1200
gaacaggagt ttgtgatatg gatctcggtg ctgactaata gtaaggagga ggctctgaac   1260
atggcatttc gtggggagca gagtgctgga gatgacagtt tggaggactt gaccaaagcc   1320
atcatcgagg acgtgctgcg cattcctgga aacgaagtct gctgtgactg tggggttcca   1380
gagcccaaat ggttatccac taacctcggc atcctgacgt gcatcgagtg ttcaggaatc   1440
cacaggaaaa tgggagtcca tatttcgcgc atccaatcca tggagcttga caaacttgga   1500
acctctgaac tcttgctggc taagaacgtg ggcaacagta gtttcaacga atattagaa    1560
gggaatctgc cgagtccttc accaaagcca gcgccatcaa gtgacatgac cgagaggaag   1620
gagtacatca atgcgaagta cgtggagcac aggttcgctc ggcgaacggc cactacagcc   1680
acagccagac agggcgactt gtacgaggcg gtgagaacgc gagacttgat ggctctcatt   1740
cagctctatg cagatggagt ggagctaatg gatcctttcc cagaagcagg acaggacccg   1800
ggagagacag ctctgcactt tgctgttcgg acatcagacc agacttccct gcacctggtg   1860
gactttcttg tccaaaacag tgggactcta gacagacaga cggagagtgg aaacgctgct   1920
ctccattact gctgcacata tgagaagcca gagtgtctca aactgctgct caggggaaaa   1980
ccgtctattg acctggttaa tcaaaacggg gagacagcat ggatatcgc cagacgactg   2040
agaaatgtac agtgtgaaga gctactggtg gaggcagcag ccgggaggtt taatcctcat   2100
gtgcatgtgg agtatgagtg gaatctgcgg ctggaggaga ttgatgagag tgacgatgac   2160
ctggatgaca agcctagtcc agtgaagaag gagcgttctc ctcgtcctca gagcttctgt   2220
cattcgtcca gcgtgtctcc tcaggagaag ttaaccctgc cggggtatct aggacacagg   2280
gacaagcaga gactgtccta tggagccttt gccaaccccg tctacagcac ctccaccgaa   2340
accccctgcat ctccagtgtc agagggaccc accatagcca gcaagacccc tgcaaaagct   2400
ccgtcctgtg ggccgcccac ctctctgccg ctgggatctc aatcgagtgc aggaggcagc   2460
tccactttgt ctaagaagag agctcctcct ccacctcccg acacaagcg cacccactca   2520
gatcccccca gtcccgtact gcagggtccg cagagcaaag gaagtgagtc cacacctcct   2580
tctgcaaatc ggacatcccc ggccaacaag tttgagggaa tccagcagca gcaaagcact   2640
acgtctatga acacaaaagc aacatttggc ccacagagttc ttcccaaact acctcaaaaa   2700
gtggcactac gaaagattga cacaatccac ctcccatcag tggacaagtc tggtcctgat   2760
gtgcttcaga accccccaca ggcccaggat gcacctccca ccagagcctc agatacaata   2820
accagaccca ctgaacctcc acctaaaatt ccacaggtcg cagaacgatc ccagcctgtg   2880
```

-continued

| | |
|---|---:|
| gatgtcccgc agaaaccgca catctcagac cttcctccca aaccgcaact atcagatctt | 2940 |
| cccccaaac cccaattgtc ggatttacca ccaaaacctc agctttctga cctgcccccg | 3000 |
| aagcctcagc ttaaggatct tccccctaag ccgcagatca gtgatctgcc atccaaaccg | 3060 |
| gccgtgtgtt ctgcgtctga ggccacacag aggcagtcaa cgcaggagga aaccagtccg | 3120 |
| aagcccagc tgacggagac acagtcattc agccagcagg aggagctctc accccgacag | 3180 |
| gccagcgagg acaccaatgg agcgcccgca ggagccttgg aaatgccagt cccaatgcca | 3240 |
| cgcaaaatta acacagtagc aaagaacaaa gcgaagcgtg tgaaaaccat ctatgattgc | 3300 |
| caggcagaca atgacgatga gctgactttt gtggagggcg aggttataat tgtcacagga | 3360 |
| gaggaagacc aggagtggtg gatcgggcac atagagggtc agcctgaaag gaaagggtc | 3420 |
| ttcccaatgt ccttcgtgca cattctgtca gactga | 3456 |

<210> SEQ ID NO 6
<211> LENGTH: 5954
<212> TYPE: DNA
<213> ORGANISM: Danio rerio
<220> FEATURE:
<221> NAME/KEY: CDS
<222> LOCATION: (433)...(3378)

<400> SEQUENCE: 6

| | |
|---|---:|
| ggagctcgcg cgcctgcagg tcgacactag tggatccaaa gaattcggca cgaggcaaaa | 60 |
| tccagcacga caacctacac tcctgtccca aaacagaaga aagcacatc accgcactgc | 120 |
| tttattatca aacgagtgga ctaaattcct acttaaactg gaagaagtga gatccgtgaa | 180 |
| agaaagagag ggaaaaagag agagatttcc ccgtcgtaca agccgcactt cagtgtagtt | 240 |
| ggctaatgat ttgtattaat tcccaacttg ttttaatcca ccgaggacaa acaccgcga | 300 |
| tgataagact ccaggacgct catgagagtt ttaattcggc gtttcatctc tgaatttcga | 360 |
| cattaagtgc accgcgaccg gccaaatcaa ggattaaaca cgacatttgt ggatttcgcc | 420 |

| | | |
|---|---|---:|
| aaaggagata ca atg cct gac cag ata aca gtg gcg gag ttt gtc acg gag | | 471 |
| Met Pro Asp Gln Ile Thr Val Ala Glu Phe Val Thr Glu | | |
| 1 5 10 | | |

| | |
|---|---:|
| aca aat gaa gat tat aaa tcg ccc acc gcc tca aac ttc acc acc aga | 519 |
| Thr Asn Glu Asp Tyr Lys Ser Pro Thr Ala Ser Asn Phe Thr Thr Arg | |
| 15 20 25 | |

| | |
|---|---:|
| atg act cac tgc agg aac aca gta tcc gca ctg gag gag gcc ctg gat | 567 |
| Met Thr His Cys Arg Asn Thr Val Ser Ala Leu Glu Glu Ala Leu Asp | |
| 30 35 40 45 | |

| | |
|---|---:|
| gtg gac cgc agt gtc ctt tac aag atg aag aag tca gtt aag gct att | 615 |
| Val Asp Arg Ser Val Leu Tyr Lys Met Lys Lys Ser Val Lys Ala Ile | |
| 50 55 60 | |

| | |
|---|---:|
| tac gcc tcg ggt ctg gct cat gtg gag aat gag gag cag tac act caa | 663 |
| Tyr Ala Ser Gly Leu Ala His Val Glu Asn Glu Glu Gln Tyr Thr Gln | |
| 65 70 75 | |

| | |
|---|---:|
| gct ctg gag aag ttc gga gag aac tgt gtg tac aga gat gac ccg gac | 711 |
| Ala Leu Glu Lys Phe Gly Glu Asn Cys Val Tyr Arg Asp Asp Pro Asp | |
| 80 85 90 | |

| | |
|---|---:|
| ctg gga tca gcc ttc ctg aag ttc tcc gtc ttc acc aag gag ctc acg | 759 |
| Leu Gly Ser Ala Phe Leu Lys Phe Ser Val Phe Thr Lys Glu Leu Thr | |
| 95 100 105 | |

| | |
|---|---:|
| gca ctc ttc aag aac ctg ttt cag aac atg aat aat atc att acc ttc | 807 |
| Ala Leu Phe Lys Asn Leu Phe Gln Asn Met Asn Asn Ile Ile Thr Phe | |
| 110 115 120 125 | |

| | |
|---|---:|
| cca ttg gac agt ctg ctg aag gga gat ctg aaa ggg gtt aaa ggg gat | 855 |
| Pro Leu Asp Ser Leu Leu Lys Gly Asp Leu Lys Gly Val Lys Gly Asp | |

-continued

|  |  |  |  |  |  |  |  |  |  |  |  |  |  |  |  |
|--|--|--|--|--|--|--|--|--|--|--|--|--|--|--|--|
|  |  |  | 130 |  |  |  | 135 |  |  |  | 140 |  |  |  |  |
| ctc | aag | aag | ccc | ttc | gat | aaa | gcc | tgg | aaa | gac | tac | gag | act | aaa | gtc | 903 |
| Leu | Lys | Lys | Pro | Phe | Asp | Lys | Ala | Trp | Lys | Asp | Tyr | Glu | Thr | Lys | Val |  |
|  |  |  | 145 |  |  |  | 150 |  |  |  | 155 |  |  |  |  |
| tct | aaa | ata | gag | aag | gag | aaa | aaa | gag | cac | gcc | cgg | cag | cac | gga | atg | 951 |
| Ser | Lys | Ile | Glu | Lys | Glu | Lys | Lys | Glu | His | Ala | Arg | Gln | His | Gly | Met |  |
|  | 160 |  |  |  |  | 165 |  |  |  |  | 170 |  |  |  |  |
| atc | cgg | acg | gag | atc | agc | gga | gca | gag | ata | gca | gaa | gag | atg | gaa | aaa | 999 |
| Ile | Arg | Thr | Glu | Ile | Ser | Gly | Ala | Glu | Ile | Ala | Glu | Glu | Met | Glu | Lys |  |
|  | 175 |  |  |  |  | 180 |  |  |  |  | 185 |  |  |  |  |
| gag | cgg | cgt | ttc | ttc | cag | ctt | cag | atg | tgt | gag | tac | ctc | ctc | aaa | gtc | 1047 |
| Glu | Arg | Arg | Phe | Phe | Gln | Leu | Gln | Met | Cys | Glu | Tyr | Leu | Leu | Lys | Val |  |
| 190 |  |  |  |  | 195 |  |  |  |  | 200 |  |  |  |  | 205 |
| aat | gaa | atc | aag | atc | aaa | aaa | ggt | gtc | gac | ctg | ctc | cag | aat | ctc | atc | 1095 |
| Asn | Glu | Ile | Lys | Ile | Lys | Lys | Gly | Val | Asp | Leu | Leu | Gln | Asn | Leu | Ile |  |
|  |  |  | 210 |  |  |  | 215 |  |  |  | 220 |  |  |  |  |
| aaa | tac | ttc | cac | gca | cag | tgc | aac | ttc | ttt | cag | gat | ggt | ctc | aaa | gcg | 1143 |
| Lys | Tyr | Phe | His | Ala | Gln | Cys | Asn | Phe | Phe | Gln | Asp | Gly | Leu | Lys | Ala |  |
|  |  | 225 |  |  |  |  | 230 |  |  |  |  | 235 |  |  |  |
| gtg | gac | aac | ctc | aaa | ccc | tca | ata | gaa | aaa | ctg | gcc | aca | gac | ttg | cac | 1191 |
| Val | Asp | Asn | Leu | Lys | Pro | Ser | Ile | Glu | Lys | Leu | Ala | Thr | Asp | Leu | His |  |
|  |  | 240 |  |  |  |  | 245 |  |  |  |  | 250 |  |  |  |
| tcg | atc | aaa | cag | gta | cag | gat | gaa | gaa | cgc | aga | cag | cta | acc | cag | tta | 1239 |
| Ser | Ile | Lys | Gln | Val | Gln | Asp | Glu | Glu | Arg | Arg | Gln | Leu | Thr | Gln | Leu |  |
| 255 |  |  |  |  | 260 |  |  |  |  | 265 |  |  |  |  |  |
| cgg | gat | gtg | cta | aaa | act | gct | ctg | caa | gtg | gag | cag | aag | gag | gac | tct | 1287 |
| Arg | Asp | Val | Leu | Lys | Thr | Ala | Leu | Gln | Val | Glu | Gln | Lys | Glu | Asp | Ser |  |
| 270 |  |  |  |  | 275 |  |  |  |  | 280 |  |  |  |  | 285 |
| cag | gtt | aga | cag | agc | gcc | acc | tac | agt | ctg | cac | cag | ccg | cag | ggc | aac | 1335 |
| Gln | Val | Arg | Gln | Ser | Ala | Thr | Tyr | Ser | Leu | His | Gln | Pro | Gln | Gly | Asn |  |
|  |  |  | 290 |  |  |  |  | 295 |  |  |  |  | 300 |  |  |
| aaa | gag | cat | ggg | act | gag | cgc | agc | ggc | aac | ctt | tac | aag | aag | agt | gac | 1383 |
| Lys | Glu | His | Gly | Thr | Glu | Arg | Ser | Gly | Asn | Leu | Tyr | Lys | Lys | Ser | Asp |  |
|  |  |  | 305 |  |  |  |  | 310 |  |  |  |  | 315 |  |  |
| ggg | ctg | cgg | aaa | gtg | tgg | cag | aag | aga | aag | tgc | aca | gta | aag | aat | gga | 1431 |
| Gly | Leu | Arg | Lys | Val | Trp | Gln | Lys | Arg | Lys | Cys | Thr | Val | Lys | Asn | Gly |  |
|  |  | 320 |  |  |  |  | 325 |  |  |  |  | 330 |  |  |  |
| tat | ttg | acc | atc | tca | cat | ggg | acg | gca | aac | aga | cct | ccc | gcc | aaa | ctc | 1479 |
| Tyr | Leu | Thr | Ile | Ser | His | Gly | Thr | Ala | Asn | Arg | Pro | Pro | Ala | Lys | Leu |  |
|  |  | 335 |  |  |  |  | 340 |  |  |  |  | 345 |  |  |  |
| aat | ctt | ctc | acc | tgt | cag | gtg | aag | cac | aac | cca | gag | gag | aag | aaa | agt | 1527 |
| Asn | Leu | Leu | Thr | Cys | Gln | Val | Lys | His | Asn | Pro | Glu | Glu | Lys | Lys | Ser |  |
| 350 |  |  |  |  | 355 |  |  |  |  | 360 |  |  |  |  | 365 |
| ttt | gac | ctc | atc | tca | cat | gac | aga | aca | tat | cat | ttc | cag | gca | gaa | gat | 1575 |
| Phe | Asp | Leu | Ile | Ser | His | Asp | Arg | Thr | Tyr | His | Phe | Gln | Ala | Glu | Asp |  |
|  |  |  | 370 |  |  |  |  | 375 |  |  |  |  | 380 |  |  |
| gag | cca | gag | tgt | caa | ata | tgg | atc | tca | gtg | ctg | cag | aac | agt | aaa | gaa | 1623 |
| Glu | Pro | Glu | Cys | Gln | Ile | Trp | Ile | Ser | Val | Leu | Gln | Asn | Ser | Lys | Glu |  |
|  |  | 385 |  |  |  |  | 390 |  |  |  |  | 395 |  |  |  |
| gag | gcg | ctc | aac | aac | gcc | ttc | aag | ggc | gac | cag | cat | gtt | ggt | gaa | aat | 1671 |
| Glu | Ala | Leu | Asn | Asn | Ala | Phe | Lys | Gly | Asp | Gln | His | Val | Gly | Glu | Asn |  |
|  |  | 400 |  |  |  |  | 405 |  |  |  |  | 410 |  |  |  |
| aac | att | gtg | cag | gag | ctc | acc | aag | gcc | atc | ctg | gga | gag | gtg | aag | cgg | 1719 |
| Asn | Ile | Val | Gln | Glu | Leu | Thr | Lys | Ala | Ile | Leu | Gly | Glu | Val | Lys | Arg |  |
|  |  | 415 |  |  |  |  | 420 |  |  |  |  | 425 |  |  |  |
| atg | gcg | ggg | aac | gat | gtc | tgc | tgc | gac | tgc | ggt | gct | ccc | ggc | ccc | aca | 1767 |
| Met | Ala | Gly | Asn | Asp | Val | Cys | Cys | Asp | Cys | Gly | Ala | Pro | Gly | Pro | Thr |  |
| 430 |  |  |  |  | 435 |  |  |  |  | 440 |  |  |  |  | 445 |
| tgg | ctc | tcc | acc | aac | ctg | ggc | atc | ctg | acc | tgc | atc | gag | tgt | tcg | ggg | 1815 |

```
                    -continued
Trp Leu Ser Thr Asn Leu Gly Ile Leu Thr Cys Ile Glu Cys Ser Gly
            450                 455                 460 atc cac aga gag ctg ggc gtc cat tac tcc cga atc cag tcc ctc aca   1863
Ile His Arg Glu Leu Gly Val His Tyr Ser Arg Ile Gln Ser Leu Thr
            465                 470                 475 ctc gac gtc ctc agc acc tcc gag ctc ttg ctg gcc aag aac gtg ggg   1911
Leu Asp Val Leu Ser Thr Ser Glu Leu Leu Leu Ala Lys Asn Val Gly
        480                 485                 490 aat gct ggc ttc aat gag atc atg gag gcc tgt ctg acg gca gaa gat   1959
Asn Ala Gly Phe Asn Glu Ile Met Glu Ala Cys Leu Thr Ala Glu Asp
    495                 500                 505 gtg atc aaa ccg aat cca gcc agt gac atg cag gcg agg aag gac ttt   2007
Val Ile Lys Pro Asn Pro Ala Ser Asp Met Gln Ala Arg Lys Asp Phe
510                 515                 520                 525 atc atg gcc aaa tac aca gag aaa cgc ttc gct cgt aag aag tgt cca   2055
Ile Met Ala Lys Tyr Thr Glu Lys Arg Phe Ala Arg Lys Lys Cys Pro
                530                 535                 540 gac gca ctg tcg aag ctg cac acg ctc tgt gat gct gtg aag gcc cgg   2103
Asp Ala Leu Ser Lys Leu His Thr Leu Cys Asp Ala Val Lys Ala Arg
            545                 550                 555 gac att ttc tct ctc atc cag gtc tat gct gaa gga gtg gat ctg atg   2151
Asp Ile Phe Ser Leu Ile Gln Val Tyr Ala Glu Gly Val Asp Leu Met
        560                 565                 570 gag ccc att cct ctg gct aat gga cat gaa caa ggt gag acg gct ctt   2199
Glu Pro Ile Pro Leu Ala Asn Gly His Glu Gln Gly Glu Thr Ala Leu
    575                 580                 585 cat ctg gcc gtg aga ctg gtg gac aga act tcc cta cac atc atc gac   2247
His Leu Ala Val Arg Leu Val Asp Arg Thr Ser Leu His Ile Ile Asp
590                 595                 600                 605 ttc ctc acc caa aac agt tta aac ctg gat aag caa acg gct aaa gga   2295
Phe Leu Thr Gln Asn Ser Leu Asn Leu Asp Lys Gln Thr Ala Lys Gly
                610                 615                 620 agc aca gct ctg cat tac tgc tgc ctg acg gac aac agc gag tgt ctc   2343
Ser Thr Ala Leu His Tyr Cys Cys Leu Thr Asp Asn Ser Glu Cys Leu
            625                 630                 635 aaa ctg ctg ctc aga gga aaa gcc tcc ata gat atc gct aat gaa gct   2391
Lys Leu Leu Leu Arg Gly Lys Ala Ser Ile Asp Ile Ala Asn Glu Ala
        640                 645                 650 gga gag acc ccg ttg gac atc gcc agg cga ctc aaa cat ctg cag tgt   2439
Gly Glu Thr Pro Leu Asp Ile Ala Arg Arg Leu Lys His Leu Gln Cys
    655                 660                 665 gag gaa ctg ctg aac cag gct ctt gca ggg aag ttc aat gct cat gtg   2487
Glu Glu Leu Leu Asn Gln Ala Leu Ala Gly Lys Phe Asn Ala His Val
670                 675                 680                 685 cat gtg gag tat gag tgg aga ctt cag cat gaa gac ctg gac gag agt   2535
His Val Glu Tyr Glu Trp Arg Leu Gln His Glu Asp Leu Asp Glu Ser
                690                 695                 700 gat gaa gat ctg gat gag aag tcg agt cct cac cgg cgg gat gag cgg   2583
Asp Glu Asp Leu Asp Glu Lys Ser Ser Pro His Arg Arg Asp Glu Arg
            705                 710                 715 ccc atc agc tgc tac aca ccg ggc agt aac tcc ctt cag ctg agt cca   2631
Pro Ile Ser Cys Tyr Thr Pro Gly Ser Asn Ser Leu Gln Leu Ser Pro
        720                 725                 730 gcc agc ctg agc cga gac ggt cga gac ctg gtt aaa gac aag caa cgc   2679
Ala Ser Leu Ser Arg Asp Gly Arg Asp Leu Val Lys Asp Lys Gln Arg
    735                 740                 745 ttt gtg cca aac ctg gtc aac aat gaa acc tac ggg acc atc att aac   2727
Phe Val Pro Asn Leu Val Asn Asn Glu Thr Tyr Gly Thr Ile Ile Asn
750                 755                 760                 765
```

-continued

| | |
|---|---|
| acc agc tca ccc gtc agc ctg tcc tct tct gct cca cct cta cca ccc<br>Thr Ser Ser Pro Val Ser Leu Ser Ser Ser Ala Pro Pro Leu Pro Pro<br>               770                    775                 780 | 2775 |
| cga aac cta gtt cag ccg tct gct ctt gca gga ctg act caa gga tct<br>Arg Asn Leu Val Gln Pro Ser Ala Leu Ala Gly Leu Thr Gln Gly Ser<br>             785                   790                 795 | 2823 |
| ccc ggc tgg aag cct ggc tct ctg gat ctg agc ggc aga cag aga tcc<br>Pro Gly Trp Lys Pro Gly Ser Leu Asp Leu Ser Gly Arg Gln Arg Ser<br>          800                   805                 810 | 2871 |
| tcc tct gac cct ccc aac atg cat cct cct gcg cct ccc tta cgg gtc<br>Ser Ser Asp Pro Pro Asn Met His Pro Pro Ala Pro Pro Leu Arg Val<br>815                   820                 825 | 2919 |
| act tcc acc tcc ctt cta atg ccc agc ggt gct gct cct cct ctg gct<br>Thr Ser Thr Ser Leu Leu Met Pro Ser Gly Ala Ala Pro Pro Leu Ala<br>830                   835                 840                 845 | 2967 |
| aaa gct act ggt atg atg gag acc atg aat atg caa ccc aaa ccc gga<br>Lys Ala Thr Gly Met Met Glu Thr Met Asn Met Gln Pro Lys Pro Gly<br>                 850                   855                 860 | 3015 |
| cag ggg cct cct gga cag aac atc aac cgg gct aca agt gcg gac aaa<br>Gln Gly Pro Pro Gly Gln Asn Ile Asn Arg Ala Thr Ser Ala Asp Lys<br>          865                   870                 875 | 3063 |
| aac ttc agc aaa agc aca ctg atg cgc tcc gga tcc atc gag aga cca<br>Asn Phe Ser Lys Ser Thr Leu Met Arg Ser Gly Ser Ile Glu Arg Pro<br>             880                   885                 890 | 3111 |
| gct aaa gaa gtc cca gga ggc cca caa aac acc act ggt caa act ctg<br>Ala Lys Glu Val Pro Gly Gly Pro Gln Asn Thr Thr Gly Gln Thr Leu<br>895                   900                 905 | 3159 |
| cct gcg acc cac atg ccc agg aaa acg tat ttg aag ccg aag cgt gtg<br>Pro Ala Thr His Met Pro Arg Lys Thr Tyr Leu Lys Pro Lys Arg Val<br>910                 915                 920               925 | 3207 |
| aag gcc atg tat aac tgt gtg gcc gat aat cca gac gag ctg acc ttc<br>Lys Ala Met Tyr Asn Cys Val Ala Asp Asn Pro Asp Glu Leu Thr Phe<br>                 930                   935                 940 | 3255 |
| tct gag gga gag ctt atc gtg gtg gat gga gag gag gac cag gag tgg<br>Ser Glu Gly Glu Leu Ile Val Val Asp Gly Glu Glu Asp Gln Glu Trp<br>          945                   950                 955 | 3303 |
| tgg ctg ggc cac att gag gga gag cca atg aga aga gga gcg ttt cct<br>Trp Leu Gly His Ile Glu Gly Glu Pro Met Arg Arg Gly Ala Phe Pro<br>             960                   965                 970 | 3351 |
| gtc acg ttt gta cag ttc att atg gac tgaagctcga gagatcacac<br>Val Thr Phe Val Gln Phe Ile Met Asp<br>          975                   980 | 3398 |
| actgaactga tgacggcact tctctgcctc tgtgtggcct cactaaccac cactatcttc | 3458 |
| atcatcatcg ttgttcttcc ctttatggtg aggcctgtat cttcaccaat cttccacaag | 3518 |
| tcctgcctct ggagaaatca gccttctggg caataaacgc acttttgaac ttaatttatc | 3578 |
| atgaacacaa tgctaatgaa tgtcaccaag atgaaggttt tgtttcagga tcattccacat | 3638 |
| ccttatttct ttagacagat ctgtgaatat agtcttatat gcccacattc cacatctggc | 3698 |
| aaggaaagac ggaagcatag tagtgaaatg acagccttt tggaggactc tgttggataa | 3758 |
| gacggctctg ttaatggtgc taaagcagga atatgctaca ggagctgtct gtcctaggag | 3818 |
| gagcgcactg atgtccccgt tttcacacta cctgccccag tgctgagtgc agaaataggt | 3878 |
| tttctccagc actcgcacat gggaaatctc tgaagtgcac tgtgtgatgg agaaactgac | 3938 |
| agactgaaga gtgcttttgc gctggctgag ggacgtgaag attaaatgaa agtaatcttg | 3998 |
| accctgaagc tgctgggatt ttggagcgtt gtgaatgttc tctggcctcc agggaaagga | 4058 |
| gaggaagagc atccaggagc tttttttctg tataggtatt tataaatcgg agctgttctg | 4118 |

-continued

```
ttttagactc tcgttgattt taacgatctt ccgcagaact tgcttcattg tgcgagcaat    4178
ctgctgaatg atgtcatttc tttttaaaga gacagaccaa accttcaaat aattaattta    4238
ctccaggagt gtcaaagttc ctggagggcc acagccctgc acagtttagt tccaaccctg    4298
ctccaacaca cttacctgca agtttcaaac aagcctgaag aacttaatta gtttgatcag    4358
gtgtttaatc agggttgtgc agagctgcgg ccctccagga actcagtttg acacctgtga    4418
tttactcaat ttacaaaatg tccagagtgc tctatatcag catttcccaa ccctcttctt    4478
gaaggcacac caacagtaca cattttcaac ctcttcctaa gcaaacacgc ctcaatcaac    4538
tcaacagacc attagaagag actctaaaac ctgaagtaaa tgagtcagat aagggagact    4598
cccaaaatat gaactgttgg tgtgcctcca ggaacactgt ttggaaacct tctctatatg    4658
ctcaatttga tgtaatccaa gttgtctgaa gacatacagt aaacttaaat gagtaaatag    4718
atgggtttta gaggaaaact aaacatttat tctcaagtct ttacaaacct tacttcagtg    4778
tttatttgga gcaatgtggg tactaaatgt aggaatctgt tcatatggaa atatatatat    4838
atatatatat atatatatat atatatatat attcaaaaaa ggtaatagtg actttaatcg    4898
taccagttct gcttatttta tatatgaaag atttgcaaca gaaaagtgca aaattgaggt    4958
ggcacaaatg gatttcaata cactgatcca attctctaaa tattgtctta tacaatgaaa    5018
tcctacagga ttgtaatagc aaattaagtt attttctgaa atcattcac tgtcattgtc     5078
aaacaaggtc aaatcatcaa cttcacattt gaatatggat tcagctttgg tttgagtatt    5138
ctggttacag ggtgaacatg tttcatcaat catactgatt aaagcactct tgccattttt    5198
cactaatcat cctctggttc aatggaagaa aaaagtcata cttttggcat gacggtgagc    5258
aaatgacagc atttacattt gtggagggg agtgactgtc tttttaagatg cttttgcaca    5318
gttttaaata gagtctgttt taatttaaac ctttggataa aagcgtctgc taaattaata    5378
aatttaaaca gattacgaag tgtgaatgac agctattttc tactagaccg ttttggtgta    5438
accctgacgg ttgttccctg tagcagtaat aactctcttt ctctctctag cgctctaatt    5498
gtattccaga gaaaatgaaa atctctctca tcacttctcc taatcctttg taaagctcat    5558
ccatcagtga gtgtgtgcag gagtaacaca gcagagcgtt ttctgtcaag agtgtttgat    5618
gtggttgcag agcaacttag cgtctgttat gtaacttta attacagtca tgttagtctt    5678
gattgagctc aggccagtgt gtatacggcc tgcagtgatt gtaaataact gtagactttt    5738
tgctttgtgc atatttaatt gtaaacagag agctaaactg atactgactg atgtgttgac    5798
gtattgttag ataagactgt tacagtacac ttttaactac tcaccccttt accataaaca    5858
ttgttgacgc taatatataa ttcatatatg tacaaataaa gagtacttct agagcggccg    5918
cgggcccatc gattttccac ccgggtgggt accagg                              5954
```

<210> SEQ ID NO 7
<211> LENGTH: 982
<212> TYPE: PRT
<213> ORGANISM: Danio rerio

<400> SEQUENCE: 7

Met Pro Asp Gln Ile Thr Val Ala Glu Phe Val Thr Glu Thr Asn Glu
 1               5                  10                  15

Asp Tyr Lys Ser Pro Thr Ala Ser Asn Phe Thr Thr Arg Met Thr His
             20                  25                  30

Cys Arg Asn Thr Val Ser Ala Leu Glu Glu Ala Leu Asp Val Asp Arg
         35                  40                  45

-continued

```
Ser Val Leu Tyr Lys Met Lys Lys Ser Val Lys Ala Ile Tyr Ala Ser
     50                  55                  60
Gly Leu Ala His Val Glu Asn Glu Gln Tyr Thr Gln Ala Leu Glu
 65                  70                  75                  80
Lys Phe Gly Glu Asn Cys Val Tyr Arg Asp Asp Pro Asp Leu Gly Ser
                     85                  90                  95
Ala Phe Leu Lys Phe Ser Val Phe Thr Lys Glu Leu Thr Ala Leu Phe
                100                 105                 110
Lys Asn Leu Phe Gln Asn Met Asn Asn Ile Ile Thr Phe Pro Leu Asp
                115                 120                 125
Ser Leu Leu Lys Gly Asp Leu Lys Gly Val Lys Gly Asp Leu Lys Lys
    130                 135                 140
Pro Phe Asp Lys Ala Trp Lys Asp Tyr Glu Thr Lys Val Ser Lys Ile
145                 150                 155                 160
Glu Lys Glu Lys Lys Glu His Ala Arg Gln His Gly Met Ile Arg Thr
                165                 170                 175
Glu Ile Ser Gly Ala Glu Ile Ala Glu Glu Met Glu Lys Glu Arg Arg
                180                 185                 190
Phe Phe Gln Leu Gln Met Cys Glu Tyr Leu Leu Lys Val Asn Glu Ile
                195                 200                 205
Lys Ile Lys Lys Gly Val Asp Leu Leu Gln Asn Leu Ile Lys Tyr Phe
        210                 215                 220
His Ala Gln Cys Asn Phe Phe Gln Asp Gly Leu Lys Ala Val Asp Asn
225                 230                 235                 240
Leu Lys Pro Ser Ile Glu Lys Leu Ala Thr Asp Leu His Ser Ile Lys
                245                 250                 255
Gln Val Gln Asp Glu Glu Arg Arg Gln Leu Thr Gln Leu Arg Asp Val
                260                 265                 270
Leu Lys Thr Ala Leu Gln Val Glu Gln Lys Glu Asp Ser Gln Val Arg
        275                 280                 285
Gln Ser Ala Thr Tyr Ser Leu His Gln Pro Gln Gly Asn Lys Glu His
    290                 295                 300
Gly Thr Glu Arg Ser Gly Asn Leu Tyr Lys Lys Ser Asp Gly Leu Arg
305                 310                 315                 320
Lys Val Trp Gln Lys Arg Lys Cys Thr Val Lys Asn Gly Tyr Leu Thr
                325                 330                 335
Ile Ser His Gly Thr Ala Asn Arg Pro Pro Ala Lys Leu Asn Leu Leu
                340                 345                 350
Thr Cys Gln Val Lys His Asn Pro Glu Glu Lys Lys Ser Phe Asp Leu
                355                 360                 365
Ile Ser His Asp Arg Thr Tyr His Phe Gln Ala Glu Asp Glu Pro Glu
        370                 375                 380
Cys Gln Ile Trp Ile Ser Val Leu Gln Asn Ser Lys Glu Glu Ala Leu
385                 390                 395                 400
Asn Asn Ala Phe Lys Gly Asp Gln His Val Gly Glu Asn Asn Ile Val
                405                 410                 415
Gln Glu Leu Thr Lys Ala Ile Leu Gly Glu Val Lys Arg Met Ala Gly
                420                 425                 430
Asn Asp Val Cys Cys Asp Cys Gly Ala Pro Gly Pro Thr Trp Leu Ser
                435                 440                 445
Thr Asn Leu Gly Ile Leu Thr Cys Ile Glu Cys Ser Gly Ile His Arg
    450                 455                 460
```

-continued

```
Glu Leu Gly Val His Tyr Ser Arg Ile Gln Ser Leu Thr Leu Asp Val
465                 470                 475                 480

Leu Ser Thr Ser Glu Leu Leu Ala Lys Asn Val Gly Asn Ala Gly
            485                 490                 495

Phe Asn Glu Ile Met Glu Ala Cys Leu Thr Ala Glu Asp Val Ile Lys
                500                 505                 510

Pro Asn Pro Ala Ser Asp Met Gln Ala Arg Lys Asp Phe Ile Met Ala
            515                 520                 525

Lys Tyr Thr Glu Lys Arg Phe Ala Arg Lys Lys Cys Pro Asp Ala Leu
            530                 535                 540

Ser Lys Leu His Thr Leu Cys Asp Ala Val Lys Ala Arg Asp Ile Phe
545                 550                 555                 560

Ser Leu Ile Gln Val Tyr Ala Glu Gly Val Asp Leu Met Glu Pro Ile
                565                 570                 575

Pro Leu Ala Asn Gly His Glu Gln Gly Glu Thr Ala Leu His Leu Ala
            580                 585                 590

Val Arg Leu Val Asp Arg Thr Ser Leu His Ile Ile Asp Phe Leu Thr
            595                 600                 605

Gln Asn Ser Leu Asn Leu Asp Lys Gln Thr Ala Lys Gly Ser Thr Ala
610                 615                 620

Leu His Tyr Cys Cys Leu Thr Asp Asn Ser Glu Cys Leu Lys Leu Leu
625                 630                 635                 640

Leu Arg Gly Lys Ala Ser Ile Asp Ile Ala Asn Glu Ala Gly Glu Thr
                645                 650                 655

Pro Leu Asp Ile Ala Arg Arg Leu Lys His Leu Gln Cys Glu Glu Leu
            660                 665                 670

Leu Asn Gln Ala Leu Ala Gly Lys Phe Asn Ala His Val His Val Glu
            675                 680                 685

Tyr Glu Trp Arg Leu Gln His Glu Asp Leu Asp Glu Ser Asp Glu Asp
            690                 695                 700

Leu Asp Glu Lys Ser Ser Pro His Arg Arg Asp Glu Arg Pro Ile Ser
705                 710                 715                 720

Cys Tyr Thr Pro Gly Ser Asn Ser Leu Gln Leu Ser Pro Ala Ser Leu
                725                 730                 735

Ser Arg Asp Gly Arg Asp Leu Val Lys Asp Lys Gln Arg Phe Val Pro
            740                 745                 750

Asn Leu Val Asn Asn Glu Thr Tyr Gly Thr Ile Ile Asn Thr Ser Ser
            755                 760                 765

Pro Val Ser Leu Ser Ser Ser Ala Pro Pro Leu Pro Pro Arg Asn Leu
770                 775                 780

Val Gln Pro Ser Ala Leu Ala Gly Leu Thr Gln Gly Ser Pro Gly Trp
785                 790                 795                 800

Lys Pro Gly Ser Leu Asp Leu Ser Gly Arg Gln Arg Ser Ser Ser Asp
            805                 810                 815

Pro Pro Asn Met His Pro Pro Ala Pro Pro Leu Arg Val Thr Ser Thr
            820                 825                 830

Ser Leu Leu Met Pro Ser Gly Ala Ala Pro Pro Leu Ala Lys Ala Thr
            835                 840                 845

Gly Met Met Glu Thr Met Asn Met Gln Pro Lys Pro Gly Gln Gly Pro
            850                 855                 860

Pro Gly Gln Asn Ile Asn Arg Ala Thr Ser Ala Asp Lys Asn Phe Ser
865                 870                 875                 880

Lys Ser Thr Leu Met Arg Ser Gly Ser Ile Glu Arg Pro Ala Lys Glu
```

|  |  | 885 |  |  |  | 890 |  |  |  | 895 |  |
|--|--|--|--|--|--|--|--|--|--|--|--|

Val Pro Gly Gly Pro Gln Asn Thr Thr Gly Gln Thr Leu Pro Ala Thr
              900                    905                    910

His Met Pro Arg Lys Thr Tyr Leu Lys Pro Lys Arg Val Lys Ala Met
         915                    920                    925

Tyr Asn Cys Val Ala Asp Asn Pro Asp Glu Leu Thr Phe Ser Glu Gly
         930                    935                    940

Glu Leu Ile Val Val Asp Gly Glu Asp Gln Glu Trp Trp Leu Gly
945                    950                    955                960

His Ile Glu Gly Glu Pro Met Arg Arg Gly Ala Phe Pro Val Thr Phe
              965                    970                    975

Val Gln Phe Ile Met Asp
         980

<210> SEQ ID NO 8
<211> LENGTH: 2949
<212> TYPE: DNA
<213> ORGANISM: Danio rerio

<400> SEQUENCE: 8

| | | | | |
|--|--|--|--|--|
| atgcctgacc agataacagt ggcggagttt gtcacggaga caaatgaaga ttataaatcg | 60 |
| cccaccgcct caaacttcac caccagaatg actcactgca ggaacacagt atccgcactg | 120 |
| gaggaggccc tggatgtgga ccgcagtgtc ctttacaaga tgaagaagtc agttaaggct | 180 |
| atttacgcct cgggtctggc tcatgtggag aatgaggagc agtacactca agctctggag | 240 |
| aagttcggag agaactgtgt gtacagagat gacccggacc tgggatcagc cttcctgaag | 300 |
| ttctccgtct tcaccaagga gctcacggca ctcttcaaga acctgtttca gaacatgaat | 360 |
| aatatcatta ccttcccatt ggacagtctg ctgaaggagg atctgaaagg ggttaaaggg | 420 |
| gatctcaaga agcccttcga taagcctgg aaagactacg agactaaagt ctctaaaata | 480 |
| gagaaggaga aaaagagca cgcccggcag cacggaatga tccggacgga gatcagcgga | 540 |
| gcagagatag cagaagagat ggaaaaagag cggcgtttct ccagcttca gatgtgtgag | 600 |
| tacctcctca agtcaatga aatcaagatc aaaaaggtg tcgacctgct ccagaatctc | 660 |
| atcaaatact ccacgcaca gtgcaacttc tttcaggatg gtctcaaagc ggtggacaac | 720 |
| ctcaaacct caatagaaaa actggccaca gacttgcact cgatcaaaca ggtacaggat | 780 |
| gaagaacgca gacagctaac ccagttacgg gatgtgctaa aaactgctct gcaagtggag | 840 |
| cagaaggagg actctcaggt tagacagagc gccacctaca gtctgcacca gccgcagggc | 900 |
| aacaaagagc atgggactga gcgcagcggc aaccttaca agaagagtga cgggctgcgg | 960 |
| aaagtgtggc agaagagaaa gtgcacagta agaatggat atttgaccat ctcacatggg | 1020 |
| acggcaaaca gacctcccgc caaactcaat cttctcacct gtcaggtgaa gcacaaccca | 1080 |
| gaggagaaga aagttttga cctcatctca catgacagaa catatcattt ccaggcagaa | 1140 |
| gatgagccag agtgtcaaat atggatctca gtgctgcaga cagtaaaga agaggcgctc | 1200 |
| aacaacgcct tcaagggcga ccagcatgtt ggtgaaaata cattgtgca ggagctcacc | 1260 |
| aaggccatcc tgggagaggt gaagcggatg gcggggaacg atgtctgctg cgactgcggt | 1320 |
| gctcccggcc ccacatggct ctccaccaac ctgggcatcc tgacctgcat cgagtgttcg | 1380 |
| gggatccaca gagagctggg cgtccattac tcccgaatcc agtccctcac actcgacgtc | 1440 |
| ctcagcacct ccgagctctt gctggccaag aacgtgggga tgctggctt caatgagatc | 1500 |
| atggaggcct gtctgacggc agaagatgtg atcaaaccga tccagccag tgacatgcag | 1560 |

-continued

```
gcgaggaagg actttatcat ggccaaatac acagagaaac gcttcgctcg taagaagtgt    1620
ccagacgcac tgtcgaagct gcacacgctc tgtgatgctg tgaaggcccg ggacattttc    1680
tctctcatcc aggtctatgc tgaaggagtg gatctgatgg agcccattcc tctggctaat    1740
ggacatgaac aaggtgagac ggctcttcat ctggccgtga gactggtgga cagaacttcc    1800
ctacacatca tcgacttcct cacccaaaac agtttaaacc tggataagca aacggctaaa    1860
ggaagcacag ctctgcatta ctgctgcctg acggacaaca gcgagtgtct caaactgctg    1920
ctcagaggaa aagcctccat agatatcgct aatgaagctg agagacccc gttggacatc     1980 gccaggcgac tcaaacatct gcagtgtgag gaactgctga accaggctct tgcagggaag    2040
ttcaatgctc atgtgcatgt ggagtatgag tggagacttc agcatgaaga cctggacgag    2100
agtgatgaag atctggatga aagtcgagt cctcaccggc gggatgagcg gcccatcagc     2160
tgctacacac cgggcagtaa ctcccttcag ctgagtccag ccagcctgag ccgagacggt    2220
cgagacctgg ttaaagacaa gcaacgcttt gtgccaaacc tggtcaacaa tgaaacctac    2280
gggaccatca ttaacaccag ctcacccgtc agcctgtcct cttctgctcc acctctacca    2340
ccccgaaacc tagttcagcc gtctgctctt gcaggactga ctcaaggatc tcccggctgg    2400
aagcctggct ctctggatct gagcggcaga cagagatcc cctctgaccc tcccaacatg     2460
catcctcctg cgcctcccct acgggtcact tccacctccc ttctaatgcc cagcggtgct    2520
gctcctcctc tggctaaagc tactggtatg atggagacca tgaatatgca acccaaaccc    2580
ggacaggggc ctcctggaca gaacatcaac cgggctacaa gtgcggacaa aaacttcagc    2640
aaaagcacac tgatgcgctc cggatccatc gagagaccag ctaaagaagt cccaggaggc    2700
ccacaaaaca ccactggtca aactctgcct gcgacccaca tgcccaggaa aacgtatttg    2760
aagccgaagc gtgtgaaggc catgtataac tgtgtggccg ataatccaga cgagctgacc    2820
ttctctgagg gagagcttat cgtggtggat ggagaggagg accaggagtg gtggctgggc    2880
cacattgagg gagagccaat gagaagagga gcgtttcctg tcacgtttgt acagttcatt    2940
atggactga                                                           2949
```

<210> SEQ ID NO 9
<211> LENGTH: 4595
<212> TYPE: DNA
<213> ORGANISM: Danio rerio
<220> FEATURE:
<221> NAME/KEY: CDS
<222> LOCATION: (300)...(3008)

<400> SEQUENCE: 9

```
ggagctcgcg cgcctgcagg tcgacactag tggatccaaa gaattcggca cgagcagaag     60
tgttgatctt gtcagctgct cgtgtgatgg agttgtttaa cgcttgtgtt caaaggcaaa    120
tcctctcctc atcggccgtt tacattttaa cttcacgcgg aaatttaaaa ctgaactaat    180
ctctaaggaa tgactgaaat ggacttgagt tgaagtctgg tttttgagcg cgaagctaca    240
actttaagca aactttcttt cttttttgga tctattgtgt agatttaaaa ggaataatc     299 atg cct gat cag ctg aca gtg act gag ttt gtg gat att acc cat gag    347
Met Pro Asp Gln Leu Thr Val Thr Glu Phe Val Asp Ile Thr His Glu
  1               5                  10                  15 gac tat aaa gca ccg aca aca tca gtg ttc tgc acg cgc atg gct cac    395
Asp Tyr Lys Ala Pro Thr Thr Ser Val Phe Cys Thr Arg Met Ala His
             20                  25                  30 tgc agg aat aca gtc gcc gct ctg gaa gag gcg ctg gat ctg gac cgc    443
```

```
Cys Arg Asn Thr Val Ala Ala Leu Glu Glu Ala Leu Asp Leu Asp Arg
         35                  40                  45 agt gta ctg cac aaa atg aag aag tca gtc aag gcc ata aac agc tct        491
Ser Val Leu His Lys Met Lys Lys Ser Val Lys Ala Ile Asn Ser Ser
 50                  55                  60 ggt cag act cat gta gag aac gag gag cag tac atc cag gcc ata gag        539
Gly Gln Thr His Val Glu Asn Glu Glu Gln Tyr Ile Gln Ala Ile Glu
 65              70                  75                  80 agg ttt acg gat aac act gtg tac aaa gat gac cct gag atg tcc aat        587
Arg Phe Thr Asp Asn Thr Val Tyr Lys Asp Asp Pro Glu Met Ser Asn
                 85                  90                  95 tac ttc ctc aca ttc gct ggt ttc acc aag gag ctt act gct ctt ttc        635
Tyr Phe Leu Thr Phe Ala Gly Phe Thr Lys Glu Leu Thr Ala Leu Phe
                100                 105                 110 aag aac ttg cta cag aac atg aat aac atc atc act ttt cca cta gac        683
Lys Asn Leu Leu Gln Asn Met Asn Asn Ile Ile Thr Phe Pro Leu Asp
            115                 120                 125 agt ctg cta aag gga gac ctc aaa gga gtc aaa ggg gat ttg aaa aag        731
Ser Leu Leu Lys Gly Asp Leu Lys Gly Val Lys Gly Asp Leu Lys Lys
130                 135                 140 cca ttt gat aaa gca tgg aag gat tat gaa acc aaa ctg agc aag att        779
Pro Phe Asp Lys Ala Trp Lys Asp Tyr Glu Thr Lys Leu Ser Lys Ile
145                 150                 155                 160 gag aaa gaa aag cga gaa cat gcc aaa cag cac ggt ctg atc cga aca        827
Glu Lys Glu Lys Arg Glu His Ala Lys Gln His Gly Leu Ile Arg Thr
                165                 170                 175 gag atc agt gga gga gag atc gca gaa gag atg gag aaa gag aga cgc        875
Glu Ile Ser Gly Gly Glu Ile Ala Glu Glu Met Glu Lys Glu Arg Arg
            180                 185                 190 ctg ttt cag ctt cag atg tgt gag tac ctc att aaa gtg aat gaa atc        923
Leu Phe Gln Leu Gln Met Cys Glu Tyr Leu Ile Lys Val Asn Glu Ile
        195                 200                 205 aaa gtc aaa aag ggg gtc gac ctg ctt cac aac ctc atc aaa tac ttt        971
Lys Val Lys Lys Gly Val Asp Leu Leu His Asn Leu Ile Lys Tyr Phe
210                 215                 220 cat gcc cag tgc aat ttc ttt cag gat ggg cta aag gtc gtg gac aat       1019
His Ala Gln Cys Asn Phe Phe Gln Asp Gly Leu Lys Val Val Asp Asn
225                 230                 235                 240 ctg aaa cct ttc atg gaa aag ctt gcc aca gac tta acc gcg aac aaa       1067
Leu Lys Pro Phe Met Glu Lys Leu Ala Thr Asp Leu Thr Ala Asn Lys
                245                 250                 255 cag act caa gat gca gaa agg aaa cag ttg ctg cag ctg aaa gaa act       1115
Gln Thr Gln Asp Ala Glu Arg Lys Gln Leu Leu Gln Leu Lys Glu Thr
            260                 265                 270 ctt aaa tct gct cta cag tct gag tgt aag gag gat gct cag tca aag       1163
Leu Lys Ser Ala Leu Gln Ser Glu Cys Lys Glu Asp Ala Gln Ser Lys
        275                 280                 285 cag aac gca ggc tac agt ctt cac cag ttg cag ggc aat aaa gct cac       1211
Gln Asn Ala Gly Tyr Ser Leu His Gln Leu Gln Gly Asn Lys Ala His
290                 295                 300 ggc acg gag cgc tct ggg atg ctc ctc aaa cgc agc gag gga ctg agg       1259
Gly Thr Glu Arg Ser Gly Met Leu Leu Lys Arg Ser Glu Gly Leu Arg
305                 310                 315                 320 aaa gtt tgg cag aaa agg aag tgc tct gtg aaa aat gga ttg ttg act       1307
Lys Val Trp Gln Lys Arg Lys Cys Ser Val Lys Asn Gly Leu Leu Thr
                325                 330                 335 att tca cat gga acg ccc aat gca ccg cca gca aac ctg aac ctc tta       1355
Ile Ser His Gly Thr Pro Asn Ala Pro Pro Ala Asn Leu Asn Leu Leu
            340                 345                 350
```

```
acc tgc caa gtg aag cgt aac cca gat gag aaa aaa tgc ttt gat ctc      1403
Thr Cys Gln Val Lys Arg Asn Pro Asp Glu Lys Lys Cys Phe Asp Leu
        355                 360                 365 ata tca cat gac aga acg tat cac ttc cag act gag gat gag gca gag      1451
Ile Ser His Asp Arg Thr Tyr His Phe Gln Thr Glu Asp Glu Ala Glu
370                 375                 380 tgt cag gta tgg gtt tct gtt ctc cag aac agt aaa gaa gag gcg ctg      1499
Cys Gln Val Trp Val Ser Val Leu Gln Asn Ser Lys Glu Glu Ala Leu
385                 390                 395                 400 aac aat gcc ttt aaa gac gat cag aat gag gga gaa aat aac att gtt      1547
Asn Asn Ala Phe Lys Asp Asp Gln Asn Glu Gly Glu Asn Asn Ile Val
            405                 410                 415 cga gag ctc act aag gcc atc gtg ggg gaa gtg aag aaa atg agc ggc      1595
Arg Glu Leu Thr Lys Ala Ile Val Gly Glu Val Lys Lys Met Ser Gly
        420                 425                 430 aat gac gtg tgc tgt gac tgt gga gct tcc aat cca aca tgg ctc tcc      1643
Asn Asp Val Cys Cys Asp Cys Gly Ala Ser Asn Pro Thr Trp Leu Ser
                435                 440                 445 aca aac ctg ggt gtg ttg att tgc att gaa tgc tct ggg atc cat cgg      1691
Thr Asn Leu Gly Val Leu Ile Cys Ile Glu Cys Ser Gly Ile His Arg
450                 455                 460 gaa atg ggc gtc cac tac tcc cga ata cag tct ctg aca ctg gac ctc      1739
Glu Met Gly Val His Tyr Ser Arg Ile Gln Ser Leu Thr Leu Asp Leu
465                 470                 475                 480 tta ggc aca tct gaa cta ttg ctt gct aac agt gtg gga aat gca gca      1787
Leu Gly Thr Ser Glu Leu Leu Leu Ala Asn Ser Val Gly Asn Ala Ala
            485                 490                 495 ttc aat gaa atc atg gaa gca aaa ctg tct tca gag atc cca aaa ccc      1835
Phe Asn Glu Ile Met Glu Ala Lys Leu Ser Ser Glu Ile Pro Lys Pro
        500                 505                 510 tac cct tct agt gac atg cag gta cga aaa gac ttc atc aca gcc aaa      1883
Tyr Pro Ser Ser Asp Met Gln Val Arg Lys Asp Phe Ile Thr Ala Lys
            515                 520                 525 tac aca gag aag cgt ttc gct cag aag aag tat gca gat aac gca gct      1931
Tyr Thr Glu Lys Arg Phe Ala Gln Lys Lys Tyr Ala Asp Asn Ala Ala
530                 535                 540 cga ctg cat gca ctg tgt gat gca gtg aag tct cgg gac atc ttc tcc      1979
Arg Leu His Ala Leu Cys Asp Ala Val Lys Ser Arg Asp Ile Phe Ser
545                 550                 555                 560 ctg atc cag gtc tat gct gaa gga ctg gac ctg atg gag acc att aat      2027
Leu Ile Gln Val Tyr Ala Glu Gly Leu Asp Leu Met Glu Thr Ile Asn
            565                 570                 575 cag cct aac caa cat gaa cca ggc gag aca tca cta cat ctt gcg gta      2075
Gln Pro Asn Gln His Glu Pro Gly Glu Thr Ser Leu His Leu Ala Val
        580                 585                 590 cga atg gtg gac cga aac tcc ctc cat att gtg gac ttt ctt gta cag      2123
Arg Met Val Asp Arg Asn Ser Leu His Ile Val Asp Phe Leu Val Gln
            595                 600                 605 aac agt ggc aat tta gac aag cag aca gcc aaa gga agc aca gcg cta      2171
Asn Ser Gly Asn Leu Asp Lys Gln Thr Ala Lys Gly Ser Thr Ala Leu
610                 615                 620 cat tat tgc tgc ttg act gat aac agt gaa tgt atg aag ctg ctg ctg      2219
His Tyr Cys Cys Leu Thr Asp Asn Ser Glu Cys Met Lys Leu Leu Leu
625                 630                 635                 640 cgg ggg aaa gca tct gtc agc att act aat gat gct gga gag act gct      2267
Arg Gly Lys Ala Ser Val Ser Ile Thr Asn Asp Ala Gly Glu Thr Ala
            645                 650                 655 ctg gat ttg gcg cag cgt ctc aaa cac tcc aaa tgc gag gag ctg ctg      2315
Leu Asp Leu Ala Gln Arg Leu Lys His Ser Lys Cys Glu Glu Leu Leu
        660                 665                 670
```

```
act cag gcg cag acg ggg aag ttc aat gtc cat gtg cat gtg gaa tat      2363
Thr Gln Ala Gln Thr Gly Lys Phe Asn Val His Val His Val Glu Tyr
            675                 680                 685 gac tgg cgt ctg cat aat gag gat ctg gac gag agc gaa gat gag atg      2411
Asp Trp Arg Leu His Asn Glu Asp Leu Asp Glu Ser Glu Asp Glu Met
    690                 695                 700 gag gac aag ccc att ccc atc agg cgt gag gag cgt cca ata agc tgt      2459
Glu Asp Lys Pro Ile Pro Ile Arg Arg Glu Glu Arg Pro Ile Ser Cys
705                 710                 715                 720 ata gtt cca ggc agt ggc ccc atg atg ccc aac atg agc gct ctg gct      2507
Ile Val Pro Gly Ser Gly Pro Met Met Pro Asn Met Ser Ala Leu Ala
                725                 730                 735 cgg gac gtg gcc aat gtg gtc aat aat aag cag agg gct ttt att ccg      2555
Arg Asp Val Ala Asn Val Val Asn Asn Lys Gln Arg Ala Phe Ile Pro
            740                 745                 750 agc atg atg atg aac gag act tac ggc acc atg ctc gat ccc aac tct      2603
Ser Met Met Met Asn Glu Thr Tyr Gly Thr Met Leu Asp Pro Asn Ser
        755                 760                 765 cca cca ctg ggt tta cca gga gta cct ggc att cct ctt tta ccc cct      2651
Pro Pro Leu Gly Leu Pro Gly Val Pro Gly Ile Pro Leu Leu Pro Pro
770                 775                 780 cgg ccc ttg gga agg gga tgg agt cca cca atg gag aac atc ggt aga      2699
Arg Pro Leu Gly Arg Gly Trp Ser Pro Pro Met Glu Asn Ile Gly Arg
785                 790                 795                 800 cag agg tca tgt tca gat cct gca aac cct caa act cct gaa caa aat      2747
Gln Arg Ser Cys Ser Asp Pro Ala Asn Pro Gln Thr Pro Glu Gln Asn
                805                 810                 815 aac tct gtg tat gtt ctg cct cct gct cct cca cct cct cct gca ccc      2795
Asn Ser Val Tyr Val Leu Pro Pro Ala Pro Pro Pro Pro Pro Ala Pro
            820                 825                 830 aag aga cct cca cct cca gat cca aag gcc agt ctt ctt cct cca gca      2843
Lys Arg Pro Pro Pro Pro Asp Pro Lys Ala Ser Leu Leu Pro Pro Ala
        835                 840                 845 gcc acg gct cct cct gca cca tcc gca ccg ctc ctt att cca cct gct      2891
Ala Thr Ala Pro Pro Ala Pro Ser Ala Pro Leu Leu Ile Pro Pro Ala
850                 855                 860 cct ctc agg cca gcg cct gta gtg ccc cct gca cca gtt atg ccc act      2939
Pro Leu Arg Pro Ala Pro Val Val Pro Pro Ala Pro Val Met Pro Thr
865                 870                 875                 880 tcg tca ctg act gat gtc aaa agt ctg ctg tct aaa gcc cag ctc aca      2987
Ser Ser Leu Thr Asp Val Lys Ser Leu Leu Ser Lys Ala Gln Leu Thr
                885                 890                 895 ttg tgc gat ttc gaa tac tac taaatgattg tagcatcaga gtgcacaagt         3038
Leu Cys Asp Phe Glu Tyr Tyr
                900 atgatccgca tgtgtccctc agttttcata atgtcagatt gaaccacagt taagatgcac   3098 caaacatgga cacgcaagaa aactcaccct ggagtttggc atcatccatc tgtgacacct   3158 tcactctact gcatcctgac atgaaacctc acggtaaaca taaacaaact gtagcaacac   3218 ttttacttac aacacgtctc agtgataacc ggaaaaggca gtggtttgaa agtgtcgttc   3278 tgattgcgtc atcagatata ccgctcctat tgattcttgg ttagacgctc gtcttaactg   3338 aattcacact tcagccaaga gtctgaacgc ccgacaccac cagaacttct tcatcagagg   3398 gaaaatctga tcgtagaggc catcaatcaa ggaatcaaaa actacagatt ttaggctagg   3458 attactggaa tcttttagga ttttccatat tagtctcaga tggccaaatc atctctgaaa   3518 ttgcacagtg tgagcagggc ttaaatcaga tcaccaaaact attgttgaga cctaacacca   3578
```

```
ctgaatattt aacaatcaat acacccctca gccatccgtg tggctaattg gtggtgtacg    3638
agacattcac aagcattaag acctcaggaa gtgttacttt gattactttg attctaagtg    3698
caattacctc tacctttaat acggaaatcg tttatgaact gtgatgagtg atatgcatta    3758
tacggggacg gtttggtttt attaagcgag atgtggttgg atgagctttt tgtgttttc     3818
agacagcagt ggcagagtga ctcctatttg gcaagtgttt aaaggcacaa tatgtaatat    3878
tcaccacaag ggggcacata ttcacaacaa acaaatggtt atgtctgtta gggtgctgca    3938
ctttgcagtg taataaaacg cacaacattt taaagcgtct ttggagtttt ctgttttct     3998
agaaaaccaa actagaaatc gaaggtgatg agcaactgga aaatgcaggt gtatgatgtc    4058
ataagcatgg agacactagt taaataact tatatctctg gatttgaaca ttcttcctaa     4118
cctttgggat aatgcaagta ctcaagccaa aatatatcac actgttttag tgattttagg    4178
atatttgaaa gaaataatc gtacatattg tgcctttaag taacatgatg aaccaggtag     4238
gttgcttctc aagatttgtt accagacaag ccattaaact tactctgctt cattttcagc    4298
cttaatatt ttttttaca aaatgttata gtggcttaga aaacgtttt tagtaacatt       4358
catgatttt gtggaaacca gattgaatag aaagaagtat ggaatttatt ttaaataata    4418
tattacatga ctgtaatatt cttaatgtgt gtactgtcat ttttcatcag tgtaatgcat    4478
ccttgctcaa taaaaacatg tattttttt ttaaaaaaaa aaaaaaaaa aaaactcgag      4538
agtacttcta gagcggccgc gggcccatcg attttccacc cgggtggggt accaggt       4595
```

<210> SEQ ID NO 10
<211> LENGTH: 903
<212> TYPE: PRT
<213> ORGANISM: Danio rerio

<400> SEQUENCE: 10

```
Met Pro Asp Gln Leu Thr Val Thr Glu Phe Val Asp Ile Thr His Glu
  1               5                  10                  15

Asp Tyr Lys Ala Pro Thr Thr Ser Val Phe Cys Thr Arg Met Ala His
             20                  25                  30

Cys Arg Asn Thr Val Ala Ala Leu Glu Glu Ala Leu Asp Leu Asp Arg
         35                  40                  45

Ser Val Leu His Lys Met Lys Ser Val Lys Ala Ile Asn Ser Ser
     50                  55                  60

Gly Gln Thr His Val Glu Asn Glu Glu Gln Tyr Ile Gln Ala Ile Glu
 65                  70                  75                  80

Arg Phe Thr Asp Asn Thr Val Tyr Lys Asp Asp Pro Glu Met Ser Asn
                 85                  90                  95

Tyr Phe Leu Thr Phe Ala Gly Phe Thr Lys Glu Leu Thr Ala Leu Phe
            100                 105                 110

Lys Asn Leu Leu Gln Asn Met Asn Asn Ile Ile Thr Phe Pro Leu Asp
        115                 120                 125

Ser Leu Leu Lys Gly Asp Leu Lys Gly Val Lys Gly Asp Leu Lys Lys
    130                 135                 140

Pro Phe Asp Lys Ala Trp Lys Asp Tyr Glu Thr Lys Leu Ser Lys Ile
145                 150                 155                 160

Glu Lys Glu Lys Arg Glu His Ala Lys Gln His Gly Leu Ile Arg Thr
                165                 170                 175

Glu Ile Ser Gly Gly Glu Ile Ala Glu Glu Met Glu Lys Glu Arg Arg
            180                 185                 190

Leu Phe Gln Leu Gln Met Cys Glu Tyr Leu Ile Lys Val Asn Glu Ile
```

-continued

```
                195                 200                 205
Lys Val Lys Gly Val Asp Leu Leu His Asn Leu Ile Lys Tyr Phe
    210                 215                 220

His Ala Gln Cys Asn Phe Gln Asp Gly Leu Lys Val Val Asp Asn
225                 230                 235                 240

Leu Lys Pro Phe Met Glu Lys Leu Ala Thr Asp Leu Thr Ala Asn Lys
                245                 250                 255

Gln Thr Gln Asp Ala Glu Arg Lys Gln Leu Leu Gln Leu Lys Glu Thr
            260                 265                 270

Leu Lys Ser Ala Leu Gln Ser Glu Cys Lys Glu Asp Ala Gln Ser Lys
            275                 280                 285

Gln Asn Ala Gly Tyr Ser Leu His Gln Leu Gln Gly Asn Lys Ala His
    290                 295                 300

Gly Thr Glu Arg Ser Gly Met Leu Leu Lys Arg Ser Glu Gly Leu Arg
305                 310                 315                 320

Lys Val Trp Gln Lys Arg Lys Cys Ser Val Lys Asn Gly Leu Leu Thr
                325                 330                 335

Ile Ser His Gly Thr Pro Asn Ala Pro Ala Asn Leu Asn Leu Leu
            340                 345                 350

Thr Cys Gln Val Lys Arg Asn Pro Asp Glu Lys Lys Cys Phe Asp Leu
            355                 360                 365

Ile Ser His Asp Arg Thr Tyr His Phe Gln Thr Glu Asp Ala Glu
    370                 375                 380

Cys Gln Val Trp Val Ser Val Leu Gln Asn Ser Lys Glu Glu Ala Leu
385                 390                 395                 400

Asn Asn Ala Phe Lys Asp Asp Gln Asn Glu Gly Glu Asn Asn Ile Val
                405                 410                 415

Arg Glu Leu Thr Lys Ala Ile Val Gly Glu Val Lys Lys Met Ser Gly
            420                 425                 430

Asn Asp Val Cys Cys Asp Cys Gly Ala Ser Asn Pro Thr Trp Leu Ser
            435                 440                 445

Thr Asn Leu Gly Val Leu Ile Cys Ile Glu Cys Ser Gly Ile His Arg
    450                 455                 460

Glu Met Gly Val His Tyr Ser Arg Ile Gln Ser Leu Thr Leu Asp Leu
465                 470                 475                 480

Leu Gly Thr Ser Glu Leu Leu Leu Ala Asn Ser Val Gly Asn Ala Ala
                485                 490                 495

Phe Asn Glu Ile Met Glu Ala Lys Leu Ser Ser Glu Ile Pro Lys Pro
            500                 505                 510

Tyr Pro Ser Ser Asp Met Gln Val Arg Lys Asp Phe Ile Thr Ala Lys
            515                 520                 525

Tyr Thr Glu Lys Arg Phe Ala Gln Lys Lys Tyr Ala Asp Asn Ala Ala
    530                 535                 540

Arg Leu His Ala Leu Cys Asp Ala Val Lys Ser Arg Asp Ile Phe Ser
545                 550                 555                 560

Leu Ile Gln Val Tyr Ala Glu Gly Leu Asp Leu Met Glu Thr Ile Asn
                565                 570                 575

Gln Pro Asn Gln His Glu Pro Gly Glu Thr Ser Leu His Leu Ala Val
            580                 585                 590

Arg Met Val Asp Arg Asn Ser Leu His Ile Val Asp Phe Leu Val Gln
            595                 600                 605

Asn Ser Gly Asn Leu Asp Lys Gln Thr Ala Lys Gly Ser Thr Ala Leu
    610                 615                 620
```

```
His Tyr Cys Cys Leu Thr Asp Asn Ser Glu Cys Met Lys Leu Leu Leu
625                 630                 635                 640

Arg Gly Lys Ala Ser Val Ser Ile Thr Asn Asp Ala Gly Glu Thr Ala
            645                 650                 655

Leu Asp Leu Ala Gln Arg Leu Lys His Ser Lys Cys Glu Glu Leu Leu
        660                 665                 670

Thr Gln Ala Gln Thr Gly Lys Phe Asn Val His Val His Val Glu Tyr
    675                 680                 685

Asp Trp Arg Leu His Asn Glu Asp Leu Asp Ser Glu Asp Glu Met
690                 695                 700

Glu Asp Lys Pro Ile Pro Ile Arg Arg Glu Arg Pro Ile Ser Cys
705                 710                 715                 720

Ile Val Pro Gly Ser Gly Pro Met Met Pro Asn Met Ser Ala Leu Ala
                725                 730                 735

Arg Asp Val Ala Asn Val Val Asn Asn Lys Gln Arg Ala Phe Ile Pro
            740                 745                 750

Ser Met Met Met Asn Glu Thr Tyr Gly Thr Met Leu Asp Pro Asn Ser
        755                 760                 765

Pro Pro Leu Gly Leu Pro Gly Val Pro Gly Ile Pro Leu Leu Pro Pro
770                 775                 780

Arg Pro Leu Gly Arg Gly Trp Ser Pro Pro Met Glu Asn Ile Gly Arg
785                 790                 795                 800

Gln Arg Ser Cys Ser Asp Pro Ala Asn Pro Gln Thr Pro Glu Gln Asn
                805                 810                 815

Asn Ser Val Tyr Val Leu Pro Ala Pro Pro Pro Pro Ala Pro
            820                 825                 830

Lys Arg Pro Pro Pro Asp Pro Lys Ala Ser Leu Leu Pro Pro Ala
            835                 840                 845

Ala Thr Ala Pro Pro Ala Pro Ser Ala Pro Leu Leu Ile Pro Pro Ala
850                 855                 860

Pro Leu Arg Pro Ala Pro Val Val Pro Pro Ala Pro Val Met Pro Thr
865                 870                 875                 880

Ser Ser Leu Thr Asp Val Lys Ser Leu Leu Ser Lys Ala Gln Leu Thr
            885                 890                 895

Leu Cys Asp Phe Glu Tyr Tyr
            900

<210> SEQ ID NO 11
<211> LENGTH: 2712
<212> TYPE: DNA
<213> ORGANISM: Danio rerio

<400> SEQUENCE: 11
atgcctgatc agctgacagt gactgagttt gtggatatta cccatgagga ctataaagca    60
ccgacaacat cagtgttctg cacgcgcatg gctcactgca ggaatacagt cgccgctctg   120
gaagaggcgc tggatctgga ccgcagtgta ctgcacaaaa tgaagaagtc agtcaaggcc   180
ataaacagct ctggtcagac tcatgtagag aacgaggagc agtacatcca ggccatagag   240
aggtttacgg ataacactgt gtacaaagat gaccctgaga tgtccaatta cttcctcaca   300
ttcgctggtt tcaccaagga gcttactgct cttttcaaga acttgctaca gaacatgaat   360
aacatcatca cttttccact agacagtctg ctaaagggag acctcaaagg agtcaaaggg   420
gatttgaaaa agccatttga taaagcatgg aaggattatg aaaccaaact gagcaagatt   480
```

-continued

```
gagaaagaaa agcgagaaca tgccaaacag cacggtctga tccgaacaga gatcagtgga    540
ggagagatcg cagaagagat ggagaaagag agacgcctgt ttcagcttca gatgtgtgag    600
tacctcatta aagtgaatga aatcaaagtc aaaaagggg tcgacctgct tcacaacctc    660
atcaaatact ttcatgccca gtgcaattc tttcaggatg ggctaaaggt cgtggacaat    720
ctgaaacctt tcatggaaaa gcttgccaca gacttaaccg cgaacaaaca gactcaagat    780
gcagaaagga aacagttgct gcagctgaaa gaaactctta aatctgctct acagtctgag    840
tgtaaggagg atgctcagtc aaagcagaac gcaggctaca gtcttcacca gttgcagggc    900
aataaagctc acggcacgga gcgctctggg atgctcctca aacgcagcga gggactgagg    960
aaagtttggc agaaaaggaa gtgctctgtg aaaaatggat tgttgactat ttcacatgga   1020
acgcccaatg caccgccagc aaacctgaac ctcttaacct gccaagtgaa gcgtaaccca   1080
gatgagaaaa aatgctttga tctcatatca catgacagaa cgtatcactt ccagactgag   1140
gatgaggcag agtgtcaggt atgggtttct gttctccaga acagtaaaga agaggcgctg   1200
aacaatgcct ttaaagacga tcagaatgag ggagaaaata acattgttcg agagctcact   1260
aaggccatcg tgggggaagt gaagaaaatg agcggcaatg acgtgtgctg tgactgtgga   1320
gcttccaatc caacatggct ctccacaaac ctgggtgtgt tgatttgcat tgaatgctct   1380
gggatccatc gggaaatggg cgtccactac tcccgaatac agtctctgac actggacctc   1440
ttaggcacat ctgaactatt gcttgctaac agtgtgggaa atgcagcatt caatgaaatc   1500
atggaagcaa aactgtcttc agagatccca aaacccctacc cttctagtga catgcaggta   1560
cgaaaagact tcatcacagc caaatacaca gagaagcgtt tcgctcagaa gaagtatgca   1620
gataacgcag ctcgactgca tgcactgtgt gatgcagtga agtctcggga catcttctcc   1680
ctgatccagg tctatgctga aggactggac ctgatggaga ccattaatca gcctaaccaa   1740
catgaaccag gcgagacatc actacatctt gcggtacgaa tggtgaccg aaactccctc   1800 catattgtgg actttcttgt acagaacagt ggcaatttag acaagcagac agccaaagga   1860
agcacagcgc tacattattg ctgcttgact gataacagtg aatgtatgaa gctgctgctg   1920
cgggggaaag catctgtcag cattactaat gatgctggag agactgctct ggatttggcg   1980
cagcgtctca aacactccaa atgcgaggag ctgctgactc aggcgcagac ggggaagttc   2040
aatgtccatg tgcatgtgga atatgactgg cgtctgcata atgaggatct ggacgagagc   2100
gaagatgaga tggaggacaa gcccattccc atcaggcgtg aggagcgtcc aataagctgt   2160
atagttccag gcagtggccc catgatgccc aacatgagcg ctctggctcg ggacgtggcc   2220
aatgtggtca ataataagca gagggctttt attccgagca tgatgatgaa cgagacttac   2280
ggcaccatgc tcgatcccaa ctctccacca ctgggtttac caggagtacc tggcattcct   2340 cttttaccccc ctcggccctt gggaagggga tggagtccac caatggagaa catcggtaga   2400
cagaggtcat gttcagatcc tgcaaaccct caaactcctg aacaaaataa ctctgtgtat   2460
gttctgcctc ctgctcctcc acctcctcct gcacccaaga gacctccacc tccagatcca   2520
aaggccagtc ttcttcctcc agcagccacg gctcctcctg caccatccgc accgctcctt   2580
attccacctg ctcctctcag gccagcgcct gtagtgcccc ctgcaccagt tatgcccact   2640
tcgtcactga ctgatgtcaa aagtctgctg tctaaagccc agctcacatt gtgcgatttc   2700
gaatactact aa                                                       2712
```

<210> SEQ ID NO 12
<211> LENGTH: 1006

```
<212> TYPE: PRT
<213> ORGANISM: Homo sapiens

<400> SEQUENCE: 12

Met Pro Asp Gln Ile Ser Val Ser Glu Phe Val Ala Glu Thr His Glu
  1               5                  10                  15

Asp Tyr Lys Ala Pro Thr Ala Ser Ser Phe Thr Thr Arg Thr Ala Gln
             20                  25                  30

Cys Arg Asn Thr Val Ala Ala Ile Glu Glu Ala Leu Asp Val Asp Arg
         35                  40                  45

Met Val Leu Tyr Lys Met Lys Lys Ser Val Lys Ala Ile Asn Ser Ser
 50                  55                  60

Gly Leu Ala His Val Glu Asn Glu Glu Gln Tyr Thr Gln Ala Leu Glu
 65                  70                  75                  80

Lys Phe Gly Gly Asn Cys Val Cys Arg Asp Asp Pro Asp Leu Gly Ser
             85                  90                  95

Ala Phe Leu Lys Phe Ser Val Phe Thr Lys Glu Leu Thr Ala Leu Phe
            100                 105                 110

Lys Asn Leu Ile Gln Asn Met Asn Asn Ile Ile Ser Phe Pro Leu Asp
            115                 120                 125

Ser Leu Leu Lys Gly Asp Leu Lys Gly Val Lys Gly Asp Leu Lys Lys
130                 135                 140

Pro Phe Asp Lys Ala Trp Lys Asp Tyr Glu Thr Lys Ile Thr Lys Ile
145                 150                 155                 160

Glu Lys Glu Lys Lys Glu His Ala Lys Leu His Gly Met Ile Arg Thr
                165                 170                 175

Glu Ile Ser Gly Ala Glu Ile Ala Glu Glu Met Glu Lys Glu Arg Arg
            180                 185                 190

Phe Phe Gln Leu Gln Met Cys Glu Tyr Leu Leu Lys Val Asn Glu Ile
            195                 200                 205

Lys Ile Lys Lys Gly Val Asp Leu Leu Gln Asn Leu Ile Lys Tyr Phe
210                 215                 220

His Ala Gln Cys Asn Phe Phe Gln Asp Gly Leu Lys Ala Val Glu Ser
225                 230                 235                 240

Leu Lys Pro Ser Ile Glu Thr Leu Ser Thr Asp Leu His Thr Ile Lys
                245                 250                 255

Gln Ala Gln Asp Glu Glu Arg Arg Gln Leu Ile Gln Leu Arg Asp Ile
            260                 265                 270

Leu Lys Ser Ala Leu Gln Val Glu Gln Lys Glu Asp Ser Gln Ile Arg
            275                 280                 285

Gln Ser Thr Ala Tyr Ser Leu His Gln Pro Gln Gly Asn Lys Glu His
            290                 295                 300

Gly Thr Glu Arg Asn Gly Ser Leu Tyr Lys Lys Ser Asp Gly Ile Arg
305                 310                 315                 320

Lys Val Trp Gln Lys Arg Lys Cys Ser Val Lys Asn Gly Phe Leu Thr
                325                 330                 335

Ile Ser His Gly Thr Ala Asn Arg Pro Pro Ala Lys Leu Asn Leu Leu
            340                 345                 350

Thr Cys Gln Val Lys Thr Asn Pro Glu Glu Lys Lys Cys Phe Asp Leu
            355                 360                 365

Ile Ser His Asp Arg Thr Tyr His Phe Gln Ala Glu Asp Glu Gln Glu
            370                 375                 380

Cys Gln Ile Trp Met Ser Val Leu Gln Asn Ser Lys Glu Glu Ala Leu
385                 390                 395                 400
```

```
Asn Asn Ala Phe Lys Gly Asp Asp Asn Thr Gly Glu Asn Asn Ile Val
                405                 410                 415
Gln Glu Leu Thr Lys Glu Ile Ile Ser Glu Val Gln Arg Met Thr Gly
            420                 425                 430
Asn Asp Val Cys Cys Asp Cys Gly Ala Pro Asp Pro Thr Trp Leu Ser
        435                 440                 445
Thr Asn Leu Gly Ile Leu Thr Cys Ile Glu Cys Ser Gly Ile His Arg
    450                 455                 460
Glu Leu Gly Val His Tyr Ser Arg Met Gln Ser Leu Thr Leu Asp Val
465                 470                 475                 480
Leu Gly Thr Ser Glu Leu Leu Leu Ala Lys Asn Ile Gly Asn Ala Gly
                485                 490                 495
Phe Asn Glu Ile Met Glu Cys Cys Leu Pro Ala Glu Asp Ser Val Lys
            500                 505                 510
Pro Asn Pro Gly Ser Asp Met Asn Ala Arg Lys Asp Tyr Ile Thr Ala
        515                 520                 525
Lys Tyr Ile Glu Arg Arg Tyr Ala Arg Lys Lys His Ala Asp Asn Ala
    530                 535                 540
Ala Lys Leu His Ser Leu Cys Glu Ala Val Lys Thr Arg Asp Ile Phe
545                 550                 555                 560
Gly Leu Leu Gln Ala Tyr Ala Asp Gly Val Asp Leu Thr Glu Lys Ile
                565                 570                 575
Pro Leu Ala Asn Gly His Glu Pro Asp Glu Thr Ala Leu His Leu Ala
            580                 585                 590
Val Arg Ser Val Asp Arg Thr Ser Leu His Ile Val Asp Phe Leu Val
        595                 600                 605
Gln Asn Ser Gly Asn Leu Asp Lys Gln Thr Gly Lys Gly Ser Thr Ala
    610                 615                 620
Leu His Tyr Cys Cys Leu Thr Asp Asn Ala Glu Cys Leu Lys Leu Leu
625                 630                 635                 640
Leu Arg Gly Lys Ala Ser Ile Glu Ile Ala Asn Glu Ser Gly Glu Thr
                645                 650                 655
Pro Leu Asp Ile Ala Lys Arg Leu Lys His Glu His Cys Glu Glu Leu
            660                 665                 670
Leu Thr Gln Ala Leu Ser Gly Arg Phe Asn Ser His Val His Val Glu
    675                 680                 685
Tyr Glu Trp Arg Leu Leu His Glu Asp Leu Asp Glu Ser Asp Asp Asp
690                 695                 700
Met Asp Glu Lys Leu Gln Pro Ser Pro Asn Arg Arg Glu Asp Arg Pro
705                 710                 715                 720
Ile Ser Phe Tyr Gln Leu Gly Ser Asn Gln Leu Gln Ser Asn Ala Val
                725                 730                 735
Ser Leu Ala Arg Asp Ala Ala Asn Leu Ala Lys Glu Lys Gln Arg Ala
            740                 745                 750
Phe Met Pro Ser Ile Leu Gln Asn Glu Thr Tyr Gly Ala Leu Leu Ser
        755                 760                 765
Gly Ser Pro Pro Ala Gln Pro Ala Ala Pro Ser Thr Thr Ser Ala
    770                 775                 780
Pro Pro Leu Pro Pro Arg Asn Val Gly Lys Val Gln Thr Ala Ser Ser
785                 790                 795                 800
Ala Asn Thr Leu Trp Lys Thr Asn Ser Val Ser Val Asp Gly Gly Ser
                805                 810                 815
```

```
Arg Gln Arg Ser Ser Ser Asp Pro Pro Ala Val His Pro Pro Leu Pro
              820                 825                 830

Pro Leu Arg Val Thr Ser Thr Asn Pro Leu Thr Pro Thr Pro Pro Pro
        835                 840                 845

Pro Val Ala Lys Thr Pro Ser Val Met Glu Ala Leu Ser Gln Pro Ser
    850                 855                 860

Lys Pro Ala Pro Pro Gly Ile Ser Gln Ile Arg Pro Pro Pro Leu Pro
865                 870                 875                 880

Pro Gln Pro Pro Ser Arg Leu Pro Gln Lys Lys Pro Ala Pro Gly Ala
                885                 890                 895

Asp Lys Ser Thr Pro Leu Thr Asn Lys Gly Gln Pro Arg Gly Pro Val
            900                 905                 910

Asp Leu Ser Ala Thr Glu Ala Leu Gly Pro Leu Ser Asn Ala Met Val
            915                 920                 925

Leu Gln Pro Pro Ala Pro Met Pro Arg Lys Ser Gln Ala Thr Lys Leu
            930                 935                 940

Lys Pro Lys Arg Val Lys Ala Leu Tyr Asn Cys Val Ala Asp Asn Pro
945                 950                 955                 960

Asp Glu Leu Thr Phe Ser Glu Gly Asp Val Ile Ile Val Asp Gly Glu
                965                 970                 975

Glu Asp Gln Glu Trp Trp Ile Gly His Ile Asp Gly Asp Pro Gly Arg
            980                 985                 990

Lys Gly Ala Phe Pro Val Ser Phe Val His Phe Ile Ala Asp
            995                 1000                1005

<210> SEQ ID NO 13
<211> LENGTH: 49
<212> TYPE: PRT
<213> ORGANISM: Gallus gallus

<400> SEQUENCE: 13

Ala Leu Tyr Asp Tyr Glu Ser Arg Thr Glu Thr Asp Leu Ser Phe Lys
 1               5                  10                  15

Lys Gly Glu Arg Leu Gln Ile Val Asn Asn Thr Glu Gly Asp Trp Trp
            20                  25                  30

Leu Ala His Leu Ser Thr Thr Gly Gln Thr Gly Tyr Ile Pro Ser Asn
        35                  40                  45

Tyr

<210> SEQ ID NO 14
<211> LENGTH: 49
<212> TYPE: PRT
<213> ORGANISM: Mus musculus

<400> SEQUENCE: 14

Ala Leu Tyr Asp Tyr Glu Ala Arg Thr Gly Asp Asp Leu Thr Phe Thr
 1               5                  10                  15

Lys Gly Glu Lys Phe His Ile Leu Asn Asn Thr Glu Tyr Asp Trp Trp
            20                  25                  30

Glu Ala Arg Ser Leu Ser Ser Gly His Arg Gly Tyr Val Pro Ser Asn
        35                  40                  45

Tyr

<210> SEQ ID NO 15
<211> LENGTH: 49
<212> TYPE: PRT
<213> ORGANISM: Homo sapiens
```

```
<400> SEQUENCE: 15

Ala Leu Tyr Asp Tyr Glu Ala Arg Thr Glu Thr Asp Leu Ser Phe His
 1               5                  10                  15

Lys Gly Glu Lys Phe Gln Ile Leu Asn Ser Ser Glu Gly Asp Trp Trp
             20                  25                  30

Glu Ala Arg Ser Leu Thr Thr Gly Glu Thr Gly Tyr Ile Pro Ser Asn
             35                  40                  45

Tyr

<210> SEQ ID NO 16
<211> LENGTH: 48
<212> TYPE: PRT
<213> ORGANISM: Mus musculus

<400> SEQUENCE: 16

Ala Leu Tyr Asp Phe Val Ala Ser Gly Asp Asn Thr Leu Ser Ile Thr
 1               5                  10                  15

Lys Gly Glu Lys Leu Arg Val Leu Gly Tyr Asn His Asn Gly Glu Trp
             20                  25                  30

Cys Glu Ala Gln Thr Lys Asn Gly Gln Gly Trp Val Pro Ser Asn Tyr
             35                  40                  45

<210> SEQ ID NO 17
<211> LENGTH: 51
<212> TYPE: PRT
<213> ORGANISM: Homo sapiens

<400> SEQUENCE: 17

Ala Leu Tyr Asp Tyr Lys Lys Glu Arg Glu Glu Asp Ile Asp Leu His
 1               5                  10                  15

Leu Gly Asp Ile Leu Thr Val Asn Lys Gly Ser Leu Val Ala Leu Gly
             20                  25                  30

Phe Ser Asp Gly Gln Glu Ala Arg Pro Glu Ile Ile Gly Trp Leu Asn
             35                  40                  45

Gly Asn Tyr
     50

<210> SEQ ID NO 18
<211> LENGTH: 48
<212> TYPE: PRT
<213> ORGANISM: Homo sapiens

<400> SEQUENCE: 18

Ala Lys Tyr Asp Phe Lys Ala Thr Ala Asp Asp Glu Leu Ser Phe Lys
 1               5                  10                  15

Arg Gly Asp Ile Leu Lys Val Leu Asn Glu Glu Cys Asp Gln Asn Trp
             20                  25                  30

Tyr Lys Ala Glu Leu Asn Gly Lys Asp Gly Phe Ile Pro Lys Asn Tyr
             35                  40                  45

<210> SEQ ID NO 19
<211> LENGTH: 9
<212> TYPE: PRT
<213> ORGANISM: Artificial sequence
<220> FEATURE:
<223> OTHER INFORMATION: src SH3 consensus binding sequence

<400> SEQUENCE: 19

Arg Ala Leu Pro Pro Leu Pro Arg Tyr
```

-continued

```
        1               5

<210> SEQ ID NO 20
<211> LENGTH: 9
<212> TYPE: PRT
<213> ORGANISM: Artificial sequence
<220> FEATURE:
<223> OTHER INFORMATION: src SH3 consensus binding sequence

<400> SEQUENCE: 20

Ala Phe Ala Pro Pro Leu Pro Arg Arg
  1               5

<210> SEQ ID NO 21
<211> LENGTH: 16
<212> TYPE: PRT
<213> ORGANISM: Bos sp.

<400> SEQUENCE: 21

Thr Glu Leu Pro Gln Lys Pro Pro Pro Gly Asp Leu Pro Pro Lys Pro
  1               5                  10                  15

<210> SEQ ID NO 22
<211> LENGTH: 16
<212> TYPE: PRT
<213> ORGANISM: Bos sp.

<400> SEQUENCE: 22

Thr Glu Leu Ala Pro Lys Pro Pro Ile Gly Asp Leu Pro Pro Lys Pro
  1               5                  10                  15

<210> SEQ ID NO 23
<211> LENGTH: 37
<212> TYPE: PRT
<213> ORGANISM: Bos sp.

<400> SEQUENCE: 23

Val Asn Pro Ser Leu Asp Ala Pro His Ser Lys Pro Thr Leu Glu Leu
  1               5                  10                  15

Pro Pro Gln Ala Lys Pro Ser Ala Asp Gly Thr Gln Pro Lys Ala Leu
                 20                  25                  30

Leu Glu Gly Leu Gln
                 35

<210> SEQ ID NO 24
<211> LENGTH: 34
<212> TYPE: PRT
<213> ORGANISM: Bos sp.

<400> SEQUENCE: 24

Gly Glu Leu Pro Pro Lys Pro Gln Leu Gly Asp Leu Pro Pro Lys Pro
  1               5                  10                  15

Gln Leu Ala Asp Leu Pro Pro Lys Pro Gln Val Lys Asp Leu Pro Pro
                 20                  25                  30

Lys Pro

<210> SEQ ID NO 25
<211> LENGTH: 34
<212> TYPE: PRT
<213> ORGANISM: Bos sp.

<400> SEQUENCE: 25

Pro Lys Pro Pro Leu Asp Lys Val Gln Pro Lys Pro Pro Leu Asp Ala
```

```
              1               5              10              15
Leu Gln Pro Lys Pro Pro Leu Asp Gly Leu Gln Pro Lys Pro Pro Leu
                    20                  25                  30
Glu Gly

<210> SEQ ID NO 26
<211> LENGTH: 37
<212> TYPE: PRT
<213> ORGANISM: Bos sp.

<400> SEQUENCE: 26

Gln Leu Gly Glu Leu Leu Ala Lys Pro Gln Thr Gly Asp Ala Ser Pro
  1               5                  10                  15

Lys Ala Gln Pro Pro Leu Glu Leu Thr Pro Lys Ser His Pro Ala Asp
                    20                  25                  30

Leu Ser Pro Asn Val
                35

<210> SEQ ID NO 27
<211> LENGTH: 16
<212> TYPE: PRT
<213> ORGANISM: Bos sp.

<400> SEQUENCE: 27

Pro Lys Pro Pro Leu Asp Gly Ile Pro Pro Lys Pro Ala Leu Glu Thr
  1               5                  10                  15

<210> SEQ ID NO 28
<211> LENGTH: 16
<212> TYPE: PRT
<213> ORGANISM: Bos sp.

<400> SEQUENCE: 28

Pro Lys Pro Pro Leu Asp Gly Pro Pro Lys Gln Pro Leu Glu Thr
  1               5                  10                  15

<210> SEQ ID NO 29
<211> LENGTH: 98
<212> TYPE: PRT
<213> ORGANISM: Artificial sequence
<220> FEATURE:
<223> OTHER INFORMATION: consensus sequence
<221> NAME/KEY: VARIANT
<222> LOCATION: 91, 95
<223> OTHER INFORMATION: Xaa = Any Amino Acid

<400> SEQUENCE: 29

Cys Ala Asp Cys Gly Ala Pro Pro Asp Trp Ala Ser Tyr Thr Leu
  1               5                  10                  15

Gly Val Phe Ile Cys Leu Ser Cys Ser Gly Ile His Arg Asn Ile Pro
                    20                  25                  30

Gln Val Ser Lys Val Lys Ser Val Arg Leu Asp Trp Glu Gln Val Glu
                35                  40                  45

Phe Met Ser Gly Asn Ala Ala Arg Ala Phe Glu Ser Val Asp Pro Phe
        50                  55                  60

Tyr Lys Arg Thr Leu Ala Ser Asp Cys Gln Leu Leu Arg Lys Gln Trp
 65                  70                  75                  80

Ile Arg Ala Lys Tyr Glu Arg Gln Glu Phe Xaa His Val Glu Xaa Gln
                    85                  90                  95

Glu Pro
```

```
<210> SEQ ID NO 30
<211> LENGTH: 134
<212> TYPE: PRT
<213> ORGANISM: Bos sp.

<400> SEQUENCE: 30

Lys Ala Ile Ile Glu Asp Val Gln Arg Leu Pro Gly Asn Asp Val Cys
  1               5                  10                  15

Cys Asp Cys Gly Ser Ala Glu Pro Thr Trp Leu Ser Thr Asn Leu Gly
                 20                  25                  30

Ile Leu Thr Cys Ile Glu Cys Ser Gly Ile His Arg Glu Met Gly Val
             35                  40                  45

His Ile Ser Arg Ile Gln Ser Leu Glu Leu Asp Lys Leu Gly Thr Ser
 50                  55                  60

Glu Leu Leu Leu Ala Lys Asn Val Gly Asn Asn Ser Phe Asn Asp Ile
 65                  70                  75                  80

Met Glu Ala Asn Leu Pro Ser Pro Ser Pro Lys Pro Thr Pro Ser Ser
                 85                  90                  95

Asp Met Thr Val Arg Lys Glu Tyr Ile Thr Ala Lys Tyr Val Asp His
                100                 105                 110

Arg Phe Ser Arg Lys Thr Cys Ser Ser Ser Ala Lys Leu Asn Glu
            115                 120                 125

Leu Leu Glu Ala Ile Lys
            130

<210> SEQ ID NO 31
<211> LENGTH: 40
<212> TYPE: PRT
<213> ORGANISM: Homo sapiens

<400> SEQUENCE: 31

Asp Pro Tyr Val Lys Ile His Leu Met Gln Asn Gly Lys Arg Leu Lys
  1               5                  10                  15

Lys Lys Lys Thr Thr Val Lys Lys Lys Thr Leu Asn Pro Tyr Phe Asn
                 20                  25                  30

Glu Ser Phe Ser Phe Glu Ile Pro
            35                  40

<210> SEQ ID NO 32
<211> LENGTH: 108
<212> TYPE: PRT
<213> ORGANISM: Homo sapiens

<400> SEQUENCE: 32

His Cys Ala Asp Cys Gly Ala Pro Asp Pro Asp Trp Ala Ser Tyr Thr
  1               5                  10                  15

Leu Gly Val Phe Ile Cys Leu Ser Cys Ser Gly Ile His Arg Asn Ile
                 20                  25                  30

Pro Gln Val Ser Lys Val Lys Ser Val Arg Leu Asp Thr Trp Glu Glu
             35                  40                  45

Pro Gln Val Glu Phe Met Ala Ser Arg Gly Asn Ser Ala Ala Arg Ala
 50                  55                  60

Val Phe Glu Ser Arg Val Pro Pro Phe Tyr Arg Pro Ser Ala Ser
 65                  70                  75                  80

Asp Cys Gln Leu Leu Arg Glu Gln Trp Ile Arg Ala Lys Tyr Glu Arg
                 85                  90                  95

Gln Glu Phe Thr His Pro Glu Arg Gln Glu Pro Tyr
            100                 105
```

<210> SEQ ID NO 33
<211> LENGTH: 38
<212> TYPE: PRT
<213> ORGANISM: Homo sapiens

<400> SEQUENCE: 33

Asp Pro Tyr Ala Thr Val Thr Leu Ala Gly Pro Phe Arg Ser Glu Ala
1               5                   10                  15

Lys Lys Thr Lys Val Lys Arg Lys Thr Asn Asn Pro Gln Phe Asp Asp
            20                  25                  30

Val Phe Tyr Phe Glu Val
        35

<210> SEQ ID NO 34
<211> LENGTH: 106
<212> TYPE: PRT
<213> ORGANISM: Homo sapiens

<400> SEQUENCE: 34

Cys Ala Asp Cys Gly Ala Pro Asp Pro Asp Trp Ala Ser Tyr Thr Leu
1               5                   10                  15

Gly Val Phe Ile Cys Leu Ser Cys Ser Gly Ile His Arg Asn Ile Pro
            20                  25                  30

Gln Val Ser Lys Val Lys Ser Val Arg Leu Asp Ala Trp Asp Glu Thr
        35                  40                  45

Gln Val Glu Phe Met Thr Ser His Gly Asn Glu Ala Ala Arg Ala Thr
    50                  55                  60

Phe Glu Ser Lys Val Pro Pro Phe Tyr Arg Pro Thr Phe Ser Asp
65                  70                  75                  80

Cys Gln Leu Leu Arg Glu Gln Trp Ile Arg Ala Lys Tyr Glu Arg Gln
                85                  90                  95

Glu Phe Leu His Val Glu Lys Gln Glu Pro
            100                 105

<210> SEQ ID NO 35
<211> LENGTH: 109
<212> TYPE: PRT
<213> ORGANISM: Artificial sequence
<220> FEATURE:
<223> OTHER INFORMATION: consensus sequence
<221> NAME/KEY: VARIANT
<222> LOCATION: 1, 45, 47, 49, 55, 57, 60, 65, 69, 72, 79, 80, 101, 103,
      105, 109
<223> OTHER INFORMATION: Xaa = Any Amino Acid

<400> SEQUENCE: 35

Xaa Cys Ala Asp Cys Gly Ala Pro Asp Pro Asp Trp Ala Ser Tyr Thr
1               5                   10                  15

Leu Gly Val Phe Ile Cys Leu Ser Cys Ser Gly Ile His Arg Asn Ile
            20                  25                  30

Pro Gln Val Ser Lys Val Lys Ser Val Arg Leu Asp Xaa Trp Xaa Glu
        35                  40                  45

Xaa Gln Val Glu Phe Met Xaa Ser Xaa Gly Asn Xaa Ala Ala Arg Ala
    50                  55                  60

Xaa Phe Glu Ser Xaa Val Pro Xaa Pro Phe Tyr Arg Pro Xaa Xaa
65                  70                  75                  80

Ser Asp Cys Gln Leu Leu Arg Glu Gln Trp Ile Arg Ala Lys Tyr Glu
                85                  90                  95

```
Arg Gln Glu Phe Xaa His Xaa Glu Xaa Gln Glu Pro Xaa
                100             105

<210> SEQ ID NO 36
<211> LENGTH: 307
<212> TYPE: PRT
<213> ORGANISM: Artificial sequence
<220> FEATURE:
<223> OTHER INFORMATION: consensus sequence

<400> SEQUENCE: 36

Met Pro Asp Gln Ile Ser Val Ser Glu Phe Val Ala Glu Thr Thr Glu
1               5                   10                  15

Asp Tyr Lys Ser Pro Thr Thr Ser Ser Phe Thr Thr Arg Leu Ala His
            20                  25                  30

Cys Arg Asn Thr Val Ala Ala Leu Glu Glu Ala Leu Asp Val Asp Arg
        35                  40                  45

Ser Val Leu Gln Lys Met Lys Lys Ser Val Lys Ala Ile Tyr Ser Ser
    50                  55                  60

Gly Gln Ala His Val Glu Asn Glu Glu Gln Tyr Thr Gln Ala Leu Glu
65                  70                  75                  80

Lys Phe Gly Ser Asn Phe Val Ser Arg Asp Asp Pro Asp Leu Gly Ser
                85                  90                  95

Ala Phe Leu Lys Phe Ser Gly Phe Thr Lys Glu Leu Thr Ala Leu Phe
            100                 105                 110

Lys Asn Leu Leu Gln Asn Met Asn Asn Ile Ile Ile Phe Pro Leu Asp
        115                 120                 125

Ser Leu Leu Lys Gly Asp Leu Lys Gly Val Lys Gly Asp Leu Lys Lys
    130                 135                 140

Pro Phe Asp Lys Ala Trp Lys Asp Tyr Glu Thr Lys Phe Thr Lys Ile
145                 150                 155                 160

Glu Lys Glu Lys Arg Glu His Ala Lys Gln His Gly Met Ile Arg Thr
                165                 170                 175

Glu Ile Ser Gly Ala Glu Ile Ala Glu Glu Met Glu Lys Glu Arg Arg
            180                 185                 190

Leu Phe Gln Leu Gln Met Cys Glu Tyr Leu Ile Lys Val Asn Glu Ile
        195                 200                 205

Lys Ile Lys Lys Gly Val Asp Leu Leu Gln Asn Leu Ile Lys Tyr Phe
    210                 215                 220

His Ala Gln Cys Asn Phe Phe Gln Asp Gly Leu Lys Ala Val Asp Asn
225                 230                 235                 240

Leu Lys Pro Ser Ile Glu Lys Leu Ala Thr Asp Leu His Asn Ile Lys
                245                 250                 255

Gln Thr Gln Asp Glu Glu Arg Lys Gln Leu Thr Gln Leu Arg Asp Leu
            260                 265                 270

Leu Lys Ser Ala Leu Gln Val Glu Gln Lys Glu Asp Ser Gln Ser Arg
        275                 280                 285

Gln Ser Ala Gly Tyr Ser Leu His Gln Leu Gln Gly Asn Lys Glu His
    290                 295                 300

Gly Thr Glu
305

<210> SEQ ID NO 37
<211> LENGTH: 7
<212> TYPE: PRT
<213> ORGANISM: Artificial Sequence
```

```
<220> FEATURE:
<223> OTHER INFORMATION: consensus binding sequence
<221> NAME/KEY: VARIANT
<222> LOCATION: 5, 6
<223> OTHER INFORMATION: Xaa = Any Amino Acid

<400> SEQUENCE: 37

Arg Pro Leu Pro Xaa Xaa Pro
 1               5

<210> SEQ ID NO 38
<211> LENGTH: 9
<212> TYPE: PRT
<213> ORGANISM: Artificial Sequence
<220> FEATURE:
<223> OTHER INFORMATION: consensus binding sequence

<400> SEQUENCE: 38

Ala Phe Ala Pro Pro Leu Pro Arg Arg
 1               5

<210> SEQ ID NO 39
<211> LENGTH: 7
<212> TYPE: PRT
<213> ORGANISM: Artificial Sequence
<220> FEATURE:
<223> OTHER INFORMATION: consensus sequence

<400> SEQUENCE: 39

Gly Asp Leu Pro Pro Lys Pro
 1               5
```

DIFFERENTIATION ENHANCING FACTORS AND USES THEREFOR

RELATED APPLICATIONS

This application claims priority to U.S. Provisional Application No. 60/038,191 filed on Feb. 14, 1997, the contents of which are incorporated herein by reference.

FUNDING

Work described herein was supported by funding from the National Institutes of Health Grants CA09134, R37DK31405 and CA43803. The U.S. government therefore may have certain rights in this invention.

BACKGROUND OF THE INVENTION

Cellular interactions can be viewed as proceeding in two steps. Initially, an extracellular molecule binds to a specific receptor on a target cell, converting the dormant receptor to an active state. Subsequently, the receptor stimulates intracellular biochemical pathways leading to a cellular response, which may involve progression through the cell cycle, as well as changes in cellular gene expression, cytoskeletal architecture, protein trafficking, endocytosis, cell adhesion, migration, proliferation and differentiation, among others. An intracellular biochemical pathway which mediates some of these cellular responses involves members of the c-src family of protein tyrosine kinases, such as $pp60^{c-src}$. Src tyrosine kinases transduce extracellular signals as diverse as responses to growth factors (for example, platelet derived growth factor (PDGF), epidermal growth factor (EGF)), antigens, cytokines, extracellular matrix molecules, among others. These extracellular signals give rise to a myriad of cellular responses, such as mitotic function, activation of Ras dependent pathways, phosphatidyl inositol 3-kinase activation and cytoskeletal reorganization.

The amino terminus of $pp60^{c-src}$ contains two motifs of approximately 100 and 60 amino acids in length named Src homology 2 and 3 domains (SH2, SH3), respectively. SH2 and SH3 domains have been identified in numerous signal transduction proteins (Pawson, T. and J. Schiessinger (1993) *J. Curr. Bio.* 3:434–442; Courtneidge et al. (1994) *Trends Cell Biol.* 4:345–347; Pawson, T. (1995) *Nature* 373: 573–580). These domains presumably function as modular units that interact with other signal transduction proteins. The importance of SH2 and SH3 domains in signal transduction is underscored by the identification of "adapter proteins", such as c-crk (Reichman et al., 1992), c-nck (Chou et al., 1992) and grb-2/ASH (Margolis et al., 1992; Matuoka et al., 1992), which lack a catalytic domain, and thus, appear to function as adaptors between membrane signaling and multiple downstream targets.

Proteins containing SH2 domains control biochemical pathways as diverse as phospholipid metabolism, tyrosine phosphorylation and dephosphorylation, activation of Ras-like GTPases, gene expression, protein trafficking and cytoskeletal architecture (Pawson, T. and J. Schlessinger (1993) *J. Curr. Bio.* 3:434–442). In vivo, SH2-containing proteins bind to phosphotyrosine (pTyr)-containing sites on activated receptors and cytoplasmic phosphoproteins (Anderson et al. (1990) *Science* 250:979–982; Matsuda et al. (1990) *Science* 248:1537–1539; Valius, M. and A. Kazlauskas (1993) *Cell* 73:321–334). Indeed, crystal structures of the SH2 domains show a pocket configuration of amino acids that interact directly with a phosphotyrosine residue of an associated protein. Based on the crystal structure, the amino acid residues adjacent to the residues in direct contact with the phosphotyrosine determine the specificity of the interaction (Waksman et al. (1993) *J. Cell* 72:779–790; Lee et al. (1994) *Structure* 2:423–438).

SH3 domains have been found in a number of proteins involved in tyrosine kinase signaling, but also in cytoskeletal components and subunits of the neutrophil cytochrome oxidase, among others (Drubin et al. (1990) *Nature* 343:288–290; Leto et al. (1990) *Science* 248:727–730). In contrast to SH2 domains which interact with phosphorylated tyrosine residues of an associated protein, phosphorylation does not appear to be necessary for a protein to interact with a SH3 domain. The first SH3 binding protein identified, 3bp-1, shows homology to rho GTPase activating protein (GAP) (Cicchetti et al., (1992) *Science* 257:803). C3G was initially identified as a GTP exchange factor for several G proteins, and was subsequently shown to have affinity for the SH3 domains of Crk and Grb-2 (Tanaka et al. (1994) *Proc. Natl. Acad. Sci. USA* 91:3443–3447). G proteins themselves may be the targets for the binding of SH3 containing proteins. As an illustration, the proline rich C-terminus of the brain specific form of dynamin binds to several SH3 domains including those found in $pp60^{c-src}$ and $pp59^{c-fyn}$, but not $pp58^{c-fgr}$ (Gout et al., 1993; Seedorf et al. (1994) *J. Biol. Chem.* 269:16009–16014). Dynamin is a microtubule-associated GTPase that is involved in endocytosis (Takel et al., 1995; Hinshaw et al., 1995). The binding of a SH3 domain to dynamin results in an increase in intrinsic GTPase activity (Gout et al., 1993).

SH3-binding sites consist of proline-rich peptides of approximately 10 amino acids (Ren et al. (1993) *Science* 259:1157–1161; Yu et al. (1994) *Cell* 76:933–945), which bind to isolated SH3 domains with dissociation constants of 5–100 $\mu$M (ref. 25). Recent structural and mutagenic analysis of peptide-SH3 complexes (Feng et al. (1994) *Science* 266:1241–1246; Lim et al. (1994) *Nature* 372:375–379; Musacchio et al. (1994) *Nature Struct. Biol.* 1:546–551; Wittekind et al. (1994) *Biochemistry* 33:13531–13539; Rickles et al. (1994) *EMBO J.* 13:5598–5604) shows that peptides associated with SH3 domains adopt a left-handed polyproline type II helix, with three residues per turn, as illustrated by a PXXP consensus sequence (P=Proline, X=any amino acid) that forms a polyproline type II helix (Yu et al. (1994) *Cell* 76:933–945). Solution and crystal structures of SH3 domains complexed with small peptides indicate a groove in the SH3 domain where the prolines of the PXXP helix are situated (Lim et al. (1994) *Nature* 372:375–379; Yu et al. (1994) *Cell* 76:933–945; Musacchio et al. (1994) *Nature Struct. Biol.* 1:546–551). Residues adjacent to the prolines also form contacts within the SH3 sequence and these interactions determine the specificity between a protein and a particular SH3 domain. For example, the arginine in "RPLPXXP" forms a salt bridge with aspartate at position 99 of $pp60^{c-src}$. However the C-terminal arginine in the sequence "AFAPPLPRR" contacts the identical aspartate in $pp60^{c-src}$, indicating that proteins may interact with SH3 domains in either a "plus" or "minus" orientation (named "class I" and "class II" binding, respectively; Yu et al. (1994) *Science* 258:1665; Lim et al. (1994) *Nature* 372:375–379).

Several proteins that interact with the SH3 domains of src-family kinases have been shown to be implicated in cellular growth. These include the regulatory subunit of phosphatidyl-inositol-3-kinase, p85 (Prasad et al. (1993) *Proc. Natl. Acad. Sci. USA* 91:2834–2838), SHC (Weng et al., 1994), and ras GTPase-activating protein (Briggs et al., 1995). Furthermore, mutants within the SH3 domains of the adapter proteins c-crk and grb-2 inhibit v-abl oncogenic activity presumably by acting as "dominant negative" signal transduction effectors (Tanaka et al. (1995) *Proc. Natl. Acad Sci. USA* 91:3443–3447).

Despite much progress in characterizing the signal trasnduction pathways involving SH3 domains, there is a great need for identifying novel mediators of these pathways, and in particular, binding proteins that interact with these SH3 domains. The identification of these novel molecules may provide for a detailed analysis of the amino acid contacts that determine the binding affinity and specificity of SH3 domains with an associated protein, which may in turn facilitate the development of therapeutic agents to be used in treating a diverse number of disorders.

SUMMARY OF THE INVENTION

The present invention is based, at least in part, on the discovery of nucleic acid molecules which encode a novel family of src SH3 binding proteins, referred to herein as "differentiation enhancing factors" or "DEF polypeptides". The DEF molecules show a highly conserved N-terminal domain and divergent C-terminus. The N-terminal domain preferably includes several structural motifs such as at least one src SH3 consensus binding sequence, at least one, and preferably four ankyrin repeats, at least one zinc finger domain, at least one pleckstrin homology domain and at least one C2 domain. The C-terminal domain diverges between family members, and may include at least one, and preferably three, more preferably six copies of a proline-rich tandem repeat and an SH3 domain. In one embodiment, DEF molecules of the invention are cytoplasmic proteins which function as mediators of signal transduction pathways of, for example, SH3 domain containing molecules, thus mediating multiple events including gene expression, cytoskeletal architecture, protein trafficking and endocytosis, cell adhesion, migration, proliferation and differentiation. In a preferred embodiment, DEF molecules of the invention modulate the differentiation of precursor cells, e.g., adipose or neural precursor cells. The DEF molecules of the invention may therefor be useful in the treatment of disorders, for example, hyperplastic and neoplastic tissues.

In one aspect, the invention provides isolated nucleic acid molecules encoding a DEF polypeptide. Such nucleic acid molecules (e.g., cDNAs) have a nucleotide sequence encoding a DEF polypeptide or biologically active portions thereof, such as a polypeptide having one or more of the following characteristics: the ability to bind to an SH3 domain in an intra- or intermolecular interaction; the ability to dimerize with like molecules or other molecules; the ability to anchor cytoskeletal elements to the plasma membrane; the ability to modulate the activity of signal transduction molecules, e.g., kinase activity, e.g., p38 MAP kinase activity, or G protein activity, e.g., GTPase activity; the ability to synergize with the activity of peroxisome proliferator activated receptor γ (PPARγ); the ability to induce expression of PPARγ; the ability to induce the terminal differentiation of a hyperproliferative cell; or the ability to induce adipogenesis or neurogenesis. In a preferred embodiment, the isolated nucleic acid molecule has a nucleotide sequence shown in FIG. 2, SEQ ID NO: 1; FIG. 13, (SEQ ID NO: 3 or SEQ ID NO: 5); FIG. 14, (SEQ ID NO: 6 or SEQ ID NO: 8); or FIG. 15, (SEQ ID NO: 9 or SEQ ID NO: 11), or a portion thereof such as the coding region of the nucleotide sequence of FIG. 2, SEQ ID NO: 1; FIG. 13, (SEQ ID NO: 3); FIG. 14, (SEQ ID NO: 6); or FIG. 15, (SEQ ID NO: 9). Other preferred nucleic acid molecules encode a protein having the amino acid sequence of FIG. 3, SEQ ID NO: 2; or FIG. 12, (SEQ ID NO: 4, SEQ ID NO: 7, or SEQ ID NO: 10). Nucleic acid molecules derived from a mammalian, preferably, a human cell (e.g., a naturally-occurring nucleic acid molecule found in a mammalian brain or an adipocyte cell) which hybridize under stringent conditions to the nucleotide sequence shown in FIG. 2, SEQ ID NO: 1; FIG. 13, (SEQ ID NO: 3 or SEQ ID NO: 5); FIG. 14, (SEQ ID NO: 6 or SEQ ID NO: 8); or FIG. 15, (SEQ ID NO: 9 or SEQ ID NO: 11) are also within the scope of the invention.

In another embodiment, the isolated nucleic acid molecule is a nucleotide sequence encoding a protein having an amino acid sequence which is at least about 80%, preferably at least about 85%, more preferably at least about 90% and most preferably at least about 95–99% overall amino acid sequence identity with an amino acid sequence shown in FIG. 3, SEQ ID NO: 2; or FIG. 12, (SEQ ID NO: 4, SEQ ID NO: 7, or SEQ ID NO: 10). This invention further pertains to nucleic acid molecules which encode a protein which includes one or more of the following: at least one SH3 consensus binding sequence having an amino acid sequence at least 80%, preferably at least 90%, more preferably at least 95–99% identical to an amino acid sequence shown in FIG. 3, SEQ ID NO: 2; or FIG. 12, (SEQ ID NO: 4, SEQ ID NO: 7, or SEQ ID NO: 10); at least one ankyrin repeat, preferably two or three, and most preferably four ankyrin repeats, having an amino acid sequence at least 80%, preferably at least 90%, more preferably at least 95–99% identical to an amino acid sequence shown in FIG. 3, SEQ ID NO: 2; or FIG. 12, (SEQ ID NO: 4, SEQ ID NO: 7, or SEQ ID NO: 10); a zinc finger domain having an amino acid sequence at least 80%, preferably at least 90%, more preferably at least 95–99% identical to an amino acid sequence shown in FIG. 3, SEQ ID NO: 2; or FIG. 12, (SEQ ID NO: 4, SEQ ID NO: 7, or SEQ ID NO: 10); a pleckstrin homology domain having an amino acid sequence at least 80%, preferably at least 90%, more preferably at least 95–99% identical to an amino acid sequence shown in FIG. 3, SEQ ID NO: 2; or FIG. 12, (SEQ ID NO: 4, SEQ ID NO: 7, or SEQ ID NO: 10); and a C2 domain having an amino acid sequence at least 80%, preferably at least 90%, more preferably at least 95–99% identical to an amino acid sequence shown in FIG. 3, SEQ ID NO: 2; or FIG. 12, (SEQ ID NO: 4, SEQ ID NO: 7, or SEQ ID NO: 10). Further within the scope of this invention are nucleic acid molecules which encode a protein which includes a proline-rich repeat having an amino acid sequence at least 80%, preferably at least about 90%, more preferably at least about 95–99% identical to an amino acid sequence shown in FIG. 3, SEQ ID NO: 2. This invention also encompasses nucleic acid molecules which encode a protein which includes an SH3 domain having an amino acid sequence at least about 80%, preferably at least about 90%, more preferably at least about 95–99% identical to an amino acid sequence shown in FIG. 3, SEQ ID NO: 2 or FIG. 12, SEQ ID NO: 4 or SEQ ID NO: 7.

Nucleic acid molecules encoding proteins which include one or more of the following: at least one SH3 consensus binding sequence having an amino acid sequence at least about 60% (preferably at least about 70%, 80%, 90%, or 95–99%) identical to an amino acid sequence shown in FIG. 3, SEQ ID NO: 2, or FIG. 12, SEQ ID NO: 4, SEQ ID NO: 7, or SEQ ID NO: 10; at least one ankyrin repeat having an amino acid sequence at least about 60% (preferably at least about 70%, 80%, 90%, or 95–99%) identical to an amino acid sequence shown in FIG. 3, SEQ ID NO: 2, or FIG. 12, SEQ ID NO: 4, SEQ ID NO: 7, or SEQ ID NO: 10, a zinc finger domain having an amino acid sequence at least about 60% (preferably at least about 70%, 80%, 90%, or 95–99%) identical to an amino acid sequence shown in FIG. 3, SEQ ID NO: 2 or FIG. 12, SEQ ID NO: 4, SEQ ID NO: 7, or SEQ ID NO: 10, a pleckstrin homology domain having an amino acid sequence at least 60% (preferably at least about 70%, 80%, 90%, or 95–99%) identical to an amino acid sequence shown in FIG. 3, SEQ ID NO: 2; or FIG. 12, (SEQ ID NO: 4, SEQ ID NO: 7, or SEQ ID NO: 10), a C2 domain having an amino acid sequence at least about 60% (preferably at least about 70%, 80%, 90%, or 95–99%) identical to an amino acid sequence shown in FIG. 3, SEQ ID NO: 2; or FIG. 12, (SEQ ID NO: 4, SEQ ID NO: 7, or SEQ ID NO: 10); a proline-rich repeat having an amino acid sequence at least about 60% (preferably at least about 70%, 80%, 90%, or 95–99%) identical to an amino acid sequence shown in FIG. 3, SEQ ID NO: 2, and an SH3 domain having an amino acid sequence at least about 60% (preferably at least about 70%, 80%, 90%, or 95–99%) identical to an amino acid sequence shown in FIG. 3, SEQ ID NO: 2 or FIG. 12, SEQ ID NO: 4 or SEQ ID NO: 7, are also within the scope of this invention.

Another aspect of this invention pertains to nucleic acid molecules encoding a DEF polypeptide fusion protein which includes a nucleotide sequence encoding a first peptide having an amino acid sequence at least about 80% (preferably at least about 90%, or 95–99%) identical to an amino acid sequence shown in FIG. 3, SEQ ID NO: 2 or FIG. 12, SEQ ID NO: 4, SEQ ID NO: 7, or SEQ ID NO: 10, and a nucleic sequence encoding a second peptide corresponding to a moiety that facilitates detection or purification or alters the solubility of this fusion protein, such as glutathione-S-transferase, or an enzymatic activity such as alkaline phosphatase, or an epitope tag.

In another embodiment, the isolated nucleic acid molecule is a nucleotide sequence encoding a polypeptide fragment of at least about 5, 10, 15, 20, 25, 30, 40, 50, 60, 70, 100, 150, 200, 250, 300, 350, 400, 450, 500, 550, 600, 650, 700, 750, 800, 850–1125 amino acid residues in length, preferably at least about 5–250 amino acid residues in length, and more preferably at least about 10–200 amino acid residues in length corresponding to a protein having at least about 80% the amino acid sequence shown in FIG. 3, (SEQ ID NO: 2) or FIG. 12, SEQ ID NO: 4, SEQ ID NO: 7, or SEQ ID NO: 10. In a preferred embodiment, the polypeptide fragment has a DEF activity, e.g., induces adipogenesis or neurogenesis.

Moreover, given the disclosure herein of a DEF polypeptide-encoding cDNA sequence (e.g., SEQ ID NO: 1, SEQ ID NO: 3, SEQ ID NO: 5, SEQ ID NO: 6, SEQ ID NO: 8, SEQ ID NO: 9 or SEQ ID NO: 11), antisense nucleic acid molecules (i.e, molecules which are complimentary to the coding strand of the DEF polypeptide cDNA sequence) are also provided by the invention. Accordingly, the DEF nucleic acid molecule can be non-coding, (e.g., probe, antisense or ribozyme molecules) or can encode a functional DEF polypeptide (e.g., a polypeptide which specifically modulates, e.g., by acting as either an agonist or antagonist, at least one biological activity of the DEF polypeptide). In a preferred embodiment, a DEF nucleic acid molecule includes the coding region of FIG. 1, (SEQ ID NO: 1, SEQ ID NO: 3, SEQ ID NO: 6, or SEQ ID NO: 9).

Furthermore, in certain preferred embodiments, the subject DEF nucleic acids will include a transcriptional regulatory sequence, e.g., at least one of a transcriptional promoter or transcriptional enhancer sequence, which regulatory sequence is operably linked to the DEF gene sequences. Such regulatory sequences can be used to render the DEF gene sequences suitable for use as an expression vector. This invention also encompasses cells transfected with said expression vector whether prokaryotic or eukaryotic and a method for producing DEF proteins by employing the expression vectors.

Accordingly, another aspect of the invention pertains to recombinant expression vectors containing the nucleic acid molecules of the invention and host cells into which such recombinant expression vectors have been introduced. In one embodiment, such a host cell is used to produce DEF polypeptide by culturing the host cell in a suitable medium. If desired, DEF polypeptide can be then isolated from the medium or the host cell.

Still another aspect of the invention pertains to isolated DEF polypeptides and active fragments thereof, such as peptides having an activity of a DEF polypeptide (e.g., at least one biological acitivity of DEF polypeptide, such as the ability to bind to a src SH3 domain, the ability to induce PPARγ expression; or the ability to induce the terminal differentiation of a cell, e.g., an adipose or a neural precursor cell, e.g., a transformed adipose or a neural precursor cell). The invention also provides an isolated preparation of a DEF polypeptide. In preferred embodiments, the DEF polypeptide comprises an amino acid sequence of FIG. 3, (SEQ ID NO: 2), or FIG. 12, (SEQ ID NO: 4, SEQ ID NO: 7, or SEQ ID NO: 10). In other embodiments, the isolated DEF polypeptide comprises an amino acid sequence at least 60% identical to an amino acid sequence of FIG. 3, (SEQ ID NO: 2) or FIG. 12, (SEQ ID NO: 4, SEQ ID NO: 7, or SEQ ID NO: 10) and, preferably has an activity of DEF polypeptide (e.g., at least one biological activity of DEF polypeptide). Preferably, the protein is at least about 70%, more preferably at least about 80%, even more preferably at least about 90% and most preferably at least about 95–99% identical to the amino acid sequence of FIG. 3, SEQ ID NO: 2 or FIG. 12, SEQ ID NO: 4, SEQ ID NO: 7, or SEQ ID NO: 10.

This invention also pertains to isolated polypeptides which include one or more of the following: a src SH3 consensus binding sequence having an amino acid sequence that is at least about 60% (preferably at least about 70%, 80%, 90%, or 95–99%) identical to an amino acid sequence shown in FIG. 3 (SEQ ID NO: 2) or FIG. 12 (SEQ ID NO: 4, SEQ ID NO: 7, or SEQ ID NO: 10), at least one ankyrin repeat, preferably two or three, and most preferably four ankyrin repeats, having an amino acid sequence that is at least 50% (preferably at least 60%, 70%, 80%, 90%, or 95–99%) identical to an amino acid sequence shown in FIG. 3 (SEQ ID NO: 2) or FIG. 12 (SEQ ID NO: 4, SEQ ID NO: 7, or SEQ ID NO: 10), a zinc finger domain having an amino acid sequence that is at least about 50% (preferably at least about 60%, 70%, 80%, 90%, or 95–99%) identical to an amino acid sequence shown in FIG. 3 (SEQ ID NO: 2) or FIG. 12 (SEQ ID NO: 4, SEQ ID NO: 7, or SEQ ID NO: 10), a pleckstrin homology domain having an amino acid sequence that is at least about 50% (preferably at least about 60%, 70%, 80%, 90%, or 95–99%) identical to an amino acid sequence shown in FIG. 3 (SEQ ID NO: 2; or FIG. 12 (SEQ ID NO: 4, SEQ ID NO: 7, or SEQ ID NO: 10), a C2 domain having an amino acid sequence that is at least about 50% (preferably at least about 60%, 70%, 80%, 90%, or 95–99%) identical to an amino acid sequence shown in FIG. 3 (SEQ ID NO: 2); or FIG. 12 (SEQ ID NO: 4, SEQ ID NO: 7, or SEQ ID NO: 10), a proline-rich tandem repeat having an amino acid sequence that is at least 50% (preferably at least about 60%, 70%, 80%, 90%, or 95–99%) identical to an amino acid sequence shown in FIG. 3 (SEQ ID NO: 2)

or FIG. 12 (SEQ ID NO: 4), and an SH3 domain having an amino acid sequence that is at least about 50% (preferably at least about 60%, 70%, 80%, 90%, or 95–99%) identical to an amino acid sequence shown in FIG. 3 (SEQ ID NO: 2) or FIG. 12 (SEQ ID NO: 4 or SEQ ID NO: 7).

The invention also provides for a DEF polypeptide comprising a first peptide having an amino acid sequence at least about 80% identical to an amino acid sequence shown in FIG. 3 (SEQ ID NO: 2) or FIG. 12 (SEQ ID NO: 4, SEQ ID NO: 7, or SEQ ID NO: 10) and a second peptide corresponding to a moiety that facilitates detection or purification or alters the solubility of this fusion protein, such as glutathione-S-transferase, or an enzymatic activity such as alkaline phosphatase, or an epitope tag.

Polypeptides comprising a polypeptide fragment of at least about 5, 10, 15, 20, 25, 30, 40, 50, 60, 70, 100, 150, 200, 250, 300, 350, 400, 450, 500, 550, 600, 650, 700, 750, 800, 850–1125 amino acid residues in length, preferably at least about 5–250 amino acid residues in length, and more preferably at least about 10–220 amino acid residues in length, and most preferably at least about 200 amino acid residues corresponding to a protein having at least about 80% the amino acid sequence shown in FIG. 3 (SEQ ID NO: 2) or FIG. 12 (SEQ ID NO: 4, SEQ ID NO: 7, or SEQ ID NO: 10). In a preferred embodiment, the polypeptide fragment has a DEF activity, e.g., induces adipogenesis or neurogenesis.

Still another aspect of the invention pertains to isolated DEF polypeptide and active fragments thereof, such as polypeptides having an activity of a DEF polypeptide (e.g., at least one biological acitivity of DEF, such as the ability to bind to an SH3 domain in an intra- or intermolecular interaction, a polypeptide capable of dimerizing to like molecules or other molecules, a polypeptide capable of anchoring cytoskeletal elements to the plasma membrane, a polypeptide capable of modulating the activity of signal transduction molecules, e.g., kinase activity, e.g., p38 MAP kinase activity, or G protein activity, e.g., GTPase activity, a polypeptide capable of inducing PPARγ expression, a polypeptide capable of inducing the terminal differentiation of a hyperproliferative cell, e.g., a transformed cell, e.g., a transformed adipose cell, or a polypeptide capable of inducing adipogenesis or neurogenesis).

The invention also provides an isolated preparation of a DEF protein. In a preferred embodiment, the isolated DEF protein comprises an amino acid sequence at least 70% identical to an amino acid sequence of FIG. 3 (SEQ ID NO: 2) or FIG. 12 (SEQ ID NO: 4, SEQ ID NO: 7, or SEQ ID NO: 10) and, preferably has an activity of DEF (e.g., at least one biological activity of DEF). Preferably, the protein is at least about 80%, more preferably at least about 90–95%, even more preferably at least about 96–98% and most preferably at least about 99% identical to the amino acid sequence of FIG. 3, (SEQ ID NO: 2) or FIG. 12 (SEQ ID NO: 4, SEQ ID NO: 7, or SEQ ID NO: 10).

In another embodiment, the DEF protein comprises an amino acid sequence of FIG. 3 (SEQ ID NO: 2) or FIG. 12 (SEQ ID NO: 4, SEQ ID NO: 7, or SEQ ID NO: 10). This invention also pertains to isolated polypeptides which include a src SH3 consensus binding sequence having an amino acid sequence that is at least 80%, preferably at least about 85%, more preferably at least about 86–99% identical to a src SH3 consensus binding sequence shown in FIG. 3, (SEQ ID NO: 2) or FIG. 12 (SEQ ID NO: 4, SEQ ID NO: 7, or SEQ ID NO: 10), at least one ankyrin repeat, preferably two or three, and most preferably four ankyrin repeats, having having an amino acid sequence that is at least about 80%, preferably at least about 85%, more preferably at least about 86–99% identical to an amino acid sequence shown in FIG. 3 (SEQ ID NO: 2) or FIG. 12 (SEQ ID NO: 4, SEQ ID NO: 7, or SEQ ID NO: 10), a zinc finger domain having an amino acid sequence that is at least about 80%, preferably at least about 85%, more preferably at least about 86–99% identical to an amino acid sequence shown in FIG. 3 (SEQ ID NO: 2) or FIG. 12 (SEQ ID NO: 4, SEQ ID NO: 7, or SEQ ID NO: 10), a pleckstrin homology domain having an amino acid sequence that is at least about 80%, preferably at least about 85%, more preferably at least about 86–99% identical to an amino acid sequence shown in FIG. 3 (SEQ ID NO: 2), or FIG. 12 (SEQ ID NO: 4, SEQ ID NO: 7, or SEQ ID NO: 10), a C2 domain having an amino acid sequence that is at least about 80%, preferably at least 85%, more preferably at least about 86–99% identical to an amino acid sequence shown in FIG. 3 (SEQ ID NO: 2), or FIG. 12, (SEQ ID NO: 4, SEQ ID NO: 7, or SEQ ID NO: 10), a proline-rich repeat having an amino acid sequence that is at least about 80%, preferably at least about 85%, more preferably at least about 86–99% identical to an amino acid sequence shown in FIG. 3 (SEQ ID NO: 2) or FIG. 12 (SEQ ID NO: 4), and an SH3 domain having an amino acid sequence that is at least about 80%, preferably at least about 85%, more preferably at least about 86–99% identical to an amino acid sequence shown in FIG. 3 (SEQ ID NO: 2) or FIG. 12 (SEQ ID NO: 4 or SEQ ID NO: 7).

The invention also provides for a DEF fusion protein comprising a first polypeptide having an amino acid sequence at least about 80% (preferably at least 90%, or 95–99%) identical to an amino acid sequence shown in FIG. 3 (SEQ ID NO: 2) or FIG. 12 (SEQ ID NO: 4, SEQ ID NO: 7, or SEQ ID NO: 10) and a nucleotide sequence encoding a second polypeptide corresponding to a moiety that facilitates detection or purification or alters the solubility of the fusion protein, such as glutathione-S-transferase, or an enzymatic activity such as alkaline phosphatase, or an epitope tag. In preferred embodiments, the fusion protein comprises one or more of a src SH3 consensus binding sequence, an ankyrin repeat, a zinc finger domain, a PH domain, a C2 domain, a proline-rich repeat, or an SH3 domain of a DEF polypeptide.

Yet another aspect of the present invention features an immunogen comprising a DEF polypeptide in an immunogenic preparation, the immunogen being capable of eliciting an immune response specific for a DEF polypeptide; e.g. a humoral response, e.g. an antibody response; e.g. a cellular response. In preferred embodiments, the immunogen includes an antigenic determinant, e.g. a unique determinant, from a protein having at least about 80%, preferably at least about 85%, more preferably at least about 87–99% identity with the amino acid sequence represented by one of FIG. 3 (SEQ ID NO: 2) or FIG. 12 (SEQ ID NO: 4, SEQ ID NO: 7, or SEQ ID NO: 10).

A still further aspect of the present invention features antibodies and antibody preparations specifically reactive with an epitope of the DEF immunogen.

The invention also features transgenic non-human animals, e.g. mice, rats, rabbits, chickens, frogs or pigs, having a transgene, e.g., animals which include (and preferably express) a heterologous form of a DEF gene described herein, or which misexpress an endogenous DEF gene, e.g., an animal in which expression of one or more of the subject DEF proteins is disrupted. Such a transgenic animal can serve as an animal model for studying cellular and tissue disorders comprising mutated or mis-expressed DEF alleles or for use in drug screening.

The invention also provides probes and primers composed of substantially purified oligonucleotides, which correspond to a region of nucleotide sequence which hybridizes to at least 6 consecutive nucleotides preferably at least 25 more preferably at least 40, 50 or at least 75 consecutive nucleotides of either sense or antisense sequences of FIG. 2 (SEQ ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11) or natually occurring mutants thereof In preferred embodiments, an oligonucleotide of the present invention specifically detects a DEF nucleic acid relative to other nucleic acid in a sample. In yet another embodiment, the probe/primer further includes a label which is capable of being detected. The label group can be selected, e.g., from a group consisting of radioisotopes, fluorescent compounds, enzymes, and enzyme co-factors. Probes of the invention can be used as a part of a diagnostic test kit for identifying dysfunctions associated with mis-expression of a DEF protein, such as for detecting in a sample of cells isolated from a patient, a level of a nucleic acid encoding a DEF protein; e.g. measuring a DEF mRNA level in a cell, or determining whether a genomic DEF gene has been mutated or deleted. These so-called "probes/primers" of the invention can also be used as a part of "antisense" therapy which refers to administration or in situ generation of oligonucleotide probes or their derivatives which specifically hybridize (e.g. bind) under cellular conditions, with the cellular mRNA and/or genomic DNA encoding one or more of the subject DEF proteins so as to inhibit expression of that protein, e.g. by inhibiting transcription and/or translation. Preferably, the oligonucleotide is at least 12 nucleotides in length, although primers of 25, 40, 50, or 75 nucleotides in length are also encompassed.

Yet another aspect of the present invention concerns a method for modulating one or more of a cell by modulating a DEF biological activity, e.g., by potentiating or disrupting certain protein-protein interactions. In general, whether carried out in vivo, in vitro, or in situ, the method includes treating the cell with an effective amount of DEF or a DEF agent so as to alter, relative to the cell in the absence of treatment, at least one or more of (i) cellular gene expression, (ii) cell proliferation, (iii) cell differentiation, e.g., differentiation of adipose or neural precursor cells, (iv) signal transduction, (v) cytoskeletal architecture, (vi) protein trafficking, (vii) adhesion of a cell. Accordingly, the method can be carried out with DEF or a DEF agents such as peptide and peptidomimetics or other molecules identified in the drug screens devised herein which agonize or antagonize the effects of signaling from a DEF protein or ligand binding of a DEF protein, e.g., an intracellular target molecule, e.g., an SH3 domain-containing molecule, a G protein, e.g., GTPase protein, or a cytoskeleton molecule. Other DEF agents include antisense constructs for inhibiting expression of DEF proteins, and different domains of the DEF proteins that may act as dominant negative mutants of DEF proteins which competitively inhibit ligand interactions upstream and signal transduction downstream of a DEF protein.

In one embodiment, the subject method of modulating a DEF biological activity can be used in the treatment of hyperproliferative cell to modulate growth arrest and terminal differentiation of a cell. In a preferred embodiment, the modulation of DEF activity occurs in an adipocyte or neural cell, in order to modulate adipocyte or neuronal differentiation. In another embodiment, the subject method is used to modulate induce growth arrest and differentiation of a cancer cell.

In yet another aspect, the invention provides a drug screening assay for screening test compounds for modulators, e.g., inhibitors, or alternatively, potentiators, of an interaction between an SH3 domain-containing protein, e.g., a DEF molecule or a c-src protein tyrosine kinases, e.g., pp60$^{c\text{-}src}$ and a DEF polypeptide or a biologically active portion thereof, e.g., an SH3 binding domain. An exemplary method includes the following (a) forming a reaction mixture including: (i) a pp60$^{c\text{-}src}$, (ii) a DEF or an SH3 binding domain, and (iii) a test compound; and (b) detecting interaction of the pp60$^{c\text{-}src}$ and DEF or an SH3 binding domain. A statistically significant change (potentiation or inhibition) in the interaction of the pp60$^{c\text{-}src}$, and DEF or an SH3 binding domain in the presence of the test compound, relative to the interaction in the absence of the test compound, indicates a potential agonist (mimetic or potentiator) or antagonist (inhibitor) of said interaction. The reaction mixture can be a cell-free protein preparation, e.g., a reconsituted protein mixture or a cell lysate, or it can be a recombinant cell including a heterologous nucleic acid recombinantly expressing the DEF polypeptide.

In another embodiment, an assay is provided for screening for modulators of an interaction between a DEF polypeptide or biologically active portions thereof, e.g., a src SH3 consensus binding sequence, an ankyrin repeat, a zinc finger domain, a PH domain, a C2 domain, a proline-rich repeat and an SH3 domain, with signaling molecules. As an illustrative embodiment, test compounds that modulate the interaction between a DEF polypeptide or an ankyrin repeat and a cytoskeletal molecule can be tested.

In preferred embodiments, the steps of the assay are repeated for a variegated library of at least 100 different test compounds, more preferably at least $10^3$, $10^4$ or $10^5$ different test compounds. The test compound can be, e.g., a peptide, a nucleic acid, a small organic molecule, or natural product extract (or fraction thereof).

Another aspect of the present invention provides a method of determining if a subject, e.g. an animal patient, is at risk for a disorder characterized by unwanted biological activity of a DEF polypeptide. The method includes detecting, in a tissue of the subject, the presence or absence of a genetic lesion characterized by at least one of (i) a mutation of a gene encoding a DEF protein; or (ii) the mis-expression of a DEF gene. In preferred embodiments, detecting the genetic lesion includes ascertaining the existence of at least one of: a deletion of one or more nucleotides from a DEF gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of soluble DEF protein.

For example, detecting the genetic lesion can include (i) providing a probe/primer including an oligonucleotide containing a region of nucleotide sequence which hybridizes to a sense or antisense sequence of a DEF gene or naturally occurring mutants thereof, or 5' or 3' flanking sequences naturally associated with the DEF gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the DEF gene and, optionally, of the flanking nucleic acid sequences. For instance, the probe/primer can be employed in a polymerase chain reaction (PCR) or in a ligation chain reaction (LCR). In alternate embodiments, the level of a DEF protein is detected in an immunoassay using an antibody which is specifically immunoreactive with the DEF protein.

Another aspect of the invention provides a method for inhibiting proliferation of a hyperproliferative cell, e.g., a neoplastic cell, comprising ectopically expressing DEF or a functional fragment thereof in a cell in order to induce differentiation of the cell. In one embodiment, ectopic expression of DEF in a precursor cell may result in the differentiation of a hyperproliferative cell, e.g., an adipocyte precursor cell, or a cells derived from an adipose tumor, e.g., lipomas, fibrolipomas, lipoblastomas, lipomatosis, hibernomas, hemangiomas and/or liposarcomas, into adipocytes. In other embodiments, activation of DEF may synergize with other signaling agents to augment the differentiated phenotype. Thus, DEF alone or in combination with other agents can be used for the treatment of, or prevention of a disorder characterized by aberrant cell growth.

For example, the subject method can be used in the treatment of disorders mediated by an aberrant activity of a PPARγ receptor. The subject method can be used in treating disorders characterized by the aberrant activity of an adipocyte precursor cell, e.g., obesity.

As another example, the subject method can be used in the treatment of sarcomas, carcinomas and/or leukemias. Exemplary disorders for which the subject method may be used as part of a treatment regimen include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In certain embodiments, the subject method can be used to treat such disorders as carcinomas forming from tissue of the breast, prostate, kidney, bladder or colon.

In other embodiments, the subject method can be used to treat hyperplastic or neoplastic disorders arising in adipose tissue, such as adipose cell tumors, e.g., lipomas, fibrolipomas, lipoblastomas, lipomatosis, hibemomas, hemangiomas and/or liposarcomas.

In still other embodiments, the subject method can be used to treat hyperplastic or neoplastic disorders of the hematopoietic system, e.g., leukemic cancers. In a preferred embodiment, the subject is a mammal, e.g., a primate, e.g., a human.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

FIG. 1A shows SDS/PAGE analysis of src SH3 binding proteins by passing bovine brain lysates over src SH3 and src SH3SH2 affinity columns. FIG. 1B depicts further analysis of proteins which bound to src SH3 and src SH3SH2 affinity columns by passing eluted proteins over an ATP agarose column. Molecular size markers in kilodaltons are indicated on the left side.

FIGS. 2A–2B is the full-length nucleotide sequence of the bovine DEF-1 gene (coding and untranslated regions; SEQ ID NO: 1).

FIG. 3 is the predicted amino acid sequence of bovine DEF-1 (SEQ ID NO: 2). The number of the last amino acid in a line is noted on the right. The following domains were identified: pleckstrin homology domain corresponding to amino acids 326–419; zinc finger domain 457–480; C2 domain corresponding to amino acids 498–557; ankyrin-related motifs corresponding to amino acids 356–374, 604–623, 640–659 and 672–692; SH3 consensus binding sequence corresponding to amino acids 794–799, 803–809, 829–835, 895–901 and 993–999; proline-rich repeat corresponding to amino acids 934–1001; and SH3 domain corresponding to amino acids 1073–1123. Key: overline= peptide sequenced; and underline=putative alternative exon.

FIG. 7A represents the putative structure of repeats 1–3 (amino acids 934–974). FIG. 7B represents the putative structure of repeats 3–6 (amino acids 966–1001). Circles represent the amino acid indicated with a single letter code.

FIGS. 12A–12D is an alignment of the amino acid sequences of DEF family members. Amino acid sequences corresponding to Majority sequence (SEQ ID NO: 36); bovine DEF-1 or P140 PROT SEQ (SEQ ID NO: 2); zebrafish DEF-1 or Zp140 Composite (SEQ ID NO: 4); zebrafish DEF-2 or Zp140 #28 Comp (SEQ ID NO: 7); zebrafish DEF-3 Zp140 #25 Comp (SEQ ID NO: 10); and human DEF-2 or Human S10 (SEQ ID NO: 12) are indicated.

FIGS. 13A–13E is the full-length nucleotide sequence of the zebrafish DEF-1 gene (coding and untranslated regions; SEQ ID NO: 3).

FIGS. 14A–14F is the full-length nucleotide sequence of the zebrafish DEF-2 gene (coding and untranslated regions; SEQ ID NO: 6).

FIGS. 15A–15E is the full-length nucleotide sequence of the zebrafish DEF-3 gene (coding and untranslated regions; SEQ ID NO: 9).

DETAILED DESCRIPTION OF THE INVENTION

Figures 1A, 1B:
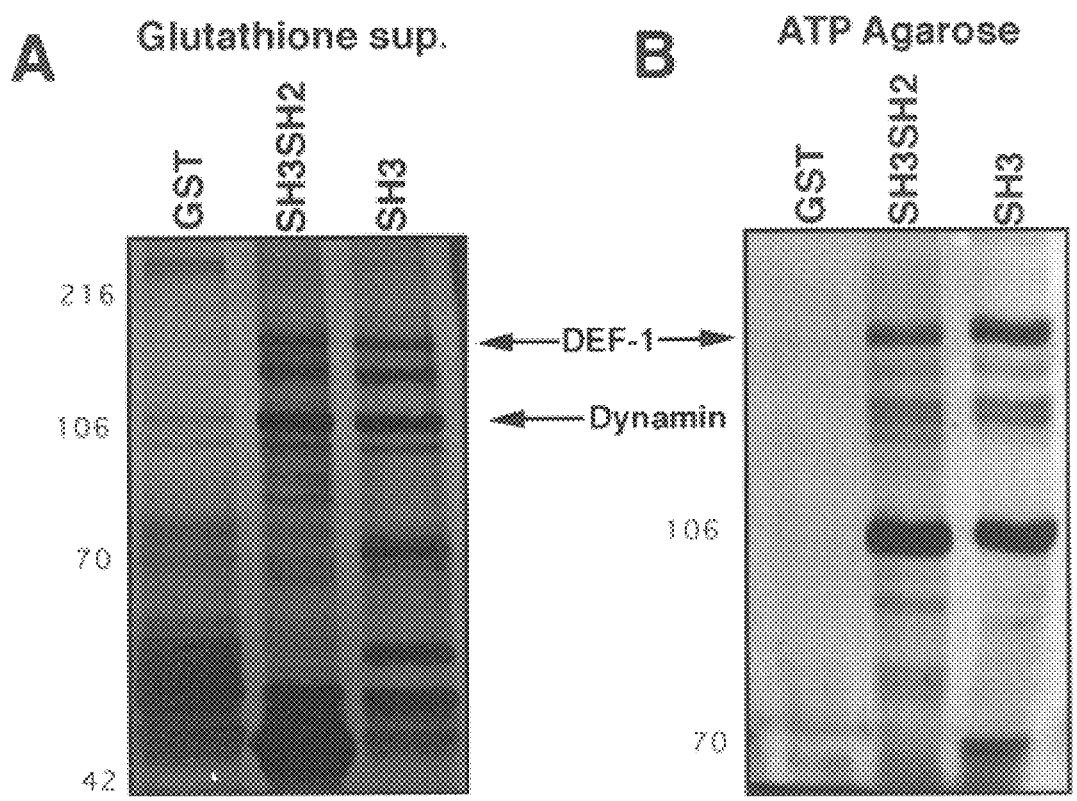
FIGS. 1A–1B are silver-stained gels depicting the SDS/PAGE electrophoretic resolution of bovine DEF-1 protein.
Figure 4:
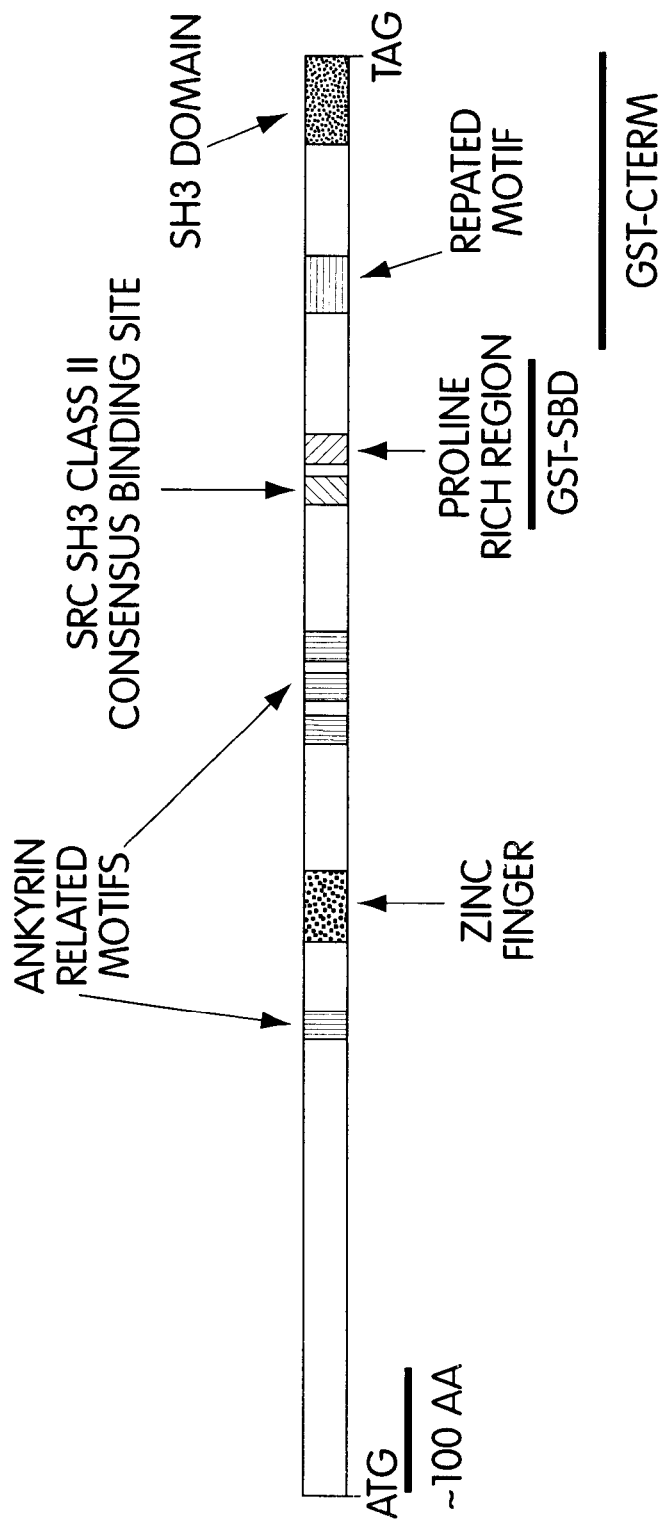
FIG. 4 is a schematic representation of the structure of bovine DEF-1.

The present invention is based on the discovery of novel molecules, referred to herein as "differentiation enhancing factors" or DEF protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain and having sufficient amino acid or nucleotide sequence homology as defined herein. Such family members can be naturally occurring and can be from either the same or different species. For example, a family can contain a first protein of human origin, as well as other, distinct proteins of human origin or alternatively, can contain homologues of non-human origin. Members of a family may also have common functional characteristics.

One aspect of the invention pertains to nucleic acids encoding DEF family members and DEF polypeptides. Preferably, a DEF family member includes at least one SH3 consensus binding sequence, at least one, preferably four ankyrin repeats, at least one zinc finger domain, at least one pleckstrin homology domain and at least one C2 domain. In another embodiment, a DEF family member has at least one or more of the above-identified domains and has an amino acid sequence which is at least about 40% identical to an amino acid sequence shown in FIG. 2 (SEQ ID NO:2).

In yet another embodiment, a DEF family member has an amino acid sequence, which is at least about 40% identical to an amino acid sequence shown in FIG. 2 (SEQ ID NO:2).

In another embodiment, a DEF family member has one or more of the above-identified domains and is encoded by a nucleic acid which encodes an amino acid sequence which is at least about 40% identical to an amino acid sequence shown in FIG. 2 (SEQ ID NO:2).

In still another embodiment, a DEF family member is encoded by a nucleic acid which encodes an amino acid sequence which is at least about 40% identical to an amino acid sequence shown in FIG. 2 (SEQ ID NO:2).

In still another embodiment, a DEF family member has at least one biological activity of a DEF polypeptide, such as the ability to bind to an SH3 domain in an intra- or intermolecular interaction, a polypeptide capable of dimerizing to like molecules or other molecules, a polypeptide capable of anchoring cytoskeletal elements to the plasma membrane, a polypeptide capable of modulating the activity of signal transduction molecules, e.g., kinase activity, e.g., p38 MAP kinase activity, or G protein activity, e.g., GTPase activity, a polypeptide capable of inducing PPARγ expression, a polypeptide capable of inducing the terminal differentiation of a hyperproliferative cell, e.g., a transformed cell, e.g., a transformed adipose cell, or a polypeptide capable of inducing adipogenesis or neurogenesis). In yet another embodiment, a DEF family member: (i) has one or more of the above-identified domains, (ii) is encoded by a nucleic acid which encodes polypeptide having an amino acid sequence, which is at least about 40% identical to an amino acid sequence shown in FIG. 2 (SEQ ID NO:2), (iii) is a polypeptide having an amino acid sequence, which is at least about 40% identical to an amino acid sequence shown in FIG. 2 (SEQ ID NO:2), and (iii) has at least one biological activity of a DEF polypeptide.

In another aspect, the invention features nucleic acids encoding a DEF-1 polypeptide, as well as DEF-1 polypeptides. Such DEF-1 nucleic acids and polypeptides have at least one SH3 consensus binding sequence, at least one, preferably four ankyrin repeats, at least one zinc finger domain, at least one pleckstrin homology domain, at least one C2 domain, at least one proline-rich repeat, and at least one SH3 domain. In one embodiment, the DEF-1 polypeptide has the above-identified domains and is encoded by a nucleic acid which is at least about 60% (preferably at least about 61–65%, 70%, 80%, 90% or 95–99%) identical to the nucleotide sequence of FIG. 2 (SEQ ID NO: 1) or FIG. 13 (SEQ ID NO: 3 or SEQ ID NO: 5). In another embodiment, the DEF-1 polypeptide is encoded by a nucleic acid which is at least about 60% (preferably at least about 61–65%, 70%, 80%, 90% or 95–99%) identical to the nucleotide sequence of FIG. 2 (SEQ ID NO: 1) or FIG. 13 (SEQ ID NO: 3 or SEQ ID NO: 5).

Figure 12A:
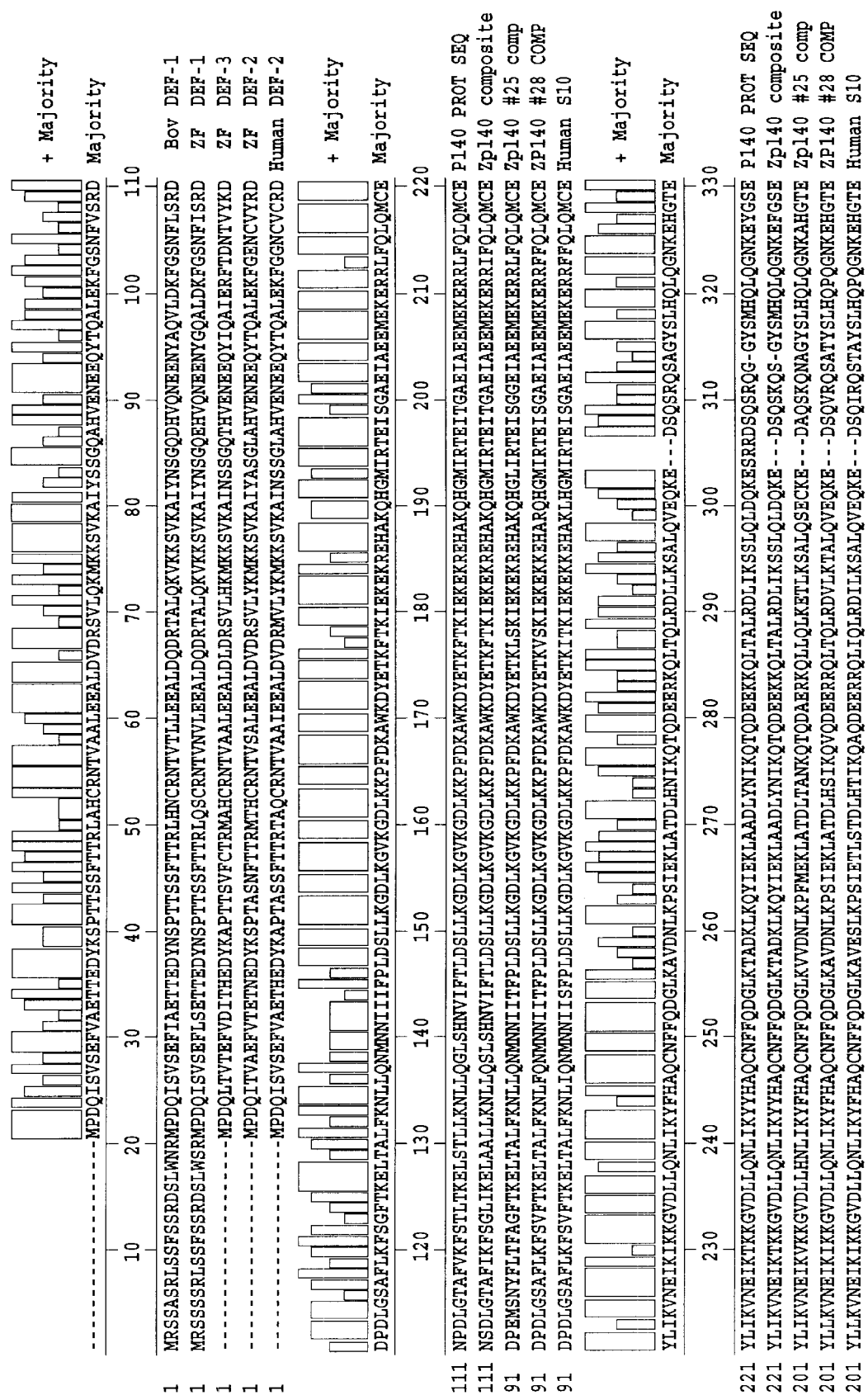
Figure 12B:
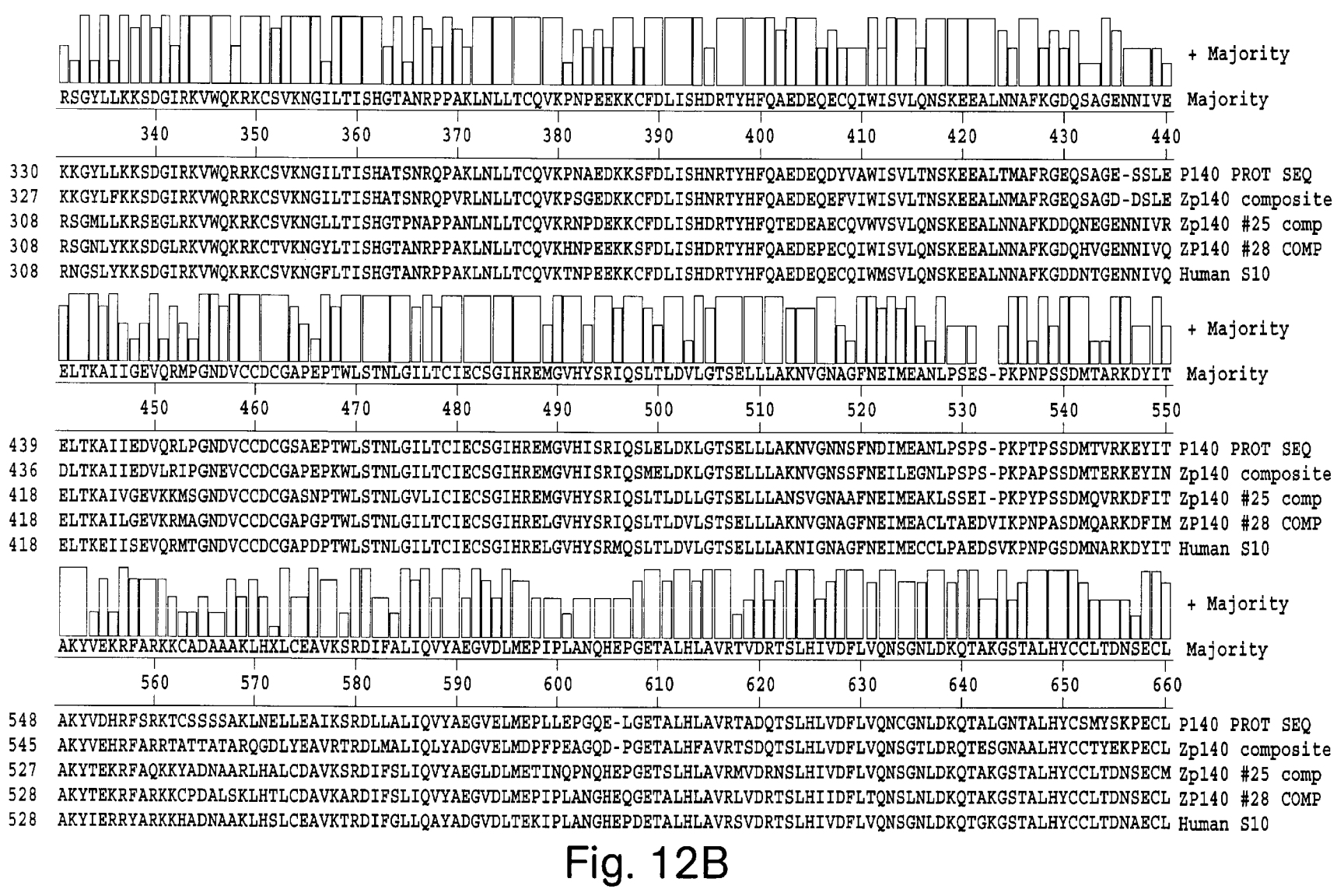
Figure 12C:
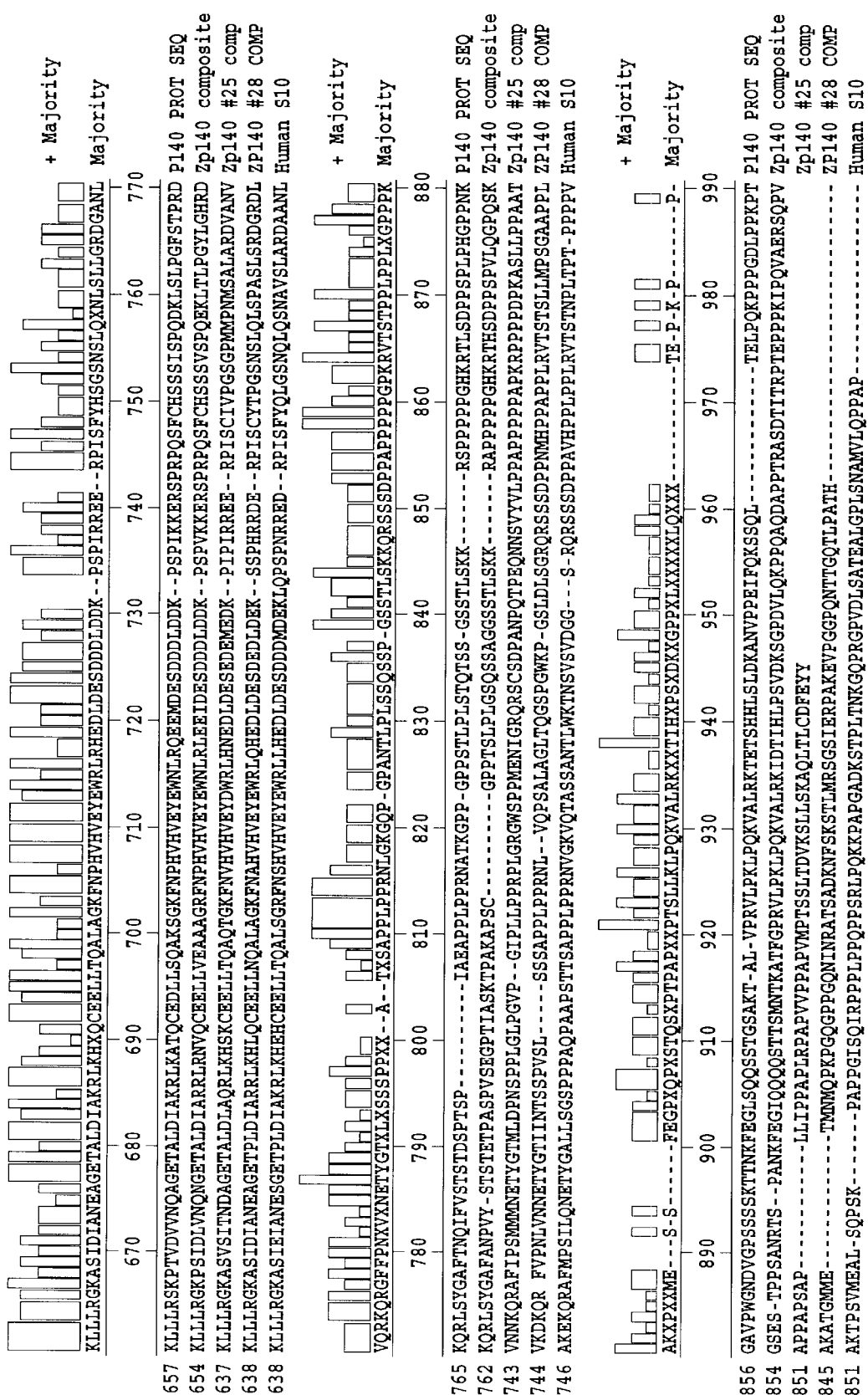
Figure 12D:
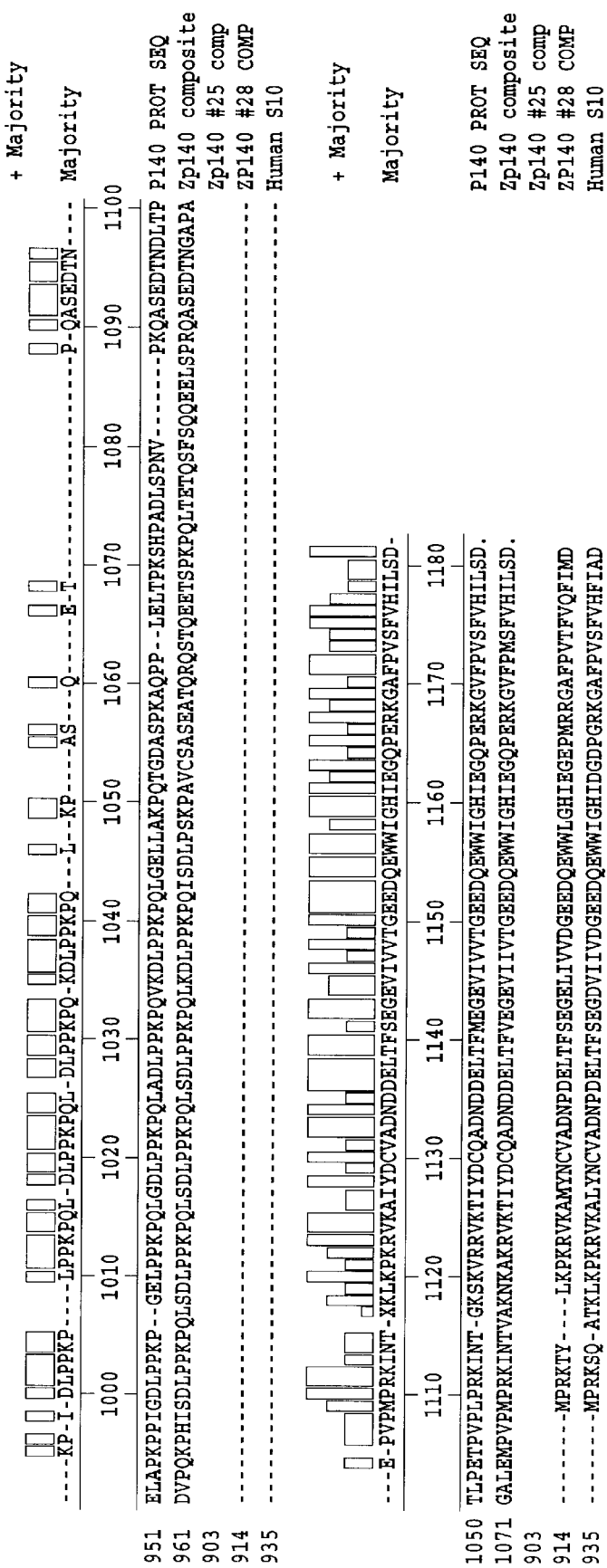

In other embodiments, the DEF-1 polypeptide has the above-identified domains and has an amino acid sequence which is at least about 60% (preferably at least about 70%, 71–74%, 75%, 80%, 90% or 95–99%) identical to the amino acid sequence of FIG. 3 (SEQ ID NO: 2) or FIG. 12 (SEQ ID NO: 4). In other embodiments, the DEF-1 polypeptide has an amino acid sequence which is at least about 60% (preferably at least about 70%, 71–74%, 75%, 80%, 90% or 95–99%) identical to the amino acid sequence of FIG. 3 (SEQ ID NO: 2) or FIG. 12 (SEQ ID NO: 4). In still another embodiment, the DEF-1 polypeptide has at least one biological activity of a DEF polypeptide. In yet another embodiment, the DEF-1 polypeptide: (i) has one or more of the above-identified domains, (ii) is encoded by the above-described nucleic acids, (iii) has the above-described amino acid sequence, and (iv) has at least one biological activity of a DEF polypeptide.

In one embodiment, the DEF-1 polypeptide is a protein of a calculated molecular weight of approximately 120–130 kDa, and preferably 125 kDa consisting of approximately 1129 amino acids and having the amino acid sequence shown in FIG. 3 (SEQ ID NO: 2) or FIG. 12 (SEQ ID NO: 4). Each DEF polypeptide consists of an amino terminal portion of about 350 amino acids (about amino acids 1–350 of the sequence shown in FIG. 2 (SEQ ID NO: 2) or FIG. 12 (SEQ ID NO: 4)) followed by four ankyrin repeats (each of about 20 amino acids in length), at least one SH3 binding site (each of about 10 amino acids), a proline-rich repeat of about 68 amino acids, a PH domain, a C2 domain of about 60 amino acids and an SH3 domain of about 50 amino acids.

In another embodiment, the DEF-1 polypeptide includes a C-terminal domain of the molecule. As used herein, a "C-terminal domain" is a polypeptide of about 100–300 amino acids, more preferably, about 150–250 amino acids, and most preferably 200 amino acids which includes at least one proline-rich repeat and at least one SH3 domain. Preferably, the C-terminal domain of DEF-1 has at least one of the above-identified domains and has an amino acid sequence which is at least about 60% (preferably at least about 70%, 71–74%, 75%, 80%, 90% or 95–99%) identical to the amino acid sequence of the last 200 amino acids of FIG. 3 (SEQ ID NO: 2) or FIG. 12 (SEQ ID NO: 4). In another embodiment, the C-terminal domain of DEF-1 has an amino acid sequence which is at least about 60% (preferably at least about 70%, 71–74%, 75%, 80%, 90% or 95–99%) identical to the amino acid sequence of the last 200 amino acids of FIG. 3 (SEQ ID NO: 2) or FIG. 12 (SEQ ID NO: 4). In still another embodiment, the C-terminal domain of DEF-1 has at least one biological activity of a DEF polypeptide, e.g., induces adipogenesis. In yet another embodiment, the C-terminal domain of DEF-1: (i) has one or more of the above-identified domains, (ii) the above-described amino acid sequence, and (iii) at least one biological activity of a DEF polypeptide.

In yet another aspect, the invention features nucleic acids encoding a DEF-2 polypeptide, as well as DEF-2 polypeptides. Such DEF-2 nucleic acids and polypeptides have at least one SH3 consensus binding sequence, at least one, preferably four ankyrin repeats, at least one zinc finger domain, at least one pleckstrin homology domain, at least one C2 domain, and at least one SH3 domain. In one embodiment, the DEF-2 polypeptide has the above-identified domains and is encoded by a nucleic acid which is at least about 60% (preferably at least about 61–65%, 70%, 80%, 90% or 95–99%) identical to the nucleotide sequence of FIG. 14 (SEQ ID NO: 6 or SEQ ID NO: 8). In another embodiment, the DEF-2 polypeptide is encoded by a nucleotide which is at least about 60% (preferably at least about 61–65%, 70%, 80%, 90% or 95–99%) identical to the nucleotide sequence of FIG. 14 (SEQ ID NO: 6 or SEQ ID NO: 8).

In other embodiments, the DEF-2 polypeptide has one or more the above-identified domains and has an amino acid sequence which is at least about 70% (preferably at least about 71–74%, 75%, 80%, 90% or 95–99%) identical to the amino acid sequence of FIG. 12 (SEQ ID NO: 7). In other embodiments, the DEF-2 polypeptide has an amino acid sequence which is at least about 60% (preferably at least about 70%, 71–74%, 75%, 80%, 90% or 95–99%) identical to the amino acid sequence of FIG. 12 (SEQ ID NO: 7). In still another embodiment, the DEF-2 polypeptide has at least one biological activity of a DEF polypeptide. In yet another embodiment, the DEF-2 polypeptide: (i) has one or more the above-identified domains, (ii) is encoded by the above-described nucleic acids, (iii) has the above-described amino acid sequence, and (iv) at least one biological activity of a DEF polypeptide.

In yet another aspect, the invention features nucleic acids encoding a DEF-3 polypeptide, and DEF-3 polypeptides. Such DEF-3 nucleic acid and polypeptide have at least one SH3 consensus binding sequence, at least one, preferably four ankyrin repeat, at least one zinc finger domain, at least one pleckstrin homology domain, and at least one C2 domain. In one embodiment, the DEF-3 polypeptide has the above-identified domains and is encoded by a nucleic acid which is at least about 60% (preferably at least about 61–65%, 70%, 80%, 90% or 95–99%) identical to the nucleotide sequence of FIG. 15 (SEQ ID NO: 9 or SEQ ID NO: 11). In another embodiment, the DEF-3 polypeptide is encoded by a nucleic acid which is at least about 60% (preferably at least about 61–65%, 70%, 80%, 90% or 95–99%) identical to the nucleotide sequence of FIG. 15 (SEQ ID NO: 9 or SEQ ID NO: 11).

In other embodiments, the DEF-3 polypeptide has the above-identified domains and has an amino acid sequence which is at least about 70% (preferably at least about 71–74%, 75%, 80%, 90% or 95–99%) identical to the amino acid sequence of FIG. 12 (SEQ ID NO: 10). In other embodiments, the DEF-3 polypeptide has an amino acid sequence which is at least about 60% (preferably at least about 70%, 71–74%, 75%, 80%, 90% or 95–99%) identical to the amino acid sequence of FIG. 12 (SEQ ID NO: 10). In still another embodiment, the DEF-3 polypeptide has at least one biological activity of a DEF polypeptide. In yet another embodiment, the DEF-3 polypeptide: (i) has one or more of the above-identified domains, (ii) is encoded by the above-described nucleic acids, (iii) has the above-described amino acid sequence, and (iv) at least one biological activity of a DEF polypeptide.

In one embodiment, DEF polypeptides include a src SH3 consensus binding sequence. As used herein, the language "src SH3 consensus binding sequence" is intended to include class I and, preferably, class II peptides which associate with an SH3 domain. The peptide ligand therefore has three spines, two contacting the SH3 domain, and the third stabilizing the PPII helix. The core ligand is a seven residue peptide containing the consensus X-P-p-X-P, where X is an aliphatic residue and the two conserved prolines (P) are necessary for high affinity binding. The intervening scaffolding residue (p) also tends to be a proline. Each X-P pair fits into a hydrophobic pocket formed by conserved SH3 aromatic residues (sites 1 and 2), providing the principal binding energy. A third pocket (site 3) is more variable, although it frequently binds an arginine. Residues adjacent to the prolines also form contacts within the SH3 sequence and these interactions determine the specificity between a protein and a particular SH3. For example, the arginine in "RPLPXXP" forms a salt bridge with aspartate 99 of pp60$^{c-src}$. However the C-terminal arginine in the sequence "AFAPPLPRR" contacts the identical aspartate in pp60$^{c-src}$. This term is intended to encompass proteins that interact with with SH3 domains in either a "plus" or "minus" orientation (named "class I" and "class II" binding, respectively; Yu et al. (1994) *Cell* 76:933–945; Lim et al. (1994) *Nature* 372:375–379). In one embodiment, the src SH3 consensus binding sequence has an amino acid sequence of up to 10 amino acids, preferably about 4–8 amino acids, most preferably about 6 amino acids and contains about amino acids 794–799, 803–809, 829–835, 895–901 or 993–999 of FIG. 3 (SEQ ID NO: 2), amino acids 827–833, 892–898 or 1005–1011 of FIG. 12 (SEQ ID NO: 4), amino acids 777–782 or 822–828 of FIG. 12 (SEQ ID NO: 7), and amino acids 780–785, 829–834, 834–840 or 867–873 of FIG. 12 (SEQ ID NO: 10).

Figure 7A:
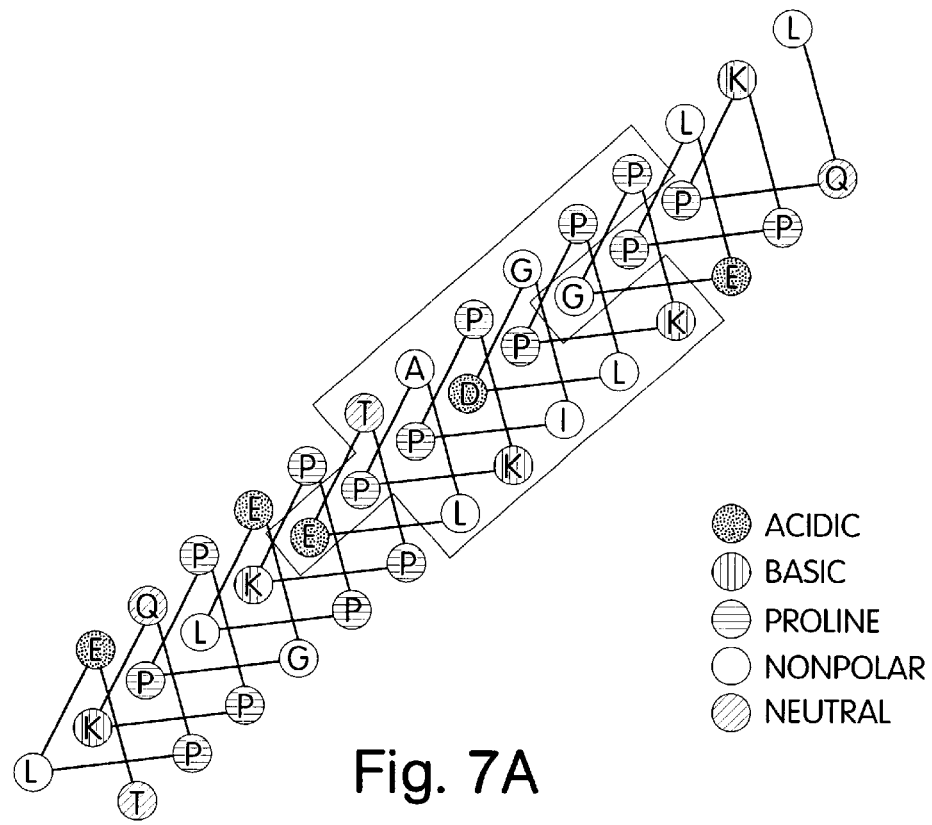
FIGS. 7A and 7B are schematic representations of the putative left-handed polyproline type II helix configuration of bovine DEF-1 proline-rich motifs SEQ ID NO: 2 (amino acids 934–1001).
Figure 7B:
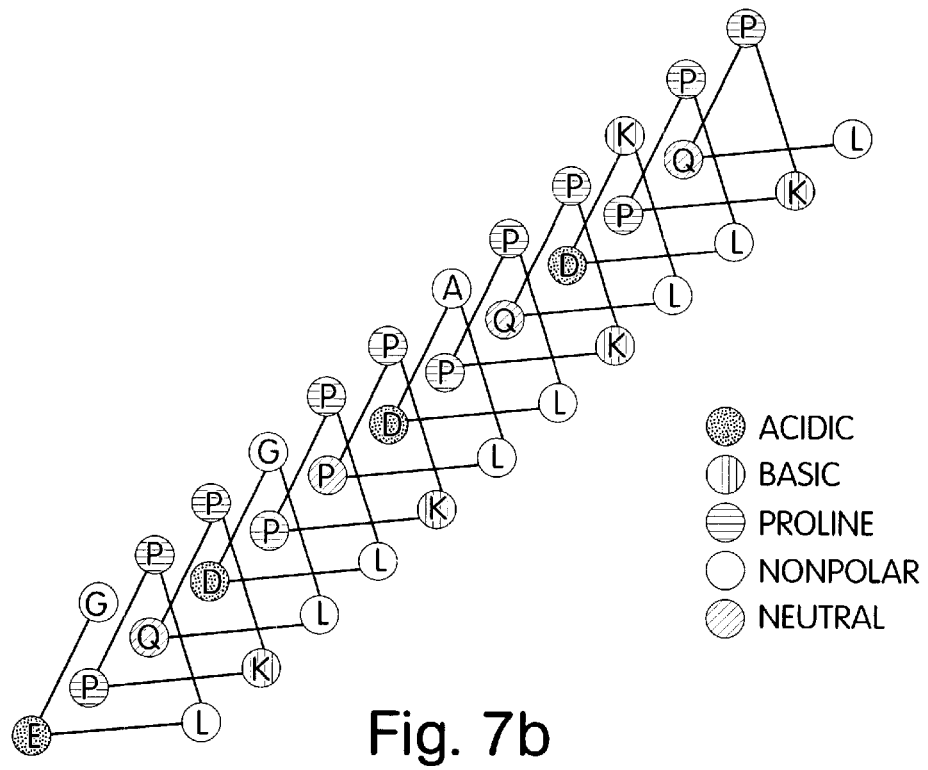

In yet another embodiment, the DEF polypeptides include at least one motif having proline-rich stretch located between the SH3 domain and the predicted SH3 binding sites in DEF-1. This region can be subdivided into six tandem repeats centered on the consensus sequence "GDLP-PKP". The number of prolines in this repeat suggests that this region forms a left-handed polyproline type II helix (Williamson, M. P. (1994) *Biochemical Journal* 297:249–60). Accordingly, the four C-terminal repeats form a trigonal prism with an acidic "edge", a basic edge, and an uncharged edge (FIGS. 7A–7B). In one embodiment, the proline-rich repeat has an amino acid sequence of up to 75 amino acids, preferably about 50–70 amino acids, most preferably about 65 amino acids and contains about amino acids 934–1001 of FIG. 3 (SEQ ID NO: 2), or amino acids 944–1013 of FIG. 12 (SEQ ID NO: 4).

In still another embodiment, the DEF polypeptides include at least one motif having homology to an ankyrin repeat. The term "ankyrin repeat" refers to an amino acid motif, preferably about 33 amino acids in length, which is typically repeated several times in an amino acid sequence, e.g., a motif repeated 24 times in the protein ankyrin, and which is believed to be involved in directing the protein to the inner face of the plasma membrane (Hatada et al., 1992 *Proc. Natl. Acad. Sci. USA* 89, 2489–2493; Michaely and Bennett, 1993; Lambert and Bennett, 1993). Ankyrin repeats have been found in several other proteins such as the transcription factor regulator, Iκ-B (Hay, 1993), and the protooncogene Bcl-3 (Ohno et al., 1990 Cell 60: 991). In one embodiment, the ankyrin repeat sequence has an amino acid sequence of up to 25 amino acids, preferably about 10–20 amino acids, most preferably about 18–19 amino acids and contains about amino acids 356–374, 604–623, 640–659 or 672–692 of FIG. 3 (SEQ ID NO: 2), amino acids 353–371, 601–620, 637–656, or 669–689 of FIG. 12 (SEQ ID NO: 4), amino acids 334–352, 585–604, 621–640, or 653–673 of FIG. 12 (SEQ ID NO: 7), and amino acids 334–352, 584–603, 620–639, or 652–672 of FIG. 12 (SEQ ID NO: 10).

In yet another embodiment, the DEF polypeptides include a pleckstrin homology (PH) domain. As used herein, a PH domain is a protein module of approximately 100 amino acids typically located at the carboxy-terminal of proteins involved in signal transduction processes (See also Haslam et al. (1993) supra; Mayer et al. (1993) supra; Musacchio et al. (1993) *TIBS* 28:343–348). Typically, PH domains are very divergent and do not occupy a specific positions in molecules; alignments of PH domains show six conserved blocks, each containing several conserved hydrophobic residues which to form a folded structure comprising seven to eight β-strands, most likely in one or two β-sheets, and a single helix (Musacchio et al. supra). PH domains have been identified in kinases and also in Vav, Dbl, Bcr, yeast cdc24, Ras-GAP, DM GAP, Ras-GRF, Sos PH, protein kinase C α, phospholipase C-δ1 (Burgering, B. M. T. and P. J. Coffer (1995) supra; Franke et al. (1995) supra; Coffer, P. J. and J. R. Woodgett (1991) supra), the serine/threonine kinase known variously as protein kinase B, Akt and Rac among others. The PH domain of β adrenergic receptor kinase may be involved in binding to G protein βγ complexes (Koch et al. (1993) *J. Biol. Chem.* 268:8256–8260). PH domains have been implicated in the binding to membranes containing PI 4,5-bisphosphate (Lemmon et al. (1995) supra), as well as to the binding of several proteins βγ subunits (Gβγ) of heterotrimeric G proteins (Touhara et al. (1994) supra; Satoshi et al. (1994) supra; Lemmon et al. (1995) supra), protein kinase C (17), WD motifs (18). In addition, the isolated PH domain of PLCg1 has been shown to specifically interact with high affinity with PI-4,5 P2 and D-myo-inositol 1,4,5 trisphosphate (Ins(1,4,5) P3) (Lemmon et al. (1995) supra). In one embodiment, the PH sequence has an amino acid sequence of up to 150 amino acids, preferably about 80–120 amino acids, most preferably about 100 amino acids and contains about amino acids 326–419 of FIG. 3 (SEQ ID NO: 2), amino acids 323–416 of FIG. 12 (SEQ ID NO: 4), amino acids 304–397 of FIG. 12 (SEQ ID NO: 7), or amino acids 303–397 of FIG. 12 (SEQ ID NO: 10).

In another embodiment, the DEF polypeptides include a zinc finger domain. As used herein the term "zinger finger domain" refers to a structural motif present in a family of transcription factors. An illustration of this class are members of the GATA family of zinc finger-containing transcription factors, e.g., GATA-1 (Trainor, C. D. et al. *Nature* 343:92–96(1990). Examples of eukaryotic proteins having a similar zinc finger motif include GCS 1 (Ireland et al., 1994), ROKα and ARFlGAP (Leung et al., 1995; Cukierman et al., 1995). This term is also intended to include motiffs that interact with G proteins and affect GTPase activity. In one embodiment, the zinger finger domain has an amino acid sequence of up to about 35 amino acids, preferably about 20–30 amino acids, most preferably about 25 amino acids and contains about amino acids 457–480 of FIG. 3 (SEQ ID NO: 2), amino acids 454–477 of FIG. 12 (SEQ ID NO: 4), amino acids 436–459 of FIG. 12 (SEQ ID NO: 7), or amino acids 436–459 of FIG. 12 (SEQ ID NO: 10).

As used herein the language "SH3 domain" refers to a domain of approximately 60 amino acids in length named Src homology 3 which has been identified in numerous signal transduction proteins (Pawson, T. and J. Schlessinger (1993) *J. Curr. Bio.* 3:434–442; Courtneidge et al. (1994) *Trends Cell Biol.* 4:345–347; Pawson, T. (1995) *Nature* 373: 573–580). These domains interact with other signal transduction proteins. In one embodiment, the SH3 domain has an amino acid sequence of up to about 100 amino acids, preferably about 40–80 amino acids, most preferably about 60 amino acids and contains about amino acids 1073–1123 of FIG. 3 (SEQ ID NO: 2), amino acids 1095–1145 of FIG. 12 (SEQ ID NO: 4), or amino acids 926–976 of FIG. 12 (SEQ ID NO: 7).

As used herein the language "C2 domain" is intended to include a domain believed to be involved in lipid binding, primarily phosphatidylinositol binding. In one embodiment, the C2 domain has an amino acid sequence of up to about 70 amino acids, preferably about 50–65 amino acids, most preferably about 60 amino acids and contains about amino acids 498–557 of FIG. 3 (SEQ ID NO: 2), amino acids 495–554 of FIG. 12 (SEQ ID NO: 4), amino acids 477–537 of FIG. 12 (SEQ ID NO: 7), or amino acids 477–536 of FIG. 12 (SEQ ID NO: 10).

In another embodiment, a portion of a DEF protein, e.g., a src SH3 binding sequence, may antagonize the biological/biochemical activities of a naturally occurring DEF protein by acting as a dominant negative regulator of a DEF protein or a fragment therof. In another embodiment, a portion of a DEF protein, e.g., a zinc finger domain, may activate the biological/biochemical activities of a naturally occurring DEF protein.

Other aspects of the present invention relate to nucleic acids encoding DEF polypeptides, the DEF polypeptides themselves (including various fragments containing domains), antibodies immunoreactive with DEF proteins, and preparations of such compositions. Moreover, the present invention provides diagnostic and therapeutic assays and reagents for detecting and treating disorders involving, for example, aberrant expression (or loss thereof) of DEF, DEF-interacting molecules (particularly src SH3 domain-containing proteins), or signal transducers thereof.

In addition, drug discovery assays are provided for identifying agents which can modulate the biological function of DEF polypeptides, such as by altering the binding of DEF molecules to DEF interacting molecules (particularly src SH3 domain-containing proteins) or other intracellular targets (for example, cytoskeletal proteins). Such agents can be useful therapeutically to alter diseases dependent on cellular gene expression, cytoskeletal architecture, protein trafficking and endocytosis, cell adhesion, migration, proliferation and differentiation.

Various aspects of the invention are described in further detail in the following subsections:

I. Nucleic Acids

As described below, one aspect of the invention pertains to isolated nucleic acids comprising nucleotide sequences encoding DEF polypeptides, and/or equivalents of such nucleic acids.

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject mammalian DEF polypeptides preferably includes no more than 10 kilobases (kb) of nucleic acid sequence which naturally immediately flanks the mammalian DEF gene in genomic DNA, more preferably no more than 5kb of such naturally occurring flanking sequences, and most preferably less than 1.5kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "equivalent" is understood to include nucleotide sequences encoding functionally equivalent DEF polypeptides or functionally equivalent polypeptides having a DEF bioactivity refer to molecules such as proteins and peptides which are capable of mimicking or antagonizing all or a portion of the biological/biochemical activities of a DEF protein. In addition a polypeptide has bioactivity if it is a specific agonist or antagonist (competitor) of a naturally-occurring form of a mammalian DEF protein. In one embodiment a DEF protein of the present invention has a DEF bioactivity if it is capable of binding to a src SH3 domain, a polypeptide capable of anchoring cytoskeletal elements to the plasma membrane, a polypeptide capable of modulating gene expression or G protein activity, e.g., GTPase activity, a polypeptide capable of inducing PPARγ mRNA and protein expression. Equivalent nucleotide sequences will include sequences that differ by one or more nucleotide substitutions, additions or deletions, such as allelic variants; and will, therefore, include sequences that differ from the nucleotide sequence of the DEF gene shown in FIG. 2 (SEQ ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11) due to the degeneracy of the genetic code.

Other equivalents of DEF include structural equivalents. Structural equivalents preferably comprise a motif, e.g., a src SH3 consensus binding sequence, a zinc finger domain, a proline-rich repeat, an SH3 domain, and an ankyrin repeat. A portion of DEF polypeptide is at least about 5, 10, 15, 20, 25, 30, 40, 50, 60, 70, 100, 150, 200, 250, 300, 350, 400, 450, 500, 550, 600, 650, 700, 750, 800, 850–1125 amino acid residues in length, preferably at least about 100–300 amino acid residues in length, more preferably at least about 140–260 amino acid residues in length, and most preferably at least about 200 amino acid residues in length corresponding to a protein having at least 80% the amino acid sequence shown in FIG. 3, (SEQ ID NO: 2), FIG. 12 (SEQ ID NO: 4, SEQ ID NO: 7, or SEQ ID NO: 10). Preferred nucleotides of the present invention include nucleic acid molecules comprising a nucleotide sequence provided in FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11), fragments thereof or equivalents thereof. Most preferred portions of the nucleic acids and DEF polypeptides include at least one, more preferable two motifs. For example, a preferred portion of a DEF polypeptide include at least one proline-rich motiff and at least one SH3 domain.

One embodiment the present invention features an isolated DEF nucleic acid molecule. In a preferred embodiment the DEF nucleic acid molecule of the present invention is isolated from a vertebrate organism. More preferred DEF nucleic acids are mammalian. Particularly preferred DEF nucleic acids are human or bovine.

A particularly preferred DEF nucleic acid is shown in SEQ ID NO:1, SEQ ID NO: 3 or SEQ ID NO: 5, SEQ ID NO: 6 or SEQ ID NO: 8, SEQ ID NO: 9 or SEQ ID NO: 11. The term DEF nucleic acid is also meant to include nucleic acic sequences which are homologous to the sequence shown in SEQ ID NO:1, SEQ ID NO: 3 or SEQ ID NO: 5, SEQ ID NO: 6 or SEQ ID NO: 8, SEQ ID NO: 9 or SEQ ID NO: 11 or a sequence which is complementary to that shown in SEQ ID NO:1, SEQ ID NO: 3 or SEQ ID NO: 5, SEQ ID NO: 6 or SEQ ID NO: 8, SEQ ID NO: 9 or SEQ ID NO: 11.

"Complementary" sequences as used herein refer to sequences which have sufficient complementarity to be able to hybridize, forming a stable duplex.

As used herein, the term "specifically hybridizes" refers to the ability of a nucleic acid probe/primer of the invention to hybridize to at least 15 consecutive nucleotides of a DEF gene, such as a DEF sequence designated in SEQ ID NO: 1, SEQ ID NO: 3 or SEQ ID NO: 5, SEQ ID NO: 6 or SEQ ID NO: 8, SEQ ID NO: 9 or SEQ ID NO: 11, or a sequence complementary thereto, or naturally occurring mutants thereof, such that it has less than 15%, preferably less than 10%, and more preferably less than 5% background hybridization to a cellular nucleic acid (e.g., mRNA or genomic DNA) encoding a protein other than a DEF protein, as defined herein.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the mammalian DEF sequences of the present invention.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

The comparison of sequences and determination of percent homology between two sequences can be accomplished using a mathematical algorithim. Preferably, the alignment can be performed using the Clustal Method. Multiple alignment paramethers include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

Additional non-limiting example of a mathematical algorithim utilized for the comparison of sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs (version 2.0) of Altschul, et al. (1990) J. Mol. Biol. 215:403–10. BLAST nucleotide searches can be performed performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Research 25(17):3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithim utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The term "ortholog" refers to genes or proteins which are homologs via speciation, e.g., closely related and assumed to have common descent based on structural and functional considerations. Orthologous proteins function as recognizably the same activity in different species. The term "paralog" refers to genes or proteins which are homologs via gene duplication, e.g., duplicated variants of a gene within a genome. See also, Fritch, W M (1970) Syst Zool 19:99–113.

Thus, nucleic acids having a sequence that differs from the nucleotide sequences shown in SEQ ID No:1 due to degeneracy in the genetic code are also within the scope of the invention. Such nucleic acids encode functionally equivalent peptides (i.e., a peptide having a biological activity of a mammalian DEF polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a mammalian DEF polypeptide. However, it is expected that DNA sequence polymorphisms that do lead to changes in the amino acid sequences of the subject DEF polypeptides will exist among mammalians. One skilled in the art will appreciate that these variations in one or more nucleotides (e.g., up to about 3–5% of the nucleotides) of the nucleic acids encoding polypeptides having an activity of a mammalian DEF polypeptide may exist among individuals of a given species due to natural allelic variation.

In a preferred embodiment a DEF nucleic acid is at least about 85% homologous to the nucleic acid sequence shown in FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11) or its complement. In more preferred embodiments a DEF nucleic acid is at least about 90–99% homologous to the nucleic acid sequence shown in FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11). In particularly preferred embodiments a DEF nucleic acid sequence is identical to the nucleotide sequence of FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11).

In another embodiment a DEF nucleic acid includes a nucleic acid sequence at least 70% homologous to the nucleotide sequence of FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11). In a preferred embodiment a DEF nucleic acid contains a sequence at least about 85% homologous to the nucleotide sequence of FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11). In a more preferred embodiment a DEF nucleic acid of the present invention contains a nucleotide sequence at least about 90–99% homologous to the nucleotide sequence of FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11). In a particularly preferred embodiment a DEF nucleic acid contains a sequence identical to the nucleotide sequence of FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11).

In another embodiment a DEF nucleic acid includes a nucleic acid sequence at least 80% homologous to the nucleotide sequence of FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11). In a preferred embodiment a DEF nucleic acid contains a sequence at least about 85% homologous to the nucleotide sequence of FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11). In a more preferred embodiment a DEF nucleic acid of the present invention contains a nucleotide sequence at least about 90% homologous to the nucleotide sequence of FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11). In a particularly preferred embodiment a DEF nucleic acid contains a sequence identical to the nucleotide sequence of FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11).

In one embodiment a DEF nucleic acid contains a nucleotide sequence at least about 70% homologous to the sequence of FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11) and encodes a polypeptide with a DEF bioactivity, e.g., induces adipogenesis or neurogenesis. In a preferred embodiment a DEF nucleic acid contains a nucleotide sequence at least about 80% homologous to the sequence of FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11) and encodes a polypeptide with a DEF bioactivity. In a more preferred embodiment a DEF nucleic acid contains a nucleotide sequence at least about 90–99% homologous to the sequence of FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11) and encodes a polypeptide with a DEF bioactivity. In a particularly preferred embodiment a DEF nucleic acid contains a nucleotide sequence identical to the sequence of FIG. 2 (SEQ. ID NO:1), FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11) and encodes a polypeptide with a DEF bioactivity.

In a preferred embodiment a DEF nucleic acid is at least about 90% homologous to the coding sequence shown in FIG. 2 (SEQ ID NO:1), FIG. 13 (SEQ ID NO: 3), FIG. 14 (SEQ ID NO: 6), or FIG. 15 (SEQ ID NO: 9) or its complement. In more preferred embodiments a DEF nucleic acid is at least about 96–97% homologous to the coding sequence shown in FIG. 2 (SEQ ID NO:1), FIG. 13 (SEQ ID NO: 3), FIG. 14 (SEQ ID NO: 6), or FIG. 15 (SEQ ID NO: 9). In particularly preferred embodiments a DEF nucleic acid sequence is identical to the coding sequence of FIG. 2 (SEQ ID NO:1), FIG. 13 (SEQ ID NO: 3), FIG. 14 (SEQ ID NO: 6), or FIG. 15 (SEQ ID NO: 9).

A DEF nucleic molecucle can include an open reading frame encoding one of the mammalian DEF polypeptides of the present invention, including both exon and (optionally) intron sequences. A "recombinant gene" refers to nucleic acid encoding a mammalian DEF polypeptide and comprising mammalian DEF-encoding exon sequences, though it may optionally include intron sequences which are either derived from a chromosomal mammalian DEF gene or from an unrelated chromosomal gene. The term "intron" refers to a DNA sequence present in a given mammalian DEF gene which is not translated into protein and is generally found between exons.

In certain embodiments the subject DEF nucleic acid molecules include the 5' and 3' untranslated sequences which flank the gene, i.e., noncoding sequences, and do not encode for amino acids of a DEF polypeptide. In a preferred embodiment a DEF nuceleic acid molecule contains the coding region of SEQ ID NO:1, SEQ ID NO: 3, SEQ ID NO: 6, or SEQ ID NO: 9.

"Transcriptional regulatory sequence" is a term used throughout the specification to refer to DNA sequences, such as initiation signals, enhancers, and promoters, which induce or control transcription of protein coding sequences with which they are operatively linked. In preferred embodiments, transcription of one of the recombinant mammalian DEF genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of DEF proteins.

Another aspect of the invention provides a nucleic acid which hybridizes under stringent conditions to a nucleic acid represented by FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11) or its complement. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In a particularly preferred embodiment, a DEF nucleic acid of the present invention will bind to SEQ. ID NO:1, SEQ ID NO: 3 or SEQ ID NO: 5, SEQ ID NO: 6 or SEQ ID NO: 8, or SEQ ID NO: 9 or SEQ ID NO: 11 under stringent conditions.

As used herein, the term "specifically hybridizes" or "specifically detects" refers to the ability of a nucleic acid molecule of the invention to hybridize to at least approximately 6, 12, 20, 30, 50, 100, 150, 200, or 300 consecutive nucleotides of a vertebrate, preferably mammalian, DEF gene, such as a DEF sequence designated in SEQ. ID NO:1, SEQ ID NO: 3 or SEQ ID NO: 5, SEQ ID NO: 6 or SEQ ID NO: 8, or SEQ ID NO: 9 or SEQ ID NO: 11, or a sequence complementary thereto, or naturally occurring mutants thereof, such that it shows more than 10 times more hybridization, preferably more than 100 times more hybridization, and even more preferably more than 100 times more hybridization than it does to to a cellular nucleic acid (e.g., mRNA or genomic DNA) encoding a protein other than a vertebrate, preferably mammalian, DEF protein as defined herein. In a particularly preferred embodiment a DEF nucleic acid fragment specifically detects a DEF, and not dynamin or dynamin-related sequences.

In a further embodiment a DEF nucleic acid sequence encodes a vertebrate DEF polypeptide. Preferred nucleic acids of the present invention encode a DEF polypeptide which includes a polypeptide sequence corresponding to all or a portion of amino acid residues of SEQ ID NO:2, SEQ ID NO: 4, SEQ ID NO: 7, or SEQ ID NO: 10, e.g., at least 5, 10, 15, 20, 25, 30, 40, 50, 60, 70, 100, 150, 200, 250, 300, 350, 400, 450, 500, 550, 600, 650, 700, 750, 800, 850–1125 amino acid residues of that region. Genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "nucleic acid sequence encoding a vertebrate DEF polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same bioactivity.

In one embodiment a DEF nucleic acid encodes a polypeptide sequence at least 85% homologous to the sequence shown in SEQ ID NO: 2, SEQ ID NO: 4, SEQ ID NO: 7 or SEQ ID NO: 10. In a preferred embodiment a DEF nucleic acid encodes a sequence at least 91–99% homologous to the sequence shown in SEQ ID NO: 2, SEQ ID NO: 2, SEQ ID NO: 4, SEQ ID NO: 7 or SEQ ID NO: 10. In a more preferred embodiment a DEF nucleic acid encodes a sequence at least about 95% homologous to the sequence shown in SEQ ID NO: 2, SEQ ID NO: 2, SEQ ID NO: 4, SEQ ID NO: 7 or SEQ ID NO: 10. In a particularly preferred embodiment the subject DEF nucleic acid molecule encodes the polypeptide shown in SEQ ID NO. 2, SEQ ID NO: 2, SEQ ID NO: 4, SEQ ID NO: 7 or SEQ ID NO: 10.

In another embodiment a DEF nucleic acid molecule encodes a polypeptide with a DEF bioactivity and contains a src consensus binding sequence, at least one ankyrin repeat, a zinc finger domain, a proline-rich repeat, a C2 domain and a PH domain.

The subject DEF nucleic acid sequences allow for the generation of nucleic acid fragments (e.g., probes and primers) designed for use in identifying and/or cloning DEF homologs in other cell types, e.g. from other tissues, as well as DEF homologs from other mammalian organisms. For instance, the present invention also provides a nucleic acid fragment that can be used as a primer. The fragment can comprise a substantially purified oligonucleotide, containing a region of nucleotide sequence that hybridizes under stringent conditions to at least approximately 12, preferably 25, more preferably 40, 50 or 75 consecutive nucleotides of sense or anti-sense sequence of SEQ ID NO:1, SEQ. ID NO:1, SEQ ID NO: 3 or SEQ ID NO: 5, SEQ ID NO: 6 or SEQ ID NO: 8, or SEQ ID NO: 9 or SEQ ID NO: 11, or naturally occurring mutants thereof. For instance, primers based on the nucleic acid represented in SEQ ID NO:1, SEQ. ID NO:1, SEQ ID NO: 3 or SEQ ID NO: 5, SEQ ID NO: 6 or SEQ ID NO: 8, or SEQ ID NO: 9 or SEQ ID NO: 11 can be used in PCR reactions to clone DEF homologs.

In another embodiment, a DEF nucleic acid fragment is an oligonucleotide probe which specifically detects a DEF nucleic acid relative to a dynamin or dynamin-related nucleic acid sequences. In a preferred embodiment the subject oligonucleotide hybridizes under stringent conditions to at least 6 consecutive nucleotides encoding the DEF nucleic acid (SEQ ID NO:1, SEQ. ID NO:1, SEQ ID NO: 3 or SEQ ID NO: 5, SEQ ID NO: 6 or SEQ ID NO: 8, or SEQ ID NO: 9 or SEQ ID NO: 11).

In preferred embodiments, the probe further contains a label group capable of detection, e.g. the label group can be a radioisotope, fluorescent compound, enzyme, or enzyme co-factor. Probes based on the subject DEF sequences can also be used to detect transcripts or genomic sequences encoding the same or homologous proteins.

As discussed in more detail below, the probes of the present invention can also be used as a part of a diagnostic test kit for identifying cells or tissue which misexpress a DEF protein, such as by measuring a level of a DEF-encoding nucleic acid in a sample of cells from a patient; e.g. detecting DEF mRNA levels or determining whether a genomic DEF gene has been mutated or deleted. Briefly, nucleotide probes can be generated from the subject DEF genes which facilitate histological screening of intact tissue and tissue samples for the presence (or absence) of DEF-encoding transcripts. Similar to the diagnostic uses of anti-DEF antibodies, the use of probes directed to DEF messages, or to genomic DEF sequences, can be used for both predictive and therapeutic evaluation of allelic mutations which might be manifest in certain disorders. Used in conjunction with immunoassays as described herein, the oligonucleotide probes can help facilitate the determination of the molecular basis for a disorder which may involve some abnormality associated with expression (or lack thereof) of a DEF protein. For instance, variation in polypeptide synthesis can be differentiated from a mutation in a coding sequence.

Another aspect of the invention relates to the use of isolated DEF nucleic acids in "antisense" therapy. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject DEF proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a mammalian DEF protein. Alternatively, the antisense construct is an oligonucleotide probe which is generated ex vivo and which, when introduced into the cell causes inhibition of expression by hybridizing with the mRNA and/or genomic sequences of a mammalian DEF gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) Biotechniques 6:958–976; and Stein et al. (1988) Cancer Res 48:2659–2668.

Antisense approaches involve the design of oligonucleotides (either DNA or RNA) that are complementary to DEF mRNA. The antisense oligonucleotides will bind to the DEF mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of a DEF gene could be used in an antisense approach to inhibit translation of endogenous DEF mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of DEF mRNA, antisense nucleic acids should be at least six nucleotides in length, and are preferably oligonucleotides ranging from 6 to about 50 nucleotides in length. In certain embodiments, the oligonucleotide is at least 10 nucleotides, at least 17 nucleotides, at least 25 nucleotides, or at least 50 nucleotides.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc. While antisense nucleotides complementary to the DEF coding region sequence could be used, those complementary to the transcribed untranslated region are most preferred.

The antisense molecules can be delivered to cells which express the DEF in vivo or in vitro. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

Since, it is often difficult to achieve intracellular concentrations of the antisense sufficient to suppress translation on endogenous mRNAs, a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous DEF transcripts and thereby prevent translation of the DEF mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpesvirus vectors may be used), in which case administration may be accomplished by another route (e.g., systematically).

Ribozyme molecules designed to catalytically cleave DEF mRNA transcripts can also be used to prevent translation of DEF mRNA and expression of DEF. (See, e.g., PCT International Publication WO90/11364, published Oct. 4, 1990; Sarver et al., 1990, Science 247:1222–1225). While ribozymes that cleave mRNA at site specific recognition sequences can be used to destroy DEF mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are numerous potential hammerhead ribozyme cleavage sites within the nucleotide sequence of human DEF cDNA. Preferably the ribozyme is engineered so that the cleavage recognition site is located near the 5' end of the DEF mRNA; i.e., to increase efficiency and minimize the intracellular accumulation of non-functional mRNA transcripts.

Ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in DEF.

As in the antisense approach, the ribozymes can be composed of modified oligonucleotides (e.g. for improved stability, targeting, etc.) and should be delivered to cells which express the DEF in vivo e.g., T cells. A preferred method of delivery involves using a DNA construct "encoding" the ribozyme under the control of a strong constitutive pol III or pol II promoter, so that transfected cells will produce sufficient quantities of the ribozyme to destroy endogenous DEF and inhibit translation. Because ribozymes unlike antisense molecules, are catalytic, a lower intracellular concentration is required for efficiency.

Endogenous DEF gene expression can also be reduced by inactivating or "knocking out" the DEF gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional DEF (or a completely unrelated DNA sequence) flanked by DNA homologous to the endogenous DEF gene (either the coding regions or regulatory regions of the DEF gene) can be used, with or without a selectable marker and/or a negative selectable marker, to transfect cells that express DEF in vivo. Insertion of the DNA construct, via targeted homologous recombination, results in inactivation of the DEF gene. Such approaches are particularly suited in the generation of animal offspring with an inactive DEF (e.g., see Thomas & Capecchi 1987 and Thompson 1989, supra). However this approach can be adapted for use in humans provided appropriate delivery means are used.

Alternatively, endogenous DEF gene expression can be reduced by targeting deoxyribonucleotide sequences complementary to the regulatory region of the DEF gene (i.e., the DEF promoter and/or enhancers) to form triple helical structures that prevent transcription of the DEF gene in target cells in the body. (See generally, Helene, C. 1991, Anticancer Drug Des., 6(6):569–84; Helene, C., et al., 1992, Ann, N.Y. Accad. Sci., 660:27–36; and Maher, L. J., 1992, Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

DEF nucleic acids can be obtained from mRNA present in any of a number of eukaryotic cells. It should also be possible to obtain nucleic acids encoding mammalian DEF polypeptides of the present invention from genomic DNA from both adults and embryos. For example, a gene encoding a DEF protein can be cloned from either a cDNA or a genomic library in accordance with protocols described herein, as well as those generally known to persons skilled in the art. Examples of tissues and/or libraries suitable for isolation of the subject nucleic acids include T cells, among others. A cDNA encoding a DEF protein can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a mammalian DEF protein can also be cloned using established polymerase chain reaction techniques in accordance with the nucleotide sequence information provided by the invention. The nucleic acid of the invention can be DNA or RNA. A preferred nucleic acid is a cDNA represented by a sequence shown in SEQ ID NO:1, SEQ. ID NO:1, SEQ ID NO: 3 or SEQ ID NO: 5, SEQ ID NO: 6 or SEQ ID NO: 8, or SEQ ID NO: 9 or SEQ ID NO: 11.

Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Any of the subject nucleic acids can also be obtained by chemical synthesis. For example, nucleic acids of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988) *Nucl. Acids Res.* 16:3209, methylphosphonate olgo-nucleotides can be prepared by use of controlled pore glass polymer supports (Sarin et al., 1988, Proc. Natl. Acad. Sci. U.S.A. 85:7448–7451), etc. Other techniques for chemically synthesizing oligodeoxyribonucleotides and oligoribonucleotides well known in the art such as for example solid phase phosphoramidite chemical synthesis.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. The subject nucleic acids may also contain modified bases. For example, a nucleic acid may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

A modified nucleic acid of the present invention may also include at least one modified sugar moiety selected from the group including but not limited to arabinose, 2-fluoroarabinose, xylulose, and hexose.

In yet another embodiment, the subject nucleic acid may include at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

II. Recombinant Expression Vectors and Host Cells

The present invention also provides for vectors containing the subject nucleic acid molecules. As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions.

This invention also provides expression vectors containing a nucleic acid encoding a DEF polypeptide, operatively linked to at least one transcriptional regulatory sequence. "Operatively linked" is intended to mean that the nucleotide sequence is linked to a regulatory sequence in a manner which allows expression of the nucleotide sequence. Transcriptional regulatory sequences are art-recognized and are selected to direct expression of the subject mammalian DEF proteins. Exemplary regulatory sequences are described in Goeddel; Gene Expression Technology: Methods in Enzymology 185, Academic Press, San Diego, Calif. (1990).

In a preferred embodiment the expression vector of the present invention is capable of replicating in a cell. In one embodiment, the expression vector includes a recombinant gene encoding a peptide having DEF bioactivity. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject mammalian DEF proteins. Thus, another aspect of the invention features expression vectors for in vivo or in vitro transfection and expression of a mammalian DEF polypeptide in particular cell types so as to reconstitute the function of, or alternatively, abrogate the function of DEF in a tissue. For example, DEF or fragments thereof may be expressed in a cell in order to induce growth arrest and/or terminal differentiation of a proliferating cell, e.g., a cancer cell. As an illustrative embodiment, transfected DEF may induce growth arrest of an adipocyte cell or a neuronal cell. Alternatively, inhibition of the cell proliferation in a subject can be obtained by abrogate the function of DEF in therapeutic intervention in diseases as cancer. In another embodiment, DEF or fragments thereof may be expressed in a mammalian cell, e.g., an adipocyte or a neural cell.

In addition to viral transfer methods, such as those described above, non-viral methods can also be employed to cause expression of a subject DEF polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject DEF polypeptide gene by the targeted cell. Exemplary targeting means of this type include liposomal derived systems, poly-lysine conjugates, and artificial viral envelopes.

The recombinant DEF genes can be produced by ligating nucleic acid encoding a DEF protein, or a portion thereof, into a vector suitable for expression in either prokaryotic cells, eukaryotic cells, or both. Expression vectors for production of recombinant forms of the subject DEF polypeptides include plasmids and other vectors. For instance, suitable vectors for the expression of a DEF polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a DEF polypeptide is produced recombinantly utilizing an expression vector generated by sub-cloning the coding sequence of one of the DEF genes represented in SEQ ID NO:1, SEQ. ID NO:1, SEQ ID NO: 3 or SEQ ID NO: 5, SEQ ID NO: 6 or SEQ ID NO: 8, or SEQ ID NO: 9 or SEQ ID NO: 11.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some instances, it may be desirable to express the recombinant DEF polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In some cases it will be desirable to express only a portion of a DEF protein. The subject vectors can also include fragments of a DEF nucleic acid encoding a fragment of a DEF protein. In a preferred embodiment, subdomains of a DEF protein are expressed.

The subject vectors can be used to transfect a host cell in order to express a recombinant form of the subject DEF polypeptides. The host cell may be any prokaryotic or eukaryotic cell. Thus, a nucleotide sequence derived from the cloning of mammalian DEF proteins, encoding all or a selected portion of the full-length protein, can be used to produce a recombinant form of a mammalian DEF polypeptide in a cell.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The present invention further pertains to methods of producing the subject DEF polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant DEF polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant DEF polypeptide is a fusion protein containing a domain which facilitates its purification, such as GST fusion protein or poly(His) fusion protein.

In other embodiments transgenic animals, described in more detail below could be used to produce recombinant proteins.

The present invention also provides for a recombinant transfection system, including a DEF gene construct operatively linked to a transcriptional regulatory sequence and a gene delivery composition for delivering the gene construct to a cell so that the cell expresses the DEF protein.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a mammalian DEF polypeptide or, in the case of anti-sense expression from the transferred gene, the expression of a naturally-occurring form of the DEF protein is disrupted.

A "delivery composition" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors).

III. Polypeptides

The present invention further pertains to isolated and/or recombinant forms of a DEF polypeptide. The terms "protein", "polypeptide" and "peptide" are used interchangably herein.

The term "recombinant protein" refers to a polypeptide of the present invention which is produced by recombinant DNA techniques, wherein generally, DNA encoding a mammalian DEF polypeptide is inserted into a suitable expression vector which is in turn used to transform a host cell to produce the heterologous protein. Moreover, the phrase "derived from", with respect to a recombinant DEF gene, is meant to include within the meaning of "recombinant protein" those proteins having an amino acid sequence of a native DEF protein, or a similar amino acid sequence which is generated by mutations including substitutions and deletions (including truncation) of a naturally occurring form of the protein.

The present invention also makes available isolated DEF polypeptides which are isolated from, or otherwise substantially free from other cellular proteins, especially other factors which may normally be associated with the DEF polypeptide. The term "substantially free of other cellular proteins" (also referred to herein as "contaminating proteins") or "substantially pure or purified preparations" are defined as encompassing preparations of DEF polypeptides having less than about 20% (by dry weight) contaminating protein, and preferably having less than about 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" are not meant to encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified DEF preparations will lack any contaminating proteins from the same animal from which DEF is normally produced, as can be accomplished by recombinant expression of, for example, a human DEF protein in a non-human cell.

In a particularly preferred embodiment a DEF protein includes the amino acid sequence shown in SEQ ID NO:2, SEQ ID NO: 4, SEQ ID NO: 7, or SEQ ID NO: 10. In particularly preferred embodiments, a DEF protein has a DEF bioactivity.

The present invention also provides for DEF proteins which have amino acid sequences evolutionarily related to the DEF proteins represented in SEQ ID NO:2, SEQ ID NO: 4, SEQ ID NO: 7, or SEQ ID NO: 10. In a preferred embodiment, a DEF protein of the present invention is a mammalian DEF protein. The term "evolutionarily related to", with respect to amino acid sequences of mammalian DEF proteins, refers to both polypeptides having amino acid sequences which have arisen naturally, and also to mutational variants of mammalian DEF polypeptides which are derived, for example, by combinatorial mutagenesis. Such evolutionarily derived DEF polypeptides preferred by the present invention have a DEF bioactivity and are at least 90% homologous and most preferably at least 95% homologous with the amino acid sequence shown in SEQ ID NO:2, SEQ ID NO: 4, SEQ ID NO: 7, or SEQ ID NO: 10.

In certain embodiments it will be advantageous to provide homologs of one of the subject DEF polypeptides which function in a limited capacity as one of either a DEF agonist (mimetic) or a DEF antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of DEF proteins.

Homologs of each of the subject DEF proteins can be generated by mutagenesis, such as by discrete point mutation(s), or by truncation. For instance, mutation can give rise to homologs which retain substantially the same, or merely a subset, of the biological activity of the DEF polypeptide from which it was derived. Alternatively, antagonistic forms of the protein can be generated which are able to inhibit the function of the naturally occurring form of the protein, such as by competitively binding to a downstream or upstream member of the DEF cascade which includes the DEF protein. In addition, agonistic forms of the protein may be generated which are constitutively active. Thus, the mammalian DEF protein and homologs thereof provided by the subject invention may be either positive or negative regulators of cell proliferation or differentiation.

The recombinant DEF polypeptides of the present invention also include homologs of the wild type DEF proteins, such as versions of those protein which are resistant to proteolytic cleavage, as for example, due to mutations which alter ubiquitination or other enzymatic targeting associated with the protein.

DEF polypeptides may also be chemically modified to create DEF derivatives by forming covalent or aggregate conjugates with other chemical moieties, such as glycosyl groups, lipids, phosphate, acetyl groups and the like.

Covalent derivatives of DEF proteins can be prepared by linking the chemical moieties to functional groups on amino acid sidechains of the protein or at the N-terminus or at the C-terminus of the polypeptide.

Modification of the structure of the subject mammalian DEF polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the DEF polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing cysteine and methionine. (see, for example, Biochemistry, 2nd ed., Ed. by L. Stryer, WH Freeman and Co.: 1981). Whether a change in the amino acid sequence of a peptide results in a functional DEF homolog (e.g. functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

In another embodiment a DEF has a DEF bioactivity and is encoded by the nucleic acid shown in FIG. 2 (SEQ. ID NO:1), FIG. 13 (SEQ ID NO: 3 or SEQ ID NO: 5), FIG. 14 (SEQ ID NO: 6 or SEQ ID NO: 8), or FIG. 15 (SEQ ID NO: 9 or SEQ ID NO: 11).

Full length proteins or fragments corresponding to one or more particular motifs and/or domains or to arbitrary sizes, for example, at least amino acids in length are within the scope of the present invention. For example, isolated DEF polypeptides can include all or a portion of an amino acid sequences corresponding to a DEF polypeptide represented in or homologous to FIG. 3 (SEQ ID NO:2), FIG. 12 (SEQ ID NO: 4, SEQ ID NO: 7, or SEQ ID NO: 10). Isolated peptidyl portions of DEF proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a DEF polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") DEF protein.

In still a further embodiment an isolated or recombinant DEF polypeptide includes a sequence corresponding to a src SH3 consensus binding sequence (794–799, 803–809, 829–835, 895–901 or 993–999 of SEQ ID NO:2; 829–833, 892–898 or 1005–1011 of SEQ ID NO: 4; 777–782, 822–828 of SEQ ID NO: 7; or 780–785, 829–834, 834–840, 867–873 of SEQ ID NO: 10), and is at least 85%, more preferably about 90%, and most preferably at least about 91, 92, 93, 94, 95, 96, 97, 98, 99% identical to a a src SH3 consensus binding sequence of the amino acid sequence shown in FIG. 3 (SEQ ID NO:2), FIG. 12 (SEQ ID NO: 4, SEQ ID NO: 7, or SEQ ID NO: 10).

In still a further embodiment an isolated or recombinant DEF polypeptide includes a sequence corresponding to a zinc finger domain (457–480 of SEQ ID NO:2; 454–477 of SEQ ID NO: 4, 436–459 of SEQ ID NO: 7, or 436–459 of SEQ ID NO: 10) and is at least 85%, more preferably about 90%, and most preferably at least about 91, 92, 93, 94, 95, 96, 97, 98, 99% identical to a zinc finger domain of the amino acid sequence shown in FIG. 3 (SEQ ID NO:2), FIG. 12 (SEQ ID NO: 4, SEQ ID NO: 7, or SEQ ID NO: 10).

In yet another embodiment an isolated or recombinant DEF polypeptide includes a sequence corresponding to an ankyrin repeat (356–374, 604–623, 640–659 and 672–692 of SEQ ID NO:2; 353–371, 601–620, 637–656 and 669–689 of SEQ ID NO: 4; 334–352, 585–604, 621–640 and 653–673 of SEQ ID NO: 7; or 334–352, 584–603, 620–639 and 652–672 of SEQ ID NO: 10) and is at least 85%, more preferably about 90%, and most preferably at least about 91, 92, 93, 94, 95, 96, 97, 98, 99% identical to an ankyrin repeat of the amino acid sequence shown in FIG. 3 (SEQ ID NO:2), FIG. 12 (SEQ ID NO: 4, SEQ ID NO: 7, or SEQ ID NO: 10).

In yet another embodiment an isolated or recombinant DEF polypeptide includes a sequence corresponding to a pleckstrin homology domain (326–419 of SEQ ID NO:2; 323–416 of SEQ ID NO: 4; 304–397 of SEQ ID NO: 7; or 303–397 of SEQ ID NO: 10) and is at least 85%, more preferably about 90%, and most preferably at least about 91, 92, 93, 94, 95, 96, 97, 98, 99% identical to an ankyrin repeat of the amino acid sequence shown in FIG. 3 (SEQ ID NO:2), FIG. 12 (SEQ ID NO: 4, SEQ ID NO: 7, or SEQ ID NO: 10).

In yet another embodiment an isolated or recombinant DEF polypeptide includes a sequence corresponding to a C2 domain (498–557 of SEQ ID NO:2; 495–554 of SEQ ID NO: 4; 477–537 of SEQ ID NO: 7; or 477–536 of SEQ ID NO: 10) and is at least 85%, more preferably about 90%, and most preferably at least about 91, 92, 93, 94, 95, 96, 97, 98, 99% identical to an ankyrin repeat of the amino acid sequence shown in FIG. 3 (SEQ ID NO:2), FIG. 12 (SEQ ID NO: 4, SEQ ID NO: 7, or SEQ ID NO: 10).

In another embodiment an isolated or recombinant DEF polypeptide includes a sequence corresponding to a proline-rich repeat (934–1001 of SEQ ID NO:2; or 944–1013 of SEQ ID NO: 4) and is at least 85%, more preferably about 90%, and most preferably at least about 91, 92, 93, 94, 95, 96, 97, 98, 99% identical to a proline-rich repeat of the amino acid sequence shown in FIG. 3 (SEQ ID NO:2), FIG. 12 (SEQ ID NO: 4).

In yet another embodiment an isolated or recombinant DEF polypeptide includes a sequence corresponding to an SH3 domain (1073–1123 of SEQ ID NO:2; 1095–1145 of SEQ ID NO: 4; or 926–976 of SEQ ID NO: 7) and is at least 85%, more preferably about 90%, and most preferably at least about 91, 92, 93, 94, 95, 96, 97, 98, 99% identical to an SH3 domain of the amino acid sequence shown in FIG. 3 (SEQ ID NO:2), FIG. 12 (SEQ ID NO: 4, or SEQ ID NO: 7).

In certain preferred embodiments, the invention features a purified or recombinant DEF polypeptide having a molecular weight of approximately 135–145 kD. It will be understood that certain post-translational modifications can increase the apparent molecular weight of the DEF protein relative to the unmodified polypeptide chain.

This invention further provides a method for generating sets of combinatorial mutants of the subject DEF proteins as well as truncation mutants, and is especially useful for identifying potential variant sequences (e.g. homologs) that modulate a DEF bioactivity. The purpose of screening such combinatorial libraries is to generate, for example, novel DEF homologs which can act as either agonists or antagonist, or alternatively, possess novel activities all together. To illustrate, combinatorially-derived homologs can be generated to have an increased potency relative to a naturally occurring form of the protein.

Likewise, DEF homologs can be generated by the present combinatorial approach to selectively inhibit (antagonize) an authentic DEF. For instance, mutagenesis can provide DEF homologs which are able to bind other signal pathway proteins (or DNA) yet prevent propagation of the signal, e.g. the homologs can be dominant negative mutants. Moreover, manipulation of certain domains of DEF by the present method can provide domains more suitable for use in fusion proteins.

In one embodiment, the variegated library of DEF variants is generated by combinatorial mutagenesis at the nucleic acid level, and is encoded by a variegated gene library. For instance, a mixture of synthetic oligonucleotides can be enzymatically ligated into gene sequences such that the degenerate set of potential DEF sequences are expressible as individual polypeptides, or alternatively, as a set of larger fusion proteins (e.g. for phage display) containing the set of DEF sequences therein.

There are many ways by which such libraries of potential DEF homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential DEF sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

Likewise, a library of coding sequence fragments can be provided for a DEF clone in order to generate a variegated population of DEF fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a DEF coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of DEF homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate DEF sequences created by combinatorial mutagenesis techniques.

In one embodiment, cell based assays can be exploited to analyze the variegated DEF library. For instance, the library of expression vectors can be transfected into a cell line ordinarily responsive to DEF. The transfected cells are then exposed to an extracellular signal and the effect of the DEF mutant can be detected, e.g. G protein activity, e.g., GTPase activity. Plasmid DNA can then be recovered from the cells which score for inhibition, or alternatively, potentiation of DEF activity, and the individual clones further characterized.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811–7815; Yourvan et al., 1992, Parallel Problem Solving from Nature, 2., In Maenner and Manderick, eds., Elsevir Publishing Co., Amsterdam, pp. 401–410; Delgrave et al., 1993, Protein Engineering 6(3):327–331).

The invention also provides for reduction of the mammalian DEF proteins to generate mimetics, e.g. peptide or non-peptide agents, which are able to disrupt binding of a mammalian DEF polypeptide of the present invention with binding proteins or interactors. Thus, such mutagenic techniques as described above are also useful to map the determinants of the DEF proteins which participate in protein-protein interactions involved in, for example, binding of the subject mammalian DEF polypeptide to proteins which may function upstream (including both activators and repressors of its activity) or to proteins or nucleic acids which may function downstream of the DEF polypeptide, whether they are positively or negatively regulated by it. To illustrate, the critical residues of a subject DEF polypeptide which are involved in molecular recognition of interactor proteins or molecules upstream or downstream of a DEF (such as, for example, a src SH3 binding site, a zinc finger domain, an ankyrin repeat) can be determined and used to generate DEF-derived peptidomimetics which competitively inhibit binding of the authentic DEF protein to that moiety. By employing, for example, scanning mutagenesis to map the amino acid residues of each of the subject DEF proteins which are involved in binding other intracellular proteins, peptidomimetic compounds can be generated which mimic those residues of the DEF protein which facilitate the interaction. Such mimetics may then be used to interfere with the normal function of a DEF protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted γ lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), and b-aminoalcohols (Gordon et al. (1985) Biochem Biophys Res Commun 126:419; and Dann et al. (1986) Biochem Biophys Res Commun 134:71).

In another embodiment, the coding sequences for the polypeptide can be incorporated as a part of a fusion gene including a nucleotide sequence encoding a different polypeptide to generate a fusion protein or chimeric protein.

A "chimeric protein" or "fusion protein" is a fusion of a first amino acid sequence encoding one of the subject mammalian DEF polypeptides with a second amino acid sequence defining a domain (e.g. polypeptide portion) foreign to and not substantially homologous with any domain of one of the mammalian DEF proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-DEF-Y, wherein DEF represents a portion of the protein which is derived from one of the mammalian DEF proteins, and X and Y are independently absent or represent amino acid sequences which are not related to one of the mammalian DEF sequences in an organism, including naturally occurring mutants.

Fusion proteins can also facilitate the expression of proteins, and accordingly, can be used in the expression of the mammalian DEF polypeptides of the present invention. For example, DEF polypeptides can be generated as glutathione-S-transferase (GST-fusion) proteins. Such GST-fusion proteins can enable easy purification of the DEF polypeptide, as for example by the use of glutathione-derivatized matrices (see, for example, Current Protocols in Molecular Biology, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

In preferred embodiments, fusion proteins of the present invention contain a detectable label or a matrix binding domain.

The preparation of fusion proteins is often desirable when producing an immunogenic fragment of a DEF protein. For example, the VP6 capsid protein of rotavirus can be used as an immunologic carrier protein for portions of the DEF polypeptide, either in the monomeric form or in the form of a viral particle. The nucleic acid sequences corresponding to the portion of a subject DEF protein to which antibodies are to be raised can be incorporated into a fusion gene construct which includes coding sequences for a late vaccinia virus structural protein to produce a set of recombinant viruses expressing fusion proteins comprising DEF epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a DEF protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple Antigen Peptide system for peptide-based immunization can also be utilized to generate an immunogen, wherein a desired portion of a DEF polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of DEF proteins can also be expressed and presented by bacterial cells.

IV. Antibodies

Another aspect of the invention pertains to an antibody specifically reactive with a mammalian DEF protein. For example, by using immunogens derived from a DEF protein, e.g. based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a mammalian DEF polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of a DEF protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a DEF protein of a mammal, e.g. antigenic determinants of a protein represented by FIG. 3 (SEQ ID NO:2), FIG. 12 (SEQ ID NO: 4, SEQ ID NO: 7, or SEQ ID NO: 10).

Following immunization of an animal with an antigenic preparation of a DEF polypeptide, anti-DEF antisera can be obtained and, if desired, polyclonal anti-DEF antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) Nature, 256: 495–497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a mammalian DEF polypeptide of the present invention and monoclonal antibodies isolated from a culture comprising such hybridoma cells.

The term antibody as used herein is intended to include fragments thereof which are also specifically reactive with one of the subject mammalian DEF polypeptides. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for a DEF protein conferred by at least one CDR region of the antibody.

Antibodies which specifically bind DEF epitopes can also be used in immunohistochemical staining of tissue samples in order to evaluate the abundance and pattern of expression of each of the subject DEF polypeptides. Anti-DEF antibodies can be used diagnostically in immuno-precipitation and immuno-blotting to detect and evaluate DEF protein levels in tissue as part of a clinical testing procedure. Likewise, the ability to monitor DEF protein levels in an individual can allow determination of the efficacy of a given treatment regimen for an individual afflicted with such a disorder. Diagnostic assays using anti-DEF antibodies can include, for example, immunoassays designed to aid in early diagnosis of a degenerative disorder, particularly ones which are manifest at birth. Diagnostic assays using anti-DEF polypeptide antibodies can also include immunoassays designed to aid in early diagnosis and phenotyping neoplastic or hyperplastic disorders.

Another application of anti-DEF antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a DEF protein, e.g. other orthologs of a particular DEF protein or other paralogs from the same species, can then be detected with antibodies, as, for example, reacting nitrocellulose filters lifted from infected plates with anti-DEF antibodies. Positive phage detected by this assay can then be isolated from the infected plate. Thus, the presence of DEF homologs can be detected and cloned from other animals, as can alternate isoforms (including splicing variants) from humans.

In certain embodiment, it will be desirable to attach a label group to the subject antibodies to facilitate detection. One means for labeling an anti-DEF protein specific antibody is via linkage to an enzyme and use in an enzyme immunoassay (EIA) (Voller, "The Enzyme Linked Immunosorbent Assay (ELISA)", Diagnostic Horizons 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) Enzyme Immunoassay, CRC Press, Boca Raton, Fla., 1980; Ishikawa, et al., (eds.) Enzyme Immunoassay, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

It is also possible to label the antibody with a fluorescent compound. When the fluorescently labeled antibody is exposed to light of the proper wave length, its presence can then be detected. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

V. Pharmaceutical Preparations

The subject modulating agents can be administered to a subject at therapeutically effective dose to treat or ameliorate a disorder benefiting from the modulation of DEF. The data obtained from cell culture assays and animal studies can be used in formulating a range of dosage for use in humans. The dosage of such compounds lies preferably within a range of circulating or tissue concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In clinical settings, the gene delivery systems for the therapeutic DEF gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). A mammalian DEF gene, such as any one of the sequences represented in SEQ ID NO:1, or a sequence homologous thereto can be delivered in a gene therapy construct by electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Pharmaceutical preparations for use in accordance with the present invention may also be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical preparations may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation, the preparations for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

The compositions may, if desired, be presented in a pack or dispenser device, or as a kit with instructions. The composition may contain one or more unit dosage forms containing the active ingredient. The pack may for example comprise metal or plastic foil, such as a blister pack. The pack or dispenser device may be accompanied by instructions for administration.

VI. Transgenic animals

The present invention also provides for transgenic animals in which expression of a genomic sequence encoding a functional DEF polypeptide is enhanced, induced, disrupted, prevented or suppressed. The transgenic animals produced in accordance with the present invention will include exogenous genetic material. As set out above, the exogenous genetic material will, in certain embodiments, be a DNA sequence which results in the production of a DEF protein (either agonistic or antagonistic), and antisense transcript, or a DEF mutant. Further, in such embodiments the sequence will be attached to a transcriptional control element, e.g., a promoter, which preferably allows the expression of the transgene product in a specific type of cell.

As used herein, the term "transgene" means a nucleic acid sequence (whether encoding or antisense to one of the mammalian DEF polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the mammalian DEF proteins, e.g. either agonistic or antagonistic forms. However, transgenic animals in which the recombinant DEF gene is silent are also encompassed, as for example, the FLP or CRE recombinase dependent constructs described below. Moreover, "transgenic animal" also includes those recombinant animals in which gene disruption of one or more DEF genes is caused by human intervention, including both recombination and antisense techniques.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that one of the recombinant mammalian DEF genes is present and/or expressed or disrupted in some tissues but not others.

These systems may be used in a variety of applications. For example, the cell- and animal-based model systems may be used to further characterize DEF genes and proteins. In addition, such assays may be utilized as part of screening strategies designed to identify compounds which are capable of ameliorating disease symptoms. Thus, the animal- and cell-based models may be used to identify drugs, pharmaceuticals, therapies and interventions which may be effective in treating disease.

One aspect of the present invention concerns transgenic animals which are comprised of cells (of that animal) which contain a transgene of the present invention and which preferably (though optionally) express an exogenous DEF protein in one or more cells in the animal. A DEF transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a DEF protein can be essential for many forms of lineage analysis and can additionally provide a means to assess the effects of, for example, lack of DEF expression which might grossly alter development in small patches of tissue within an otherwise normal embryo. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject DEF proteins. For example, excision of a target sequence which interferes with the expression of a recombinant DEF gene, such as one which encodes an antagonistic homolog or an antisense transcript, can be designed to activate expression of that gene. This interference with expression of the protein can result from a variety of mechanisms, such as spatial separation of the DEF gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) PNAS 89:6232–6236; Orban et al. (1992) PNAS 89:6861–6865) or the FLP recombinase system of *Saccharomyces cerevisiae* (O'Gorman et al. (1991) Science 251:1351–1355; PCT publication WO 92/15694) can be used to generate in vivo site-specific genetic recombination systems.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant DEF protein can be regulated via control of recombinase expression.

Use of the cre/loxP recombinase system to regulate expression of a recombinant DEF protein requires the construction of a transgenic animal containing transgenes encoding both the Cre recombinase and the subject protein. Animals containing both the Cre recombinase and a recombinant DEF gene can be provided through the construction of "double" transgenic animals. A convenient method for providing such animals is to mate two transgenic animals each containing a transgene, e.g., a DEF gene and recombinase gene.

One advantage derived from initially constructing transgenic animals containing a DEF transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic DEF transgene is silent will allow the study of progeny from that founder in which disruption of DEF mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the DEF transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a DEF transgene could remain silent into adulthood until "turned on" by the introduction of the trans-activator.

In one embodiment, gene targeting, which is a method of using homologous recombination to modify an animal's genome, can be used to introduce changes into cultured embryonic stem cells. By targeting a DEF gene of interest e.g., in embryonic stem (ES) cells, these changes can be introduced into the germlines of animals to generate chimeras. The gene targeting procedure is accomplished by introducing into tissue culture cells a DNA targeting construct that includes a segment homologous to a target DEF locus, and which also includes an intended sequence modification to the DEF genomic sequence (e.g., insertion, deletion, point mutation). The treated cells are then screened for accurate targeting to identify and isolate those which have been properly targeted.

Methods of culturing cells and preparation of knock out constructs for insertion are known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) Current Topics in Devel. Biol. 20:357–371); and by Hogan et al. (Manipulating the Mouse Embryo: A Laboratory Manual, Cold Spring Harbor Laboratory Press, Cold Spring Harbor, N.Y. [1986]).

Introduction of the transgenic constructs nucleotide sequence into the embryo may be accomplished by any means known in the art such as, for example, microinjection, electroporation, calcium phosphate, or lipofection. Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260–1264).

Other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a DEF-gene can be controlled by recombinase sequences.

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

USES AND METHODS OF THE INVENTION

VII. Drug Screening Assays

The present invention also provides for assays which can be used to screen for compounds, including DEF homologs, which are either agonists or antagonists of the normal cellular function of the subject DEF polypeptides, or portions thereof such as an SH3 domain or a src SH3 consensus binding sequence. Screened compounds, for example agonist of DEF bioactivity, may be useful in treating many diseases involving cell proliferation, e.g., metastasis of cancer cells. In other embodiments, antagonists of DEF are provided.

For example, potentiators, or alternatively, inhibitors, of an interaction between a src SH3 consensus binding sequence and an interacting protein, e.g., a protein containing an SH3 domain, e.g., $pp60^{src}$. A variety of assay formats can be used for the subject assays. An exemplary method includes the steps of (a) forming a reaction mixture including: (i) a $pp60^{src}$, (ii) a DEF or a src SH3 consensus binding sequence, and (iii) a test compound; and (b) detecting interaction of the $pp60^{src}$ and a DEF polypeptide or a src SH3 consensus binding sequence polypeptides. A statistically significant change (potentiation or inhibition) in the interaction of the $pp60^{src}$ and a DEF polypeptide or a src SH3 consensus binding sequence in the presence of the test compound, relative to the interaction in the absence of the test compound, indicates a potential agonist (mimetic or potentiator) or antagonist (inhibitor) of said interaction. The reaction mixture can be a cell-free protein preparation, e.g., a reconsistuted protein mixture or a cell lysate, or it can be a recombinant cell including a heterologous nucleic acid recombinantly expressing the DEF polypeptide.

In one embodiment, an assay is provided for screening for modulators of an interaction between a DEF polypeptide or various domains thereof, e.g., SH3 domain or a src SH3 consensus binding sequence, with signaling molecules.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements.

In an exemplary screening assay of the present invention, the compound of interest is contacted with proteins which may function upstream (including both activators and repressors of its activity) or to proteins or nucleic acids which may function downstream of the DEF polypeptide, whether they are positively or negatively regulated by it. To the mixture of the compound and the upstream or downstream element is then added a composition containing a DEF polypeptide. Detection and quantification of the interaction of DEF with its upstream or downstream elements provide a means for determining a compound's efficacy at inhibiting (or potentiating) complex formation between DEF and the DEF-binding elements. The term "interact" as used herein is meant to include detectable interactions between molecules, such as can be detected using, for example, a yeast two hybrid assay. The term interact is also meant to include "binding" interactions between molecules. Interactions may be protein-protein or protein-nucleic acid in nature.

The efficacy of the compound can be assessed by generating dose response curves from data obtained using various concentrations of the test compound. Moreover, a control assay can also be performed to provide a baseline for comparison. In the control assay, isolated and purified DEF polypeptide is added to a composition containing the DEF-binding element, and the formation of a complex is quantitated in the absence of the test compound.

Complex formation between the DEF polypeptide and a DEF binding element may be detected by a variety of techniques. Modulation of the formation of complexes can be quantitated using, for example, detectably labeled proteins such as radiolabeled, fluorescently labeled, or enzymatically labeled DEF polypeptides, by immunoassay, or by chromatographic detection. Typically, it will be desirable to immobilize either DEF or its binding protein to facilitate separation of complexes from uncomplexed forms of one or both of the proteins, as well as to accommodate automation of the assay.

Binding of DEF to an upstream or downstream element, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/DEF (GST/DEF) fusion proteins can be adsorbed onto glutathione sepharose beads (Sigma Chemical, St. Louis, Mo.) or glutathione derivatized microtitre plates, which are then combined with the cell lysates, e.g. an 35S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of DEF-binding protein found in the bead fraction quantitated from the gel using standard electrophoretic techniques such as described in the appended examples.

Other techniques for immobilizing proteins on matrices are also available for use in the subject assay. For instance, either DEF or its cognate binding protein can be immobilized utilizing conjugation of biotin and streptavidin. For instance, biotinylated DEF molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with DEF but which do not interfere with binding of upstream or downstream elements can be derivatized to the wells of the plate, and DEF trapped in the wells by antibody conjugation. As above, preparations of a DEF-binding protein and a test compound are incubated in the DEF-presenting wells of the plate, and the amount of complex trapped in the well can be quantitated. Exemplary methods for detecting such complexes, in addition to those described above for the GST-immobilized complexes, include immunodetection of complexes using antibodies reactive with the DEF binding element, or which are reactive with DEF protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the DEF-BP. To illustrate, the DEF-BP can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2, 4-dinitrobenzene (Habig et al (1974) J Biol Chem 249:7130).

For processes which rely on immunodetection for quantitating one of the proteins trapped in the complex, antibodies against the protein, such as anti-DEF antibodies, can be used. Alternatively, the protein to be detected in the complex can be "epitope tagged" in the form of a fusion protein which includes, in addition to the DEF sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

In addition to cell-free assays, such as described above, the readily available source of mammalian DEF proteins provided by the present invention also facilitates the generation of cell-based assays for identifying small molecule agonists/antagonists and the like. For example, cells can be caused to overexpress a recombinant DEF protein in the presence and absence of a test compound of interest, with the assay scoring for modulation in DEF responses by the target cell mediated by the test agent. As with the cell-free assays, compounds which produce a statistically significant change in DEF-dependent responses (either inhibition or potentiation) can be identified. In an illustrative embodiment, the expression or activity of a DEF is modulated embryos or cells and the effects of compounds of interest on the readout of interest (such as apoptosis) are measured. For example, the expression of genes which are up- or down-regulated in response to a DEF-dependent signal cascade can be assayed. In preferred embodiments, the regulatory regions of such genes, e.g., the 5' flanking promoter and enhancer regions, are operatively linked to a marker (such as luciferase) which encodes a gene product that can be readily detected.

Monitoring the influence of compounds on cells may be applied not only in basic drug screening, but also in clinical trials. In such clinical trials, the expression of a panel of genes may be used as a "read out" of a particular drug's therapeutic effect.

In another aspect of the invention, the subject DEF polypeptides can be used to generate a "two hybrid" assay (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), for isolating coding sequences for other cellular proteins which bind to or interact with DEF ("DEF-binding proteins" or "DEF-bp". Such DEF-binding proteins would likely regulators of DEF bioactivity.

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a DEF polypeptide. The second hybrid protein encodes a transcriptional activation domain fused in frame to a sample gene from a cDNA library. If the bait and sample hybrid proteins are able to interact, e.g., form a DEF-dependent complex, they bring into close proximity the two domains of the transcriptional activator. This proximity is sufficient to cause transcription of a reporter gene which is operatively linked to a transcriptional regulatory site responsive to the transcriptional activator, and expression of the reporter gene can be detected and used to score for the interaction of the DEF and sample proteins.

VIII. Diagnostic and Prognostic Assays

The invention provides a method for detecting the presence of DEF in a biological sample. The method involves contacting the biological sample with an agent capable of detecting DEF protein or mRNA such that the presence of DEF is detected in the biological sample. A preferred agent for detecting DEF mRNA is a labeled or labelable nucleic acid probe capable of hybridizing to DEF mRNA. The nucleic acid probe can be, for example, the full-length DEF cDNA of SEQ ID NO: 1, SEQ ID NO: 3 or SEQ ID NO: 5, SEQ ID NO: 6 or SEQ ID NO: 8, or SEQ ID NO: 9 or SEQ ID NO: 11, or a portion thereof, such as an oligonucleotide of at least 15, 30, 50, 100, 250 or 500 nucleotides in length and sufficient to specifically hybridize under stringent conditions to DEF mRNA. A preferred agent for detecting DEF protein is a labeled or labelable antibody capable of binding to DEF protein. Antibodies can be polyclonal, or more preferably, monoclonal. An intact antibody, or a fragment thereof (e.g., Fab or F(ab')$_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect DEF mRNA or protein in a biological sample in vitro as well as in vivo. For example, in vitro techniques for detection of DEF mRNA include Northern hybridizations and in situ hybridizations. In vitro techniques for detection of DEF protein include enzyme linked immunosorbent assays (ELISAs), Western blots, immunoprecipitations and immunofluorescence. Alternatively, DEF protein can be detected in vivo in a subject by introducing into the subject a labeled anti-DEF antibody. For example, the antibody can be labeled with a radioactive marker whose presence and location in a subject can be detected by standard imaging techniques.

Accordingly, the invention provides a diagnostic method comprising:

contacting a sample from a subject with an agent capable of detecting DEF protein or mRNA;

determining the amount of DEF protein or mRNA expressed in the sample;

comparing the amount of DEF protein or mRNA expressed in the sample to a control sample; and forming a diagnosis based on the amount of DEF protein or mRNA expressed in the sample as compared to the control sample.

The invention also encompasses kits for detecting the presence of DEF in a biological sample. For example, the kit can comprise a labeled or labelable agent capable of detecting DEF protein or mRNA in a biological sample; means for determining the amount of DEF in the sample; and means for comparing the amount of DEF in the sample with a standard. The agent can be packaged in a suitable container. The kit can further comprise instructions for using the kit to detect DEF mRNA or protein.

The diagnostic methods of the present invention are elaborated further below. In preferred embodiments, the methods can be characterized as comprising detecting, in a sample of cells from the subject, the presence or absence of a genetic lesion characterized by at least one of (i) an alteration affecting the integrity of a gene encoding a DEF-protein, or (ii) the mis-expression of the DEF gene. To illustrate, such genetic lesions can be detected by ascertaining the existence of at least one of (i) a deletion of one or more nucleotides from a DEF gene, (ii) an addition of one or more nucleotides to a DEF gene, (iii) a substitution of one or more nucleotides of a DEF gene, (iv) a gross chromosomal rearrangement of a DEF gene, (v) a gross alteration in the level of a messenger RNA transcript of a DEF gene, (vii) aberrant modification of a DEF gene, such as of the methylation pattern of the genomic DNA, (vii) the presence of a non-wild type splicing pattern of a messenger RNA transcript of a DEF gene, (viii) a non-wild type level of a DEF-protein, (ix) allelic loss of a DEF gene, and (x) inappropriate post-translational modification of a DEF-protein. As set out below, the present invention provides a large number of assay techniques for detecting lesions in a DEF gene, and importantly, provides the ability to discern between different molecular causes underlying DEF-dependent aberrant bioactivity of a DEF popypeptide.

In an exemplary embodiment a nucleic acid composition is provided which contains an oligonucleotide probe previously described. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) PNAS 91:360–364), the latter of which can be particularly useful for detecting point mutations in the DEF-gene (see Abravaya et al. (1995) Nuc Acid Res 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a DEF gene under conditions such that hybridization and amplification of the DEF-gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In another embodiment of the subject assay, mutations in a DEF gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the DEF gene and detect mutations by comparing the sequence of the sample DEF with the corresponding wild-type (control) sequence. Exemplary sequencing reactions include those based on techniques developed by Maxim and Gilbert (Proc. Natl Acad Sci USA (1977) 74:560) or Sanger (Sanger et al (1977) Proc. Nat. Acad. Sci 74:5463). Any of a variety of automated sequencing procedures may be utilized when performing the subject assays (Biotechniques (1995) 19:448), including by sequencing by mass spectrometry (see, for example PCT publication WO 94/16101; Cohen et al. (1996) Adv Chromatogr 36:127–162; and Griffin et al. (1993) Appl Biochem Biotechnol 38:147–159). It will be evident to one skilled in the art that, for certain embodiments, the occurence of only one, two or three of the nucleic acid bases need be determined in the sequencing reaction. For instance, A-tract sequencing where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA heteroduplexes (Myers, et al. (1985) Science 230:1242). In general, the art technique of "mismatch cleavage" starts by providing heteroduplexes formed by hybridizing (labelled) RNA or DNA containing the wild-type DEF sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in DEF cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a DEF sequence, e.g., a wild-type DEF sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in DEF genes. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) Mutat Res 285:125–144; and Hayashi (1992) *Genet Anal Tech Appl* 9:73–79). Single-stranded DNA fragments of sample and control DEF nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al (1989) Proc. Natl Acad. Sci USA 86:6230). Such allele speicific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a DEF gene.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant DEF proteins, which are discussed, above, may also be used in disease diagnostics and prognostics. Such diagnostic methods, may be used to detect abnormalities in the level of DEF protein expression, or abnormalities in the structure and/or tissue, cellular, or subcellular location of DEF protein. Structural differences may include, for example, differences in the size, electronegativity, or antigenicity of the mutant DEF protein relative to the normal DEF protein. Protein from the tissue or cell type to be analyzed may easily be detected or isolated using techniques which are well known to one of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of DEF proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the DEF protein, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

Moreover, any of the above methods for detecting alterations in a DEF gene or gene product can be used to monitor the course of treatment or therapy.

IX. Methods of Modulating Cell Differentiation

In another aspect, this invention features methods for inhibiting the proliferation and/or reversing the transformed phenotype of a hyperproliferative cells by the ectopic expression of DEF, or by contacting the cells with a DEF agonist. In general, the method includes a step of contacting pathological hyperproliferative cells with an amount of a DEF agonist effective for promoting the differentiation of the hyperproliferative cells. Alternatively, the a method of ectopic expression of DEF in a hyperproliferative cell is described in Examples 7 and 8. The present method can be performed on cells in culture, e.g., in vitro or ex vivo, or can be performed on cells present in an animal subject, e.g., as part of an in vivo therapeutic protocol. The therapeutic regimen can be carried out on a human or other animal subject.

While the DEF activation can be utilized alone, the subject method can be combined with other therapeutics, e.g., such as cell cycle inhibitors, agents which promote apoptosis, agents which strengthen the immune response, and/or PPARγ agonists.

In one embodiment, the cells to be treated are hyperproliferative cells of adipocytic lineage, e.g., arising from adipose or adipose precursor cells. In certain embodiments, the adipose cells show an aberrant activity of at least one process mediated by PPARγ. As employed herein, the phrase "processes mediated by PPARγ" refers to biological, physiological, endocrinological, and other bodily processes which are mediated by receptor or receptor combinations which are responsive to the PPAR-γ-selective prostaglandin or prostaglandin-like compounds described herein. Such processes include cell differentiation to produce lipid-accumulation cells, modulation of blood glucose levels and insulin sensitivity, regulation of leptin levels and subsequent feeding levels (for the control of satiety and/or appetite), regulation of thermogenesis and fatty acid metabolism, regulation of fat levels for the treatment of lipodystrophies, control of cell differentiation for the treatment of myxoid liposarcomas, regulation of triglyceride levels and lipoproteins for the treatment of hyperlipidemia, modulation of genes expressed in adipose cells (e.g., leptin, lipoprotein, lipase, uncoupling protein, and the like), and the like.

The term "PPARγ" refers to members of the peroxisome proliferator-activated receptors family which are expressed, inter alia, in adipocytic and hematopoietic cells (Braissant, O. et al. *Endocrinology* 137(1): 354–66), and which function as key regulators of differentiation. Contemplated within this definition are variants thereof, as for example, PPARγ1 and PPARγ2 which are two isoforms having a different N-terminal generated by alternate splicing of a primary RNA transcript (Tontonoz, P. et al. (1994), *Genes & Dev.* 8:1224–34; Zhu et al. (1993) *J. Biol. Chem.* 268: 26817–20).

In other embodiments, the instant method can be carried out to prevent the proliferation of an adipose cell tumor. The adipose tumor cells can be of a liposarcoma. The term "liposarcoma" is recognized by those skilled in the art and refers to a malignant tumor characterized by large anaplastic lipoblasts, sometimes with foci of normal fat cells. Exemplary liposarcoma types which are can be treated by the present invention include, but are not limited to, well differentiated/dedifferentiated, myxoid/round cell and pleiomorphic (reviewed in Sreekantaiah, C. et al., (1994) supra).

Another adipose cell tumor which may be treated by the present method include lipomas, e.g., benign fatty tumors usually composed of mature fat cells. Likewise, the method of the present invention can be used in the treatment and/or prophylaxis of lipochondromas, lipofibromas and lipogranulomas. Lipochondroma are tumors composed of mature lipomatous and cartilaginous elements; lipofibromas are lipomas containing areas of fibrosis; and lipogranuloma are characterized by nodules of lipoid material associated with granulomatous inflammation.

The subject method may also be used to inhibit the proliferation of hyperplastic/neoplastic cells of hematopoietic origin, e.g., arising from myeloid, lymphoid or erythroid lineages, or precursor cells thereof.

As used herein, the terms "hyperproliferative" and "neoplastic" are used interchangeably, and refer to those cells an abnormal state or condition characterized by rapid proliferation or neoplasm. The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth.

The term "adipose cell tumor" refers to all cancers or neoplasias arising from cells of adipocytic lineage, e.g., arising from adipose or adipose precursor cells. The adipose cell tumors include both common and uncommon, benign and malignant lesions, such as lipoma, intramuscular and intermuscular lipoma, neural fibrolipoma, lipoblastoma, lipomatosis, hibernoma, hemangioma and liposarcoma, as well as lesions that may mimic fat-containing soft-tissue masses.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is recognized by those skilled in the art and refers to malignant tumors of mesenchymal derivation.

As used herein the term "leukemic cancer" refers to all cancers or neoplasias of the hemopoietic and immune systems (blood and lymphatic system). The acute and chronic leukemias, together with the other types of tumors of the blood, bone marrow cells (myelomas), and lymph tissue (lymphomas), cause about 10% of all cancer deaths and about 50% of all cancer deaths in children and adults less than 30 years old. Chronic myelogenous leukemia (CML), also known as chronic granulocytic leukemia (CGL), is a neoplastic disorder of the hematopoietic stem cell. The term "leukemia" is recognized by those skilled in the art and refers to a progressive, malignant disease of the blood-forming organs, marked by distorted proliferation and development of leukocytes and their precursors in the blood and bone marrow.

For instance, the present invention provides for the treatment of various myeloid disorders including, but not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267–97). Lymphoid malignancies which may be treated by the subject method include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas contemplated by the treatment method of the present invention include, but are not limited to, non-Hodgkin's lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

The subject method can also be useful in treating malignancies of the various organ systems, such as those affecting lung, breast, lymphoid, gastrointestinal, and genito-urinary tract as well as adenocarcinomas which include malignancies such as most colon cancers, renal-cell carcinoma, prostate cancer and/or testicular tumors, non-small cell carcinoma of the lung, cancer of the small intestine and cancer of the esophagus. According to the general paradigm of PPARγ involvement in differentiation of transformed cells, exemplary solid tumors that can be treated according to the method of the present invention include sarcomas and carcinomas with PPARγ-responsive phenotypes, such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In another embodiment, the present methods can be used in vitro to induce and/or maintain the differentiation of neural crest cells into glial cells, schwann cells, chromaffin cells, cholinergic sympathetic or parasympathetic neurons, as well as peptidergic and serotonergic neurons. The DEF protein can be used alone, or can be used in combination with other neurotrophic factors which act to more particularly enhance a particular differentiation fate of the neuronal progenitor cell.

In addition to cell culture applicationst and other in vitro uses described above, yet another aspect of the present invention concerns the therapeutic application of a DEF molecules to enhance survival of neurons and other neuronal cells in both the central nervous system and the peripheral nervous system. The ability of DEF molecules to regulate neuronal differentiation during development of the nervous system and also presumably in the adult state indicates that certain of the DEF molecules can be reasonably expected to facilitate control of adult neurons with regard to maintenance, functional performance, and aging of normal cells; repair and regeneration processes in chemically or mechanically lesioned cells; and prevention of degeneration and premature death which result from loss of differentiation in certain pathological conditions. In light of this understanding, the present invention specifically contemplates applications of the subject method to the treatment of (prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis.

Many neurological disorders are associated with degeneration of discrete populations of neuronal elements and may be treatable with a therapeutic regimen which includes a hedgehog agonist. For example, Alzheimer's disease is associated with deficits in several neurotransmitter systems, both those that project to the neocortex and those that reside with the cortex. For instance, the nucleus basalis in patients with Alzheimer's disease have been observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex.

However, some forms of dementia are associated with degeneration of the thalmus or the white matter underlying the cerebral cortex. Here, the cognitive dysfunction results from the isolation of cortical areas by the degeneration of efferents and afferents. Huntington's disease involves the degeneration of intrastraital and cortical cholinergic neurons and GABAergic neurons. Pick's disease is a severe neuronal degeneration in the neocortex of the frontal and anterior temporal lobes, sometimes accompanied by death of neurons in the striatum. Treatment of patients suffering from such degenerative conditions can include the application of DEF molecules, or agents which mimic their effects, in order to control, for example, differentiation and apoptotic events which give rise to loss of neurons (e.g. to enhance survival of existing neurons) as well as promote differentiation and repopulation by progenitor cells in the area affected. In preferred embodiments, a source of a DEF agent (DEF agonist) is stereotactically provided within or proximate the area of degeneration.

In addition to degenerative-induced dementias, a pharmaceutical preparation of one or more of the subject DEF molecules can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. The present method is amenable to the treatment of disorders of the cerebellum which result in hypotonia or ataxia, such as those lesions in the cerebellum which produce disorders in the limbs ipsilateral to the lesion.

This invention is further illustrated by the following examples which should not be construed as limiting. The contents of all references, patents and published patent applications cited throughout this application are hereby incorporated by reference.

EXAMPLE 1

Purification of Bovine DEF-1 Protein

Experimental Procedures

SH3 binding proteins from bovine brain were purified using a src SH3 and src SH3SH2 affinity columns. The affinity columns were constructed by cloning the avian src SH3 or src SH3SH2 domains (amino acids 88–136 and 88–240, respectively) into the plasmid vector pGEX-2T (Pharmacia) using standard PCR techniques. The resulting glutathione-S-transferase src SH3 domain fusion protein was secured to glutathione-coupled sepharose beads. Lck SH3, was constructed in a similar fashion using a murine c-lck gene as the initial template. The GST-DEF-1 constructs were made by cloning in the appropriate blunt-ended, Bgl II fragment into the Sma I site of pGEX-2T. Calf brain lysates were made by homogenization in the presence of hypotonic Lysis buffer (0.25M Sucrose, 20 mM Tris pH 8.0, 1 mM EDTA, 1 mM , 8-mercaptoethanol, 2 mM PMSF) and passed over the respective columns. Each column was washed once in NP40 Lysis buffer, twice in 0.5M LiCl/20 mM Tris pH 8.0, and once with PBS. Samples were eluted with 10 mM glutathione in 120 mM NaCl/100 mM Tris 8.0 and passed over an ATP-agarose column (Sigma) or eluted with SDS sample buffer and loaded onto a 10% SDS/PAGE gel. Samples passed over the ATP-agarose column were washed twice with PBS, eluted with SDS sample buffer and electrophoresed on a 5% SDS/PAGE gel. The gel was electroblotted using PVDF membrane (Biorad) in CAPS buffer and the band corresponding to DEF-1 was excised. Following in situ digestion with trypsin (Fernandez et al. (1994) *Analytical Biochemistry* 218:112–7) the resulting peptide mixture was separated by microbore HPLC using a Zorbax C18 1.0 mm by 150 mm reverse-phase column on a Hewlett-Packard 1090 HPLC/1040 diode array detector. Optimum fractions from the chromatogram were chosen based on differential UV absorbance at 205 nm, 277 nm, and 292 nm, peak symmetry and resolution. Peaks were further screened for length and homogeneity by matrix-assisted laser desorption time-of-flight mass spectrometry on a Finnigan Lasermat 200 (Hemel, England) and selected fractions underwent automated Edman degradation on a Perkin Elmer/Applied Biosystems 494A, 477A (Foster City, Calif.). Details of strategies for the selection of peptide fractions and their microsequencing have been previously described (Lane et al. (1991) *Journal of Protein Chemistry* 10:151–60). Lysates made with NP40 Lysis buffer from NIH-3T3 cells expressing pLNSL7 alone (vector) or HA tagged DEF-1 (DEF-1) were passed over the noted columns and washed as described above. Bound proteins were immunoblotted with the anti-HA antibody, 12CA5 (Babco). pp60$^{c-src}$ was detected using the monoclonal antibody "327", a gift from J. Brugge.

To identify novel src SH3 binding proteins, proteins isolated from bovine brain extracts that bound to a glutathione-S-transferase src SH3 (GST-SRC SH3) affinity column were analyzed. Resolution of the associated proteins by SDS/PAGE showed several species that bound to the src SH3 but not the GST beads alone (FIG. 1A). This included a prominent band of approximately 100 kD which was subsequently identified as dynamin (Gout, I. et al. (1993) *Cell* 75:25–36). Because dynamin also shows affinity for ATP agarose (Scaife et al. (1990) *Journal of Cell Biology* 111:3023–33), the ability of the src SH3 associated proteins to bind to an ATP affinity matrix was determined. This led to the identification of a small number of proteins that bound to both affinity columns, including a protein of approximately 140 kD (DEF-1) which showed high abundance and good separation relative to the other proteins (FIG. 1B). Therefore, a sufficient quantity of DEF-1 was purified to enable a determination of its partial amino acid sequence.

A large-scale preparation from bovine brain was prepared and the proteins that bound to both columns were separated by SDS/PAGE and blotted to polyvinylidene diflouride membrane resulting in approximately 20 µg of purified protein. The band corresponding to DEF-1 was cut from the filter and sequenced. Following elution of the protein from the filter and digestion with endopeptidase, the peptides were separated by HPLC. Six peaks from the HPLC column were selected and sequenced. The partial amino acid sequence obtained did not correspond with any protein in the Genbank database, suggesting that DEF-1 was a previously unidentified src SH3 binding protein.

EXAMPLE 2

Cloning of Bovine DEF-1 cDNA cDNA cloning using degenerate primers in PCR reactions was performed essentially as described (Lee, C. C. et al.

(I1990) *A Guide to Methods and Applications* (ed. M. A. Innis et al) Academic Press, pp. 46–53. Degenerate oligonucleotides were designed based on the resultant amino acid sequence of six tryptic peptides and used as primers in a series of nested PCR reactions using bovine brain mRNA as the initial template. Bovine brain RNA was reverse transcribed with the downstream primer "RTCRTTNGTRT-CYTC" (SEQ ID NO: 13). The cDNA from this reaction was used in a PCR reaction with the same downstream primer and "CAYGTICARAAYGARGARAA" (SEQ ID NO: 14) as the upstream primer. This reaction was used as a template for a subsequent PCR reaction using the nested upstream primer, "GARGARAAYTAYGCICARGT" (SEQ ID NO: 15) and the downstream primer. The product from this reaction was sequenced and subsequently determined to encode amino acids 92–3 84 of bovine DEF-1.

This PCR product was used to screen a bovine brain random primed cDNA library in the vector λZapll (Stratagene) obtained from Dr. Akio Yamakawa. This resulted in six unique clones, five of which contained DEF-1 coding sequences. The sixth appears to be a related gene. A segment of one clone was used to rescreen the library which resulted in three novel DEF-1 clones including the remainder of the coding sequence. Positives clones were used to isolate eight overlapping clones which resulted in approximately 5300 bp of contiguous sequence. The composite sequence contained an open reading frame encoding a protein of 1129 amino acids. The nucleotide and amino acid sequence is shown in FIG. 2 (SEQ ID NO: 1) and FIG. 3 (SEQ ID NO:2), respectively. All six peptides sequenced were found in the predicted translation product. The DEF-1 cDNA (comprised of clones S9 and R27) with the HA tag, "MVYPYDVPDYAG" (SEQ ID NO: 16), at the N-terminus was cloned into the expression vector, "pLNSL7" and transfected into ψ2 cells to obtain infectious retroviral supernatants (Marth J. D. et al. (1989) *Journal of Immunology* 142:1430–7).

EXAMPLE 3

Tissue Expression and Structural Features of Bovine DEF-1

Northern blot analysis indicated that DEF-1 mRNA is expressed in several tissues and cell lines examined. This result suggests that expression of DEF is ubiquitous. Expression of DEF-1 mRNA is higher in adipose tissues compared to other tissues, suggesting a role for this molecule in adipogenesis. In addition, adipose cells obtained from obese or diabetic mouse models show higher levels of expression than normal mice. The pattern of expression of DEF-1 mRNA appears developmentally regulated. For example, the expression of DEF-1 mRNA is relatively high in the developing rat brain, and decreases after birth to levels similar to the ones detected in the adult brain.

Figure 9A:
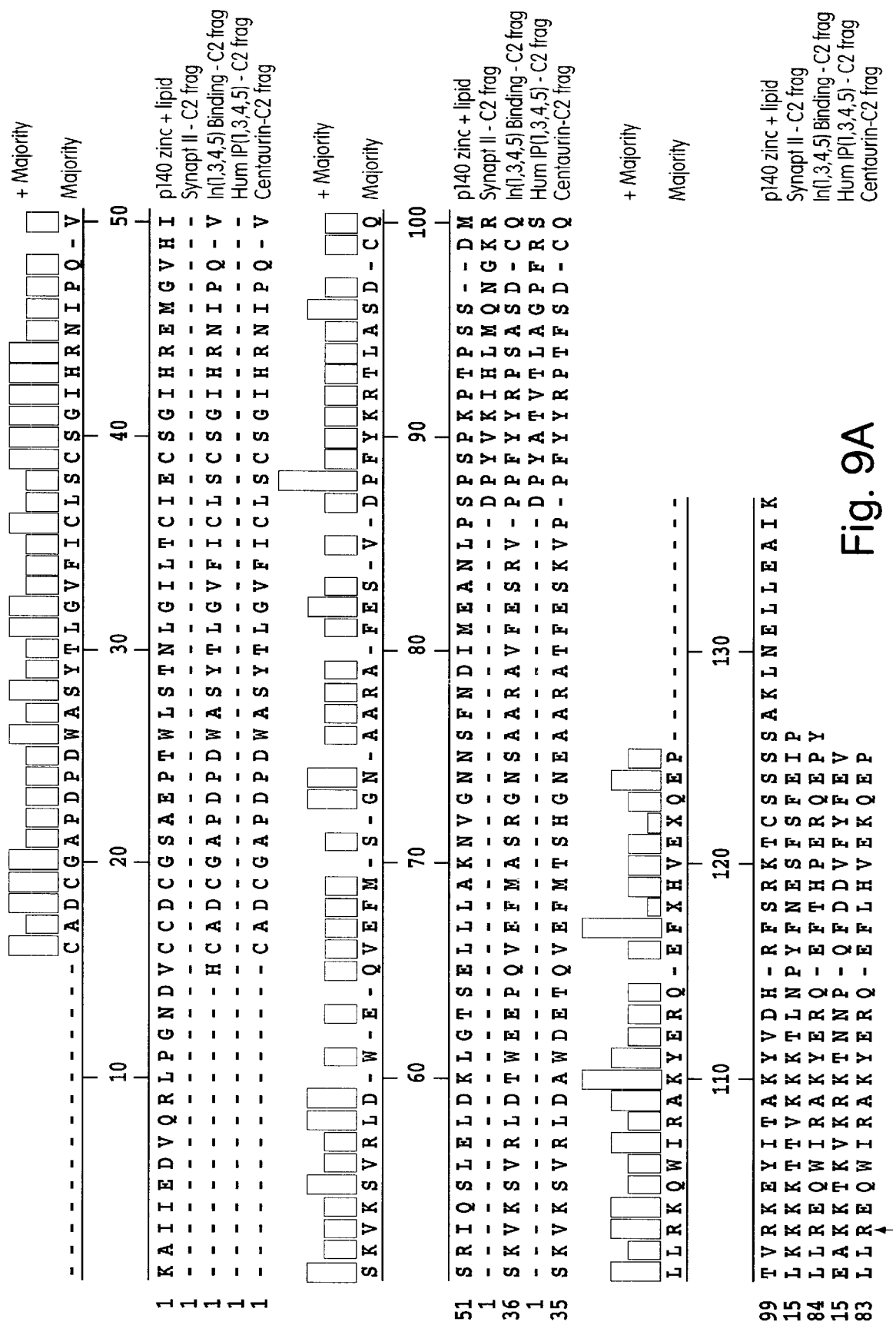
FIGS. 9A is an alignment of the amino acid sequences of the C2 domain (amino acids 498–557) of bovine DEF-1 (DEF zinc) with other C2 containing proteins (Majority sequence (SEQ ID NO: 29); p140 zinc+lipid (SEQ ID NO:30; Synapt II—C2 frag. (SEQ ID NO: 31); In(1,3,4,5) Binding—C2 frag. (SEQ ID NO: 32); Hum IP(1,3,4,5)—C2 frag. (SEQ ID NO: 33); Centaurin-C2 frag (SEQ ID NO: 34)).
Figure 9B:
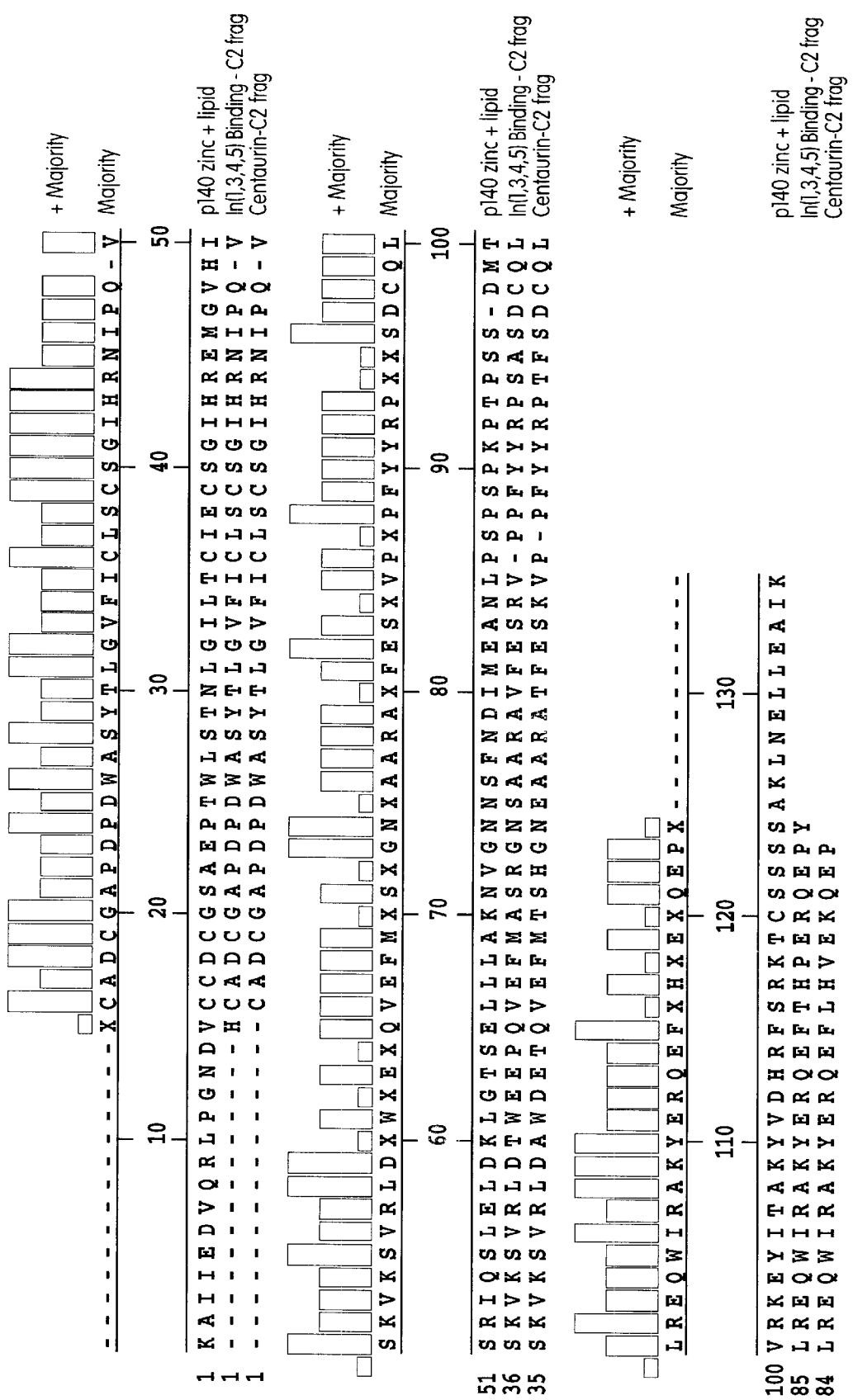
FIG. 9B is an alignment of the amino acid sequences of the C2 domain (amino acids 498–557) of bovine DEF-1 (DEF zinc) with other C2 containing proteins that also contain a zinc finger domain. (Majority sequence (SEQ ID NO: 35); p140 zinc+lipid (SEQ ID NO:30; In(1,3,4,5) Binding—C2 frag. (SEQ ID NO: 32); Centaurin-C2 frag (SEQ ID NO: 34)).

Genbank database searches of the cloned DEF-1 sequences for related protein sequences failed to identify any significant homologies. However, the best matches from the data base search indicated that DEF-1 shares several motifs with other proteins which are illustrated in FIG. 3 and described below as follows. Comparison of the amino acid sequence of bovine DEF-1 protein revealed several motifs including four ankyrin repeats, three of which are in close proximity to each other (FIG. 3) corresponding to amino acids 356–374, 604–623, 640–659 and 672–692. Ankyrin is a protein that "anchors" cytoskeleton elements to the plasma membrane (Michaely, P. and Bennett, V. (1993) *Journal of Biological Chemistry* 268:22703–9). A 33 amino acid motif is repeated 24 times within ankyrin and this region is believed to be involved in directing the protein to the inner face of the plasma membrane (Michaely, P. and Bennett, V. (1993) *Journal of Biological Chemistry* 268:22703–9). This repeat has been found in several other proteins such as the transcription factor regulator, Iκ-B (Hay, 1993). The presence of the ankyrin repeats suggests that DEF-1 may be targeted to the plasma membrane. DEF-1 protein also includes a C2 domain located approximately at amino acids 498–557. FIG. 9A is an alignment of the amino acid sequences of the C2 domain (amino acids 498–557) of bovine DEF-1 (DEF zinc) with other C2 containing proteins. A comparison of these sequence reveals about 27.1% identity with In(1,3,4,5) binding protein, and 28.3% identity with Centaurin. FIG. 9B is an alignment of the amino acid sequences of the C2 domain (amino acids 498–557) of bovine DEF-1 (DEF zinc) with other C2 containing proteins that also contain a zinc finger domain (Cullen, P. J. et al. (1995) *Nature* 376: 527). A comparison of these sequence reveals a 16.7, 22,2, 13.9 and 25% identity with Synaptogemin, In(1,3,4,5) binding protein, human IP(1,3,4, 5) and Centaurin, respectively. C2 domains are believed to be involved in lipid binding, primarily phosphatidylinositol binding. This finding suggests that DEF-1 may interact with a component of the plasma membrane, which may in turn regulate DEF-1 activity.

Bovine DEF-1 also contains a pleckstrin homology (PH) domain located approximately at amino acids 326–419. The PH domain is a domain of about 100 amino acids located at the carboxy-terminal of several proteins involved in signal transduction processes or as constituents of the cytoskeleton (Haslam et al. (1993) *Nature* 363:309–310; Mayer et al. (1993) *Cell* 73:629–630; Musacchio et al. (1993) *Trends Biochem. Sci.* 18:343–348). Bovine DEF-1 also contains one zinc finger domain located approximately at amino acids 457–480. Several matches found from the database search shared homology to the zinc finger found in ARF1 GTPase activating protein (Trainor, C. D. et al.(1990) *Nature* 343:92–96). Interestingly, these proteins bind to different G proteins and are believed to affect their GTPase activity. Since it is possible that the G protein dynamin copurified with DEF-1, this shared motif suggests that DEF-1 is also a modulator of a G protein activity.

Additionally, DEF-1 contains an SH3 domain located at approximately amino acids 1073–1123. Furthermore, bovine DEF-1 contains several proline rich stretches including multiple src SH3 consensus binding sequences located at about amino acids 794–799, 803–809, 829–835, 895–901 and 993–999 (Rickles, R. J. et al (1995) *Proceedings of the National Academy of Sciences of the United States of America* 92:10909–13; Weng, Z. et al (1995) *Molecular & Cellular Biology* 15:5627–34; Sparks, A. B. et al. (1995) *Methods in Enzymology* 255:498–509; Alexandropoulos K. et al (1995) *Proceedings of the National Academy of Sciences of the United States of America* 92:3110–4). No previously described motifs that would account for DEF-1's affinity for ATP agarose were apparent.

Figures 6A, 6B:
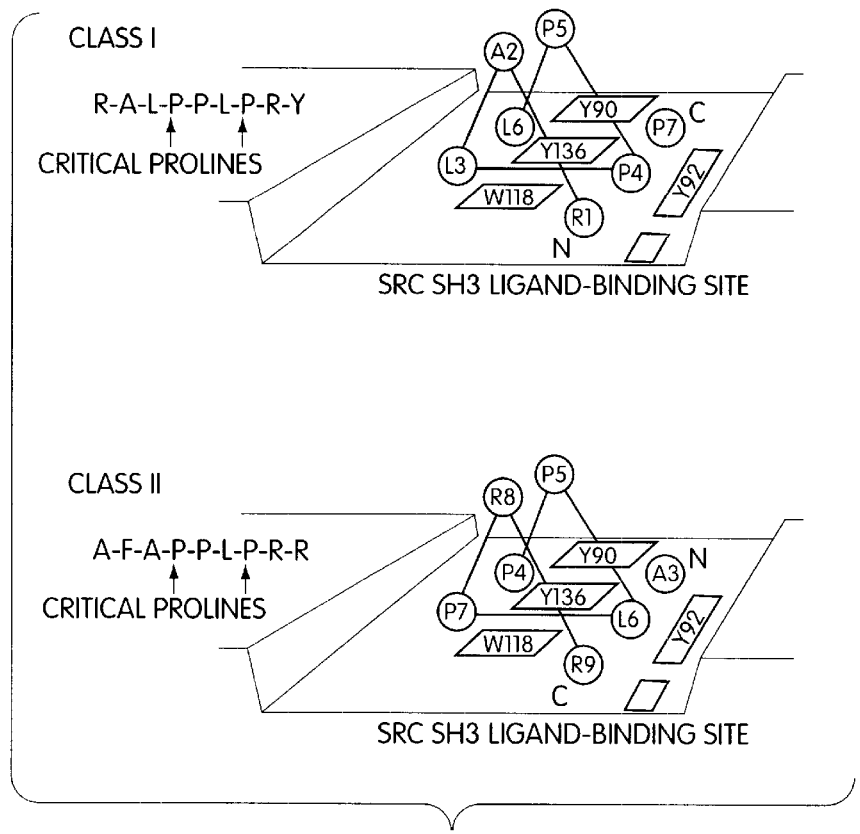
FIG. 6A is an alignment of the amino acid sequences of various SH3 domains found in c-src (SEQ ID NO: 13), c-fgr (SEQ ID NO: 14), c-fyn (SEQ ID NO: 15), c-abl (SEQ ID NO: 16), p85 (SEQ ID NO: 17) and grb-2N (SEQ ID NO: 18). Highly conserved residues that are presumably in direct contacts with SH3-binding sites are indicated.
FIG. 6B is a schematic representation of the interaction of a src SH3 consensus binding sequence adopting a polyproline type II helix conformation and an SH3 domain.

In addition to the readily identifiable motifs described above, an unusual proline-rich stretch located between the SH3 domain and the predicted SH3 binding sites in DEF-1 was noted (amino acids 934–1001). This region can be subdivided into six tandem repeats centered on the consensus sequence "GDLPPKP". Although this motif has the PXXP motif found in SH3 binding proteins, it would not be predicted to form a high affinity interaction with src SH3 since it lacks a basic amino acid residue at the proper position (with the exception of the last repeat; Rickles, R. J.

et al (1995) *Proceedings of the National Academy of Sciences of the United States of America* 92:10909–13. However, the preponderance of prolines in this repeat suggests that this region forms a polyproline type II helix (Williamson, M. P. (1994) *Biochemical Journal* 297:249–60). FIG. 6B is a schematic of the interaction of a Src SH3 ligand binding site and an SH3 domain (adapted from Feng, S. et al. (1994) *Science* 266: 1241–1247). Based on this assumption, the four C-terminal repeats form a trigonal prism with an acidic "edge", a basic edge, and an uncharged edge (with the exception noted above; FIGS. 7A–7B). The two longer repeats (amino acids 934–965) have a similar pattern yet the relative charge rotates between the repeats. FIGS. 7A and 7B are schematic representations of the putative left-handed polyproline type II helix configuration of bovine DEF-1 proline-rich motifs (amino acids 934–1001). FIG. 7A represents the putative structure of repeats 1–3 (amino acids 934–974). FIG. 7B represents the putative structure of repeats 3–6 (amino acids 966–1001).

The presence of these six proline repeats is significantly different to any SH3 binding sequence reported thus far. In this regard, a motif termed "WW" or "WWP" domain (so called because of conserved tryptophans) has been shown to associate with proline rich sequences. These proline rich regions tend to lack the basic amino acid near the proline helix common to SH3 binding proteins. This suggests that the C-terminus of DEF-1 could potentially associate with a WW/WWP domain containing protein. The repeated motif in DEF-1 does have charged amino acids albeit in the improper location for SH3 binding.

If the repeated motif described above acts as a SH3 binding site then this is the first reported case where such a motif has been found in such a repetitive fashion. Consequently, this sequence may represent an unique opportunity to determine what amino acids are crucial for an SH3 interaction. The other motifs described above also suggest where DEF-1 is localized within a cell and how it is involved in signal transduction.

EXAMPLE 4

Identification of DEF-1 as a src SH3 Binding Protein

To confirm that the DEF-1 cDNA encoded a src SH3 binding protein, the full length DEF-1 coding sequence fused with a hemaglutinin tag (HA) at the amino terminus was expressed in NIH-3T3 cells. Lysates from the subsequent drug selected, DEF-1 expressing cells were passed over a src SH3 column and probed with an anti-HA antibody. The protein produced by the DEF-1 cDNA associated with the src SH3 beads, which strongly suggests that it encodes the protein detected in FIG. 1A.

Bovine DEF-1 co-purified with dynamin, a protein known to associate with numerous SH3 domains and ATP agarose (Gout, I. et al. (1993) *Cell* 75:25–36; Scaife, R. and Margolis, R. L. (1990) *Journal of Cell Biology* 111:3023–33). Therefore, the interaction between DEF-1 and src SH3 may have been dependent upon an intermediary such as dynamin. To provide evidence that DEF-1 associated with src SH3 directly, two GST fusion proteins spanning regions of DEF-1 that had SH3 consensus binding sequences were constructed. Lysates made from bovine brain or insect cells infected with baculovirus pp60$^{c-src}$ were passed over the respective columns and the washed beads were immunoblotted with an anti- pp60$^{c-src}$ antibody. pp60$^{c-src}$ isolated from either lysate associated efficiently with amino acids 777–926 of DEF-1 (FIG. 6). The results in FIG. 6 can be explained by a direct interaction existing between this amino acids 777–926 of DEF-1 and the SH3 domain in pp60$^{c-src}$. Even though amino acids 928–1129 contains a consensus src SH3 binding site, no interaction with pp60$^{c-src}$ was detected. However, it is not clear if an intramolecular interaction with the DEF-1 SH3 domain in this construct might interfere with src SH3 binding.

EXAMPLE 5

Binding of DEF Proteins to other SH3 Containing Proteins

In order to examine the possibility that one repeat of the hexa-motif contained in DEF is capable of binding to the SH3 domain of p85, tissue or cell lysates prepared as described in Example 1 can be passed over the GST-pDEFBH beads as described. The precipitate can be examined by Western blot using an anti-p85 antibody. If p85 does interact with this region, then the other five repeats may reflect the binding site for a different SH3 containing protein. Tissue extracts can be precipitated with the GST-pDEFBH and analyzed by AllPro stain to determine if any proteins specifically associate with this region. The identity of the isolated proteins can be assessed by determining the electrophoretic mobility as analyzed by 2D and SDS-PAGE gels.

EXAMPLE 6

Binding of DEF Proteins to other SH3 Containing Proteins

As described in Example 1, DEF was purified by its ability to efficiently bind to a Src SH3 column. Experiments can be performed to demonstrate that p140 binds to Src SH3 in vitro and to map the Src SH3 binding site on DEF. To accomplish this, full length DEF can be cloned into a bacterial expression vector in order to make a lacZ-p140 fusion protein. The resultant bacterial lysate will be incubated with Src SH3 beads to determine if DEF can be precipitated. In the event that expression of DEF may be toxic to bacteria, DEF cDNA can be expressed in a baculovirus expression vector.

EXAMPLE 7

Induction of Adipogenesis by Overexpression of Bovine DEF-1 in Fibroblastic Cell Lines To determine the phenotype associated with DEF (over) expression, the DEF cDNA was introduced into the fibroblastic cell line Balb/3T3. Briefly, Balb/c-3T3 or NIH-3T3 cells were infected with the vector alone or DEF-1 retroviral supernatants and selected with 400 μg/ml G418. Only pools of cells derived from more than ~1000 infected cells were assayed. Upon confluence, the derivative NIH-3T3 cells were cultured in 10% FCS/DMEM and supplemented with combinations of 1 μM dexamethasone (Sigma), 5 μM insulin (Sigma), and 10 μM pioglitazone, as indicated (Tontonoz, P. et al. (1994) *Cell* 79:11147–56). The medium was changed every other day. After two weeks at confluence, a small number of cells expressing exogenous DEF-1 formed shiny vacuoles. This morphology is indicative of lipid droplets found in adipocytes, which suggests that DEF may be involved in the differentiation of fibroblasts into adipocytes. Cell culture conditions and differentiation assays were performed as described in Hu, E. et al. (1996) *Science* 274: 2100–2103.

The formation of lipid droplets in the DEF-1/Balb/c-3T3 cells prompted the study of the role of DEF-1 in adipogenesis using NIH-3T3 cells as a model system (Cornelius, P. (1994) *Annual Review of Nutrition* 14:99–129). A selected pool of NIH-3T3 cells infected with the DEF-1 retrovirus (DEF-1/NIH-3T3) kept at confluence in 10%FCS/DMEM demonstrated no visible signs of adipogenesis. However, parallel cultures supplemented with factors that have been previously shown to enhance differentiation in pre-adipocytic cell lines, particularly dexamethasone, insulin, and the thiazolidinedione, pioglitazone, demonstrated considerable levels of lipid accumulation as compared to the vector alone (Cao, Z. et al. (1991) *Genes & Development* Kletzien, R. F. et al. (1992) *Molecular Pharmacology* 41:393–8; Forman, B. M. et al. (1995) *Cell* 83:803–12). Lipid droplets turned red when stained with Oil-red-O, which is indicative of adipocyte differentiation. Northern blot analysis with the adipocyte specific marker aP2 confirmed that the cultures of treated DEF-1/NIH-3T3 cells that presented lipid droplets underwent adipogenesis (Tontonoz P. et al. (1994) *Genes & Development* 8:1224–34; Spiegelman, B. M. et al. *Cell* 87:377–89).

EXAMPLE 8

Cells Overexpressing Bovine DEF-1 Show Augmented Levels of PPARγ

The adipogenic activity seen in the DEF-1/NIH 3T3 cells was dependent upon the presence of pioglitazone, which is a potent and specific stimulator of the nuclear receptor PPARγ (Lehmann, J. M. et al. (1995) *Journal of Biological Chemistry* 272:5367–70). NIH-3T3 cells normally demonstrate no discernible phenotypic changes during pioglitazone treatment presumably due to low levels of PPARγ expression (Tontonoz, P. et al. (1994) *Cell* 79:1147–56). However, ectopic expression of PPARγ in NIH/3T3 cells followed by treatment with PPARγ activating ligands has been shown to be sufficient to promote conspicuous adipogenesis (Forman, B. M. (1995) *Cell* 83:803–12).

While assaying for the expression of adipocytic markers in DEF-1 expressing cells, elevated levels of PPARγ mRNA in cells that had been treated with the complete differentiation cocktail were detected. Since PPARγ levels increase during adipogenesis, this result suggests that either DEF-1 promotes PPARγ expression or that augmented PPARγ levels are the result of DEF-1 induced fibroblastic differentiation (Tontonoz, P. et al. (1994) *Genes & Development* 8:1224–34). However, the culture of DEF-1/NIH-3T3 cells supplemented only with dexamethasone and insulin demonstrated increased levels of PPARγ mRNA as compared to control cells. This suggests that heightened expression of DEF-1 synergizes with the effects of dexamethasone and insulin treatment to increase PPARγ levels. Further supplementation of pioglitazone activates the augmented levels of PPARγ resulting in the adipogenic phenotype. Elevated levels of PPARγ mRNA expression were mirrored by elevated protein levels of the receptor.

DEF-1 mRNA expression is found in adipose tissue suggesting that DEF-1 may have a role in adipogenesis in vivo. In fact, elevated expression of DEF-1 mRNA has been identified in obesity mouse models relative to non-obese mice, suggesting that DEF-1 may be an inportant regulator of adipocytic differentiation in normal and pathological conditions. Thus, strategies for modulating DEF-1 activity may be important in treating disorders involving aberrant adipose cell activity such as obesity.

The relationship between DEF-1 and PPARγ expression may extend beyond fibroblastic differentiation since both have been detected in several different tissues (Tontonoz, P. et al. (1994) *Cell* 79:1147–56. However, there are tissues that express DEF-1 in the absence of detectable levels of PPARγ (e.g. brain) suggesting a target for DEF-1 other than PPARγ in particular cell types.

EXAMPLE 9

DEF-1 Enhances PPARγ Activity in Cells Co-Expressing DEF-1 and PPARγ

To characterize the potential interaction of DEF-1 and PPARγ NIH3T3 cells transfected with PPARγ alone, or co-transfected with PPARγ and bovine DEF-1. Transfection studies were performed as described above. Results were characterized based on cell morphology, staining of lipid droplets with oil-red-o, and expression of adipocytic markers. Cells co-transfected with PPARγ and DEF-1 compared to cells transfected with PPARγ alone showed a greater response to the differentiation cocktail, i.e., dexamethasone, insulin and pioglitazone, suggesting a synergistic differentiation effect.

Figure 10:
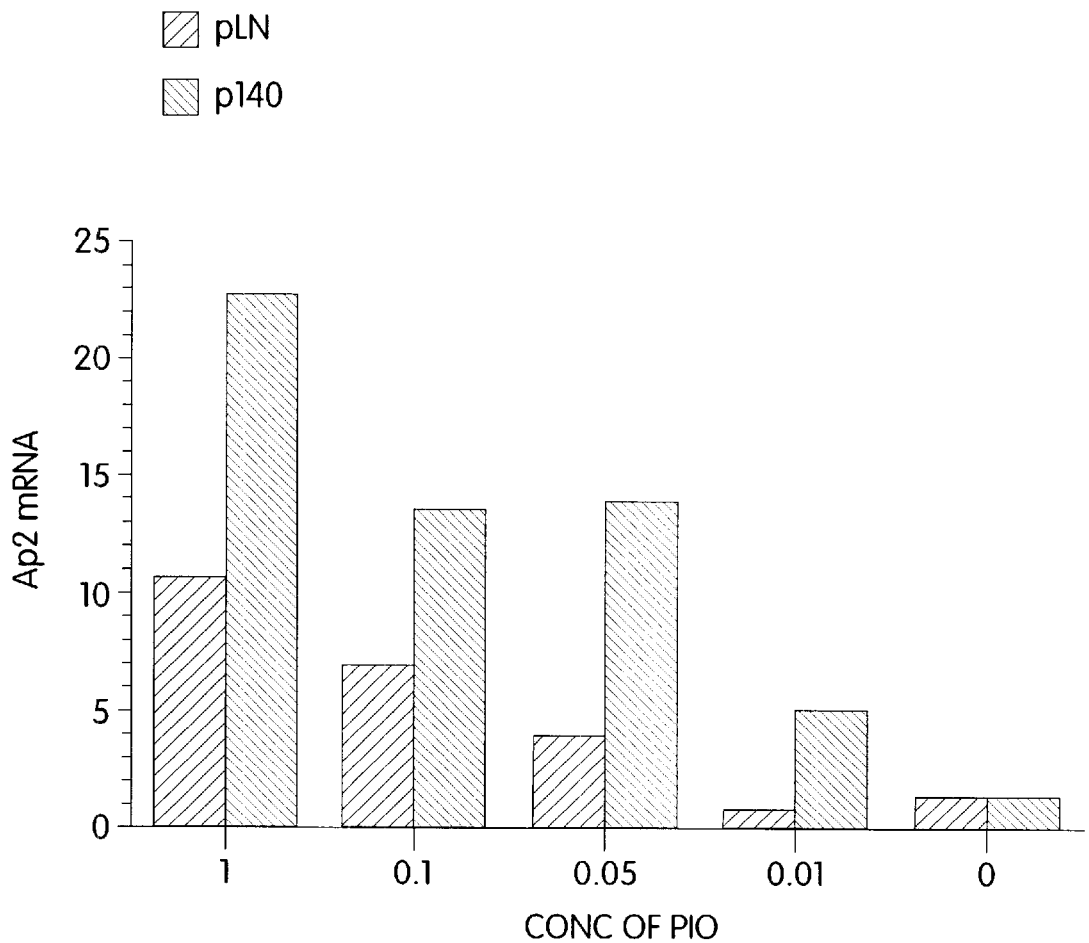
FIG. 10 is a bar graph summarizing the enhanced level of adipocytic differentiation in control PPARγ-expressing Balb/3T3 cells (left, solid bar) compared to Balb/3T3 cells co-expressing PPARγ and DEF-1 (right, spleckled bar) in the presence of the indicated concentrations of pioglitazone (pio).

FIG. 10 summarizes the quantitation of the level of adipocytic differentiation in control PPARγ-expressing cells (left, solid bar) compared to PPARγ, DEF-1-co-expressing cells (right, speckled bar) in the presence of the indicated concentrations of pioglitazone. Adipocyte differentiation was detected by the expression of the adipocyte marker, AP2 mRNA. A potentiation of the pioglitazone-induced differentiation of NIH3T3 cells was observed in DEF-1-transfected cells relative to the control cells. As shown in FIG. 10, the expression of DEF-1 increases the levels of AP2 mRNA roughly four fold over control cells at low levels of pioglitazone. The level of the AP2 mRNA was quantitated using a phosphorimager. Thus, if both DEF-1 and PPARγ are overexpressed in NIH3T3 cells, a similar effect can be seen if the cells are supplemented with lower levels of pioglitazone than cells expressing PPARγ only. This results suggests that therapeutic strategies targeting PPARγ-dependent pathways can be expanded to include modulators of DEF-1 activity or expression.

EXAMPLE 10

Deletion Analysis of Bovine DEF-1

Figure 11:
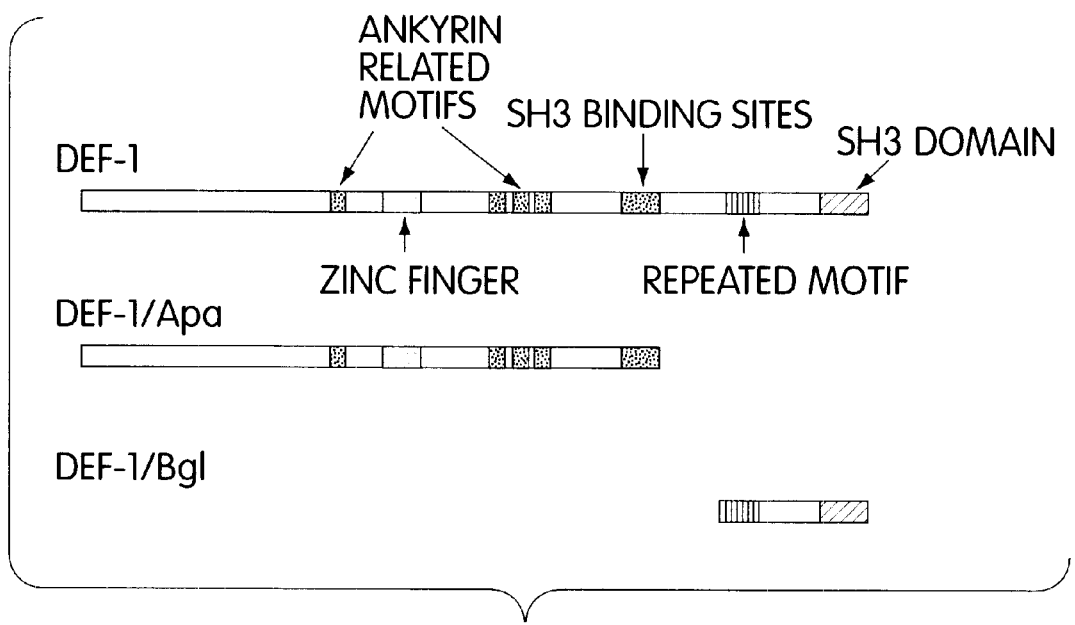
FIG. 11 is a schematic representation of deletion mutants of bovine DEF-1. DEF-1/Apa mutants (amino acids 1–800) and DEF-1/Bgl mutants (last 200 amino acids of bovine DEF-1) are indicated.

To localize the domains of bovine DEF-1 necessary for biological activity, deletion analysis of the DEF-1 construct was performed. To generate these mutants, full length bovine DEF-1 cDNA was digested with the appropriate restriction enzyme (either Apa or Bgl enzymes) to generate two sets of mutants: DEF-1/Apa mutants which encode amino acids 1–800 and DEF-1/Bgl which encode the last 200 amino acids of bovine DEF-1. Digested fragments were subcloned into cloned into the expression vector, "pLNSL7" and transfected into ψ2 cells to obtain infectious retroviral supernatants (Marth, J. D. et al. (1989) *Journal of Immunology* 142:2430–7). FIG. 11 is a schematic representation of deletion mutants of bovine DEF-1. DEF-1/Apa mutants (amino acids 1–800) and DEF-1/Bgl mutants (last 200 amino acids of bovine DEF-1 containing the proline-rich repeat and the SH3 domain).

To assay for the ability of these mutants to induce adipogenesis, Balb/c-3T3 or NIH-3T3 cells were transfected as described in Example 7. Transfected and control cells were cultured and assayed for adipogenic activity as described above. Induction of adipogenesis was observed with the two constructs tested. However, DEF-1/Bgl mutants showed even higher activity than the full length clone, which indicates that the last 200 amino acids of DEF-1 are sufficient to induce adipogenesis.

EXAMPLE 11

Signal Transduction Mechanism of DEF Proteins

Preliminary studies indicate that PPARγ is a substrate for MAP Kinase (MAPK) p42/44$^{MAPK}$. When MAPK is active (as it is growing cells), PPARγ is phosphorylated and its activity is down-regulated. A constitutively active form of PPARγ can be made by mutating the MAPK phosphorylation site. Therefore, DEF may be able to enhance adipogenesis by inhibiting MAPK and indirectly activating PPARγ.

Preliminary experiments indicate that expression of DEF increases the levels of active p38$^{MAPK}$ in cells as detected by Western blots in NIH3T3 cells transfected with DEF relative to the untransfected controls. This result suggests that DEF is an upstream effector of p38MAPK and activates a pathway distinct from PPARγ. Therefore, these two pathways may be able to complement each other in enhancing the differentiation of fibroblasts.

EXAMPLE 12

Mechanism of Action of DEF Proteins

Described above is a novel signal transduction molecule, DEF-1, whose overexpression in fibroblasts participates in augmentation of PPARγ levels and induction of cellular differentiation in fibroblasts. The increase in PPARγ in DEF-1 expressing cells may be a consequence of DEF-1 induced fibroblastic differentiation or may result from DEF-1 signal transduction targeting PPARγ expression. The latter hypothesis appears more likely since PPARγ expression was noted in DEF-1/NIH-3T3 cells treated with dexamethasone and insulin in the absence of discernible differentiation.

The mechanism by which dexamethasone and insulin treatment synergizes with ectopic expression of DEF-1 in NIH-3T3 cells to augment PPARγ levels is unclear at the present. Dexamethasone and insulin have been shown to induce or maintain the expression of particular members of the PPAR and C/EBP families of transcription factors (Spiegelman, B. M. and Flier, J. S. (1996) *Cell* 87:377–89; Brun, R. P. (1996) *Genes & Development* 10:974–84; Mandrup, S. and Lane, M. D. (1997) *Journal of Biological Chemistry* 272:5367–70). For example, dexamethasone has been shown to induce the expression of C/EBPβ which cooperates with C/EBPβ to promote the synthesis of PPARγ in pre-adipocytes (Yeh, W. C. et al. (1995) *Genes and Development* 9:168–81; Wu, Z. et al. (1996) *Molecular & Cellular Biology* 16:4128–36). Elevation of PPARγ levels in DEF-1 cells may result from the expression of a C/EBP family member (such as C/EBPβ) or an unknown factor that regulates the amount of PPARγ. These uncharacterized components may also be affected by dexamethasone since constitutive C/EBPβ expression does not appear to compensate entirely for dexamethasone treatment in the induction of adipogenesis (Wu, Z. N. (1996) *Molecular & Cellular Biology* 16:4128–36).

Figure 8:
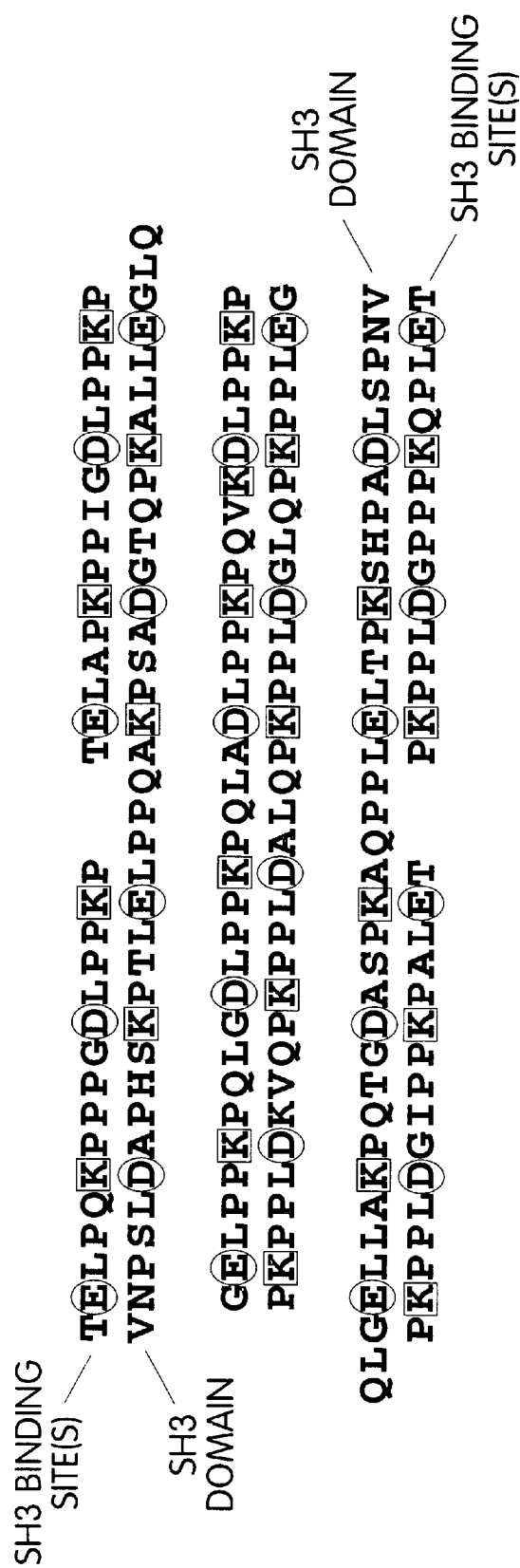
FIG. 8 is an alignment of the amino acid sequences in the SH3 domain of bovine DEF-1 with its SH3 binding site. The first line of FIG. 8 includes SEQ ID NOs: 21 and 22, respectively. The second, third, fourth, and fifth lines of FIG. 8 include SEQ ID NOs: 23, 24, 25, and 26, respectively. The sixth line of FIG. 8 includes SEQ ID NOs: 27 and 28, respectively. Represented in between the SH3 domains is an alignment of the proline-rich repeats in a homodimer configuration. The Interacting basic and acidic residues are indicated by squares and circles, respectively.

DEF-1 has several motifs which suggests that it interacts with other presently unidentified proteins to achieve its biological effects and, therefore, may act as a "scaffolding" protein (FIGS. 3, 7 and 8). Potential DEF-1 associating proteins are likely localized to the cytoplasm since we have several lines of evidence (including the purification of DEF-1 using a hypotonic lysis buffer) suggesting that DEF-1 has a cytosolic subcellular localization (FIG. 1A). However, the presence of ankyrin repeats implies that DEF-1 may have at least a transient association with the plasma membrane (Michaely, P. and Bennet, V. (1993) *Journal of Biological Chemistry* 268:22703–9). The zinc finger or DEF-1 is closely related to several proteins in the database including a GTPase activating protein (Trainor, C. D. et al (1990) *Nature* 343:92–6). Interestingly, DEF-1 co-purified with the GTPase, dynamin (FIG. 1A).

Figure 5:
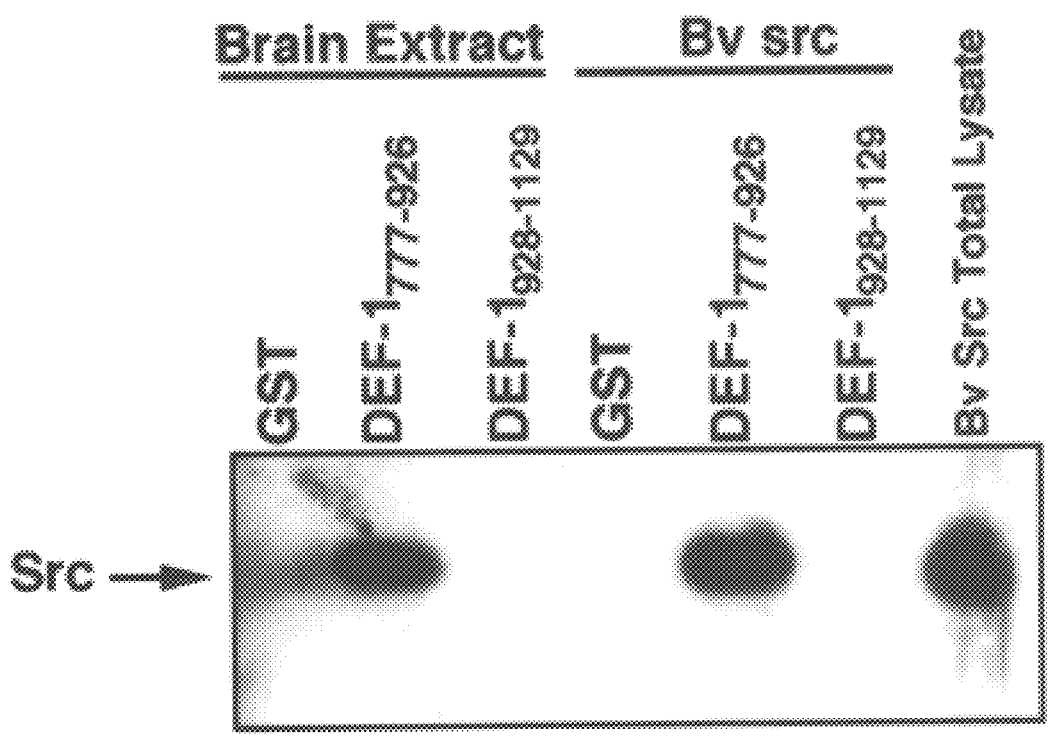
FIG. 5 is a Western blot depicting the association of bovine DEF-1 with src SH3 by passing lysates made from bovine brain (brain extract) or insect cells infected with baculovirus pp60$^{c-src}$ (Bv src) over afinity columns containing two glutathione S-transferase (GST) fusion proteins spanning regions of bovine DEF-1. The fusion proteins were: GST-src binding domain (GST-DEF-1 amino acids 777–926) and GST-C terminal of DEF-1 (GST-C 928–1129) as indicated. Bound proteins were resolved by SDS-PAGE electrophoresis and detected using an anti-src antibody.

The purification of DEF-1 involved a src SH3 affinity column which implies pp60$^{c-src}$ is potentially involved in the DEF-1 induced phenotypes observed. Although a pp60$^{c-src}$ binding site has been mapped to a region of DEF-1 containing src SH3 consensus binding sequences (FIG. 5), a reproducible interaction between the two full length proteins has not been demonstrated. However, this potential interaction may be regulated. The presence of both an SH3 domain and SH3 binding sites in DEF-1 suggests that these regions are involved in an intramolecular interaction or dimerization between two DEF-1 molecules. However, the proline rich repeats between these two regions (amino acids 934–1001) could act as a rigid "spacer" which likely would discourage intramolecular folding. Furthermore, this repetitive motif may play a role in DEF-1 homodimerization: this region of DEF-1 can be aligned with the identical sequence written in the opposite orientation resulting in almost every charged amino acid residue being paired with a residue of opposite charge (FIG. 8). The significance of this charge distribution becomes more evident if this region forms a polyproline type II helix and takes on the conformation modeled in FIGS. 7A and 7B. This would enable the polyproline type II helices from two DEF-1 molecules to array in a manner where "edges" of opposite charges align (FIG. 8). Altogether, this model of DEF-1 dimerization suggests a mechanism whereby the accessibility to the SH3 domain and possibly SH3 binding sites within DEF-1 is regulated.

The proline-rich repeat may also function as a long, rigid structure that keeps the two parts of the DEF-1 protein separated. For example, this repeat prevents the SH3 domain of a DEF-1 monomer from interacting with the SH3 binding sites. This is supported by the fact that the first lysine in the last proline-rich repeat is rare for this location, where aliphatic amino acids are typically seen. A lysine residue at this location is evolutionary conserved among different species such as human and zebrafish, suggesting an inportant function. The lysine at this position makes the last proline repeat an SH3 binding consensus sequence, therefore, a protein that has an SH3 domain might bind at this location. In addition, there are signal transduction proteins that have two SH3 domains (such as GRB-2). Thus, a protein having two SH3 domains may bind to DEF-1 using this last repeat. Then, the rest of the proline-rich repeats would provide a spacer to keep the two SH3 binding sequences at the proper spacing for the target protein to bind.

The ubiquitous expression of DEF-1 implies that DEF-1 signal transduction is not restricted to adipogenesis. Moreover, amino acid sequence of partial cDNAs corresponding to DEF-1 homologues reveal that DEF-1 has been extremely well conserved between zebrafish, mice, rats, cows, and humans which argues that DEF-1 is a signal transduction component within a variety of species (Yamabhai, M. and Kay, B. K. (1997) *Analytical Biochemistry* 247:143–51).

EXAMPLE 13

Cloning of Zebrafish DEF Family Members

Experimental Procedures

Bovine DEF-1 cDNA XbaI-EcoRI fragment (~4kb) was used as probe to screen zebrafish 18-hour and 24-hour embryo cDNA libraries in the vector ZAPExpress (Stratagene). In this library screen, ~1×10⁶ plaques were plated, transferred to nylon membranes (Genescreen plus, NEN Life Science Products) and hybridized at low stringency in 30% formamide at 42° C. (Chan and Watt (1991) *Oncogene* 6:1057–1061). The DNA probe was labeled with [α³²P]-dCTP using a random primed labeling kit (Boehringer Mannheim) and washed in 15 mM sodium chloride, 1.5 mM sodium citrate and 0. 1% sodium dodecyl sulphate at 42° C. Plaque-purified ZAPEX press phages were automatically excised using the helper phage Exassist into the plasmid pBK-CMV (Stratagene). Plasmid DNAs were sequenced using the dideoxy method following standard protocols. Zebrafish cDNAs encoding full-length DEF related proteins, ZDEF-1, ZDEF-2, and ZDEF-3, were analyzed using the DNA Star Sequence Analysis Programs. Full-length nucleotide sequences of the zebrafish genes are provided herein as follows: DEF-1 gene (FIG. 13; SEQ ID NO: 3 (coding and untranslated regions); SEQ ID NO: 5 coding sequence only); DEF-2 gene (FIG. 14; SEQ ID NO: 6 (coding and untranslated regions); SEQ ID NO: 8 coding sequence only); and DEF-3 gene (FIG. 15; SEQ ID NO: 10 (coding and untranslated regions); SEQ ID NO: 11 coding sequence only).

Figure 16:
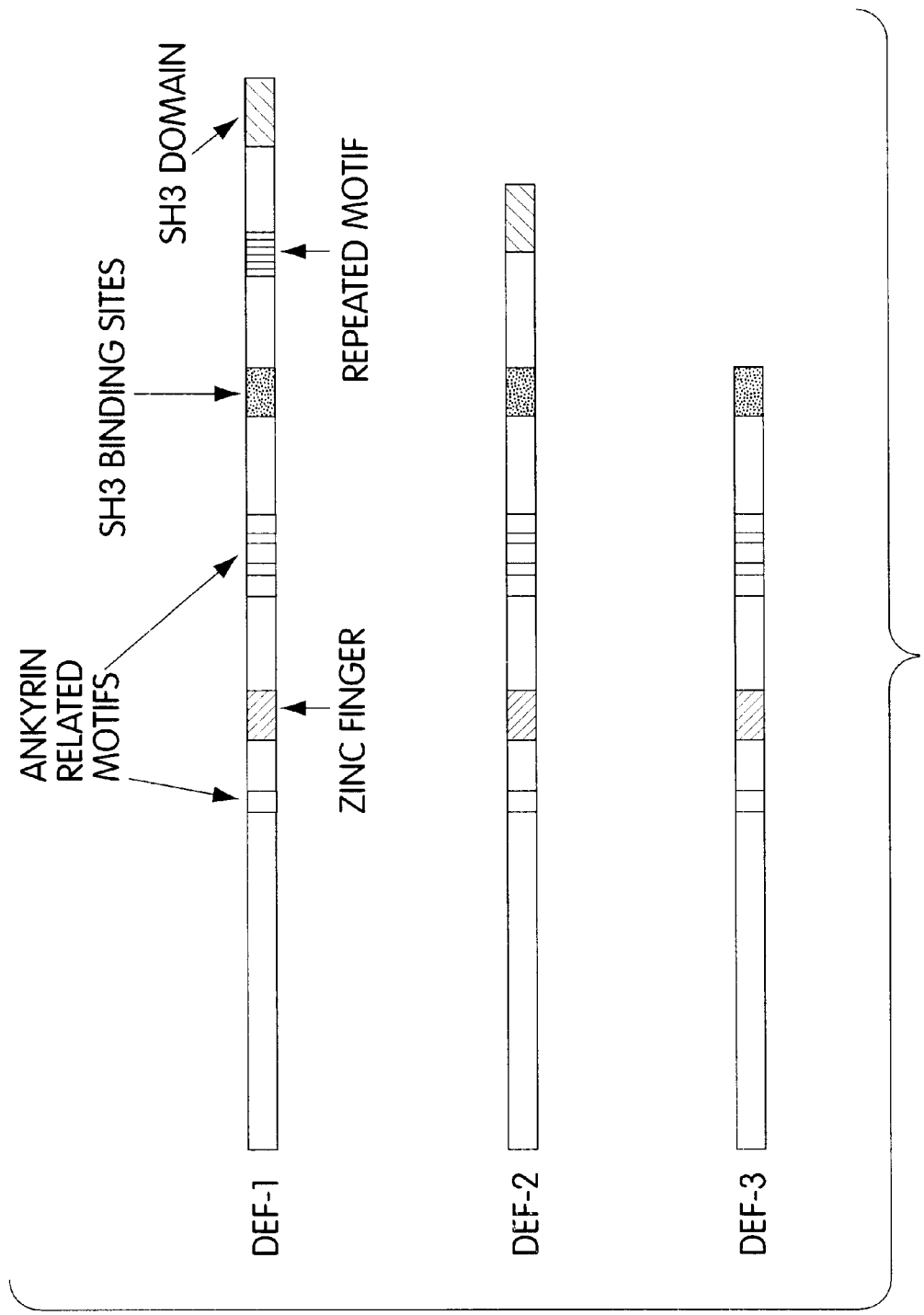
FIG. 16 is a schematic representation of zebrafish DEF family structure.

An alignment of the amino acid sequences of DEF family members is shown in FIG. 12. Amino acid sequences corresponding to bovine DEF-1 (SEQ ID NO: 2); zebrafish DEF-1 (SEQ ID NO: 4); zebrafish DEF-2 (SEQ ID NO: 7); zebrafish DEF-3 (SEQ ID NO: 10); and human DEF-2 (SEQ ID NO: 12) are indicated. A schematic representation of zebrafish DEF family structure is depicted in FIG. 16.

A comparison of the amino acid sequences of the zebrafish family members indicated a highly conserved N-terminal domain of about 750 amino acids with higher variation at the C-termini. A comparison of the full length sequences between zebrafish DEF-1 and DEF-2 revealed about 55.7% amino acid identity, whereas the amino acid sequence identity of the N-terminal domains was about 52.2%. A similar comparison between the zebrafish DEF-1 and DEF-3 sequences revealed about 51% identity of the full length protein, compared to 52.7% identity of the N-terminal domain. Similarly, a 62.3% full length identity was found between zebrafish DEF-2 and DEF-3, compared to 66% identity between the N-terminal domains. As represented in schematic form in FIG. 16 and detailed below as Table 1, zebrafish DEF-1 contains the same domains as bovine DEF-1 showing: four ankyrin related motifs, one zinc finger, SH3 binding sites, a proline-rich repeated motif and an SH3 domain. Zebrafish DEF-2 differs from DEF-1 sequence by lacking the proline-rich repeated motiff as depicted in FIG. 16. Zebrafish DEF-3 which is the shorter version of the three DEF proteins lacks the proline-rich repeated motiff and the SH3 domain. The approximate amino acid location of these domains is indicated in Table 1 below.

TABLE 1

Approximate Location of the Domains in DEF Family Members

|  | Bovine Def-1 SEQ ID NO: 2 | ZDEF-1 SEQ ID NO:4 | ZDEF-2 SEQ ID NO:7 | ZDEF-3 SEQ ID NO:10 |
|---|---|---|---|---|
| PH | 326–419 | 323–416 | 304–397 | 303–397 |
| Zn finger | 457–480 | 454–477 | 436–459 | 436–459 |
| C2 domain | 498–557 | 495–554 | 477–537 | 477–536 |
| Ankyrin #1 | 356–374 | 353–371 | 334–352 | 334–352 |
| Ankyrin #2 | 604–623 | 601–620 | 585–604 | 584–603 |
| Ankyrin #3 | 640–659 | 637–656 | 621–640 | 620–639 |
| Ankyrin #4 | 672–692 | 669–689 | 653–673 | 652–672 |
| Proline Rich Domain | 934–1001 | 944–1013 |  |  |
| SH3 domain | 1073–1123 | 1095–1145 | 926–976 |  |
| SH3 Binding Sites |  |  |  |  |
| Site #1 | 794–799 |  | 777–782 | 780–785 |
| Site #2 | 803–809 |  |  |  |
| Site #3 | 829–835 | 827–833 |  |  |
| Site #4 |  |  | 822–828 |  |
| Site #5 |  |  |  | 829–834 |
| Site #6 |  |  |  | 834–840 |
| Site #7 | 895–901 | 892–898 |  | 867–873 |
| Site #8 | 993–999 | 1005–1011 |  |  |

Bovine DEF-1 and zebrafish DEF-1 showed the highest degree of sequence identity in terms of full length nucleotide sequence (61.1% identity) and amino acid sequence (74.0%). A comparison of the amino acid sequence of the N-terminal domain (amino acids 1–750) between bovine DEF-1 and zebrafish DEF revealed about 85.2% identity, compared to 59.4% identity at the C-termini (last 200 amino acids). A comparison of zebrafish DEF-2 and human DEF-2 (Accession Number AB007860; SEQ ID NO: 12) revealed 62.3% and 73.9% identity at the nucleotide and amino acid level, respectively.

The alignment was performed using the Clustal Method. Multiple alignment paramethers include GAP Penalty=10, Gap Length Penalty=10. For DNA alignments, the pairwise alignment paramenters were Htuple=2, Gap penalty=5, Window=4, and Diagonal saved=4. For protein alignments, the pairwise alignment parameters were Ktuple=1, Gap penalty=3, Window=5, and Diagonals Saved=5.

EXAMPLE 14

In Situ Distribution of DEF Family Members

Experimental Procedures

Generation of plasmids containing only the 3' untranslated regions of ZDEF-1, ZDEF-2, ZDEF-3 cDNAs in addition to full-length plasmids were used to determine the tissue distribution of their mRNAs in the developing zebrafish embryo. Zebrafish embryos at several stages of development were fixed and processed for in situ antisense RNA hybridization as described in *The Zebrafish Book* (Westerfield, M. Editor) University of Oregon Press, 1995 and Chen, J.-N. and Fishman, M. C. (1996) *Development* 122:3809–3816. Digoxigenin-labeled antisense full-length and 3' untranslated constructs of ZDef-1, Zdef-2 and ZDef-3 were transcribed using T7 RNA polymerase (Promega). The embryos were fixed in 4% paraformaldehyde, rehydrated, treated with proteinase K, and then hybridized with various zebrafish Def-1 family antisense probes at 68° C. overnight. Alkaline phosphatase conjugated anti-digoxigenin antibody (Boehringer Mannheim) was used to detect the of ZDef-1, ZDef-2, ZDef-3 signals using the colorimetric NBT and BCIP alkaline phosphatase substrates (Boehringer Mannheim).

The in situ hybridization studies described above revealed that the expression pattern of DEF-1 increases within the zebrafish brain during development. In zebrafish, the expression of DEF-1 is spread throughout the body after 10 hour of development. By 72 hours, the majority of detectable DEF-1 is localized in the brain. Unlike the change in the distribution of DEF-1 expression upon development, the expression of DEF-3 is found primarily in the brain.

In the rat brain, expression of DEF-2 increases during gestation and then decreases near birth. These data indicate that DEF family members may function in the developing brain.

All of the above-cited references and publications are hereby incorporated by reference.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention.

We claim:

1. An isolated nucleic acid molecule wherein the nucleic acid molecule encodes a DEF polypeptide comprising the amino acid sequence of SEQ ID NO:2.

2. The isolated nucleic acid molecule of claim 1, wherein the polypeptide induces adipogenesis or neurogenesis.

3. The isolated nucleic acid molecule of claim 1, further comprising a second isolated nucleic acid molecule which encodes a second polypeptide having an amino acid sequence unrelated to the DEF polypeptide sequence, wherein the isolated nucleic acid molecule encodes a DEF fusion polypeptide.

4. A vector comprising the nucleic acid molecule of claim 1.

5. The vector of claim 4, which is a recombinant expression vector.

6. A host cell containing the vector of claim 4.

7. An isolated nucleic acid molecule comprising the nucleotide sequence of SEQ ID NO:1.

8. The isolated nucleic acid molecule of claim 1, comprising the coding region of SEQ ID NO:1, nucleotides 211 to 3595.

9. A method for producing a DEF polypeptide comprising culturing a host cell comprising the expression vector of claim 5.

10. The isolated nucleic acid molecule of claim 7, wherein the polypeptide induces adipogenesis or neurogenesis.

11. The isolated nucleic acid molecule of claim 7, further comprising a second isolated nucleic acid molecule which encodes a second polypeptide having an amino acid sequence unrelated to the DEF polypeptide sequence, wherein the isolated nucleic acid molecule encodes a DEF fusion polypeptide.

12. A vector comprising the nucleic acid molecule of claim 7.

* * * * *